United States Patent
Brentjens et al.

(10) Patent No.: US 10,590,196 B2
(45) Date of Patent: *Mar. 17, 2020

(54) ANTIBODIES TARGETING G-PROTEIN COUPLED RECEPTOR AND METHODS OF USE

(71) Applicants: MEMORIAL SLOAN-KETTERING CANCER CENTER, New York, NY (US); EUREKA THERAPEUTICS, INC., Emeryville, CA (US)

(72) Inventors: Renier J. Brentjens, New York, NY (US); Eric L. Smith, New York, NY (US); Cheng Liu, Emeryville, CA (US)

(73) Assignees: MEMORIAL SLOAN-KETTERING CANCER CENTER, New York, NY (US); EUREKA THERAPEUTICS, INC., Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/614,290

(22) Filed: Jun. 5, 2017

(65) Prior Publication Data

US 2018/0118822 A1    May 3, 2018

Related U.S. Application Data

(63) Continuation of application No. PCT/US2015/064122, filed on Dec. 4, 2015.

(60) Provisional application No. 62/088,228, filed on Dec. 5, 2014.

(51) Int. Cl.
| | |
|---|---|
| C07K 16/28 | (2006.01) |
| A61K 47/68 | (2017.01) |
| A61P 35/00 | (2006.01) |
| G01N 33/68 | (2006.01) |

(52) U.S. Cl.
CPC .......... *C07K 16/28* (2013.01); *A61K 47/6849* (2017.08); *A61P 35/00* (2018.01); *C07K 16/2809* (2013.01); *G01N 33/6872* (2013.01); *C07K 2317/21* (2013.01); *C07K 2317/24* (2013.01); *C07K 2317/31* (2013.01); *C07K 2317/34* (2013.01); *C07K 2317/622* (2013.01); *C07K 2317/92* (2013.01); *C07K 2319/21* (2013.01); *G01N 2333/705* (2013.01)

(58) Field of Classification Search
CPC ................ C07K 16/28; C07K 2317/21; C07K 2317/56; C07K 2317/565; A61K 47/6849
USPC ................................ 424/133.1, 136.1, 178.1
See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 5,399,346 A | 3/1995 | Anderson et al. | |
| 7,446,190 B2 | 11/2008 | Sadelain et al. | |
| 7,807,163 B2 | 10/2010 | Law et al. | |
| 8,389,282 B2 | 3/2013 | Sadelain et al. | |
| 2003/0207288 A1 | 11/2003 | Lewin et al. | |
| 2005/0019320 A1 | 1/2005 | Sugaru et al. | |
| 2005/0196754 A1 | 9/2005 | Drmanac et al. | |
| 2008/0057063 A1 | 3/2008 | Rinkenberger et al. | |
| 2011/0166330 A1 | 7/2011 | Kobilka et al. | |
| 2013/0130379 A1 | 5/2013 | Adams et al. | |
| 2014/0322183 A1 | 10/2014 | Milone et al. | |
| 2018/0118803 A1* | 5/2018 | Brentjens ............... C07K 16/28 |

FOREIGN PATENT DOCUMENTS

| | | |
|---|---|---|
| EP | 1 468 694 A1 | 10/2004 |
| RU | 2 526 517 C2 | 8/2014 |
| WO | WO 2004/072117 A2 | 8/2004 |
| WO | WO 2005/019258 A2 | 3/2005 |
| WO | WO 2009/039192 A2 | 3/2009 |
| WO | WO 2011/083088 A2 | 7/2011 |
| WO | WO 2012/009790 A1 | 1/2012 |
| WO | WO 2013/033626 A2 | 3/2013 |
| WO | WO 2014/087010 A1 | 6/2014 |
| WO | WO 2014/114800 A1 | 7/2014 |
| WO | WO 2014/127261 A1 | 8/2014 |
| WO | WO 2014/191128 A1 | 12/2014 |
| WO | WO 2015/142675 A2 | 9/2015 |
| WO | WO 2016/001810 A1 | 1/2016 |
| WO | WO 2016/014530 A1 | 1/2016 |

OTHER PUBLICATIONS

Smith et al. (Sci Transl Med. Mar. 27, 2019;11(485)).*
U.S. Appl. No. 15/613,800 (U.S. 2018/0118803), filed Jun. 5, 2017 (May 3, 2018).
Culture of Animal Cells: A Manual of Basic Technique and Specialized Applications, Sixth Edition, Freshney, 2010 (Table of Contents).
The Polymerase Chain Reaction. Mullis, 1994 (Foreword and Table of Contents).
Anderson, "Prospects for Human Gene Therapy," Science 226(4673):401-409 (1984).
Bataille et al., "The phenotype of normal, reactive and malignant plasma cells. Identification of 'many and multiple myelomas' and of new targets for myeloma therapy," Haematologica 91:1234-1240 (2006).
Benton et al., "Screening Xgt Recombinant Clones by Hybridization to Single Plaques in situ," Science 196(4286):180-182 (1977).
Bertilaccio et al., "Low-Dose Lenalidomide Improves CAR-Based Immunotherapy in CLL by Reverting T-Cell Defects In Vivo," Blood 122:4171 (2013).
Blömer et al., "Highly Efficient and Sustained Gene Transfer in Adult Neurons with a Lentivirus Vector," Journal of Virology 71(9):6641-6649 (1997).
Boyd et al., "The Clinical Impact and Molecular Biology of del(17p) in Multiple Myeloma Treated with Conventional or Thalidomide-Based Therapy," Genes, Chromosomes & Cancer 50:765-774 (2011).

(Continued)

*Primary Examiner* — Lynn A Bristol
(74) *Attorney, Agent, or Firm* — Baker Botts L.L.P.

(57) ABSTRACT

The presently disclosed subject matter provides antibodies that bind to GPRC5D and methods of using the same.

46 Claims, 17 Drawing Sheets

Specification includes a Sequence Listing.

(56) References Cited

OTHER PUBLICATIONS

Bregni et al., "Human Peripheral Blood Hematopoietic Progenitors Are Optimal Targets of Retroviral-Mediated Gene Transfer," Blood 80(6):1418-1422 (1992).
Brentjens et al., "CD19-Targeted T Cells Rapidly Induce Molecular Remissions in Adults with Chemotherapy-Refractory Acute Lymphoblastic Leukemia," Science Translational Medicine 5:177ra38 (2013).
Brentjens et al., "Eradication of systemic B-cell tumors by genetically targeted human T lymphocytes co-stimulated by CD80 and interleukin-15," Nature Medicine 9(3):279-286 (2003).
Brentjens et al., "Genetically Targeted T Cells Eradicate Systemic Acute Lymphoblastic Leukemia Xenografts," Clin Cancer Res 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Cornetta et al., "Gene Transfer into Primates and Prospects for Gene Therapy in Humans," Progress in Nucleic Acid Research and Molecular Biology 36:311-322 (1987).
Danos et al., "Safe and efficient generation of recombinant retroviruses with amphotropic and ecotropic host ranges," PNAS USA 85:6460-6464 (1988).
Davila et al., "Efficacy and Toxicity Management of 19-28z CAR T Cell Therapy in B Cell Acute Lymphoblastic Leukemia," Science Translational Medicine 6:224ra25 (2014).
Dudley et al., "Adoptive Cell Therapy for Patients with Metastatic Melanoma: Evaluation of Intensive Myeloablative Chemoradiation Preparative Regimens," J Clin Oncol 26:5233-5239 (2008).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).
Eglitis et al., "Retroviral Vectors for Introduction of Genes into Mammalian Cells," BioTechniques 6(7):608-614 (1988).
Extended European Search Report dated Jul. 10, 2018 in Application No. EP 15865633.
Felgner et al., "Lipofection: A highly efficient, lipid-mediated DNA-transfection procedure," PNAS USA 84:7413-7417 (1987).
Friedmann, "Progress toward Human Gene Therapy," Science 244(4910):1275-1281 (1989).
Gade et al., "Targeted Elimination of Prostate Cancer by Genetically Directed Human T Lymphocytes," Cancer Res 65(19):9080-9088 (2005).
Gahrton et al., "Allogeneic Bone Marrow Transplantation in Multiple Myeloma," N Engl J Med 325:1267-1273 (1991).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).
Grunstein et al., "Colony hybridization: A method for the isolation of cloned DNAs that contain a specific gene," PNAS USA 72(10):3961-3965 (1975).
Hollyman et al., "Manufacturing Validation of Biologically Functional T Cells Targeted to CD19 Antigen for Autologous Adoptive Cell Therapy," J Immunother 32:169-180 (2009).
Hughes et al., "Retroviral Gene Transfer to Primitive Normal and Leukemic Hematopoietic Cells Using Clinically Applicable Procedures," J. Clin. Invest. 89:1817-1824 (1992).

Hunder et al., "Treatment of Metastatic Melanoma with Autologous CD4+ T Cells against NY-ESO-1," N Engl J Med 358:2698-2703 (2008).
International Search Report dated Apr. 8, 2016 in International Application No. PCT/US15/64102.
Johnson, "Gene Therapy for Cystic Fibrosis," Chest 107:77S-83S (1995).
Kershaw et al., "Gene-Engineered T cells as a Superior Adjuvant Therapy for Metastatic Cancer," J Immunol 173:2143-2150 (2004).
Kido et al., "Use of a retroviral vector with an internal opsin promoter to direct gene expression to retinal photoreceptor cells," Current Eye Research 15:833-844 (1996).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Le Gal La Salle et al., "An Adenovirus Vector for Gene Transfer into Neurons and Glia in the Brain," Science 259(5097):988-990 (1993).
Lyddane et al., "Cutting Edge: CD28 Controls Dominant Regulatory T Cell Activity during Active Immunization," J. Immunol. 176:3306-3310 (2006).
Maher et al., "Human T-lymphocyte cytotoxicity and proliferation directed by a single chimeric TCRζ/CD28 receptor," Nat. Biotechnol. 20:70-75 (2002).
Miller et al., "Improved Retroviral Vectors for Gene Transfer and Expression," Biotechniques 7(9):980-990 (1989).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Miyoshi et al., "Stable and efficient gene transfer into the retina using an HIV-based lentiviral vector," PNAS USA 94:10319-10323 (1997).
Moen, "Directions in Gene Therapy," Blood Cells 17:407-416 (1991).
Morgan et al., "Case Report of a Serious Adverse Event Following the Administration of T Cells Transduced with a Chimeric Antigen Receptor Recognizing ERBB2," Molecular Therapy 18(4):843-851 (2010).
Morgan et al., "Cancer Regression in Patients After Transfer of Genetically Engineered Lymphocytes," Science 314:126-129 (2006).
Naldini et al., "In Vivo Gene Delivery and Stable Transduction of Nondividing Cells by a Lentiviral Vector," Science 272(5259):263-267 (1996).
Ono et al., "Plasmid DNAs directly injected into mouse brain with lipofectin can be incorporated and expressed by brain cells," Neuroscience Letters, 117:259-263 (1990).
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus-specific cytotoxic T lymphocytes by artificial antigen-presenting cells expressing a single HLA allele," Blood 102:2498-2505 (2003).
Pegram et al., "Tumor-targeted T cells modified to secrete IL-12 eradicate systemic tumors without need for prior conditioning," Blood 119(18):4133-4141 (2012).
Posthumus et al., "Analysis and Simulation of a Neutralizing Epitope of Transmissible Gastroenteritis Virus," J. Virology, 64(7):3304-3309 (1990).
Riviere et al., "Novel Strategies for Cancer Therapy: The Potential of Genetically Modified T Lymphocytes," Curr Hematol Rep 3:290-297 (2004).
Rosenberg et al., "Adoptive cell transfer: a clinical path to effective cancer immunotherapy," Nature Reviews Cancer 8:299-308 (2008).
Rosenberg et al., "Gene Transfer into Humans," N. Engl. J. Med 323(9):570-578 (1990).

(56) References Cited

OTHER PUBLICATIONS

Sadelain et al., "The basic principles of chimeric antigen receptor (CAR) design," Cancer Discovery 3(4):388-398 (2013).
Sadelain et al., "The promise and potential pitfalls of chimeric antigen receptors," Curr Opin Immunol 21:215-223 (2009).
Sadelain et al., "Targeting Tumours With Genetically Enhanced T Lymphocytes," Nat Rev Cancer 3:35-45 (2003).
Sambrook et al., Molecular Cloning: A Laboratory Manual, 2nd ed. Cold Spring Harbor Laboratory Press, New York (1989).
Sharp, "Gene Therapy," The Lancet 337:1277-1278 (1991).
Shaughnessy, Jr., et al., "A validated gene expression model of high-risk multiple myeloma is defined by deregulated expression of genes mapping to chromosome 1," Blood 109:2276-2284 (2007).
Siegel et al., "Cancer Statistics, 2013," CA Cancer J Clin 63:11-30 (2013).
Straubinger et al., "Liposomes as Carriers for Intracellular Delivery of Nucleic Acids," Methods in Enzymology, 101:512-527 (1983).
Stephan et al., "T cell-encoded CD80 and 4-1BBL induce auto- and transcostimulation, resulting in potent tumor rejection," Nat. Med 13(12):1440-1449 (2007).
Tolstoshev et al., "Gene expression using retroviral vectors," Current Opinion in Biotechnology 1:55-61 (1990).
Wahl et al., "Improved Radioimaging and Tumor Localization with Monoclonal F(ab')2," J. Nucl. Med. 24:316-325 (1983).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry, 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xu et al., "Correction of the enzyme deficiency in hematopoietic cells of Gaucher patients using a clinically acceptable retroviral supernatant transduction protocol," Exp. Hemat. 22:223-230 (1994).
Abdiche et al., "Probing the binding mechanism and affinity of tanezumab, a recombinant humanized anti-NGF monoclonal antibody, using a repertoire of biosensors," Protein Science 17:1326-1335 (2008).
Allen, "Ligand-Targeted Therapeutics in Anticancer Therapy," Nat. Rev. Cancer 2:750-763 (2002).
Altschul et al., "Gapped BLAST and PSI-BLAST: a new generation of protein database search programs," Nucleic Acids Res. 25(17):3389-3402 (1997).
Altschul, et al., "Basic Local Alignment Search Tool," J. Mol. Biol. 215:403-410 (1990).
Amon et al., "Monoclonal Antibodies for Immunotargeting of Drugs in Cancer Therapy," in Monoclonal Antibodies and Cancer Therapy, Reisfeld et al. (eds.), pp. 243-256 (1985).
Atamaniuk et al., "Overexpression of G protein-coupled receptor 5D in the bone marrow is associated with poor prognosis in patients with multiple myeloma," European Journal of Clinical Investigation, 42(9):953-960 (2012).
Azinovic et al., "Survival benefit associated with human anti-mouse antibody (HAMA) in patients with B-cell malignancies," Cancer Immunol Immunother 55:1451-1458 (2006).
Baeuerle et al., "Bispecific T-cell Engaging Antibodies for Cancer Therapy," Cancer Res., 69(12):4941-4944 (2009).
Bam et al., "GPRC5D Is a Cell Surface Plasma Cell Marker Whose Expression Is High in Myeloma Cells and Reduced Following Coculture With Osteoclasts," Blood 122:3099 (2013).
Bird et al., "Single-Chain Antigen-Binding Proteins," Science 242(4877):423-426 (1988).
Brennan et al., "Preparation of Bispecific Antibodies by Chemical Recombination of Monoclonal Immunoglobulin G1 Fragments," Science 229:81-83 (1985).
Brocks et al., "A TNF receptor antagonistic scFv, which is not secreted in mammalian cells, is expressed as a soluble mono- and bivalent scFv derivative in insect cells," Immunotechnology 3:173-184 (1997).
Brown et al., "Tolerance to Single, but not Multiple, Amino Acid Replacements in Antibody V-H CDR2: A Means of Minimizing B Cell Wastage from Somatic Hypermutation?" The Journal of Immunology, The American Association of Immunologists, 156:3285-3291 (1996).
Caron et al., "Engineered Humanized Dimeric Forms of IgG are More Effective Antibodies," J Exp. Med 176:1191-1195 (1992).
Chen et al., "Selection and Analysis of an Optimized Anti-VEGF Antibody: Crystal Structure of an Affinity-matured Fab in Complex with Antigen," J. Mol. Biol. 293:865-881(1999).
Cohen et al., "GPRC5D is a promising marker for monitoring the tumor load and to target multiple myeloma cells," Hematology 18(6):348-351 (2013).
Cuesta et al., "Multivalent antibodies: when design surpasses evolution," Trends in Biotechnology 28(7):355-362 (2010).
Fife et al., "Inhibition of T cell activiation and autoimmune diabetes using a B cell surface-linked CTLA-4 agonist," J Clin Invest 116(8):2252-2261 (2006).
Flatman et al., "Process analytics for purification of monoclonal antibodies," J. Chromatogr. B 848:79-87 (2007).
Frigyesi et al., "Robust isolation of malignant plasma cells in multiple myeloma," Blood 123(9):1336-1340 (2014).
Gershoni et al., "Epitope mapping—The first step in developing epitope-based vaccines," Biod, Adis International Ltd., NZ, 21(3):145-156 (2007).
Giomarelli et al., "Inhibition of thrombin-induced platelet aggregation using human single-chain Fv antibodies specific for TREM-like transcript- I," Thromb Haemost 97:955-963 (2007).
Glennie et al., "Preparation and performance of bispecific F(ab' gamma)2 antibody containing thioether-linked Fab' gamma fragments," J. Immunol. 139:2367-2375 (1987).
Harris et al., "Crystallographic Structure of an Intact IgG1 Monoclonal Antibody," Journal of Molecular Biology 275:861-872 (1998).
Hellstrom et al., "Antibodies for Drug Delivery," in Controlled Drug Delivery (2nd Ed.), Robinson et al. (eds.), pp. 623-653 (1987).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Huston et al., "Protein engineering of antibody binding sites: Recovery of specific activity in an anti-digoxin single-chain Fv analogue produced in *Escherichia coli*," PNAS USA 85:5879-5883 (1988).
International Search Report dated May 19, 2016 in International Application No. PCT/US15/64122.
Kabat et al., Sequences of Proteins of Immunological Interest, 4th U. S. Department of Health and Human Services, National Institutes of Health (1987), Table of Contents.
Kabat, E. A., et al. (1991) Sequences of Proteins of Immunological Interest, vol. I, Fifth Edition, U.S. Department of Health and Human Services, NIH Publication No. 91-3242).
Karpovsky et al., "Production of Target-Specific Effector Cells Using Hetero-Cross-Linked Aggregates Containing Anti-Target Cell and Anti-Fcy Receptor Antibodies," J. Exp. Med. 160:1686-1701 (1984).
Klechevsky et al., "Antitumor activity of immunotoxins with T-cell receptor-like specificity against human melanoma xenografts," Cancer Res 68(15):6360-6367 (2008).
Ledbetter et al., "Agonistic Activity of a CD40-Specific Single-Chain Fv Constructed from the Variable Regions of mAb G28-5," Crit Rev Immunol. 17:427-435 (1997).
Liu et al., "Heteroantibody duplexes target cells for lysis by cytotoxic T lymphocytes," Proc. Natl. Acad. Sci. USA 82:8648-8652 (1985).
McCafferty et al., "Phage antibodies: filamentous phage displaying antibody variable domains," Nature 348:552-554 (1990).
Meyers et al., "Optimal alignments in linear space," Cabios 4(1):11-17 (1988).
Moosmayer et al., "A single-chain TNF receptor antagonist is an effective inhibitor of TNF mediated cytotoxicity," Therapeutic Immunol. 2:31-40 (1995).

(56) References Cited

OTHER PUBLICATIONS

Needleman et al., "A General Method Applicable to the Search for Similarities in the Amino Acid Sequence of Two Proteins," J. Mol. Biol. 48:443-453 (1970).
Pastan et al., "Immunotoxins in cancer therapy," Curr. Opin. Investig. Drugs 3(7):1089-1091 (2002).
Paulus, "Preparation and Biomedical Applications of Bispecific Antibodies," Behring Ins. Mitt. 78:118-132 (1985).
Payne, "Progress in immunoconjugate cancer therapeutics," Cancer Cell 3:207-212 (2003).
Persic et al., "An integrated vector system for the eukaryotic expression of antibodies or their fragments after selection from phage display libraries," Gene 187:9-18 (1997).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the 132-Adrenergic Receptor," J Biol. Chem. 278(38):36740-36747 (2003).
Queen et al., "A humanized antibody that binds to the interleukin 2 receptor," Proc Natl Acad Sci USA 86:10029-10033 (1989).
Riechmann et al., "Reshaping human antibodies for therapy," Nature 332:323-327 (1988).
Ritter et al., "Serological Analysis of Human Anti-Human Antibody Responses in Colon Cancer Patients Treated with Repeated Doses of Humanized Monoclonal Antibody A33," Cancer Res 61:6851-6859 (2001).
Roberts et al., "Vaccination with CD20 peptides induces a biologically active, specific immune response in mice," Blood 99: 3748-3755 (2002).
Saito et al., "Drug delivery strategy utilizing conjugation via reversible disulfide linkages: role and site of cellular reducing activities," Adv. Drug Deliv. Rev. 55:199-215 (2003).
Senter et al., "Selective activation of anticancer prodrugs by monoclonal antibody—enzyme conjugates," Adv. Drug Deliv. Rev. 53:247-264 (2001).
Shen et al., "Engineering Peptide Linkers for scFv Immunosensors," Anal Chem. 80(6):1910-1917 (2008).
Shieh et al., "Transgenic Expression of Single-Chain Anti-CTLA-4 Fv on β Cells Protects Nonobese Diabetic Mice from Autoimmune Diabetes," J Immunol 183:2277-2285 (2009).
Supplemental Partial European Search Report dated May 4, 2018 in Application No. EP 15865989.
Thorpe et al., "The Preparation and Cytotoxic Properties of Antibody-Toxin Conjugates," Immunol. Rev., 62:119-158 (1982).
Thorpe, "Antibody Carriers of Cytotoxic Agents in Cancer Therapy: A Review," in Monoclonal Antibodies '84: Biological and Clinical Applications, Pinchera et al. (eds.), pp. 475-506 (1985).
Timmerman et al., "Functional reconstruction and synthetic mimicry of a conformational epitope using CLIPS™ technology," J. Mol. Recognit. 20:283-299 (2007).
Tjandra et al., "Development of human anti-murine antibody (HAMA) response in patients," Immunol Cell Biol. 68:367-376 (1990).
Tomimatsu et al., "Production of Human Monoclonal Antibodies against FcεRIα by a Method Combining *in Vitro*Immunization with Phage Display," Biosci Biotechnol Biochem 73(7):1465-1469 (2009).
Trail et al., "Monoclonal antibody drug immunoconjugates for targeted treatment of cancer," Cancer Immunol. Immunother. 52:328-337 (2003).
Ward et al., "Binding activities of a repertoire of single immunoglobulin variable domains secreted from *Escherichia coli*," Nature 341:544-546 (1989).
Xie et al., "Direct demonstration of MuSK involvement in acetylcholine receptor clustering through identification of agonist ScFv," Nat Biotech 15:768-771 (1997).
Zhao et al., "Characteristics of an scFv Antibody Fragment That Binds to Immunoglobulin G of Graves' Disease Patients and Inhibits Autoantibody-Mediated Thyroid-Stimulating Activity," Hybridoma 27(6):445-451 (2008).
Clinical Immunology and Allergology: in 3 volumes / edited by L. Yeger; translated from German by S.S. Kirzon, A.P. Portnova, Editor Academician R.V.Petrov—[$2^{nd}$ edition, reworked and updated].—Moscow: Meditsina, 1990. 1:219-222 (with full English translation).
Koyko, R. Immunology: Textbook for Post-Graduate Education of Physicians / R. Koyko, D. Sunshine, E. Benjamin; translated from English, Editor N. B. Serebryanaya. -Moscow: Akademiya; Saint-Petersburg: Philology Department of The S.-Petersburg State University, 2008, 1:37 (with full English translation).
Ozhegov, S.I. The Thesaurus of the Russian Language: 80,000 words and idioms / S.I. Ozhegov and N. Yu Shvedova; Russian Academy of Sciences, Institute of the Russian Language named after V.V. Vinogradov.—$4^{th}$ Edition, updated—Moscow: [A Temp}, 2006. 1:375 (with full English translation).
Abbas et al., Cellular and Molecular Immunology, p. 54 (1991).
Edwards et al., "The Remarkable Flexibility of the Human Antibody Repertoire; Isolation of Over One Thousand Different Antibodies to a Single Protein, BLyS," J. Mol. Biol. 334:103-118 (2003).
Hirano et al., "Novel reciprocal regulation of cAMP signaling and apoptosis by orphan G-protein-coupled receptor GPRC5A gene expression," Biochemical and Biophysical Research Communications 351:185-191 (2006).
Lippincott-Schwartz et al., "Antibodies as Cell Biological Tools," Chapter 16 in Current Protocols in Cell Biology Supplement 13, 16.0.1-16.0.2 (2002), 2 pages.
Lloyd et al., "Modelling the human immune response: performance of a 10^11 human antibody repertoire against a broad panel of therapeutically relevant antigens," Protein Engineering, Design & Selection 22(3):159-168 (2009).
Mariuzza et al., "The Structural Basis of Antigen-Antibody Recognition," Annual Review of Biophysics and Biophysical Chemistry 16:139-159 (1987).
Parkman, R., "Clonal analysis of murine graft-vs-host disease. I. Phenotypic and functional analysis of T lymphocyte clones," J. Immunol. 136:3543-3548 (1986).
Search Report in Russian Application No. 2017123545 received by Applicant dated Dec. 11, 2019.

\* cited by examiner

| Loop 1 | Loop 2 | ELISA |
|---|---|---|
| C(SEQ ID NO.: 416) MDYDFKVKLSSERERC | (SEQ ID NO.: 420) WAIGCIFAELLTSEPC | −0.01 |
| C(SEQ ID NO.: 416) MDYDFKVKLSSERERC | (SEQ ID NO.: 421) CIFAELLTSEPIFHCC | 0.79 |
| C(SEQ ID NO.: 416) MDYDFKVKLSSERERC | (SEQ ID NO.: 422) ELLTSEPIFHCRQEDC | 1.21 |
| C(SEQ ID NO.: 416) MDYDFKVKLSSERERC | (SEQ ID NO.: 423) SEPIFHCRQEDIKTSC | 0.36 |
| C(SEQ ID NO.: 417) FKVKLSSERERVEDLC | (SEQ ID NO.: 420) WAIGCIFAELLTSEPC | 0.17 |
| C(SEQ ID NO.: 417) FKVKLSSERERVEDLC | (SEQ ID NO.: 421) CIFAELLTSEPIFHCC | 1.19 |
| C(SEQ ID NO.: 417) FKVKLSSERERVEDLC | (SEQ ID NO.: 422) ELLTSEPIFHCRQEDC | 1.24 |
| C(SEQ ID NO.: 417) FKVKLSSERERVEDLC | (SEQ ID NO.: 423) SEPIFHCRQEDIKTSC | 0.56 |
| C(SEQ ID NO.: 418) LSSERERVEDLFEYEC | (SEQ ID NO.: 420) WAIGCIFAELLTSEPC | 0.61 |
| C(SEQ ID NO.: 418) LSSERERVEDLFEYEC | (SEQ ID NO.: 421) CIFAELLTSEPIFHCC | 1.21 |
| C(SEQ ID NO.: 418) LSSERERVEDLFEYEC | (SEQ ID NO.: 422) ELLTSEPIFHCRQEDC | 1.41 ← |
| C(SEQ ID NO.: 418) LSSERERVEDLFEYEC | (SEQ ID NO.: 423) SEPIFHCRQEDIKTSC | 0.58 |
| C(SEQ ID NO.: 419) RERVEDLFEYEGCKVC | (SEQ ID NO.: 420) WAIGCIFAELLTSEPC | 0.10 |
| C(SEQ ID NO.: 419) RERVEDLFEYEGCKVC | (SEQ ID NO.: 421) CIFAELLTSEPIFHCC | 0.83 |
| C(SEQ ID NO.: 419) RERVEDLFEYEGCKVC | (SEQ ID NO.: 422) ELLTSEPIFHCRQEDC | 1.21 |
| C(SEQ ID NO.: 419) RERVEDLFEYEGCKVC | (SEQ ID NO.: 423) SEPIFHCRQEDIKTSC | −0.02 |

FIG. 5A

SEQUENCE LISTING

```
<160> NUMBER OF SEQ ID NOS: 415

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ser Glu Leu Lys Lys Pro Gly Ala
1               5                   10                  15

Ser Val Arg Val Ser Cys Thr Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Val Ile Asn Pro Asn Ala Gly Ser Thr Arg Tyr Ala Gln Lys Phe
    50                  55                  60
```

Gln Gly Arg Val Thr Met Ser Thr Asp Thr Ser Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Met Tyr Arg Ser Leu Leu Phe Tyr Asp Pro Trp Gly Gln
            100                 105                 110

Gly Thr Leu Val Thr Val Ser Ser
        115                 120

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Ala Ala Pro Gly Gln
1               5                   10                  15

Lys Val Thr Ile Pro Cys Ser Gly Ser Arg Ser Asn Val Gly Asn Tyr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Gly Ser Leu
                85                  90                  95

Ser Ala His Val Phe Gly Thr Gly Thr Lys Val Thr Val Leu Gly
            100                 105                 110

<210> SEQ ID NO 3
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caggtgcagc tggtgcagtc tgggtctgag ttgaagaagc ctggggcctc agtcagagtc    60
tcctgcacgg cttctggata caccttcacc agttactata tgcactgggt gcgacaggcc   120
cctggacaag gcttgagtg gatgggagta atcaaccctc atgctggcag cacaagatac    180
gcacagaaat tccagggcag agtcaccatg agcactgaca cgtccacgag cacagcctac   240
atggacctga gcagtctgag atctgaggac acggccgtgt attactgtgc gcgcggtatg   300
taccgttctc tgctgttcta cgatccgtgg ggtcaaggta ctctggtgac cgtctcctca   360

<210> SEQ ID NO 4
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cagtctgtgt tgacgcagcc gccctcagtg tctgcggccc caggacagaa ggtcaccatc    60

```
ccctgctctg gaagccgttc caacgttggg aattattatg tgtcctggta ccagcaactc    120
ccaggaacag cccccaaact cctcatttat gacaataata gcgaccctc agggattcct     180 gaccgattct ctggctccaa gtctggcacg tcagccaccc tgggcatcac cggactccag    240
actggggacg aggccgatta tttctgcgga acatgggatg cagcctgag tgcccatgtc     300 ttcggaactg ggaccaaggt caccgtccta ggt                                 333
```

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Val Arg Tyr Thr Asp Ile Trp Gly Gln Gly Thr Leu Val
            100                 105                 110

Thr Val Ser Ser
        115
```

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 6

```
Asn Phe Met Leu Thr Gln Pro His Ser Val Ser Glu Ser Pro Gly Lys
1               5                   10                  15

Thr Val Ser Ile Ser Cys Thr Arg Thr Ser Gly Ala Ile Ala Gly Ala
            20                  25                  30

Tyr Val Gln Trp Phe Gln Gln Arg Pro Gly Ser Ala Pro Thr Thr Val
        35                  40                  45

Ile Tyr Asp Asp Asn Lys Arg Pro Ser Gly Val Pro Asp Arg Phe Ser
    50                  55                  60

Gly Ser Ile Asp Lys Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Ser Ser Asn Val Leu Phe Gly Gly Gly Thr Lys Leu Thr Val Leu
            100                 105                 110

Gly
```

<210> SEQ ID NO 7
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gaggtgcagc tggtggagtc tgggggaggc ttggtacagc ctggggggtc cctgagactc    60
tcctgtgcag cctctggatt cacctttagc aactatgcca tgagttgggt ccgccaggct   120
ccagggaagg gactggagtg ggtctcagct attagtggta gtggtaacac atactacgca   180
gactccgtga agggccggtt caccatctcc agagacaatt ccaagaacac gctgtatctg   240
caaatgaaca gcctgagagc cgaggacacg gccgtatatt actgtgcgcg cggttctgtt   300
cgttacactg atatctgggg tcaaggtact ctggtgaccg tctcctca                348
```

<210> SEQ ID NO 8
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
aattttatgc tgactcagcc ccactcagtg tcggagtctc cggggaagac ggtaagcatc    60
tcctgcaccc gcaccagtgg cgccattgcc ggcgcctatg tgcagtggtt ccagcagcgc   120
ccgggcagtg cccccaccac tgtgatctat gacgataaca aaagaccctc tggggtccct   180
gatcggttct ctgggtccat cgacaagtcc tccaactctg cctccctcac catctctgga   240
ctgaagactg aggacgaggc tgactattat tgtcagtctt atgattatga tagcagcaat   300
gtgctattcg gcggagggac caagctgacc gtcctaggt                          339
```

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Glu Val Gln Leu Val Gln Ser Gly Gly Gly Leu Val Gln Pro Gly Gly
1               5                   10                  15

Ser Leu Arg Leu Ser Cys Ala Thr Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Ala Asp Ser Val
    50                  55                  60

Arg Gly Arg Phe Thr Ile Ser Arg Asp Asn Ala Lys Asn Ser Leu Ser
65                  70                  75                  80

Leu Gln Leu Asn Asn Leu Arg Ala Glu Asp Thr Ala Val Tyr Tyr Cys
                85                  90                  95

Ala Arg Ser Met Ser Thr Ala Trp Gly Tyr Asp Glu Trp Gly Gln Gly
            100                 105                 110

Thr Leu Val Thr Val Ser Ser
        115

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Ala Asp Phe Ala Thr Tyr Tyr Cys Gln Gln Ser Tyr Ser Val Pro Tyr
                85                  90                  95

Thr Phe Gly Gln Gly Thr Lys Leu Glu Ile Lys Arg
            100                 105

<210> SEQ ID NO 11
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagc tggtgcagtc tgggggaggc ttggtccagc ctggggggtc cctgagactc      60
tcctgtgcaa cctctggatt cacctttaat aactattgga tgagttgggt ccgccaggct     120
ccagggaagg ggctggagtg ggtggccaac ataaagcaag atggaagtga aaaatactac     180
gcggactctg tgaggggccg attcaccatc tccagagaca acgccaagaa ctcactgtct     240
ctgcaattga acaacctgag agccgaggac acggccgtgt attactgtgc gcgctctatg     300
tctactgctt ggggttacga tgaatggggt caaggtactc tggtgaccgt ctcctca       357

<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacatccagt tgacccagtc tccatcctcc ctgtctgcat ctgtcggaga cagagtcacc      60
atcacttgcc gggcaagtca gagcattagc agctatttaa attggtatca acagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gcagattttg caacttacta ctgtcaacag agttacagtg tcccgtacac ttttggccag    300

```
gggaccaagc tggagatcaa acgt                                          324
```

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Arg Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ser Arg Trp Gly Gly Trp Thr Gly Asp Tyr Trp Gly
                100                 105                 110

Gln Gly Thr Leu Val Thr Val Ser Ser
            115                 120

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Phe Val Ser Trp Tyr Gln Gln His Pro Gly Lys Ala Pro Lys Val
            35                  40                  45

Met Ile Tyr Asp Val Ser Lys Arg Pro Ser Gly Ile Ser Asn Arg Phe
        50                  55                  60

Ser Gly Ser Lys Ser Gly Asn Thr Ala Ser Leu Thr Ile Ser Gly Leu
65                  70                  75                  80

Gln Val Glu Asp Glu Ala Glu Tyr Tyr Cys Ser Ser Tyr Thr Ser Thr
                85                  90                  95

Arg Thr Val Ile Phe Ala Gly Gly Thr Lys Val Thr Val Leu Gly
                100                 105                 110

<210> SEQ ID NO 15
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

-continued

```
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg atgggaata  atcaaccccta gtggtggtag cacaaggtac     180
gcacagaagt tccagggcag agtcaccatg accaggdaca cgtcaacgag cacagtctac     240
atggagctga gcagcctgag atctgaggac acggccgtgt attactgtgc gcgcggttct     300
tctcgctggg gtggttggac tggtgattac tggggtcaag gtactctggt gaccgtctcc     360
tca                                                                  363
```

<210> SEQ ID NO 16
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
caatctgccc tgactcagcc tgcctccgtg tctgggtctc ctggacagtc gatcaccatc      60
tcctgcactg gaaccagcag tgacgttggt ggttataact ttgtctcctg gtaccaacag     120
cacccaggca agcccccaa  agtcatgatt tatgatgtca gtaagcggcc ctcagggatt     180
tctaatcgct tctctggctc caagtctggc aacacggcct ccctgaccat ctctgggctc     240
caggttgagg acgaggctga atattactgc agctcatata caagcactag aactgtgata     300
ttcgccggag ggaccaaggt caccgtccta ggt                                 333
```

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Thr Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Lys Ser Ser Lys Asp His Trp Gly Gln Gly Thr Leu
            100                 105                 110

Val Thr Val Ser Ser
        115

<210> SEQ ID NO 18
<211> LENGTH: 111
<212> TYPE: PRT
<213> ORGANISM: Artificial Sequence
<220> FEATURE:

-continued

<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Any amino acid

<400> SEQUENCE: 18

Gln Ser Val Leu Thr Gln Pro Pro Ser Leu Ser Gly Ala Pro Gly Gln
1               5                   10                  15

Arg Val Thr Ile Ser Cys Ser Gly Ser Arg Ser Asn Ile Gly Thr Asn
            20                  25                  30

Tyr Val Ser Trp Xaa Gln Gln Leu Pro Gly Thr Ala Pro Lys Leu Leu
        35                  40                  45

Ile Tyr Arg Asn His Gln Trp Pro Ser Gly Val Pro Asp Arg Phe Thr
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Val Val Phe Gly Gly Gly Thr Lys Leu Thr Val Leu Gly
            100                 105                 110

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gaggtgcagc tggtggagac tgggggaggc ttggtacagc ctggggggtc cctgagactc     60
tcctgtgcag cctctggatc cacctttagc agctatgcca tgagctgggt ccgccaggct    120
ccagggaagg ggctggagtg ggtctcagct attagtggtc gtggtcgtag cacatactac    180
gcagactccg tgaagggccg gttcaccatc tccagagaca attccaagaa cacgctgtat    240
ctgcaaatga acagcctgag agccgaggac acggccgtat attactgtgc gcgctactac    300
aaatcttcta agatcattg ggtcaaggt actctggtga ccgtctccta a                351

<210> SEQ ID NO 20
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (109)..(109)
<223> OTHER INFORMATION: a, c, t, g, unknown or other

<400> SEQUENCE: 20
cagtctgtgt tgacgcagcc gccctcactg tctggggccc cagggcagag ggtcaccatc     60
tcttgttccg gaagcaggtc caacatcgga actaattatg tatcctggna ccagcaactc    120
ccaggaacgg cccccaaact cctcatctat aggaatcatc agtggccctc agggtccct    180 gaccgattca ctggctccaa gtctggcacc tcagcctccc tggccatcag tgggctccgg    240
tccgaggatg aggctgatta ctactgtgca gcatgggatg acaatttgag tggtgtggtg    300
ttcggcggag ggaccaagct gaccgtccta ggt                                  333

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Gln Arg Pro Gly Ala
1               5                   10                  15

Ser Val Arg Val Ser Cys Lys Ala Ile Ala Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Lys Ser Gly Arg Thr Gln Tyr Ala Pro Lys Phe
    50                  55                  60

Gln Asp Arg Val Thr Leu Ala Arg Glu Thr Pro Ile Ser Thr Ala Ser
65                  70                  75                  80

Met Glu Leu Arg Gly Leu Thr Ser Asp Asp Thr Ala Val Tyr Tyr Cys
                85                  90                  95

Ala Arg Val Tyr Gly Tyr Ser Arg Trp Ser Gly Phe Asp Leu Trp Gly
            100                 105                 110

Gln Gly Thr Leu Val Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 23
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
caggtccagc tggtgcagtc tggggctgag gtgcagaggc ctggggcctc agtgagggtc    60
tcctgcaagg ctattgcgta caccttcacc gactactata tccactgggt gcgacaggcc   120
cctggacaag ggcctgagtg gatggggtgg atcaaccctta aaagtggtcg cacacagtat   180
gcaccgaagt ttcaagacag ggtcaccctg gccagggaga cgcccatcag cacagcctcc   240
atggagctgc gcggactgac atctgacgac acggccgtgt attactgtgc gcgcgtttac   300
ggttactctc gttggtctgg tttcgatctg tggggtcaag gtactctggt gaccgtctcc   360
tca                                                                 363
```

<210> SEQ ID NO 24
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
caggctgtgc tgactcagcc accctcagcg tctgggaccc ccgggcagag ggtcaccatc    60
tcttgttctg gaagcagctc caacatcgga agtaattatg tatactggta ccagcagctc   120
ccaggaacgg ccccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggttatgtc   300
ttcggaactg ggaccaaggt caccgtccta ggt                                333
```

<210> SEQ ID NO 25
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Gln Pro Gly Ala
1               5                   10                  15

Ser Val Lys Val Ser Cys Gln Ala Ser Gly Tyr Thr Phe Thr Thr Tyr
                20                  25                  30

Tyr Met His Trp Val Arg Gln Ala Pro Gly Gln Gly Leu Glu Trp Met
            35                  40                  45

Gly Ile Ile Asn Pro Asn Gly Gly Thr Phe Tyr Ala Gln Lys Phe
        50                  55                  60

Gln Asp Arg Val Thr Met Thr Arg Asp Thr Ser Thr Gly Thr Val Tyr
65                  70                  75                  80

Met Glu Leu Ser Ser Leu Arg Ser Asp Asp Thr Ala Val Tyr Tyr Cys
                85                  90                  95

Ala Arg Gly His Lys Val Tyr Lys Ser His Pro Thr Gly Gly Tyr Asp
                100                 105                 110

Arg Trp Gly Gln Gly Thr Leu Val Thr Val Ser Ser
        115                 120

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 26

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Phe Gly Thr Gly Thr Lys Val Thr Val Leu Gly
            100                 105                 110

<210> SEQ ID NO 27
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtgcagc tggtgcaatc tggggctgag gtgaagcagc ctggggcctc agtgaaggtt      60
tcctgccagg catctggata caccttcacc acttattata tgcactgggt gcgacaggcc    120
cctggacaag gcttgagtg gatgggaata atcaaccta atggtggtgg cacattctac      180
gcacagaagt tccaggacag agtcaccatg accagggaca cgtccacggg cacagtctac    240
atggaactga gcagcctgag atctgacgac actgccgtgt attactgtgc gcgcggtcat    300
aaagtttaca atctcatcc gactggtggt tacgatcgtt ggggtcaagg tactctggtg    360
accgtctcct ca                                                        372

<210> SEQ ID NO 28
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
caatctgccc tgactcagcc tgcctccgtg tctgggtctc ctggacagtc gatcaccatc      60
tcctgcactg gaaccagccg tgacgttggt ggttataact atgtctcctg gtaccaacag    120
tacccaggca agcccccaa actcatgatt tatgaggtca gtaagcggcc ctcagggggtt    180 tctaatcgct tctctggctc caagtctggc aacacggcct ccctgaccat ctctgggctc    240
caggctgagg acgaggctga ttattactgc agctcatata ccagtagcag cactttagac    300
ttcggaactg ggaccaaggt caccgtccta ggt                                  333

<210> SEQ ID NO 29
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 29

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Lys Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Val Ala Trp Ser Leu Leu Asp Tyr Trp Gly Gln Gly
            100                 105                 110

Thr Leu Val Thr Val Ser Ser
        115

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly
            100                 105                 110

<210> SEQ ID NO 31
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtccagc tggtgcagtc tggggctgag gtgaagaagc ctgggtcctc ggtgaaggtc       60
tcctgcaagg cttctggagg caccttcagc agctatgcta tcagctgggt gcgacaggcc      120
cctggacaag gccttgagtg gatgggaggg attatcccta tctttggtac agcaaaatat      180
gcacagaagt tccagggcag agtcacgatt accgcggacg aatccacgag cacagcctac      240

```
atggagctga gcagcctgag atctgaggac acggccgtgt attactgtgc gcgctctcat      300
gttgcttggt ctctgctgga ttactggggt caaggtactc tggtgaccgt ctcctca        357
```

<210> SEQ ID NO 32
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
tcctatgagc tgactcagcc accctcagcg tctgggaccc ccgggcagag ggtcaccatc       60
tcttgttctg gaagcagctc caacatcgga agtaattatg tatcctggta ccagcagctc     120
ccaggaacgg cccccaaact cctcatctat aggaataatc agcggccctc aggggtccct     180
gaccgattct ctggctccaa gtctggcacc tcagcctccc tggccatcag tgggctccgg     240
tccgaggatg aggctgatta ttactgtgca gcatgggatg acagcctgag tggtgtggta     300
ttcggcggag ggaccaagct gaccgtccta ggt                                  333
```

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gln Ser Tyr Lys Gly Ser Gln Ser Asp Ser Trp Gly Gln
            100                 105                 110

Gly Thr Leu Val Thr Val Ser Ser
        115                 120
```

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu Gly
            100                 105                 110
```

<210> SEQ ID NO 35
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
caggtgcagc tggtgcagtc tggggctgag gtgaagaagc ctgggtcctc agtgaaggtc      60
tcctgcaagg cttctggagg caccttcagc agctatgcta tcagctgggt gcgacaggcc     120
cctggacaag gcttgagtg gatgggatgg atgaaccta acagtggtaa cacaggctat      180
gcacagaagt tccagggcag agtcaccatg accaggaaca cctccataag cacagcctac     240
atggagctga gcagcctgag atctgaggac acggccgtgt attactgtgc gcgctaccag     300
tcttacaaag gttctcagtc tgattcttgg ggtcaaggta ctctggtgac cgtctcctca     360
```

<210> SEQ ID NO 36
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
cagtctgtgt tgacgcagcc accctcagcg tctgggaccc ccgggcagag ggtcaccatc      60
tcttgttctg gaagcagctc caacatcgga agtaattatg tatactggta ccagcagctc     120
ccaggaacgg cccccaaact cctcatctat aggaataatc agcggccctc aggggtccct     180
gaccgattct ctggctccaa gtctggcacc tcagcctccc tggccatcag tgggctccgg     240
tccgaggatg aggctgatta ttactgtgca gcatgggatg acagcctgag tggttgggtg     300
ttcggcggag ggaccaagct gaccgtccta ggt                                  333
```

<210> SEQ ID NO 37
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30
```

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Lys Lys Trp Ser Gly Glu Lys Trp Arg Arg Glu
            100                 105                 110

Asn Phe Asp Tyr Trp Gly Gln Gly Thr Leu Val Thr Val Ser Ser
        115                 120                 125

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
                85                  90                  95

Ser Thr Glu Val Phe Gly Gly Gly Thr Lys Leu Thr Val Leu Gly
            100                 105                 110

<210> SEQ ID NO 39
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaggtccagc tggtacagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac    180
gcacagaagt tccagggcag agtcaccatg accagggaca cgtccacgag cacagtctac   240
atggagctga gcagcctgag atctgaggac acggccgtgt attactgtgc gcgcggtggt   300
tctaaaaaat ggtctggtga aaaatggcgt cgtgaaaact tcgattactg gggtcaaggt   360
actctggtga ccgtctcctc a                                            381

<210> SEQ ID NO 40
<211> LENGTH: 333
<212> TYPE: DNA

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
caatctgccc tgactcagcc tgcctccgtg tctgggtctc ctggacagtc gatcaccatc    60
tcctgcactg gaaccagcag tgacgttggt ggttataact atgtctcctg gtaccaacag   120
cacccaggca aagcccccaa actcatgatt tatgatgtca gtaagcggcc ctcaggggtt   180
tctaatcgct tctctggctc caagtctggc aacacggcct ccctgaccat ctctgggctc   240
caggctgagg acgaggctga ttattactgc agctcatata caagaagcag cactgaggta   300
ttcggcggag ggaccaagct gaccgtccta ggt                                333
```

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Met Gln Leu Val Gln Ser Gly Ala Glu Val Lys Lys Pro Gly Ala
1               5                   10                  15

Ser Val Lys Val Ser Cys Lys Ala Ser Glu Tyr Thr Phe Thr Arg His
                20                  25                  30

Ile Leu His Trp Val Arg Gln Ala Pro Gly Gln Ser Leu Glu Trp Met
            35                  40                  45

Gly Trp Ile Asn Pro Gly Asn Gly Asn Thr Lys Tyr Ser Gln Lys Phe
        50                  55                  60

Gln Val Arg Val Thr Phe Thr Arg Asp Thr Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Pro Asp Gln Trp Gly Gln Gly Thr Leu Val Thr Val Ser
            100                 105                 110

Ser
```

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80
```

Ser Glu Asp Glu Ala Asp Tyr Tyr Cys Ala Ala Trp Asp Asp Ser Leu
                85                  90                  95

Ser Gly Leu Phe Gly Thr Gly Thr Lys Val Thr Val Leu Gly
            100                 105                 110

<210> SEQ ID NO 43
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cagatgcagc tggtgcagtc tggggctgag gtgaagaagc ctggggcctc agtgaaggtt      60
tcctgcaagg cttctgaata caccttcact aggcatattc tacattgggt gcgccaggct     120
cccggacaaa gccttgagtg gatgggatgg atcaacccag caatggtaa tacaaaatat     180 tcacagaagt tccaggtcag agtcaccttt accagggaca catccgcgag cacagtctat     240
atggagctga gcagcctgag atctgaagac acggccgtgt attactgtgc gcgcctgccg     300
gatcagtggg gtcaaggtac tctggtgacc gtctcctca                            339

<210> SEQ ID NO 44
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
tcctatgtgc tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat aggaataatc agcggccctc aggggtccct     180
gaccgattct ctggctccaa gtctggcacc tcagcctccc tggccatcag tgggctccgg     240
tccgaggatg aggctgatta ttactgtgca gcatgggatg acagcctgag tggtctcttc     300
ggaactggga ccaaggtcac cgtcctaggt                                      330

<210> SEQ ID NO 45
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                    85                  90                  95
Ala Arg Ser Lys Gln Asp Tyr Trp Gly Gln Gly Thr Leu Val Thr Val
               100                 105                 110

Ser Ser

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Arg Asp Ala Gly Gly Tyr
            20                  25                  30

Asn Tyr Phe Ser Trp Tyr Gln Gln His Pro Gly Lys Ala Pro Lys Leu
        35                  40                  45

Leu Ile Tyr Glu Val Thr Lys Arg Pro Ser Gly Val Pro Asp Arg Phe
    50                  55                  60

Ser Gly Ser Lys Ser Gly Lys Thr Ala Ser Leu Thr Val Ser Gly Leu
65                  70                  75                  80

Gln Ala Asp Asp Glu Ala Val Tyr Tyr Cys Ser Ser Tyr Gly Gly Ser
                85                  90                  95

Asn Asn Phe Arg Val Phe Gly Gly Gly Thr Lys Leu Thr Val Leu Gly
               100                 105                 110

<210> SEQ ID NO 47
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gaggtgcagc tggtggagtc tgggggaggt gtggtacggc ctgggggtc cctgagactc    60 tcctgtgcag cctctggatt caccttggt gattatggca tgagctgggt ccgccaagct   120
ccagggaagg ggctggagtg gtctctggt attaattgga atggtggtag cacaggttat   180
gcagactctg tgaagggccg attcaccatc tccagagaca cgccaagaa ctccctgtat   240 ctgcaaatga acagtctgag agccgaggac acggccgtat attactgtgc gcgctctaaa   300
caggattact ggggtcaagg tactctggtg accgtctcct ca                     342

<210> SEQ ID NO 48
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cagtctgccc tgactcagcc tccctccgcg tccgggtctc ctggacagtc agtcaccatc    60
tcctgcactg gaaccagcag ggacgctggt ggttataatt atttctcctg gtaccaacaa   120
cacccaggca aagcccccaa actcctgatt tatgaggtca ctaagcggcc ctcaggggtc   180
```

```
cctgatcgct tctctggctc caagtctggc aagacggcct ccctgaccgt ctctgggctc    240
caggctgacg atgaggctgt atattactgc agctcatatg gaggcagcaa caactttcgg    300
gtgttcggcg agggaccaa gctgaccgtc ctaggt                                336
```

<210> SEQ ID NO 49
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Glu Val Gln Leu Val Glu Thr Gly Gly Asn Leu Val Gln Pro Gly Ala
1               5                   10                  15

Ser Leu Arg Leu Ser Cys Ala Ala Ser Gly Phe Ser Phe Ser Gly Thr
            20                  25                  30

Ala Met His Trp Val Arg Gln Ala Pro Gly Lys Gly Leu Glu Trp Val
        35                  40                  45

Ser Thr Ile Ser Ser Thr Gly Arg Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Val Ser Phe Asp Tyr Trp Gly Gln Gly Thr Leu Val Thr Val
            100                 105                 110

Ser Ser
```

<210> SEQ ID NO 50
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Tyr Val Phe Gly Thr Gly Thr Lys Leu Thr Val Leu
            100                 105                 110

Gly
```

<210> SEQ ID NO 51
<211> LENGTH: 342
<212> TYPE: DNA
<213> ORGANISM: Artificial Sequence -continued

```
<220> FEATURE:
<223> OTHER INFORMATION: Description of Artificial Sequence: Synthetic
      polynucleotide

<400> SEQUENCE: 51
gaggtgcagc tggtggagac tgggggaaac ttggtacagc cggggggcgtc cctgagactc    60 tcctgtgcag cctctggatt cagctttagt ggcactgcca tgcactgggt ccgccaggct   120
ccagggaagg ggctggaatg ggtctcgact attagtagta ctgggcgtag cacatactac   180
agagactccg tgaagggccg gttcaccatc tccagagaca attccaagaa cacgctgtat   240
ctgcaaatga acagcctgag aggcgaggac acggccgtat attactgtgc gcgcgtttct   300
ttcgattact ggggtcaagg tactctggtg accgtctcct ca                     342

<210> SEQ ID NO 52
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
cagtctgtcg tgacgcagcc gcccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggctcc   300
tacgtcttcg gaactgggac caagctgacc gtcctaggt                         339

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Ala Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Ser Gly Arg Gly Arg Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr His Ala Gly Ala Phe Asp Leu Trp Gly Gln Gly Thr
            100                 105                 110

Leu Val Thr Val Ser Ser
        115

<210> SEQ ID NO 54
<211> LENGTH: 111
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ser Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly
            100                 105                 110

<210> SEQ ID NO 55
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gaggtgcagc tggtggagtc tgggggagcc tttgtacagc ctgggggtc cctgagactc      60 tcctgtgcag cctctggatt cacctttagc agctatgcca tgacctgggt ccgccaggct    120
ccagggaagg gcctggaatg ggtctcgact attagtggtc gtggtcgtag cacattctac    180
gcagactccg tgaagggccg gtttaccatc tccagagaca attccaagaa cacgctatat    240
ctgcaaatga acagtctgag agccgaggac acggccgtat attactgtgc gcgctactac    300
catgctggtg cttttcgatct gtggggtcaa ggtactctgg tgaccgtctc ctca         354

<210> SEQ ID NO 56
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
cagtctgtcg tgacgcagcc tgcctccgtg tctgggtctc ctggacagtc gatcaccatc     60
tcctgcactg gaaccagcag tgacgttggt ggttataact atgtctcctg gtaccaacag    120
cacccaggca aagcccccaa actcatgatt tatgatgtca gtaagcggcc ctcaggggtt    180
tctaatcgct tctctggctc caagtctggc aacacggcct ccctgaccat ctctgggctc    240
caggctgagg acgaggctga ttattactgc agctcatata caagcagcag cactttggta    300
ttcggcggag ggaccaagct gaccgtccta ggt                                 333

<210> SEQ ID NO 57
<211> LENGTH: 114
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 57

```
Gln Met Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Asn Arg Tyr
            20                  25                  30
Ala Ile Thr Trp Val Arg Gln Ala Pro Gly Gln Gly Leu Glu Trp Met
        35                  40                  45
Gly Trp Ile Ser Ala Tyr Asn Gly Asn Ser His Tyr Ala Gln Lys Leu
    50                  55                  60
Gln Gly Arg Val Thr Met Thr Thr Asp Thr Ser Thr Gly Thr Ala Tyr
65                  70                  75                  80
Met Glu Leu Arg Arg Leu Arg Ser Asp Thr Ala Val Tyr Tyr Cys
                85                  90                  95
Ala Arg Met Ala Tyr Asp Ser Trp Gly Gln Gly Thr Leu Val Thr Val
            100                 105                 110
Ser Ser
```

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Gln Ser Val Leu Thr Gln Pro Ala Ser Val Ser Gly Ser Pro Gly Gln
1               5                   10                  15
Ser Leu Thr Ile Ser Cys Thr Gly Thr Ser Asn Asp Val Gly Ala Tyr
            20                  25                  30
Lys Tyr Val Ser Trp Tyr Gln Gln Tyr Pro Gly Lys Ala Pro Lys Leu
        35                  40                  45
Ile Leu Tyr Asp Val Phe Lys Arg Pro Ser Gly Val Ser Asn Arg Phe
    50                  55                  60
Ser Gly Ser Lys Ser Asp Asn Thr Ala Ser Leu Thr Ile Ser Gly Leu
65                  70                  75                  80
Gln Ala Glu Asp Glu Ala Asp Tyr Tyr Cys Phe Ser Leu Thr Ser Ser
                85                  90                  95
Asn Thr Tyr Val Phe Gly Thr Gly Thr Lys Val Thr Val Leu Gly
            100                 105                 110
```

<210> SEQ ID NO 59
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
cagatgcagc tggtgcagtc tggagctgag gtgaagaagc ctggggcctc agtgaaggtc      60
tcctgcaagg cttctggtta cacctttaac agatatgcta tcacctgggt gcgacaggcc     120
cctggacaag gccttgagtg gatgggatgg atcagcgctt acaatggtaa ttcacactat     180
```

```
gcacagaagc tccagggcag agtcaccatg accacagaca catccacggg cacagcctat    240
atggagctga ggaggctgag atctgacgac acggccgtgt attactgtgc gcgcatggct    300
tacgattctt ggggtcaagg tactctggtg accgtctcct ca                      342
```

<210> SEQ ID NO 60
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
cagtctgtgt tgacgcagcc tgcctccgtg tctgggtctc ctggacagtc gctcaccatc    60
tcctgcactg gaaccagcaa tgacgttggt gcttataagt atgtctcctg gtatcaacag   120
tacccaggca agccccccaa actcatactt tatgatgtct ttaagcggcc ctcaggggtc   180
tctaatcgct tctctggctc caagtctgac aacacggcct ccctgaccat ctctgggctc   240
caggctgagg acgaggctga ttattactgc ttctcactta caagcagtaa cacttatgtc   300
ttcggaactg ggaccaaggt caccgtccta ggt                                333
```

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Lys Ala Tyr Asp Gln Trp Gly Gln Gly Thr Leu
            100                 105                 110

Val Thr Val Ser Ser
        115
```

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Val Gly Gly Asn
```

```
                20                  25                  30

Tyr Val Phe Trp Tyr Gln Gln Val Pro Gly Ala Thr Pro Lys Leu Leu
            35                  40                  45

Ile Tyr Arg Ser Asn Gln Arg Pro Ser Gly Val Pro Asp Arg Phe Ala
        50                  55                  60

Gly Ser Lys Ser Gly Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Phe Val Phe Gly Thr Gly Thr Lys Val Thr Val Leu Gly
            100                 105                 110

<210> SEQ ID NO 63
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtat attactgtgc gcgcggttac     300
ggtaaagctt acgatcagtg ggtcaaggt actctggtga ccgtctcctc a               351

<210> SEQ ID NO 64
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
cagtctgtgt tgactcagcc accctcagcg tctgggaccc ccggacagag ggtcaccatc      60
tcttgttctg gaagcaggtc caacgtagga ggtaattatg tattttggta ccagcaagtc     120
cccggagcga ccccaaaact cctcatctat aggagtaatc agcggccctc gggggtccct     180
gaccgattcg ctggctccaa gtctggctcc tcagcctccc tggccatcag tggactccgg     240
tccgaggatg aggctgatta ttactgtgca acatgggatg acagcctgag tggttttgtc     300
ttcggaactg ggaccaaggt caccgtccta ggt                                  333

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Leu Val His Pro Gly Gly
1               5                  10                  15

Ser Leu Arg Leu Ser Cys Ala Ala Ser Gly Phe Thr Phe Arg Ser His
            20                  25                  30
```

Ser Met Asn Trp Val Arg Gln Ala Pro Gly Lys Gly Leu Glu Trp Val
            35                  40                  45

Ser Ser Ile Ser Ser Asp Ser Thr Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Gly Gln Trp Lys Tyr Tyr Asp Tyr Trp Gly Gln Gly
            100                 105                 110

Thr Leu Val Thr Val Ser Ser
        115

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                 85                  90                  95

Pro Val Val Phe Gly Gly Gly Thr Lys Leu Thr Val Leu Gly
            100                 105                 110

<210> SEQ ID NO 67
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
caggtgcagc tggtggagtc tgggggaggc ctggtccacc ctggggggtc cctgagactc        60
tcctgtgcag cctctggatt caccttcaga agccatagca tgaactgggt ccgccaggct       120
ccagggaagg ggctggagtg gtctcatcc attagtagtg atagtactta cacatactac       180
gcagactcag tgaagggccg attcaccatc tccagagaca acgccaagaa ctcactgtat       240
ctgcaaatga acagcctgag agccgaggac acggccgtat attactgtgc gcgctctggt       300
ggtcagtgga aatactacga ttactggggt caaggtactc tggtgaccgt ctcctca         357

<210> SEQ ID NO 68
<211> LENGTH: 330
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 68
tcttctgagc tgactcagga ccctgctgtg tctgtggcct tgggacagac agtcaggatc      60
acatgccaag agacagcct cagaagctat tatgcaagct ggtaccagca gaagccagga      120
caggcccctg tacttgtcat ctatggtaaa aacaaccggc cctcagggat cccagaccga    180
ttctctggct ccagctcagg aaacacagct tccttgacca tcactggggc tcaggcggaa    240
gatgaggctg actattactg taactcccgg gacagcagtg gtaaccccc tgtggtattc    300 ggcggaggga ccaagctgac cgtcctaggt                                    330

<210> SEQ ID NO 69
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Thr Ile Asn Gly Arg Gly Ser Ser Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Tyr Ile Ser Arg Gly Leu Gly Asp Ser Trp Gly Gln Gly Thr
            100                 105                 110

Leu Val Thr Val
        115

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ser Val Val Thr Gln Pro Pro Ser Met Ser Ala Ala Pro Gly Gln
1               5                   10                  15

Gln Val Thr Ile Ser Cys Ser Gly Gly Asn Ser Asn Ile Glu Arg Asn
            20                  25                  30

Tyr Val Ser Trp Tyr Leu Gln Leu Pro Gly Thr Ala Pro Lys Leu Val
        35                  40                  45

Ile Phe Asp Asn Asp Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80
```

Thr Gly Asp Glu Ala Asp Tyr Tyr Cys Gly Thr Trp Asp Ser Ser Leu
            85                  90                  95

Arg Gly Trp Val Phe Gly Gly Thr Lys Leu Thr Val Leu Gly
            100                 105                 110

<210> SEQ ID NO 71
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gaggtgcagc tggtggagtc cggggggaggc ttgatacagc ctggggggtc cctgagactc        60
tcctgtgcag cctctggatt cacctttagc aactatgcca tgaactgggt ccgccaggct        120
ccagggaagg ggctggagtg ggtctcaact attaatggtc gtggtagtag tacaatctac        180
gcagactccg tgaagggccg gttcaccatc tccagagaca attccaagaa cacgctgtat        240
ctgcaaatga acagcctgag agccgaggac acagccacgt attactgtgc gcgctacatc        300
tctcgtggtc tgggtgattc ttggggtcaa ggtactctgg tgaccgtctc ctca             354

<210> SEQ ID NO 72
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cagtctgtcg tgacgcagcc gccctcaatg tctgcggccc caggacagca agtcaccatc        60
tcctgctctg gaggcaactc caacattgag agaaattatg tatcctggta cctccagctc       120
cctggaacag cccccaaact cgtcattttt gacaatgata gcgaccctc agggattcct        180 gaccgattct ctggctccaa gtctggcacg tcagccaccc tgggcatcac cggactccag        240 actgggacg aggccgatta ttactgcgga acatgggata gcagcctgag aggttgggtg        300
ttcggcggag ggaccaagct gaccgtccta ggt                                   333

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                    85                  90                  95
Ala Arg Ala Gly Met Gly Met Asp Thr Trp Gly Gln Gly Thr Leu Val
                100                 105                 110

Thr Val Ser Ser
        115

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly
                100                 105                 110

<210> SEQ ID NO 75
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
cagatgcagc tggtgcagtc tggggctgag gtgaagaagc ctggggcctc agtgaaggtt     60
tcctgcaagg catctggata caccttcacc agctactata tgcactgggt gcgacaggcc   120
cctggacaag gcttgagtg gatgggaata tcaaccctat gtggtggtag cacaagctac   180
gcacagaagt tccagggcag agtcaccatg accaggacac gtccacgag cacagtctac   240 atggagctga gcagcctgag atctgaggac acggccgtgt attactgtgc gcgcgctggt   300
atgggtatgg atacttgggg tcaaggtact ctggtgaccg tctcctca               348

<210> SEQ ID NO 76
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
cagtctgccc tgactcagcc tccctccgcg tccgggtctc ctggacagtc agtcaccatc     60
tcctgcactg gaaccagcag tgacgttggt ggttataact atgtctcctg gtaccaacag   120
cacccaggca aagcccccaa actcatgatt tatgaggtca gtaagcggcc ctcaggggtc   180
```

```
cctgatcgct tctctggctc caagtctggc aacacggcct ccctgaccgt ctctgggctc    240
caggctgagg atgaggctga ttattactgc agctcatatg caggcagcaa caccttggtg    300
ttcggcggag ggaccaagct gaccgtccta ggt                                 333
```

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Ala Tyr
            20                  25                  30

Ser Leu His Trp Val Arg Gln Ala Pro Gly Gln Gly Leu Glu Trp Met
        35                  40                  45

Gly Trp Ile Asn Pro Ser Ser Gly Gly Ala Val Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Asn Val Gly Gly Gln Ala Asp Asp Trp Gly Gln Gly Thr Leu
            100                 105                 110

Val Thr Val Ser Ser
        115
```

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95

Lys Thr Leu Val Phe Gly Gly Gly Thr Lys Leu Thr Val Leu Gly
            100                 105                 110
```

<210> SEQ ID NO 79
<211> LENGTH: 351
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 79
caggtgcagc tggtgcagtc tggggctgag gtgaagaagc ctggggcctc agtgaaggtc    60
tcctgcaggg cttctggata caccttcacc gcctactctt tacactgggt gcgacaggcc   120
cctggacaag gcttgagtg gatgggatgg atcaaccta gcagtggtgg cgcagtttat     180
gcacagaaat ttcagggtag ggtcaccatg accagggaca cgtccatcag cacagcctac   240
atggagctga gtggcctgag atctgacgac acggccgtgt attactgtgc gcgcaacgtt   300
ggtggtcagg ctgatgactg gggtcaaggt actctggtga ccgtctcctc a            351

<210> SEQ ID NO 80
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
caatctgccc tgactcagcc tccctccgcg tccgggtctc ctggacagtc agtcaccatc    60
tcctgcactg gaaccagcag tgacattggt ggttataact atgtctcctg gtaccaacag   120
cacccaggca agcccccaa actcatgatt tatgaggtca ataagcggcc ctcaggggtc    180
cctgatcgct tctcgggctc caagtctggc aacacggcct ccctgaccgt ctctgggctc   240
caggctgagg atgaggctga ttattactgc gcctcatttg cgggcaggaa gacattggtc   300
ttcggcggag ggaccaagct gaccgtccta ggt                                333

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Ala Tyr
            20                  25                  30

Ser Leu His Trp Val Arg Gln Ala Pro Gly Gln Gly Leu Glu Trp Met
        35                  40                  45

Gly Trp Ile Asn Pro Ser Ser Gly Gly Ala Val Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Asn Val Gly Gly His Ala Asp Asp Trp Gly Gln Gly Thr Leu
            100                 105                 110

Val Thr Val Ser Ser
        115

<210> SEQ ID NO 82
<211> LENGTH: 111
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Thr Asp Ile Gly Gly Tyr
            20                  25                  30

Asn Tyr Val Ser Trp Tyr Gln His Pro Ser Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95

Lys Thr Leu Val Phe Gly Gly Gly Thr Lys Leu Thr Val Leu Gly
            100                 105                 110

<210> SEQ ID NO 83
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggtgcagc tggtgcagtc tggggctgag gtgaaaaagc ctggggcctc agtgaaagtc      60
tcctgcaggg cttctggata caccttcacc gcctactctt tacactgggt gcgacaggcc     120
cctggacaag gcttgagtg gatgggatgg atcaaccta gcagtggtgg cgcagtttat      180
gcacagaaat tcagggtag gtcaccatg accagggaca cgtccatcag cacagcctac      240
atggagctga gtggcctgag atctgacgac acggccgtgt attactgtgc gcgcaacgtt     300
ggtggtcacg ctgatgactg gggtcaaggt actctggtga ccgtctcctc a              351

<210> SEQ ID NO 84
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caatctgccc tgactcagcc tccctccgcg tccgggtctc ctggacagtc agtcaccatc      60
tcctgcactg gaaccagcac tgacattggt ggttataact atgtctcctg gtaccaacac     120
cacccaagca aagcccccaa actcatgatt tatgaggtca ataagcggcc ctcaggggtc     180
cctgatcgct tctcgggctc caagtctggc aacacggcct ccctgaccgt ctctgggctc     240
caggctgagg atgaggctga ttattactgc gcctcatttg cgggcaggaa gacattggtc     300
ttcggcggag ggaccaagct gaccgtccta ggt                                  333

<210> SEQ ID NO 85
<211> LENGTH: 129
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Gln Ser Gly Gly Glu Val Lys Lys Pro Gly Ala
1               5                   10                  15

Ser Val Lys Val Ser Cys Lys Ala Ser Gly Phe Thr Phe Asn Thr Tyr
            20                  25                  30

Gly Ile Ser Trp Val Arg Gln Ala Pro Gly Gln Gly Leu Glu Trp Met
        35                  40                  45

Gly Trp Ile Ser Ala Asn Asn Gly His Thr Lys Ser Ala Gln Arg Phe
    50                  55                  60

Gln Asp Arg Val Ala Met Ala Thr Asp Thr Ser Thr Ser Thr Ala Tyr
65                  70                  75                  80

Met Glu Leu Arg Ser Leu Lys Phe Asp Thr Ala Val Tyr Tyr Cys
                85                  90                  95

Ala Arg Gly Gly Tyr His His Gln Met Gln Arg Tyr Tyr Lys Ala Thr
            100                 105                 110

Ser Val Tyr Ser Asp Tyr Trp Gly Gln Gly Thr Leu Val Thr Val Ser
        115                 120                 125

Ser

<210> SEQ ID NO 86
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
            100                 105                 110

<210> SEQ ID NO 87
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
caggtccagc tggtgcagtc tggaggtgag gtgaagaagc ctggggcctc agtgaaggtc      60
tcctgcaagg cttctggttt caccttt aac acctatggca tcagttgggt gcgacaggcc     120

```
cctggacaag ggcttgagtg gatgggatgg atcagcgcta acaatggtca cacaaagtct    180
gcacagaggt tccaggacag agtcgccatg gccacagaca catccacgag cacggcctac    240
atggagctga ggagcctgaa atttgacgac acggccgtgt attactgtgc gcgcggtggt    300
taccatcatc agatgcagcg gtactacaaa gctacttctg tttactctga ttactggggt    360
caaggtactc tggtgaccgt ctcctca                                        387

<210> SEQ ID NO 88
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
cagtctgtcg tgacgcagcc gccctcagtg tctgcggccc caggacagaa ggtcaccatc     60
tcctgctctg gaagcagctc caacattggg aataattatg tatcctggta ccagcaactc    120
ccaggaacag ccccaaaact cctcatttat gacaataata gcgaccctc agggattcct     180 gaccgattct ctggctccaa gtctggcacg tctgccaccc tgggcatcac cggactccag    240
actggggacg aggccgatta ttactgcgga acatgggata gcagcctgag tggtgtggta    300
ttcggcggag ggaccaagct gaccgtccta ggt                                 333

<210> SEQ ID NO 89
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Gly Met Gly Met Asp Thr Trp Gly Gln Gly Thr Leu Val
            100                 105                 110

Thr Val Ser Ser
        115

<210> SEQ ID NO 90
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90
```

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65              70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly
            100                 105                 110

<210> SEQ ID NO 91
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
cagatgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccta gtggtggtag ctcaagctac       180
gcacagaagt tccagggcag agtcaccatg accagggaca cgtccacgag cacagtctac     240
atggagctga gcagcctgag atctgaggac acggccgtgt attactgtgc gcgcgctggt     300
atgggtatgg atacttgggg tcaaggtact ctggtgaccg tctcctca                  348

<210> SEQ ID NO 92
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
cagtctgccc tgactcagcc tccctccgcg tccgggtctc ctggacagtc agtcaccatc      60
tcctgcactg gaaccagcag tgacgttggt ggttataact atgtctcctg gtaccaacag     120
cacccaggca aagcccccaa actcatgatt tatgaggtca gtaagcggcc ctcaggggtc     180
cctgatcgct tctctggctc caagtctggc aacacggcct ccctgaccgt ctctgggctc     240
caggctgagg atgaggctga ttattactgc agctcatatg caggcagcaa caccttggtg     300
ttcggcggag ggaccaagct gaccgtccta ggt                                  333

<210> SEQ ID NO 93
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Ile Ser Gly Phe Asp Ser Trp Gly Gln Gly Thr Leu
            100                 105                 110

Val Thr Val Ser Ser
            115

<210> SEQ ID NO 94
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Ser Pro Gly Lys Ala Pro Arg Leu
        35                  40                  45

Met Ile Tyr Gly Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Val
                85                  90                  95

Asn Asn Leu Met Phe Gly Gly Gly Thr Lys Leu Thr Val Leu Gly
            100                 105                 110

<210> SEQ ID NO 95
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
caggtgcagc tggtgcaatc tggggctgag gtgaagaagc ctggggcctc agtgaaggtt      60
tcctgcaagg catctggata caccttcacc agctactata tgcactgggt gcgacaggcc    120
cctggacaag gcttgagtg gatgggaata atcaacccta gtggtggtag cacaagctac    180
gcacagaagt tccagggcag agtcaccatg accagggaca cgtccacgag cacagtctac    240
atggagctga gcagcctgag atctgaggac actgccgtgt attactgtgc gcgcgacgtt    300
atctctggtt tcgattcttg gggtcaaggt actctggtga ccgtctcctc a             351

<210> SEQ ID NO 96
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
cagtctgccc tgactcagcc tgcctccgtg tctgggtctc ctggacagtc gatcaccatc      60
tcctgcactg gaaccagcag tgacgttggt ggttataact atgtctcctg gtaccaacaa     120
tccccaggca agccccccag actcatgatt tatggggtca gtaagcggcc ctctggggtc     180
cctgatcgct tctctggctc caagtctggc aacacggcct ccctgaccgt ctctgggctc     240
caggctgaag atgaggctga ttattactgc agctcatatg caggcgtcaa caatttaatg     300
ttcggcggag ggaccaagct gaccgtccta ggt                                  333
```

<210> SEQ ID NO 97
<211> LENGTH: 345
<212> TYPE: PRT
<213> ORGANISM: Homo sapiens

<400> SEQUENCE: 97

```
Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Cys Val Ser Phe Ser Trp Thr Thr
        115                 120                 125

Ile Leu Cys Ile Ala Ile Gly Cys Ser Leu Leu Gln Ile Ile Ile Ala
    130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
        195                 200                 205

Thr Val Leu Phe Ser Ile Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255
```

```
Tyr Ile Val Pro Glu Leu Cys Ile Leu Tyr Arg Ser Cys Arg Gln Glu
                260                 265                 270

Cys Pro Leu Gln Gly Asn Ala Cys Pro Val Thr Ala Tyr Gln His Ser
            275                 280                 285

Phe Gln Val Glu Asn Gln Glu Leu Ser Arg Ala Arg Asp Ser Asp Gly
        290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
                325                 330                 335

Ser Pro Gln Gln Asp Ala Gly Gly Val
            340                 345

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 99
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tctagaggtg gtggtggtag cggcggcggc ggctctggtg gtggtggatc cctcgagatg      60
gcc                                                                   63

<210> SEQ ID NO 100
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ser Val Leu Thr Gln Pro Pro Ser Val Ser Ala Ala Pro Gly Gln
1               5                   10                  15

Lys Val Thr Ile Pro Cys Ser Gly Ser Arg Ser Asn Val Gly Asn Tyr
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Gly Ser Leu
                85                  90                  95
```

```
Ser Ala His Val Phe Gly Thr Gly Thr Lys Val Thr Val Leu Gly Ser
            100                 105                 110

Arg Gly Gly Gly Gly Ser Gly Gly Gly Ser Gly Gly Gly Ser
        115                 120                 125

Leu Glu Met Ala Gln Val Gln Leu Val Gln Ser Gly Ser Glu Leu Lys
        130                 135                 140

Lys Pro Gly Ala Ser Val Arg Val Ser Cys Thr Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Val Ile Asn Pro Asn Ala Gly Ser Thr Arg Tyr
            180                 185                 190

Ala Gln Lys Phe Gln Gly Arg Val Thr Met Ser Thr Asp Thr Ser Thr
        195                 200                 205

Ser Thr Ala Tyr Met Asp Leu Ser Ser Leu Arg Ser Glu Asp Thr Ala
        210                 215                 220

Val Tyr Tyr Cys Ala Arg Gly Met Tyr Arg Ser Leu Leu Phe Tyr Asp
225                 230                 235                 240

Pro Trp Gly Gln Gly Thr Leu Val Thr Val Ser Ser
                245                 250

<210> SEQ ID NO 101
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asn Phe Met Leu Thr Gln Pro His Ser Val Ser Glu Ser Pro Gly Lys
1               5                   10                  15

Thr Val Ser Ile Ser Cys Thr Arg Thr Ser Gly Ala Ile Ala Gly Ala
            20                  25                  30

Tyr Val Gln Trp Phe Gln Gln Arg Pro Gly Ser Ala Pro Thr Thr Val
        35                  40                  45

Ile Tyr Asp Asp Asn Lys Arg Pro Ser Gly Val Pro Asp Arg Phe Ser
50                  55                  60

Gly Ser Ile Asp Lys Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Ser Ser Asn Val Leu Phe Gly Gly Gly Thr Lys Leu Thr Val Leu
            100                 105                 110

Gly Ser Arg Gly Gly Gly Gly Ser Gly Gly Gly Gly Ser Gly Gly Gly
        115                 120                 125

Gly Ser Leu Glu Met Ala Glu Val Gln Leu Val Glu Ser Gly Gly Gly
        130                 135                 140

Leu Val Gln Pro Gly Gly Ser Leu Arg Leu Ser Cys Ala Ala Ser Gly
145                 150                 155                 160

Phe Thr Phe Ser Asn Tyr Ala Met Ser Trp Val Arg Gln Ala Pro Gly
                165                 170                 175

Lys Gly Leu Glu Trp Val Ser Ala Ile Ser Gly Ser Gly Asn Thr Tyr
            180                 185                 190

Tyr Ala Asp Ser Val Lys Gly Arg Phe Thr Ile Ser Arg Asp Asn Ser
        195                 200                 205
```

Lys Asn Thr Leu Tyr Leu Gln Met Asn Ser Leu Arg Ala Glu Asp Thr
            210                 215                 220

Ala Val Tyr Tyr Cys Ala Arg Gly Ser Val Arg Tyr Thr Asp Ile Trp
225                 230                 235                 240

Gly Gln Gly Thr Leu Val Thr Val Ser Ser
            245                 250

<210> SEQ ID NO 102
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Ala Asp Phe Ala Thr Tyr Tyr Cys Gln Gln Ser Tyr Ser Val Pro Tyr
                85                  90                  95

Thr Phe Gly Gln Gly Thr Lys Leu Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Glu Val Gln Leu Val Gln Ser Gly Gly Gly Leu Val Gln Pro Gly
    130                 135                 140

Gly Ser Leu Arg Leu Ser Cys Ala Thr Ser Gly Phe Thr Phe Asn Asn
145                 150                 155                 160

Tyr Trp Met Ser Trp Val Arg Gln Ala Pro Gly Lys Gly Leu Glu Trp
                165                 170                 175

Val Ala Asn Ile Lys Gln Asp Gly Ser Glu Lys Tyr Tyr Ala Asp Ser
            180                 185                 190

Val Arg Gly Arg Phe Thr Ile Ser Arg Asp Asn Ala Lys Asn Ser Leu
        195                 200                 205

Ser Leu Gln Leu Asn Asn Leu Arg Ala Glu Asp Thr Ala Val Tyr Tyr
    210                 215                 220

Cys Ala Arg Ser Met Ser Thr Ala Trp Gly Tyr Asp Glu Trp Gly Gln
225                 230                 235                 240

Gly Thr Leu Val Thr Val Ser Ser
                245

<210> SEQ ID NO 103
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Ala Leu Thr Gln Pro Ala Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Val
            35                  40                  45

Met Ile Tyr Asp Val Ser Lys Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Glu Tyr Tyr Cys Ser Ser Tyr Thr Ser Thr
                85                  90                  95

Arg Thr Val Ile Phe Ala Gly Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Gln Val Gln Leu Val Gln Ser Gly Ala Glu Val Lys
            130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Arg Tyr
            180                 185                 190

Ala Gln Lys Phe Gln Gly Arg Val Thr Met Thr Arg Asp Thr Ser Thr
            195                 200                 205

Ser Thr Val Tyr Met Glu Leu Ser Ser Leu Arg Ser Glu Asp Thr Ala
    210                 215                 220

Val Tyr Tyr Cys Ala Arg Gly Ser Ser Arg Trp Gly Trp Thr Gly
225                 230                 235                 240

Asp Tyr Trp Gly Gln Gly Thr Leu Val Thr Val Ser Ser
                245                 250

<210> SEQ ID NO 104
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Any amino acid

<400> SEQUENCE: 104

Gln Ser Val Leu Thr Gln Pro Pro Ser Leu Ser Gly Ala Pro Gly Gln
1               5                   10                  15

Arg Val Thr Ile Ser Cys Ser Gly Ser Arg Ser Asn Ile Gly Thr Asn
            20                  25                  30

Tyr Val Ser Trp Xaa Gln Gln Leu Pro Gly Thr Ala Pro Lys Leu Leu
            35                  40                  45

Ile Tyr Arg Asn His Gln Trp Pro Ser Gly Val Pro Asp Arg Phe Thr
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Ala Ala Trp Asp Asp Asn Leu
                85                  90                  95

Ser Gly Val Val Phe Gly Gly Thr Lys Leu Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Glu Thr Gly Gly Gly Leu Val
            130                 135                 140

Gln Pro Gly Gly Ser Leu Arg Leu Ser Cys Ala Ala Ser Gly Ser Thr
145                 150                 155                 160

Phe Ser Ser Tyr Ala Met Ser Trp Val Arg Gln Ala Pro Gly Lys Gly
                165                 170                 175

Leu Glu Trp Val Ser Ala Ile Ser Gly Arg Gly Arg Ser Thr Tyr Tyr
            180                 185                 190

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
    210                 215                 220

Val Tyr Tyr Cys Ala Arg Tyr Tyr Lys Ser Ser Lys Asp His Trp Gly
225                 230                 235                 240

Gln Gly Thr Leu Val Thr Val Ser Ser
                245

<210> SEQ ID NO 105
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Gln Val Gln Leu Val Gln Ser Gly Ala Glu Val Gln
            130                 135                 140

Arg Pro Gly Ala Ser Val Arg Val Ser Cys Lys Ala Ile Ala Tyr Thr
145                 150                 155                 160

Phe Thr Asp Tyr Tyr Ile His Trp Val Arg Gln Ala Pro Gly Gln Gly
                165                 170                 175

Pro Glu Trp Met Gly Trp Ile Asn Pro Lys Ser Gly Arg Thr Gln Tyr
            180                 185                 190
```

```
Ala Pro Lys Phe Gln Asp Arg Val Thr Leu Ala Arg Glu Thr Pro Ile
        195                 200                 205

Ser Thr Ala Ser Met Glu Leu Arg Gly Leu Thr Ser Asp Asp Thr Ala
    210                 215                 220

Val Tyr Tyr Cys Ala Arg Val Tyr Gly Tyr Ser Arg Trp Ser Gly Phe
225                 230                 235                 240

Asp Leu Trp Gly Gln Gly Thr Leu Val Thr Val Ser Ser
                245                 250
```

<210> SEQ ID NO 106
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Val Gln Leu Val Gln Ser Gly Ala Glu Val Lys
130                 135                 140

Gln Pro Gly Ala Ser Val Lys Val Ser Cys Gln Ala Ser Gly Tyr Thr
145                 150                 155                 160

Phe Thr Thr Tyr Tyr Met His Trp Val Arg Gln Ala Pro Gly Gln Gly
                165                 170                 175

Leu Glu Trp Met Gly Ile Ile Asn Pro Asn Gly Gly Thr Phe Tyr
            180                 185                 190

Ala Gln Lys Phe Gln Asp Arg Val Thr Met Thr Arg Asp Thr Ser Thr
        195                 200                 205

Gly Thr Val Tyr Met Glu Leu Ser Ser Leu Arg Ser Asp Asp Thr Ala
    210                 215                 220

Val Tyr Tyr Cys Ala Arg Gly His Lys Val Tyr Lys Ser His Pro Thr
225                 230                 235                 240

Gly Gly Tyr Asp Arg Trp Gly Gln Gly Thr Leu Val Thr Val Ser Ser
                245                 250                 255
```

<210> SEQ ID NO 107
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Gly Ile Ile Pro Ile Phe Gly Thr Ala Lys Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Ser His Val Ala Trp Ser Leu Leu Asp Tyr
225                 230                 235                 240

Trp Gly Gln Gly Thr Leu Val Thr Val Ser Ser
                245                 250
```

<210> SEQ ID NO 108
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
```

```
                        85                  90                  95
Ser Gly Trp Val Phe Gly Gly Thr Lys Leu Thr Val Leu Gly Ser
                100                 105                 110
Arg Gly Gly Gly Ser Gly Gly Gly Ser Gly Gly Gly Gly Ser
        115                 120                 125
Leu Glu Met Ala Gln Val Gln Leu Val Gln Ser Gly Ala Glu Val Lys
    130                 135                 140
Lys Pro Gly Ser Ser Val Lys Val Ser Cys Lys Ala Ser Gly Gly Thr
145                 150                 155                 160
Phe Ser Ser Tyr Ala Ile Ser Trp Val Arg Gln Ala Pro Gly Gln Gly
                165                 170                 175
Leu Glu Trp Met Gly Trp Met Asn Pro Asn Ser Gly Asn Thr Gly Tyr
                180                 185                 190
Ala Gln Lys Phe Gln Gly Arg Val Thr Met Thr Arg Asn Thr Ser Ile
                195                 200                 205
Ser Thr Ala Tyr Met Glu Leu Ser Ser Leu Arg Ser Glu Asp Thr Ala
        210                 215                 220
Val Tyr Tyr Cys Ala Arg Tyr Gln Ser Tyr Lys Gly Ser Gln Ser Asp
225                 230                 235                 240
Ser Trp Gly Gln Gly Thr Leu Val Thr Val Ser Ser
                245                 250
```

<210> SEQ ID NO 109
<211> LENGTH: 259
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
                20                  25                  30
Asn Tyr Val Ser Trp Tyr Gln Gln His Pro Gly Lys Ala Pro Lys Leu
            35                  40                  45
Met Ile Tyr Asp Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Arg Ser
                85                  90                  95
Ser Thr Glu Val Phe Gly Gly Gly Thr Lys Leu Thr Val Leu Gly Ser
                100                 105                 110
Arg Gly Gly Gly Ser Gly Gly Gly Ser Gly Gly Gly Gly Ser
        115                 120                 125
Leu Glu Met Ala Glu Val Gln Leu Val Gln Ser Gly Ala Glu Val Lys
    130                 135                 140
Lys Pro Gly Ala Ser Val Lys Val Ser Cys Lys Ala Ser Gly Tyr Thr
145                 150                 155                 160
Phe Thr Ser Tyr Tyr Met His Trp Val Arg Gln Ala Pro Gly Gln Gly
                165                 170                 175
Leu Glu Trp Met Gly Ile Ile Asn Pro Ser Gly Gly Ser Thr Ser Tyr
                180                 185                 190
```

```
Ala Gln Lys Phe Gln Gly Arg Val Thr Met Thr Arg Asp Thr Ser Thr
            195                 200                 205

Ser Thr Val Tyr Met Glu Leu Ser Ser Leu Arg Ser Glu Asp Thr Ala
    210                 215                 220

Val Tyr Tyr Cys Ala Arg Gly Gly Ser Lys Lys Trp Ser Gly Glu Lys
225                 230                 235                 240

Trp Arg Arg Glu Asn Phe Asp Tyr Trp Gly Gln Gly Thr Leu Val Thr
                245                 250                 255

Val Ser Ser

<210> SEQ ID NO 110
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Leu Phe Gly Thr Gly Thr Lys Val Thr Val Leu Gly Ser Arg
            100                 105                 110

Gly Gly Gly Gly Ser Gly Gly Gly Ser Gly Gly Gly Gly Ser Leu
            115                 120                 125

Glu Met Ala Gln Met Gln Leu Val Gln Ser Gly Ala Glu Val Lys Lys
    130                 135                 140

Pro Gly Ala Ser Val Lys Val Ser Cys Lys Ala Ser Glu Tyr Thr Phe
145                 150                 155                 160

Thr Arg His Ile Leu His Trp Val Arg Gln Ala Pro Gly Gln Ser Leu
                165                 170                 175

Glu Trp Met Gly Trp Ile Asn Pro Gly Asn Gly Asn Thr Lys Tyr Ser
            180                 185                 190

Gln Lys Phe Gln Val Arg Val Thr Phe Thr Arg Asp Thr Ser Ala Ser
        195                 200                 205

Thr Val Tyr Met Glu Leu Ser Ser Leu Arg Ser Glu Asp Thr Ala Val
    210                 215                 220

Tyr Tyr Cys Ala Arg Leu Pro Asp Gln Trp Gly Gln Gly Thr Leu Val
225                 230                 235                 240

Thr Val Ser Ser

<210> SEQ ID NO 111
<211> LENGTH: 247
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 111

```
Gln Ser Ala Leu Thr Gln Pro Pro Ser Ala Ser Gly Ser Pro Gly Gln
1               5                   10                  15
Ser Val Thr Ile Ser Cys Thr Gly Thr Ser Arg Asp Ala Gly Gly Tyr
            20                  25                  30
Asn Tyr Phe Ser Trp Tyr Gln Gln His Pro Gly Lys Ala Pro Lys Leu
        35                  40                  45
Leu Ile Tyr Glu Val Thr Lys Arg Pro Ser Gly Val Pro Asp Arg Phe
    50                  55                  60
Ser Gly Ser Lys Ser Gly Lys Thr Ala Ser Leu Thr Val Ser Gly Leu
65                  70                  75                  80
Gln Ala Asp Asp Glu Ala Val Tyr Tyr Cys Ser Ser Tyr Gly Gly Ser
                85                  90                  95
Asn Asn Phe Arg Val Phe Gly Gly Gly Thr Lys Leu Thr Val Leu Gly
            100                 105                 110
Ser Arg Gly Gly Gly Gly Ser Gly Gly Gly Ser Gly Gly Gly Gly Gly
        115                 120                 125
Ser Leu Glu Met Ala Glu Val Gln Leu Val Glu Ser Gly Gly Gly Val
    130                 135                 140
Val Arg Pro Gly Gly Ser Leu Arg Leu Ser Cys Ala Ala Ser Gly Phe
145                 150                 155                 160
Thr Phe Gly Asp Tyr Gly Met Ser Trp Val Arg Gln Ala Pro Gly Lys
                165                 170                 175
Gly Leu Glu Trp Val Ser Gly Ile Asn Trp Asn Gly Gly Ser Thr Gly
            180                 185                 190
Tyr Ala Asp Ser Val Lys Gly Arg Phe Thr Ile Ser Arg Asp Asn Ala
        195                 200                 205
Lys Asn Ser Leu Tyr Leu Gln Met Asn Ser Leu Arg Ala Glu Asp Thr
    210                 215                 220
Ala Val Tyr Tyr Cys Ala Arg Ser Lys Gln Asp Tyr Trp Gly Gln Gly
225                 230                 235                 240
Thr Leu Val Thr Val Ser Ser
                245
```

<210> SEQ ID NO 112
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Gln Ser Val Val Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
```

```
                85                  90                  95
Leu Ser Gly Ser Tyr Val Phe Gly Thr Gly Thr Lys Leu Thr Val Leu
            100                 105                 110
Gly Ser Arg Gly Gly Gly Ser Gly Gly Gly Ser Gly Gly Gly
            115                 120                 125
Gly Ser Leu Glu Met Ala Glu Val Gln Leu Val Glu Thr Gly Gly Asn
130                 135                 140
Leu Val Gln Pro Gly Ala Ser Leu Arg Leu Ser Cys Ala Ala Ser Gly
145                 150                 155                 160
Phe Ser Phe Ser Gly Thr Ala Met His Trp Val Arg Gln Ala Pro Gly
            165                 170                 175
Lys Gly Leu Glu Trp Val Ser Thr Ile Ser Ser Thr Gly Arg Ser Thr
            180                 185                 190
Tyr Tyr Arg Asp Ser Val Lys Gly Arg Phe Thr Ile Ser Arg Asp Asn
            195                 200                 205
Ser Lys Asn Thr Leu Tyr Leu Gln Met Asn Ser Leu Arg Gly Glu Asp
            210                 215                 220
Thr Ala Val Tyr Tyr Cys Ala Arg Val Ser Phe Asp Tyr Trp Gly Gln
225                 230                 235                 240
Gly Thr Leu Val Thr Val Ser Ser
            245

<210> SEQ ID NO 113
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Ser Val Val Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
            35                  40                  45
Met Ile Tyr Asp Val Ser Lys Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
            85                  90                  95
Ser Thr Leu Val Phe Gly Gly Gly Thr Lys Leu Thr Val Leu Gly Ser
            100                 105                 110
Arg Gly Gly Gly Ser Gly Gly Gly Ser Gly Gly Gly Gly Ser
            115                 120                 125
Leu Glu Met Ala Glu Val Gln Leu Val Glu Ser Gly Gly Ala Phe Val
            130                 135                 140
Gln Pro Gly Gly Ser Leu Arg Leu Ser Cys Ala Ala Ser Gly Phe Thr
145                 150                 155                 160
Phe Ser Ser Tyr Ala Met Thr Trp Val Arg Gln Ala Pro Gly Lys Gly
            165                 170                 175
Leu Glu Trp Val Ser Thr Ile Ser Gly Arg Gly Arg Ser Thr Phe Tyr
            180                 185                 190
```

```
Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
    210                 215                 220

Val Tyr Tyr Cys Ala Arg Tyr Tyr His Ala Gly Ala Phe Asp Leu Trp
225                 230                 235                 240

Gly Gln Gly Thr Leu Val Thr Val Ser Ser
                245                 250

<210> SEQ ID NO 114
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Ser Val Leu Thr Gln Pro Ala Ser Val Ser Gly Ser Pro Gly Gln
1               5                   10                  15

Ser Leu Thr Ile Ser Cys Thr Gly Thr Ser Asn Asp Val Gly Ala Tyr
            20                  25                  30

Lys Tyr Val Ser Trp Tyr Gln Gln Tyr Pro Gly Lys Ala Pro Lys Leu
        35                  40                  45

Ile Leu Tyr Asp Val Phe Lys Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Phe Ser Leu Thr Ser Ser
                85                  90                  95

Asn Thr Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Asn Arg Tyr Ala Ile Thr Trp Val Arg Gln Ala Pro Gly Gln Gly
                165                 170                 175

Leu Glu Trp Met Gly Trp Ile Ser Ala Tyr Asn Gly Asn Ser His Tyr
            180                 185                 190

Ala Gln Lys Leu Gln Gly Arg Val Thr Met Thr Thr Asp Thr Ser Thr
        195                 200                 205

Gly Thr Ala Tyr Met Glu Leu Arg Arg Leu Arg Ser Asp Asp Thr Ala
    210                 215                 220

Val Tyr Tyr Cys Ala Arg Met Ala Tyr Asp Ser Trp Gly Gln Gly Thr
225                 230                 235                 240

Leu Val Thr Val Ser Ser
                245

<210> SEQ ID NO 115
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 115

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Val Gly Gly Asn
            20                  25                  30

Tyr Val Phe Trp Tyr Gln Gln Val Pro Gly Ala Thr Pro Lys Leu Leu
        35                  40                  45

Ile Tyr Arg Ser Asn Gln Arg Pro Ser Gly Val Pro Asp Arg Phe Ala
50                  55                  60

Gly Ser Lys Ser Gly Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Phe Val Phe Gly Thr Gly Thr Lys Val Thr Val Leu Gly Ser
            100                 105                 110

Arg Gly Gly Gly Ser Gly Gly Gly Ser Gly Gly Gly Ser
            115                 120                 125

Leu Glu Met Ala Glu Val Gln Leu Val Glu Ser Gly Gly Gly Leu Val
130                 135                 140

Lys Pro Gly Gly Ser Leu Arg Leu Ser Cys Ala Ala Ser Gly Phe Thr
145                 150                 155                 160

Phe Ser Asp Tyr Tyr Met Ser Trp Ile Arg Gln Ala Pro Gly Lys Gly
                165                 170                 175

Leu Glu Trp Val Ser Tyr Ile Ser Ser Ser Gly Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
210                 215                 220

Val Tyr Tyr Cys Ala Arg Gly Tyr Gly Lys Ala Tyr Asp Gln Trp Gly
225                 230                 235                 240

Gln Gly Thr Leu Val Thr Val Ser Ser
                245

<210> SEQ ID NO 116
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95
```

```
Pro Val Val Phe Gly Gly Gly Thr Lys Leu Thr Val Leu Gly Ser Arg
            100                 105                 110

Gly Gly Gly Gly Ser Gly Gly Gly Ser Gly Gly Gly Gly Ser Leu
        115                 120                 125

Glu Met Ala Gln Val Gln Leu Val Glu Ser Gly Gly Leu Val His
    130                 135                 140

Pro Gly Gly Ser Leu Arg Leu Ser Cys Ala Ala Ser Gly Phe Thr Phe
145                 150                 155                 160

Arg Ser His Ser Met Asn Trp Val Arg Gln Ala Pro Gly Lys Gly Leu
                165                 170                 175

Glu Trp Val Ser Ser Ile Ser Ser Asp Ser Thr Tyr Thr Tyr Tyr Ala
            180                 185                 190

Asp Ser Val Lys Gly Arg Phe Thr Ile Ser Arg Asp Asn Ala Lys Asn
            195                 200                 205

Ser Leu Tyr Leu Gln Met Asn Ser Leu Arg Ala Glu Asp Thr Ala Val
    210                 215                 220

Tyr Tyr Cys Ala Arg Ser Gly Gly Gln Trp Lys Tyr Tyr Asp Tyr Trp
225                 230                 235                 240

Gly Gln Gly Thr Leu Val Thr Val Ser Ser
                245                 250

<210> SEQ ID NO 117
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Ser Val Val Thr Gln Pro Pro Ser Met Ser Ala Ala Pro Gly Gln
1               5                   10                  15

Gln Val Thr Ile Ser Cys Ser Gly Gly Asn Ser Asn Ile Glu Arg Asn
            20                  25                  30

Tyr Val Ser Trp Tyr Leu Gln Leu Pro Gly Thr Ala Pro Lys Leu Val
        35                  40                  45

Ile Phe Asp Asn Asp Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Arg Gly Trp Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Gly Gly Leu Ile
    130                 135                 140

Gln Pro Gly Gly Ser Leu Arg Leu Ser Cys Ala Ala Ser Gly Phe Thr
145                 150                 155                 160

Phe Ser Asn Tyr Ala Met Asn Trp Val Arg Gln Ala Pro Gly Lys Gly
                165                 170                 175

Leu Glu Trp Val Ser Thr Ile Asn Gly Arg Gly Ser Ser Thr Ile Tyr
            180                 185                 190

Ala Asp Ser Val Lys Gly Arg Phe Thr Ile Ser Arg Asp Asn Ser Lys
```

```
                    195                 200                 205

Asn Thr Leu Tyr Leu Gln Met Asn Ser Leu Arg Ala Glu Asp Thr Ala
        210                 215                 220

Thr Tyr Tyr Cys Ala Arg Tyr Ile Ser Arg Gly Leu Gly Asp Ser Trp
225                 230                 235                 240

Gly Gln Gly Thr Leu Val Thr Val
                245

<210> SEQ ID NO 118
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Ala Gly Met Gly Met Asp Thr Trp Gly Gln
225                 230                 235                 240

Gly Thr Leu Val Thr Val Ser Ser
                245

<210> SEQ ID NO 119
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 119

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95

Lys Thr Leu Val Phe Gly Gly Thr Lys Leu Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Gln Val Gln Leu Val Gln Ser Gly Ala Glu Val Lys
        130                 135                 140

Lys Pro Gly Ala Ser Val Lys Val Ser Cys Arg Ala Ser Gly Tyr Thr
145                 150                 155                 160

Phe Thr Ala Tyr Ser Leu His Trp Val Arg Gln Ala Pro Gly Gln Gly
                165                 170                 175

Leu Glu Trp Met Gly Trp Ile Asn Pro Ser Ser Gly Gly Ala Val Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Ser Gly Leu Arg Ser Asp Asp Thr Ala
    210                 215                 220

Val Tyr Tyr Cys Ala Arg Asn Val Gly Gly Gln Ala Asp Asp Trp Gly
225                 230                 235                 240

Gln Gly Thr Leu Val Thr Val Ser Ser
                245

<210> SEQ ID NO 120
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Thr Asp Ile Gly Gly Tyr
            20                  25                  30

Asn Tyr Val Ser Trp Tyr Gln His His Pro Ser Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95
```

```
Lys Thr Leu Val Phe Gly Gly Gly Thr Lys Leu Thr Val Leu Gly Ser
                100                 105                 110

Arg Gly Gly Gly Gly Ser Gly Gly Gly Ser Gly Gly Gly Ser
            115                 120                 125

Leu Glu Met Ala Gln Val Gln Leu Val Gln Ser Gly Ala Glu Val Lys
            130                 135                 140

Lys Pro Gly Ala Ser Val Lys Val Ser Cys Arg Ala Ser Gly Tyr Thr
145                 150                 155                 160

Phe Thr Ala Tyr Ser Leu His Trp Val Arg Gln Ala Pro Gly Gln Gly
                165                 170                 175

Leu Glu Trp Met Gly Trp Ile Asn Pro Ser Ser Gly Gly Ala Val Tyr
            180                 185                 190

Ala Gln Lys Phe Gln Gly Arg Val Thr Met Thr Arg Asp Thr Ser Ile
            195                 200                 205

Ser Thr Ala Tyr Met Glu Leu Ser Gly Leu Arg Ser Asp Asp Thr Ala
    210                 215                 220

Val Tyr Tyr Cys Ala Arg Asn Val Gly Gly His Ala Asp Asp Trp Gly
225                 230                 235                 240

Gln Gly Thr Leu Val Thr Val Ser Ser
                245

<210> SEQ ID NO 121
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly Ser
                100                 105                 110

Arg Gly Gly Gly Gly Ser Gly Gly Gly Ser Gly Gly Gly Ser
            115                 120                 125

Leu Glu Met Ala Gln Val Gln Leu Val Gln Ser Gly Gly Glu Val Lys
            130                 135                 140

Lys Pro Gly Ala Ser Val Lys Val Ser Cys Lys Ala Ser Gly Phe Thr
145                 150                 155                 160

Phe Asn Thr Tyr Gly Ile Ser Trp Val Arg Gln Ala Pro Gly Gln Gly
                165                 170                 175

Leu Glu Trp Met Gly Trp Ile Ser Ala Asn Asn Gly His Thr Lys Ser
            180                 185                 190

Ala Gln Arg Phe Gln Asp Arg Val Ala Met Ala Thr Asp Thr Ser Thr
            195                 200                 205
```

Ser Thr Ala Tyr Met Glu Leu Arg Ser Leu Lys Phe Asp Asp Thr Ala
    210                 215                 220

Val Tyr Tyr Cys Ala Arg Gly Gly Tyr His His Gln Met Gln Arg Tyr
225                 230                 235                 240

Tyr Lys Ala Thr Ser Val Tyr Ser Asp Tyr Trp Gly Gln Gly Thr Leu
                245                 250                 255

Val Thr Val Ser Ser
            260

<210> SEQ ID NO 122
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Met Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Ser Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Ala Gly Met Gly Met Asp Thr Trp Gly Gln
225                 230                 235                 240

Gly Thr Leu Val Thr Val Ser Ser
                245

<210> SEQ ID NO 123
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln Ser Pro Gly Lys Ala Pro Arg Leu
        35                  40                  45
Met Ile Tyr Gly Val Ser Lys Arg Pro Ser Gly Val Pro Asp Arg Phe
    50                  55                  60
Ser Gly Ser Lys Ser Gly Asn Thr Ala Ser Leu Thr Val Ser Gly Leu
65                  70                  75                  80
Gln Ala Glu Asp Glu Ala Asp Tyr Tyr Cys Ser Ser Tyr Ala Gly Val
                85                  90                  95
Asn Asn Leu Met Phe Gly Gly Gly Thr Lys Leu Thr Val Leu Gly Ser
            100                 105                 110
Arg Gly Gly Gly Gly Ser Gly Gly Gly Gly Ser Gly Gly Gly Gly Ser
        115                 120                 125
Leu Glu Met Ala Gln Val Gln Leu Val Gln Ser Gly Ala Glu Val Lys
    130                 135                 140
Lys Pro Gly Ala Ser Val Lys Val Ser Cys Lys Ala Ser Gly Tyr Thr
145                 150                 155                 160
Phe Thr Ser Tyr Tyr Met His Trp Val Arg Gln Ala Pro Gly Gln Gly
                165                 170                 175
Leu Glu Trp Met Gly Ile Ile Asn Pro Ser Gly Gly Ser Thr Ser Tyr
            180                 185                 190
Ala Gln Lys Phe Gln Gly Arg Val Thr Met Thr Arg Asp Thr Ser Thr
        195                 200                 205
Ser Thr Val Tyr Met Glu Leu Ser Ser Leu Arg Ser Glu Asp Thr Ala
    210                 215                 220
Val Tyr Tyr Cys Ala Arg Asp Val Ile Ser Gly Phe Asp Ser Trp Gly
225                 230                 235                 240
Gln Gly Thr Leu Val Thr Val Ser Ser
                245
```

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Gly Tyr Thr Phe Thr Ser Tyr Tyr
1               5
```

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Gly Tyr Thr Phe Thr Ser Tyr Tyr
1               5
```

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Arg Gly Met Tyr Arg Ser Leu Leu Phe Tyr Asp Pro
1               5                   10

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ser Asn Val Gly Asn Tyr Tyr
1               5

<210> SEQ ID NO 128
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Asn Asn
1

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Thr Trp Asp Gly Ser Leu Ser Ala His Val
1               5                   10

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Phe Thr Phe Ser Asn Tyr Ala
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 131

Ile Ser Gly Ser Gly Asn Thr
1               5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Arg Gly Ser Val Arg Tyr Thr Asp Ile
1               5                   10

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gly Ala Ile Ala Gly Ala Tyr
1               5

<210> SEQ ID NO 134
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Asp Asn
1

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Ser Tyr Asp Tyr Asp Ser Ser Asn Val Leu
1               5                   10

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Phe Thr Phe Asn Asn Tyr Trp
1               5

<210> SEQ ID NO 137
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ile Lys Gln Asp Gly Ser Glu Lys
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Arg Ser Met Ser Thr Ala Val
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Ser Ile Ser Ser Tyr
1               5

<210> SEQ ID NO 140
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ala Ser
1

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Gln Ser Tyr Ser Val Pro Tyr Thr
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Tyr Thr Phe Thr Ser Tyr Tyr
```

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Asn Pro Ser Gly Gly Ser Thr
1               5

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Arg Gly Ser Ser Arg Trp Gly Gly Trp Thr Gly Asp Tyr
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Ser Asp Val Gly Gly Tyr Asn Phe
1               5

<210> SEQ ID NO 146
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Val Ser
1

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Ser Tyr Thr Ser Thr Arg Thr Val Ile Phe Ala Gly Gly Thr Lys
1               5                   10                  15

Val Thr Val Leu
            20

<210> SEQ ID NO 148
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 148

Gly Ser Thr Phe Ser Ser Tyr Ala
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Ser Gly Arg Gly Arg Ser Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Arg Tyr Tyr Lys Ser Lys Asp His
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Ser Asn Ile Gly Thr Asn Tyr
1               5

<210> SEQ ID NO 152
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Asn His
1

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Ala Trp Asp Asp Asn Leu Ser Gly Val Val
1               5                   10
```

```
<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Tyr Thr Phe Thr Asp Tyr Tyr
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ile Asn Pro Lys Ser Gly Arg Thr
1               5

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Arg Val Tyr Gly Tyr Ser Arg Trp Ser Gly Phe Asp Leu
1               5                   10

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Ser Asn Ile Gly Ser Asn Tyr
1               5

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Asn Asn
1

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 159

Ala Ala Trp Asp Asp Ser Leu Ser Gly Tyr Val
1               5                   10

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Tyr Thr Phe Thr Thr Tyr Tyr
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ile Asn Pro Asn Gly Gly Gly Thr
1               5

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Arg Gly His Lys Val Tyr Lys Ser His Pro Thr Gly Gly Tyr Asp
1               5                   10                  15

Arg

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Arg Asp Val Gly Gly Tyr Asn Tyr
1               5

<210> SEQ ID NO 164
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Val Ser
1
```

```
<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Ser Tyr Thr Ser Ser Ser Thr Leu Asp
1               5                   10

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Gly Thr Phe Ser Ser Tyr Ala
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ile Ile Pro Ile Phe Gly Thr Ala
1               5

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Arg Ser His Val Ala Trp Ser Leu Leu Asp Tyr
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Ser Asn Ile Gly Ser Asn Tyr
1               5

<210> SEQ ID NO 170
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170
```

Arg Asn Asn
1

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Ala Trp Asp Asp Ser Leu Ser Gly Val Val
1               5                   10

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gly Thr Phe Ser Ser Tyr Ala
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Met Asn Pro Asn Ser Gly Asn Thr
1               5

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Arg Tyr Gln Ser Tyr Lys Gly Ser Gln Ser Asp Ser
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ser Asn Ile Gly Ser Asn Tyr
1               5

<210> SEQ ID NO 176
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 176

Arg Asn Asn
1

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ala Trp Asp Asp Ser Leu Ser Gly Trp Val
1               5                   10

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Tyr Thr Phe Thr Ser Tyr Tyr
1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ile Asn Pro Ser Gly Gly Ser Thr
1               5

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Arg Gly Gly Ser Lys Lys Trp Ser Gly Glu Lys Trp Arg Arg Glu
1               5                   10                  15

Asn Phe Asp Tyr
            20

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181
```

Ser Ser Asp Val Gly Gly Tyr Asn Tyr
1               5

<210> SEQ ID NO 182
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Val Ser
1

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ser Tyr Thr Arg Ser Ser Thr Glu Val
1               5                   10

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Tyr Thr Phe Thr Arg His Ile
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ile Asn Pro Gly Asn Gly Asn Thr
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Arg Leu Pro Asp Gln
1               5

<210> SEQ ID NO 187
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 187

Ser Ser Asn Ile Gly Ser Asn Thr
1               5

<210> SEQ ID NO 188
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Asn Asn
1

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Ala Trp Asp Asp Ser Leu Ser Gly Leu
1               5                   10

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Thr Phe Gly Asp Tyr Gly
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ile Asn Trp Asn Gly Gly Ser Thr
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Arg Ser Lys Gln Asp Tyr
1               5
```

```
<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Arg Asp Ala Gly Gly Tyr Asn Tyr
1               5

<210> SEQ ID NO 194
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Val Thr
1

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Ser Tyr Gly Gly Ser Asn Asn Phe Arg Val
1               5                   10

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Phe Ser Phe Ser Gly Thr Ala
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ile Ser Ser Thr Gly Arg Ser Thr
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198
```

```
Ala Arg Val Ser Phe Asp Tyr
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Ser Asn Ile Gly Ala Gly Tyr Asp
1               5

<210> SEQ ID NO 200
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Asn Ser
1

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gln Ser Tyr Asp Ser Ser Leu Ser Gly Ser Tyr Val
1               5                   10

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Phe Thr Phe Ser Ser Tyr Ala
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ile Ser Gly Arg Gly Arg Ser Thr
1               5

<210> SEQ ID NO 204
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 204

Ala Arg Tyr Tyr His Ala Gly Ala Phe Asp Leu
1               5                   10

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Ser Asp Val Gly Gly Tyr Asn Tyr
1               5

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Val Ser
1

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Ser Tyr Thr Ser Ser Ser Thr Leu Val
1               5                   10

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Tyr Thr Phe Asn Arg Tyr Ala
1               5

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ile Ser Ala Tyr Asn Gly Asn Ser
1               5
```

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Arg Met Ala Tyr Asp Ser
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Asn Asp Val Gly Ala Tyr Lys Tyr
1               5

<210> SEQ ID NO 212
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Val Phe
1

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Phe Ser Leu Thr Ser Ser Asn Thr Tyr Val
1               5                   10

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Phe Thr Phe Ser Asp Tyr Tyr
1               5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 215

Ile Ser Ser Ser Gly Ser Thr Ile
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Arg Gly Tyr Gly Lys Ala Tyr Asp Gln
1               5                   10

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ser Asn Val Gly Gly Asn Tyr
1               5

<210> SEQ ID NO 218
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Ser Asn
1

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Thr Trp Asp Asp Ser Leu Ser Gly Phe Val
1               5                   10

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Phe Thr Phe Arg Ser His Ser
1               5

<210> SEQ ID NO 221
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 221

Ile Ser Ser Asp Ser Thr Tyr Thr
1               5

<210> SEQ ID NO 222
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Arg Ser Gly Gly Gln Trp Lys Tyr Tyr Asp Tyr
1               5                   10

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ser Leu Arg Ser Tyr Tyr
1               5

<210> SEQ ID NO 224
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Lys Asn
1

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asn Ser Arg Asp Ser Ser Gly Asn Pro Pro Val Val
1               5                   10

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Phe Thr Phe Ser Asn Tyr Ala
1               5
```

```
<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ile Asn Gly Arg Gly Ser Ser Thr
1               5

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Arg Tyr Ile Ser Arg Gly Leu Gly Asp Ser
1               5                   10

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asn Ser Asn Ile Glu Arg Asn Tyr
1               5

<210> SEQ ID NO 230
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Asn Asp
1

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Thr Trp Asp Ser Ser Leu Arg Gly Trp Val
1               5                   10

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 232

Gly Tyr Thr Phe Thr Ser Tyr Tyr
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Asn Pro Ser Gly Gly Ser Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ala Arg Ala Gly Met Gly Met Asp Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Ser Asp Val Gly Gly Tyr Asn Tyr
1               5

<210> SEQ ID NO 236
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Glu Val Ser
1

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Ser Tyr Ala Gly Ser Asn Thr Leu Val
1               5                   10

<210> SEQ ID NO 238
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Tyr Thr Phe Thr Ala Tyr Ser
1               5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ile Asn Pro Ser Ser Gly Gly Ala
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Arg Asn Val Gly Gly Gln Ala Asp Asp
1               5                   10

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Ser Asp Ile Gly Gly Tyr Asn Tyr
1               5

<210> SEQ ID NO 242
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Glu Val Asn
1

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Ser Phe Ala Gly Arg Lys Thr Leu Val
```

```
                1               5                   10
```

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Tyr Thr Phe Thr Ala Tyr Ser
1               5

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ile Asn Pro Ser Ser Gly Gly Ala
1               5

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Arg Asn Val Gly Gly His Ala Asp Asp
1               5                   10

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ser Thr Asp Ile Gly Gly Tyr Asn Tyr
1               5

<210> SEQ ID NO 248
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Val Asn
1

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Ala Ser Phe Ala Gly Arg Lys Thr Leu Val
1               5                   10

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Phe Thr Phe Asn Thr Tyr Gly
1               5

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ile Ser Ala Asn Asn Gly His Thr
1               5

<210> SEQ ID NO 252
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Arg Gly Gly Tyr His His Gln Met Gln Arg Tyr Tyr Lys Ala Thr
1               5                   10                  15

Ser Val Tyr Ser Asp Tyr
            20

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Ser Asn Ile Gly Asn Asn Tyr
1               5

<210> SEQ ID NO 254
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Asn Asn
1

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Thr Trp Asp Ser Ser Leu Ser Gly Val Val
1               5                   10

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Tyr Thr Phe Thr Ser Tyr Tyr
1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ile Asn Pro Ser Gly Gly Ser Ser
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Arg Ala Gly Met Gly Met Asp Thr
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ser Ser Asp Val Gly Gly Tyr Asn Tyr
1               5

<210> SEQ ID NO 260
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Glu Val Ser
1

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ser Ser Tyr Ala Gly Ser Asn Thr Leu Val
1               5                   10

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Tyr Thr Phe Thr Ser Tyr Tyr
1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ile Asn Pro Ser Gly Gly Ser Thr
1               5

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Arg Asp Val Ile Ser Gly Phe Asp Ser
1               5                   10

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ser Ser Asp Val Gly Gly Tyr Asn Tyr
1               5

<210> SEQ ID NO 266
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Val Ser
1

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Ser Tyr Ala Gly Val Asn Asn Leu Met
1               5                   10

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Phe Thr Phe Gly Asp Tyr Gly
1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Asn Trp Asn Gly Gly Ser Thr
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Arg Ser Lys Gln Gly Tyr
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Arg Asp Ala Gly Gly Tyr Asn Tyr
```

```
<210> SEQ ID NO 272
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Val Thr
1

<210> SEQ ID NO 273
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ser Ser Tyr Gly Gly Ser Asn Asn Phe Arg Val
1               5                   10

<210> SEQ ID NO 274
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Gln Asp Tyr Trp Gly Gln Gly Thr Leu Val Thr Val
            100                 105                 110

Ser Ser

<210> SEQ ID NO 275
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Met Lys Lys Thr Ala Ile Ala Ile Ala Val Ala Leu Ala Gly Phe Ala
1               5                   10                  15

Thr Val Ala Gln Ala Ala Glu Leu Gln Ser Ala Leu Thr Gln Pro Pro
```

```
            20                  25                  30
Ser Ala Ser Gly Ser Pro Gly Gln Ser Val Thr Ile Ser Cys Thr Gly
        35                  40                  45

Thr Ser Arg Asp Ala Gly Gly Tyr Asn Tyr Phe Ser Trp Tyr Gln Gln
    50                  55                  60

His Pro Gly Lys Ala Pro Lys Leu Leu Ile Tyr Glu Val Thr Lys Arg
65                  70                  75                  80

Pro Ser Gly Val Pro Asp Arg Phe Ser Gly Ser Lys Ser Gly Lys Thr
                85                  90                  95

Ala Ser Leu Thr Val Ser Gly Leu Gln Ala Asp Asp Glu Ala Val Tyr
            100                 105                 110

Tyr Cys Ser Ser Tyr Gly Gly Ser Asn Asn Phe Arg Val Phe Gly Gly
        115                 120                 125

Gly Thr Lys Leu Thr Val Leu Gly
        130                 135

<210> SEQ ID NO 276
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Met Lys Lys Thr Ala Ile Ala Ile Ala Val Ala Leu Ala Gly Phe Ala
1               5                   10                  15

Thr Val Ala Gln Ala Ala Glu Leu Gln Ser Ala Leu Thr Gln Pro Pro
            20                  25                  30

Ser Ala Ser Gly Ser Pro Gly Gln Ser Val Thr Ile Ser Cys Thr Gly
        35                  40                  45

Thr Ser Arg Asp Ala Gly Gly Tyr Asn Tyr Phe Ser Trp Tyr Gln Gln
    50                  55                  60

His Pro Gly Lys Ala Pro Lys Leu Leu Ile Tyr Glu Val Thr Lys Arg
65                  70                  75                  80

Pro Ser Gly Val Pro Asp Arg Phe Ser Gly Ser Lys Ser Gly Lys Thr
                85                  90                  95

Ala Ser Leu Thr Val Ser Gly Leu Gln Ala Asp Asp Glu Ala Val Tyr
            100                 105                 110

Tyr Cys Ser Ser Tyr Gly Gly Ser Asn Asn Phe Arg Val Phe Gly Gly
        115                 120                 125

Gly Thr Lys Leu Thr Val Leu Gly Ser Arg Gly Gly Gly Ser Gly
        130                 135                 140

Gly Gly Ser Gly Gly Gly Ser Leu Glu Met Ala Glu Val Gln
145                 150                 155                 160

Leu Val Glu Ser Gly Gly Val Val Arg Pro Gly Gly Ser Leu Arg
                165                 170                 175

Leu Ser Cys Ala Ala Ser Gly Phe Thr Phe Gly Asp Tyr Gly Met Ser
            180                 185                 190

Trp Val Arg Gln Ala Pro Gly Lys Gly Leu Glu Trp Val Ser Gly Ile
        195                 200                 205

Asn Trp Asn Gly Gly Ser Thr Gly Tyr Ala Asp Ser Val Lys Gly Arg
    210                 215                 220

Phe Thr Ile Ser Arg Asp Asn Ala Lys Asn Ser Leu Tyr Leu Gln Met
225                 230                 235                 240
```

```
Asn Ser Leu Arg Ala Glu Asp Thr Ala Val Tyr Tyr Cys Ala Arg Ser
            245                 250                 255

Lys Gln Asp Tyr Trp Gly Gln Gly Thr Leu Val Thr Val Ser Ser
        260                 265                 270
```

<210> SEQ ID NO 277
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277

```
gaggtgcagc tggtggagtc tgggggaggt gtggtacggc ctgggggtc cctgagactc      60 tcctgtgcag cctctggatt cacctttggt gattatggca tgagctgggt ccgccaagct    120
ccagggaagg gctggagtg gtctctggt attaattgga atggtggtag cacaggttat     180
gcagactctg tgaagggccg attcaccatc tccagagaca cgccaagaa ctccctgtat    240 ctgcaaatga acagtctgag agccgaggac acggccgtat attactgtgc gcgctctaaa   300
caggattact ggggtcaagg tactctggtg accgtctcct ca                      342
```

<210> SEQ ID NO 278
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278

```
atgaaaaaga cagctatcgc gattgcagtg gcactggctg gtttcgctac cgtggcccag     60
gcggccgagc tccagtctgc cctgactcag cctccctccg cgtccgggtc tcctggacag   120
tcagtcacca tctcctgcac tggaaccagc agggacgctg gtggttataa ttatttctcc   180
tggtaccaac aacacccagg caaagccccc aaactcctga tttatgaggt cactaagcgg   240
ccctcagggg tccctgatcg cttctctggc tccaagtctg gcaagacggc ctccctgacc   300
gtctctgggc tccaggctga cgatgaggct gtatattact gcagctcata tggaggcagc   360
aacaactttc gggtgttcgg cggagggacc aagctgaccg tcctaggt              408
```

<210> SEQ ID NO 279
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279

```
atgaaaaaga cagctatcgc gattgcagtg gcactggctg gtttcgctac cgtggcccag     60
gcggccgagc tccagtctgc cctgactcag cctccctccg cgtccgggtc tcctggacag   120
tcagtcacca tctcctgcac tggaaccagc agggacgctg gtggttataa ttatttctcc   180
tggtaccaac aacacccagg caaagccccc aaactcctga tttatgaggt cactaagcgg   240
ccctcagggg tccctgatcg cttctctggc tccaagtctg gcaagacggc ctccctgacc   300
gtctctgggc tccaggctga cgatgaggct gtatattact gcagctcata tggaggcagc   360
aacaactttc gggtgttcgg cggagggacc aagctgaccg tcctaggttc tagaggtggt   420
```

```
ggtggtagcg gcggcggcgg ctctggtggt ggtggatccc tcgagatggc cgaggtgcag    480
ctggtggagt ctgggggagg tgtggtacgg cctgggggt ccctgagact ctcctgtgca     540
gcctctggat tcacctttgg tgattatggc atgagctggg tccgccaagc tccagggaag    600
gggctggagt gggtctctgg tattaattgg aatggtggta gcacaggtta tgcagactct    660
gtgaagggcc gattcaccat ctccagagac aacgccaaga actccctgta tctgcaaatg    720
aacagtctga gaccgagga cacggccgta tattactgtg cgcgctctaa acaggattac    780 tgggggtcaag gtactctggt gaccgtctcc tca                                813
```

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Phe Thr Phe Ser Asn Tyr Ala
1               5

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ile Thr Asn Ser Gly Arg Ser Thr
1               5

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Arg Val Thr His Arg Arg Tyr Gly Ser Thr Phe Asp Ser
1               5                   10

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Ser Asn Ile Gly Ser Asn Thr
1               5

<210> SEQ ID NO 284
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ser Asn Asn
1

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Ala Trp Asp Asp Ser Val Asn Gly Tyr Val
1               5                   10

<210> SEQ ID NO 286
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Leu Gln Leu Gln Glu Ser Gly Gly Gly Ser Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Asn Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Ser Ser Leu Arg Ala Glu Asp Thr Ala Val Tyr Tyr Cys
                85                  90                  95

Ala Arg Val Thr His Arg Arg Tyr Gly Ser Thr Phe Asp Ser Arg Gly
            100                 105                 110

Gln Gly Thr Leu Val Thr Val Ser Ser
        115                 120

<210> SEQ ID NO 287
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Met Lys Lys Thr Ala Ile Ala Ile Ala Val Ala Leu Ala Gly Phe Ala
1               5                   10                  15

Thr Val Ala Gln Ala Ala Glu Leu Ser Tyr Glu Leu Thr Gln Pro Pro
            20                  25                  30

Ser Ala Ser Gly Thr Pro Gly Gln Arg Val Ser Ile Ser Cys Ser Gly
        35                  40                  45

Ser Ser Ser Asn Ile Gly Ser Asn Thr Val Asn Trp Tyr Gln Gln Phe
    50                  55                  60

Pro Gly Thr Ala Pro Lys Leu Leu Ile His Ser Asn Asn Gln Arg Pro
65                  70                  75                  80

```
Ser Gly Val Pro Asp Arg Phe Ser Gly Ser Lys Ser Gly Thr Ser Ala
                85                  90                  95

Ser Leu Ala Ile Ser Gly Pro Gln Ser Glu Asp Glu Ala Asp Tyr Tyr
            100                 105                 110

Cys Ala Ala Trp Asp Asp Ser Val Asn Gly Tyr Val Phe Gly Thr Gly
        115                 120                 125

Thr Lys Val Thr Val Leu Gly
        130             135
```

<210> SEQ ID NO 288
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

```
Met Lys Lys Thr Ala Ile Ala Ile Ala Val Ala Leu Ala Gly Phe Ala
1               5                   10                  15

Thr Val Ala Gln Ala Ala Glu Leu Ser Tyr Glu Leu Thr Gln Pro Pro
            20                  25                  30

Ser Ala Ser Gly Thr Pro Gly Gln Arg Val Ser Ile Ser Cys Ser Gly
        35                  40                  45

Ser Ser Ser Asn Ile Gly Ser Asn Thr Val Asn Trp Tyr Gln Gln Phe
    50                  55                  60

Pro Gly Thr Ala Pro Lys Leu Leu Ile His Ser Asn Asn Gln Arg Pro
65                  70                  75                  80

Ser Gly Val Pro Asp Arg Phe Ser Gly Ser Lys Ser Gly Thr Ser Ala
                85                  90                  95

Ser Leu Ala Ile Ser Gly Pro Gln Ser Glu Asp Glu Ala Asp Tyr Tyr
            100                 105                 110

Cys Ala Ala Trp Asp Asp Ser Val Asn Gly Tyr Val Phe Gly Thr Gly
        115                 120                 125

Thr Lys Val Thr Val Leu Gly Ser Arg Gly Gly Gly Ser Gly Gly
        130             135                 140

Gly Gly Ser Gly Gly Gly Ser Leu Glu Met Ala Gln Leu Gln Leu
145                 150                 155                 160

Gln Glu Ser Gly Gly Ser Val Gln Pro Gly Gly Ser Leu Arg Leu
                165                 170                 175

Ser Cys Ala Ala Ser Gly Phe Thr Phe Ser Asn Tyr Ala Met Ser Trp
            180                 185                 190

Val Arg Gln Ala Pro Gly Lys Gly Leu Glu Trp Val Ser Ala Ile Thr
        195                 200                 205

Asn Ser Gly Arg Ser Thr Tyr Tyr Ala Asp Ser Val Lys Gly Arg Phe
    210                 215                 220

Thr Ile Ser Arg Asp Asn Ser Lys Asn Thr Leu Ser Leu Gln Met Ser
225                 230                 235                 240

Ser Leu Arg Ala Glu Asp Thr Ala Val Tyr Tyr Cys Ala Arg Val Thr
                245                 250                 255

His Arg Arg Tyr Gly Ser Thr Phe Asp Ser Arg Gly Gln Gly Thr Leu
            260                 265                 270

Val Thr Val Ser Ser
        275
```

<210> SEQ ID NO 289
<211> LENGTH: 385
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 289

```
cagctgcagc tgcaggagtc gggggggaggc tcggtacagc cggggggggtc tctgagactg      60
tcctgtgcag cctctggatt cacctttagc aactatgcca tgagctgggt ccgccaggct     120
ccagggaagg gctggagtg gtctcagct atcactaata gtggtcgtag tacatactac     180
gcagactccg tgaagggccg gttcaccatc tccagagaca attccaagaa cacgctgtct     240
ttgcaaatga gcagcctgag agccgaagac acggccgtgt attactgtgc gcgcgttact     300
catcgtcgtt acggttctac tttcgattct cggggtcaag gtactctggt gaccgtctcc     360
tcaactagtg gccaggccgg ccagc                                           385
```

<210> SEQ ID NO 290
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290

```
atgaaaaaga cagctatcgc gattgcagtg gcactggctg gtttcgctac cgtggcccag      60
gcggccgagc tcctatga gctgactcag ccaccctcag cgtctgggac ccccgggcag     120
agggtcagca tctcttgttc tggaagcagc tccaacatcg ggagtaatac tgtaaactgg     180
taccaacagt tccccggaac ggcccccaaa ctcctcatcc atagtaataa tcagcggccc     240
tcagggggtcc ctgaccgatt ctctggctcc aagtctggca cctcagcctc cctggccatc     300
agtgggcccc agtctgagga tgaggctgat tattactgtg cagcttggga tgacagtgtg     360
aatggttatg tcttcggaac tgggaccaag gtcaccgtcc taggt                     405
```

<210> SEQ ID NO 291
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 291

```
atgaaaaaga cagctatcgc gattgcagtg gcactggctg gtttcgctac cgtggcccag      60
gcggccgagc tcctatga gctgactcag ccaccctcag cgtctgggac ccccgggcag     120
agggtcagca tctcttgttc tggaagcagc tccaacatcg ggagtaatac tgtaaactgg     180
taccaacagt tccccggaac ggcccccaaa ctcctcatcc atagtaataa tcagcggccc     240
tcagggggtcc ctgaccgatt ctctggctcc aagtctggca cctcagcctc cctggccatc     300
agtgggcccc agtctgagga tgaggctgat tattactgtg cagcttggga tgacagtgtg     360
aatggttatg tcttcggaac tgggaccaag gtcaccgtcc taggttctag aggtggtggt     420
ggtagcggcg gcggcggctc tggtggtggt ggatccctcg agatggccca gctgcagctg     480
caggagtcgg ggggaggctc ggtacagccg gggggtctc tgagactgtc ctgtgcagcc     540
tctggattca cctttagcaa ctatgccatg agctgggtcc gccaggctcc agggaagggg     600
```

```
ctggagtggg tctcagctat cactaatagt ggtcgtagta catactacgc agactccgtg    660
aagggccggt tcaccatctc cagagacaat tccaagaaca cgctgtcttt gcaaatgagc    720
agcctgagag ccgaagacac ggccgtgtat tactgtgcgc gcgttactca tcgtcgttac    780
ggttctactt tcgattctcg gggtcaaggt actctggtga ccgtctcctc a             831
```

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Gly Thr Phe Arg Ser Tyr Ala
1               5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Ile Pro Met Leu Asp Ile Thr
1               5

<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Arg Thr Tyr Ser Arg Ser Pro Phe His Met Glu Asp Phe
1               5                   10

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ser Ser Asn Ile Gly Gly Asn Thr
1               5

<210> SEQ ID NO 296
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Arg Asn Asn
1

```
<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ala Ala Trp Asp Ala Ser Arg Gln Gly Val
1               5                   10

<210> SEQ ID NO 298
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Ile Thr Trp Val Arg Gln Ala Pro Gly Gln Gly Leu Glu Trp Met
        35                  40                  45

Gly Arg Ile Ile Pro Met Leu Asp Ile Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Ser Arg Ser Pro Phe His Met Glu Asp Phe Trp Gly
            100                 105                 110

Gln Gly Thr Leu Val Thr Val Ser Ser
        115                 120

<210> SEQ ID NO 299
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Lys Lys Thr Ala Ile Ala Ile Ala Val Ala Leu Ala Gly Phe Ala
1               5                   10                  15

Thr Val Ala Gln Ala Ala Glu Leu Gln Pro Val Leu Thr Gln Pro Pro
            20                  25                  30

Ser Ala Ser Gly Thr Pro Gly Gln Arg Val Thr Ile Ser Cys Ser Gly
        35                  40                  45

Ser Ser Ser Asn Ile Gly Gly Asn Thr Val Ser Trp Tyr Gln Gln Val
    50                  55                  60

Pro Gly Thr Ala Pro Arg Leu Leu Ile Phe Arg Asn Asn Gln Arg Pro
65                  70                  75                  80

Pro Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
```

```
              100                 105                 110
Cys Ala Ala Trp Asp Ala Ser Arg Gln Gly Val Phe Gly Gly Gly Thr
            115                 120                 125

Lys Leu Thr Val Leu Gly
        130

<210> SEQ ID NO 300
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Met Lys Lys Thr Ala Ile Ala Ile Ala Val Ala Leu Ala Gly Phe Ala
1               5                   10                  15

Thr Val Ala Gln Ala Ala Glu Leu Gln Pro Val Leu Thr Gln Pro Pro
            20                  25                  30

Ser Ala Ser Gly Thr Pro Gly Gln Arg Val Thr Ile Ser Cys Ser Gly
        35                  40                  45

Ser Ser Ser Asn Ile Gly Gly Asn Thr Val Ser Trp Tyr Gln Gln Val
    50                  55                  60

Pro Gly Thr Ala Pro Arg Leu Leu Ile Phe Arg Asn Asn Gln Arg Pro
65                  70                  75                  80

Pro Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
            100                 105                 110

Cys Ala Ala Trp Asp Ala Ser Arg Gln Gly Val Phe Gly Gly Gly Thr
            115                 120                 125

Lys Leu Thr Val Leu Gly Ser Arg Gly Gly Gly Ser Gly Gly Gly
        130                 135                 140

Gly Ser Gly Gly Gly Gly Ser Leu Glu Met Ala Gln Val Gln Leu Val
145                 150                 155                 160

Gln Ser Gly Ala Glu Val Lys Lys Pro Gly Ser Ser Val Lys Val Ser
                165                 170                 175

Cys Lys Ala Ser Gly Gly Thr Phe Arg Ser Tyr Ala Ile Thr Trp Val
            180                 185                 190

Arg Gln Ala Pro Gly Gln Gly Leu Glu Trp Met Gly Arg Ile Ile Pro
        195                 200                 205

Met Leu Asp Ile Thr Asn Tyr Ala Gln Lys Phe Gln Gly Arg Val Thr
    210                 215                 220

Ile Thr Ala Asp Lys Ser Thr Ser Thr Ala Tyr Met Glu Leu Ser Ser
225                 230                 235                 240

Leu Arg Ser Glu Asp Thr Ala Val Tyr Tyr Cys Ala Arg Thr Tyr Ser
                245                 250                 255

Arg Ser Pro Phe His Met Glu Asp Phe Trp Gly Gln Gly Thr Leu Val
            260                 265                 270

Thr Val Ser Ser
        275

<210> SEQ ID NO 301
<211> LENGTH: 402
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 301
atgaaaaaga cagctatcgc gattgcagtg gcactggctg gtttcgctac cgtggcccag      60
gcggccgagc tccagcctgt gctgactcag ccaccctcag cgtctgggac ccccgggcag     120
agggtcacca tctcttgttc tggaagcagc tccaatatcg aggtaacac tgtcagctgg      180 taccagcagg tcccaggaac ggcccccaga ctcctcattt ttaggaataa tcaacggccc     240
ccaggggtcc ctgaccgatt ctctggctcc aagtctggca cctcagcctc cctggccatc    300
agtgggctcc ggtctgagga tgaggctgat tattactgtg cagcatggga cgccagtcga    360 caagggtgt tcggcggagg gaccaagctg accgtcctag gt                         402

<210> SEQ ID NO 302
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302
atgaaaaaga cagctatcgc gattgcagtg gcactggctg gtttcgctac cgtggcccag      60
gcggccgagc tccagcctgt gctgactcag ccaccctcag cgtctgggac ccccgggcag     120
agggtcacca tctcttgttc tggaagcagc tccaatatcg aggtaacac tgtcagctgg      180 taccagcagg tcccaggaac ggcccccaga ctcctcattt ttaggaataa tcaacggccc     240
ccaggggtcc ctgaccgatt ctctggctcc aagtctggca cctcagcctc cctggccatc    300
agtgggctcc ggtctgagga tgaggctgat tattactgtg cagcatggga cgccagtcga    360 caagggtgt tcggcggagg gaccaagctg accgtcctag gttctagagg tggtggtggt    420
agcggcggcg gcggctctgg tggtggtgga tccctcgaga tggcccaggt gcagctggtg    480
cagtctgggg ctgaggtgaa gaagcctggg tcctcggtga aggtctcctg caaggcttct    540
ggaggcacct tccgcagcta tgctatcacc tgggtgcgac aggcccctgg acaagggctt    600
gagtggatgg gaaggatcat ccctatgctt gatataacaa actacgcaca gaagttccag    660
ggcagagtca cgattaccgc ggacaaatcc acgagcacag cctacatgga gctgagcagc    720
ctgagatctg aggacacggc cgtgtattac tgtgcgcgca cttactctcg ttctccgttc    780
catatggaag atttctgggg tcaaggtact ctggtgaccg tctcctca                 828

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gly Phe Thr Phe Ser Ser Tyr Ala
1               5

<210> SEQ ID NO 304
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 304

Ile Ser Gly Ser Gly Gly Ser Thr
1               5

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Arg Lys Tyr Gln Asp Val
1               5

<210> SEQ ID NO 306
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Ser Asn Ile Gly Ser Asn Thr
1               5

<210> SEQ ID NO 307
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Asn Asn
1

<210> SEQ ID NO 308
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ala Ala Trp Asp Asp Ser Leu Ser Gly Arg Val
1               5                   10

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Gly Gly Gly Ser Gly Gly Gly Ser Gly Gly Gly Gly Ser
1               5                   10                  15

<210> SEQ ID NO 310

```
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Gln Asp Val Trp Gly Gln Gly Thr Leu Val Thr Val
            100                 105                 110

Ser Ser

<210> SEQ ID NO 311
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Ala Ser Gly Thr Pro Gly Gln Arg Val Thr Ile Ser Cys Ser Gly
        35                  40                  45

Ser Ser Ser Asn Ile Gly Ser Asn Thr Val Asn Trp Tyr Gln Gln Leu
    50                  55                  60

Pro Gly Thr Ala Pro Lys Leu Leu Ile Tyr Arg Asn Asn Gln Arg Pro
65                  70                  75                  80

Ser Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
            100                 105                 110

Cys Ala Ala Trp Asp Asp Ser Leu Ser Gly Arg Val Phe Gly Gly Gly
        115                 120                 125

Thr Lys Leu Thr Val Leu Gly
    130                 135

<210> SEQ ID NO 312
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 312

```
Met Lys Lys Thr Ala Ile Ala Ile Ala Val Ala Leu Ala Gly Phe Ala
1               5                   10                  15
Thr Val Ala Gln Ala Ala Glu Leu Gln Ser Val Leu Thr Gln Pro Pro
                20                  25                  30
Ser Ala Ser Gly Thr Pro Gly Gln Arg Val Thr Ile Ser Cys Ser Gly
            35                  40                  45
Ser Ser Ser Asn Ile Gly Ser Asn Thr Val Asn Trp Tyr Gln Gln Leu
    50                  55                  60
Pro Gly Thr Ala Pro Lys Leu Leu Ile Tyr Arg Asn Asn Gln Arg Pro
65                  70                  75                  80
Ser Gly Val Pro Asp Arg Phe Ser Gly Ser Lys Ser Gly Thr Ser Ala
                85                  90                  95
Ser Leu Ala Ile Ser Gly Leu Arg Ser Glu Asp Glu Ala Asp Tyr Tyr
            100                 105                 110
Cys Ala Ala Trp Asp Asp Ser Leu Ser Gly Arg Val Phe Gly Gly Gly
            115                 120                 125
Thr Lys Leu Thr Val Leu Gly Ser Arg Gly Gly Gly Ser Gly Gly
            130                 135                 140
Gly Gly Ser Gly Gly Gly Gly Ser Leu Glu Met Ala Glu Val Gln Leu
145                 150                 155                 160
Val Glu Ser Gly Gly Gly Leu Val Gln Pro Gly Gly Ser Leu Arg Leu
                165                 170                 175
Ser Cys Ala Ala Ser Gly Phe Thr Phe Ser Ser Tyr Ala Met Ser Trp
            180                 185                 190
Val Arg Gln Ala Pro Gly Lys Gly Leu Glu Trp Val Ser Ala Ile Ser
            195                 200                 205
Gly Ser Gly Gly Ser Thr Tyr Tyr Ala Asp Ser Val Lys Gly Arg Phe
    210                 215                 220
Thr Ile Ser Arg Asp Asn Ala Lys Asn Thr Leu Tyr Leu Gln Met Asn
225                 230                 235                 240
Ser Leu Arg Ala Glu Asp Thr Ala Val Tyr Tyr Cys Ala Arg Lys Tyr
                245                 250                 255
Gln Asp Val Trp Gly Gln Gly Thr Leu Val Thr Val Ser Ser
            260                 265                 270
```

<210> SEQ ID NO 313
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 313

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac   180
gcagactccg tgaagggccg gttcaccatc tccagagaca atgccaagaa cacgctgtat   240
ctgcaaatga acagcctgag agccgaggac acggccgtat attactgtgc gcgcaaatac   300
caggatgttt ggggtcaagg tactctggtg accgtctcct ca                       342
```

<210> SEQ ID NO 314
<211> LENGTH: 405

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 314
atgaaaaaga cagctatcgc gattgcagtg gcactggctg gtttcgctac cgtggcccag      60
gcggccgagc tccagtctgt gctgacgcag ccgccctcag cgtctgggac ccccgggcag     120
agggtcacca tctcttgttc tggaagcagc tccaacatcg aagtaatac tgtaaactgg      180 taccagcagc tcccaggaac ggcccccaaa ctcctcatct ataggaataa tcagcggccc     240 tcagggtgtcc ctgaccgatt ctctggctcc aagtctggca cctcagcctc cctggccatc    300
agtgggctcc ggtccgagga tgaggctgat tattactgtg cagcatggga tgacagcctg     360
agtggtaggg tgttcggcgg agggaccaag ctgaccgtcc taggt                    405

<210> SEQ ID NO 315
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 315
atgaaaaaga cagctatcgc gattgcagtg gcactggctg gtttcgctac cgtggcccag      60
gcggccgagc tccagtctgt gctgacgcag ccgccctcag cgtctgggac ccccgggcag     120
agggtcacca tctcttgttc tggaagcagc tccaacatcg aagtaatac tgtaaactgg      180 taccagcagc tcccaggaac ggcccccaaa ctcctcatct ataggaataa tcagcggccc     240 tcagggtgtcc ctgaccgatt ctctggctcc aagtctggca cctcagcctc cctggccatc    300
agtgggctcc ggtccgagga tgaggctgat tattactgtg cagcatggga tgacagcctg     360
agtggtaggg tgttcggcgg agggaccaag ctgaccgtcc taggttctag aggtggtggt     420
ggtagcggcg gcggcggctc tggtggtggt ggatccctcg agatggccga ggtgcagctg     480
gtggagtctg ggggaggctt ggtacagcct ggggggtccc tgagactctc ctgtgcagcc     540
tctggattca cctttagcag ctatgccatg agctgggtcc gccaggctcc agggaagggg     600
ctggagtggg tctcagctat tagtggtagt ggtggtagca catactacgc agactccgtg     660
aagggccggt tcaccatctc cagagacaat gccaagaaca cgctgtatct gcaaatgaac     720
agcctgagag ccgaggacac ggccgtatat tactgtgcgc gcaaatacca ggatgtttgg     780
ggtcaaggta ctctggtgac cgtctcctca                                      810

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Phe Ser Phe Ser Gly Thr Ala
1               5

<210> SEQ ID NO 317
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 317

Ile Ser Ser Thr Gly Arg Ser Thr
1               5

<210> SEQ ID NO 318
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ala Arg Pro Val Ser Ser Met Thr Leu Ser Ile Gln Ser Asp Gly
1               5                  10                  15

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ser Ser Asn Ile Gly Ala Gly Tyr Asp
1               5

<210> SEQ ID NO 320
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Asn Ser
1

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Ser Tyr Asp Ser Ser Leu Arg Gly Tyr Val
1               5                  10

<210> SEQ ID NO 322
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Gln Val Gln Leu Val Gln Ser Gly Gly Gly Val Val Gln Pro Gly Arg
1               5                  10                  15
```

```
Ser Leu Arg Leu Ser Cys Ala Ala Ser Gly Phe Ser Phe Ser Gly Thr
            20                  25                  30

Ala Met His Trp Val Arg Gln Ala Pro Gly Lys Gly Leu Glu Trp Val
        35                  40                  45

Ser Thr Ile Ser Ser Thr Gly Arg Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Pro Val Ser Ser Met Thr Leu Ser Ile Gln Ser Asp Gly Trp
            100                 105                 110

Gly Gln Gly Thr Leu Val Thr Val Ser Ser
            115                 120
```

<210> SEQ ID NO 323
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Val Ser Gly Ala Pro Gly Gln Arg Val Thr Ile Ser Cys Thr Gly
        35                  40                  45

Ser Ser Ser Asn Ile Gly Ala Gly Tyr Asp Val His Trp Tyr Gln Gln
    50                  55                  60

Leu Pro Gly Arg Ala Pro Lys Leu Leu Ile Tyr Gly Asn Ser Asn Arg
65                  70                  75                  80

Pro Ser Gly Val Pro Asp Arg Phe Ser Gly Ser Lys Ser Gly Thr Ser
                85                  90                  95

Ala Ser Leu Ala Ile Thr Gly Leu Gln Ala Glu Asp Glu Ala Asp Tyr
            100                 105                 110

Tyr Cys Gln Ser Tyr Asp Ser Ser Leu Arg Gly Tyr Val Phe Gly Thr
            115                 120                 125

Gly Thr Lys Val Thr Val Leu Gly
        130                 135
```

<210> SEQ ID NO 324
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Val Ser Gly Ala Pro Gly Gln Arg Val Thr Ile Ser Cys Thr Gly
        35                  40                  45
```

Ser Ser Ser Asn Ile Gly Ala Gly Tyr Asp Val His Trp Tyr Gln Gln
            50                  55                  60

Leu Pro Gly Arg Ala Pro Lys Leu Leu Ile Tyr Gly Asn Ser Asn Arg
 65                  70                  75                  80

Pro Ser Gly Val Pro Asp Arg Phe Ser Gly Ser Lys Ser Gly Thr Ser
                 85                  90                  95

Ala Ser Leu Ala Ile Thr Gly Leu Gln Ala Glu Asp Glu Ala Asp Tyr
            100                 105                 110

Tyr Cys Gln Ser Tyr Asp Ser Ser Leu Arg Gly Tyr Val Phe Gly Thr
        115                 120                 125

Gly Thr Lys Val Thr Val Leu Gly Ser Arg Gly Gly Gly Gly Ser Gly
    130                 135                 140

Gly Gly Gly Ser Gly Gly Gly Ser Leu Glu Met Ala Gln Val Gln
145                 150                 155                 160

Leu Val Gln Ser Gly Gly Gly Val Val Gln Pro Gly Arg Ser Leu Arg
                165                 170                 175

Leu Ser Cys Ala Ala Ser Gly Phe Ser Phe Ser Gly Thr Ala Met His
            180                 185                 190

Trp Val Arg Gln Ala Pro Gly Lys Gly Leu Glu Trp Val Ser Thr Ile
        195                 200                 205

Ser Ser Thr Gly Arg Ser Thr Tyr Tyr Arg Asp Ser Val Lys Gly Arg
    210                 215                 220

Phe Thr Ile Ser Arg Asp Asn Ser Lys Asn Thr Leu Tyr Leu Gln Met
225                 230                 235                 240

Asn Ser Leu Arg Gly Glu Asp Thr Ala Val Tyr Tyr Cys Ala Arg Pro
                245                 250                 255

Val Ser Ser Met Thr Leu Ser Ile Gln Ser Asp Gly Trp Gly Gln Gly
            260                 265                 270

Thr Leu Val Thr Val Ser Ser
        275

<210> SEQ ID NO 325
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325
caggtgcagc tggtgcagtc tgggggaggc gtggtccagc ctggggaggtc cctgagactc      60 tcctgtgcag cctctggatt cagctttagt ggcactgcca tgcactgggt ccgccaggct     120
ccagggaagg gctggaatg gtctcgact attagtagta ctgggcgtag cacatactac       180
agagactccg tgaagggccg gttcaccatc tccagagaca attccaagaa cacgctgtat     240
ctgcaaatga acagcctgag aggcgaggac acggccgtat attactgtgc gcgcccggtt     300
tcttctatga ctctgtctat ccagtctgat ggttggggtc aaggtactct ggtgaccgtc     360
tcctca                                                                366

<210> SEQ ID NO 326
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326

```
atgaaaaaga cagctatcgc gattgcagtg gcactggctg gtttcgctac cgtggcccag     60
gcggccgagc tccagtctgt gttgacgcag ccgccctcag tgtctggggc cccagggcag    120
aggtcacca tctcctgcac tgggagcagc tccaacatcg gggcaggtta tgatgtacac    180
tggtaccagc agcttccagg aagagccccc aaactcctca tctatggtaa cagcaatcgg    240
ccctcagggg tccctgaccg attctctggc tccaagtctg gcacctcagc ctccctggcc    300
atcactgggc tccaggctga ggatgaggct gattattact gccagtccta tgacagcagc    360
ctgagaggtt atgtcttcgg aactgggacc aaggtcaccg tcctaggt                 408
```

<210> SEQ ID NO 327
<211> LENGTH: 837
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 327

```
atgaaaaaga cagctatcgc gattgcagtg gcactggctg gtttcgctac cgtggcccag     60
gcggccgagc tccagtctgt gttgacgcag ccgccctcag tgtctggggc cccagggcag    120
aggtcacca tctcctgcac tgggagcagc tccaacatcg gggcaggtta tgatgtacac    180
tggtaccagc agcttccagg aagagccccc aaactcctca tctatggtaa cagcaatcgg    240
ccctcagggg tccctgaccg attctctggc tccaagtctg gcacctcagc ctccctggcc    300
atcactgggc tccaggctga ggatgaggct gattattact gccagtccta tgacagcagc    360
ctgagaggtt atgtcttcgg aactgggacc aaggtcaccg tcctaggttc tagaggtggt    420
ggtggtagcg gcggcggcgg ctctggtggt ggtggatccc tcgagatggc caggtgcag    480
ctggtgcagt ctgggggagg cgtggtccag cctgggaggt ccctgagact ctcctgtgca    540
gcctctggat tcagctttag tggcactgcc atgcactggg tccgccaggc tccagggaag    600
gggctggaat gggtctcgac tattagtagt actgggcgta gcacatacta cagagactcc    660
gtgaagggcc ggttcaccat ctccagagac aattccaaga acacgctgta tctgcaaatg    720
aacagcctga gagccgagga cacggccgta tattactgtg cgcgcccggt ttcttctatg    780
actctgtcta tccagtctga tggttggggt caaggtactc tggtgaccgt ctcctca      837
```

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Gly Tyr Thr Phe Thr Ser Tyr Tyr
1               5

<210> SEQ ID NO 329
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

```
<400> SEQUENCE: 329

Ile Asn Pro Ser Gly Gly Ser Thr
1               5

<210> SEQ ID NO 330
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ala Arg Gly Gln Lys Tyr His Ser Gln Tyr Ser Arg Gly Gly Thr Gly
1               5                   10                  15

Gly Gly Met Thr Gln Asp Met
            20

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ser Ser Asn Ile Gly Asn Asn Tyr
1               5

<210> SEQ ID NO 332
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Asn Asn
1

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Thr Trp Asp Ser Ser Leu Arg Asn Trp Val
1               5                   10

<210> SEQ ID NO 334
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                20                  25                  30
Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gln Lys Tyr His Ser Gln Tyr Ser Arg Gly Gly Thr Gly
             100                 105                 110

Gly Gly Met Thr Gln Asp Met Trp Gly Gln Gly Thr Leu Val Thr Val
         115                 120                 125

Ser Ser
    130

<210> SEQ ID NO 335
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Met Lys Lys Thr Ala Ile Ala Ile Ala Val Ala Leu Ala Gly Phe Ala
 1               5                  10                  15

Thr Val Ala Gln Ala Ala Glu Leu Gln Ser Val Val Thr Gln Pro Pro
             20                  25                  30

Ser Val Ser Ala Ala Pro Gly Gln Arg Val Thr Ile Ser Cys Ser Gly
         35                  40                  45

Gly Ser Ser Asn Ile Gly Asn Asn Tyr Val Ser Trp Phe Gln Gln Leu
     50                  55                  60

Pro Arg Thr Ala Pro Lys Leu Leu Ile Tyr Asp Asn Asn Lys Arg Pro
 65                  70                  75                  80

Ser Gly Ile Pro Asp Arg Phe Ser Gly Ser Lys Ser Gly Thr Ser Ala
                 85                  90                  95

Ala Leu Asp Ile Thr Val Leu Gln Thr Gly Asp Glu Ala Asp Tyr Tyr
             100                 105                 110

Cys Gly Thr Trp Asp Ser Ser Leu Arg Asn Trp Val Phe Gly Gly Gly
         115                 120                 125

Thr Lys Leu Thr Val Leu Gly
    130                 135

<210> SEQ ID NO 336
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Met Lys Lys Thr Ala Ile Ala Ile Ala Val Ala Leu Ala Gly Phe Ala
 1               5                  10                  15

Thr Val Ala Gln Ala Ala Glu Leu Gln Ser Val Val Thr Gln Pro Pro
             20                  25                  30

Ser Val Ser Ala Ala Pro Gly Gln Arg Val Thr Ile Ser Cys Ser Gly
```

-continued

```
            35                  40                  45
Gly Ser Ser Asn Ile Gly Asn Asn Tyr Val Ser Trp Phe Gln Gln Leu
         50                  55                  60
Pro Arg Thr Ala Pro Lys Leu Leu Ile Tyr Asp Asn Asn Lys Arg Pro
 65                  70                  75                  80
Ser Gly Ile Pro Asp Arg Phe Ser Gly Ser Lys Ser Gly Thr Ser Ala
                 85                  90                  95
Ala Leu Asp Ile Thr Val Leu Gln Thr Gly Asp Glu Ala Asp Tyr Tyr
            100                 105                 110
Cys Gly Thr Trp Asp Ser Ser Leu Arg Asn Trp Val Phe Gly Gly Gly
        115                 120                 125
Thr Lys Leu Thr Val Leu Gly Ser Arg Gly Gly Gly Ser Gly Gly
130                 135                 140
Gly Gly Ser Gly Gly Gly Ser Leu Glu Met Ala Gln Met Gln Leu
145                 150                 155                 160
Val Gln Ser Gly Ala Glu Val Lys Lys Pro Gly Ala Ser Val Lys Val
                165                 170                 175
Ser Cys Lys Ala Ser Gly Tyr Thr Phe Thr Ser Tyr Tyr Met His Trp
            180                 185                 190
Val Arg Gln Ala Pro Gly Gln Gly Leu Glu Trp Met Gly Ile Ile Asn
        195                 200                 205
Pro Ser Gly Gly Ser Thr Ser Tyr Ala Gln Lys Phe Gln Gly Arg Val
    210                 215                 220
Thr Met Thr Arg Asp Thr Ser Thr Ser Thr Val Tyr Met Glu Leu Ser
225                 230                 235                 240
Ser Leu Arg Ser Glu Asp Thr Ala Val Tyr Tyr Cys Ala Arg Gly Gln
                245                 250                 255
Lys Tyr His Ser Gln Tyr Ser Arg Gly Gly Thr Gly Gly Gly Met Thr
            260                 265                 270
Gln Asp Met Trp Gly Gln Gly Thr Leu Val Thr Val Ser Ser
        275                 280                 285
```

<210> SEQ ID NO 337
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 337

```
cagatgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac   180
gcacaaaagt tccagggcag agtcaccatg accaggaca cgtccacgag cacagtctac   240
atggagctga gcagcctgag atctgaggac acggccgtgt attactgtgc gcgcggtcag   300
aaataccatt ctcagtactc tcgtggtggt actggtggtg gtatgactca ggatatgtgg   360
ggtcaaggta ctctggtgac cgtctcctca                                     390
```

<210> SEQ ID NO 338
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 338

| | |
|---|---|
| atgaaaaaga cagctatcgc gattgcagtg gcactggctg gtttcgctac cgtggcccag | 60 |
| gcggccgagc tccagtctgt cgtgacgcag ccgccctctg tgtctgcggc cccaggacag | 120 |
| agggtcacca tctcctgctc tggaggtagt tccaacattg gaataatta tgtttcctgg | 180 |
| ttccaacaac tcccacgaac agccccaaa ctcctcattt atgacaataa taagcgaccc | 240 |
| tcagggattc ctgaccgatt ctctggctcc aagtctggca cgtcagccgc cctggacatc | 300 |
| accgttctcc agactgggga cgaggccgat tattactgcg gaacttggga tagcagcctg | 360 |
| agaaattggg tgttcggcgg agggaccaag ctgaccgtcc taggt | 405 |

<210> SEQ ID NO 339
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 339

| | |
|---|---|
| atgaaaaaga cagctatcgc gattgcagtg gcactggctg gtttcgctac cgtggcccag | 60 |
| gcggccgagc tccagtctgt cgtgacgcag ccgccctctg tgtctgcggc cccaggacag | 120 |
| agggtcacca tctcctgctc tggaggtagt tccaacattg gaataatta tgtttcctgg | 180 |
| ttccaacaac tcccacgaac agccccaaa ctcctcattt atgacaataa taagcgaccc | 240 |
| tcagggattc ctgaccgatt ctctggctcc aagtctggca cgtcagccgc cctggacatc | 300 |
| accgttctcc agactgggga cgaggccgat tattactgcg gaacttggga tagcagcctg | 360 |
| agaaattggg tgttcggcgg agggaccaag ctgaccgtcc taggttctag aggtggtggt | 420 |
| ggtagcggcg gcggcggctc tggtggtggt ggatccctcg agatggccca gatgcagctg | 480 |
| gtgcagtctg gggctgaggt gaagaagcct ggggcctcag tgaaggtttc ctgcaaggca | 540 |
| tctggataca ccttcaccag ctactatatg cactgggtgc gacaggcccc tggacaaggg | 600 |
| cttgagtgga tgggaataat caaccctagt ggtggtagca caagctacgc acaaaagttc | 660 |
| cagggcagag tcaccatgac cagggacacg tccacgagca cagtctacat ggagctgagc | 720 |
| agcctgagat ctgaggacac ggccgtgtat tactgtgcgc gcggtcagaa ataccattct | 780 |
| cagtactctc gtggtggtac tggtggtggt atgactcagg atatgtgggg tcaaggtact | 840 |
| ctggtgaccg tctcctca | 858 |

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Tyr Thr Phe Ser Arg Tyr Tyr
1               5

<210> SEQ ID NO 341
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 341

Met Asn Pro Asn Ser Gly Asn Thr
1               5

<210> SEQ ID NO 342
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ala Arg Gly Arg Tyr His Val Ile Asp Tyr
1               5                   10

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ser Ser Asp Val Gly Gly Tyr Asn His
1               5

<210> SEQ ID NO 344
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Glu Val Thr
1

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ser Ser Tyr Ala Gly Ser Ala His Trp Val
1               5                   10

<210> SEQ ID NO 346
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr

```
            20                  25                  30
Tyr Ile His Trp Val Arg Gln Ala Pro Gly Gln Gly Leu Glu Trp Met
            35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Arg Tyr His Val Ile Asp Tyr Trp Gly Gln Gly Thr Leu
                100                 105                 110

Val Thr Val Ser Ser
            115

<210> SEQ ID NO 347
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Met Lys Lys Thr Ala Ile Ala Ile Ala Val Ala Leu Ala Gly Phe Ala
 1               5                  10                  15

Thr Val Ala Gln Ala Ala Glu Leu Gln Ser Val Leu Thr Gln Pro Pro
            20                  25                  30

Ser Ala Ser Gly Ser Pro Gly Gln Ser Leu Thr Ile Ser Cys Thr Gly
            35                  40                  45

Thr Ser Ser Asp Val Gly Gly Tyr Asn His Val Ser Trp Tyr Gln Gln
 50                  55                  60

Tyr Pro Gly Lys Ala Pro Lys Leu Met Ile Tyr Glu Val Thr Lys Arg
 65                  70                  75                  80

Pro Ser Gly Val Pro Asp Arg Phe Ser Gly Ser Lys Ser Gly Asn Thr
                85                  90                  95

Ala Ser Leu Thr Val Ser Gly Leu Gln Ala Glu Asp Glu Ala Asp Tyr
                100                 105                 110

Tyr Cys Ser Ser Tyr Ala Gly Ser Ala His Trp Val Phe Gly Gly Gly
                115                 120                 125

Thr Lys Leu Thr Val Leu Gly
            130                 135

<210> SEQ ID NO 348
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Met Lys Lys Thr Ala Ile Ala Ile Ala Val Ala Leu Ala Gly Phe Ala
 1               5                  10                  15

Thr Val Ala Gln Ala Ala Glu Leu Gln Ser Val Leu Thr Gln Pro Pro
            20                  25                  30

Ser Ala Ser Gly Ser Pro Gly Gln Ser Leu Thr Ile Ser Cys Thr Gly
            35                  40                  45

Thr Ser Ser Asp Val Gly Gly Tyr Asn His Val Ser Trp Tyr Gln Gln
```

```
                50                  55                  60
Tyr Pro Gly Lys Ala Pro Lys Leu Met Ile Tyr Glu Val Thr Lys Arg
 65                  70                  75                  80

Pro Ser Gly Val Pro Asp Arg Phe Ser Gly Ser Lys Ser Gly Asn Thr
                 85                  90                  95

Ala Ser Leu Thr Val Ser Gly Leu Gln Ala Glu Asp Glu Ala Asp Tyr
                100                 105                 110

Tyr Cys Ser Ser Tyr Ala Gly Ser Ala His Trp Val Phe Gly Gly Gly
            115                 120                 125

Thr Lys Leu Thr Val Leu Gly Ser Arg Gly Gly Gly Ser Gly Gly
        130                 135                 140

Gly Gly Ser Gly Gly Gly Ser Leu Glu Met Ala Glu Val Gln Leu
145                 150                 155                 160

Val Gln Ser Gly Ala Glu Val Lys Lys Pro Gly Ala Ser Val Lys Val
                165                 170                 175

Ser Cys Lys Ala Ser Gly Tyr Thr Phe Ser Arg Tyr Tyr Ile His Trp
            180                 185                 190

Val Arg Gln Ala Pro Gly Gln Gly Leu Glu Trp Met Gly Trp Met Asn
            195                 200                 205

Pro Asn Ser Gly Asn Thr Gly Tyr Ala Gln Lys Phe Gln Gly Arg Val
            210                 215                 220

Thr Met Thr Arg Asn Thr Ser Ile Ser Thr Ala Tyr Met Glu Leu Ser
225                 230                 235                 240

Ser Leu Arg Ser Glu Asp Thr Ala Val Tyr Tyr Cys Ala Arg Gly Arg
                245                 250                 255

Tyr His Val Ile Asp Tyr Trp Gly Gln Gly Thr Leu Val Thr Val Ser
            260                 265                 270

Ser

<210> SEQ ID NO 349
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 349
gaggtccagc tggtgcagtc tggggctgag gtgaagaagc ctggggcctc agtgaaggtt      60
tcctgcaagg catctggata caccttcagc aggtactata tacactgggt gcgacaggcc     120
cctggacaag ggcttgagtg gatgggatgg atgaaccctca acagtggtaa cacaggctat    180
gcacagaagt tccagggcag agtcaccatg accaggaaca cctccataag cacagcctac    240
atggagctga gcagcctgag atctgaggac acggccgtgt attactgtgc gcgcggtcgt    300
taccatgtta tcgattactg gggtcaaggt actctggtga ccgtctcctc a              351

<210> SEQ ID NO 350
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350
atgaaaaaga cagctatcgc gattgcagtg gcactggctg gtttcgctac cgtggcccag      60
```

-continued

```
gcggccgagc tccagtctgt gttgactcag ccaccctccg cgtccgggtc tcctggacag      120
tcactcacca tctcctgcac tggaaccagc agtgacgttg gtggttataa ccatgtctcc      180
tggtaccaac agtacccagg caaagccccc aaactcatga tttatgaggt cactaagcgg      240
ccctcagggg tccctgatcg cttctctggc tccaagtctg gcaacacggc ctccctgacc      300
gtctctgggc tccaggctga ggatgaggct gattattact gcagctcata tgcaggcagc      360
gcccattggg tgttcggcgg agggaccaag ctgaccgtcc taggt                     405
```

<210> SEQ ID NO 351
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351

```
atgaaaaaga cagctatcgc gattgcagtg gcactggctg gtttcgctac cgtggcccag       60
gcggccgagc tccagtctgt gttgactcag ccaccctccg cgtccgggtc tcctggacag      120
tcactcacca tctcctgcac tggaaccagc agtgacgttg gtggttataa ccatgtctcc      180
tggtaccaac agtacccagg caaagccccc aaactcatga tttatgaggt cactaagcgg      240
ccctcagggg tccctgatcg cttctctggc tccaagtctg gcaacacggc ctccctgacc      300
gtctctgggc tccaggctga ggatgaggct gattattact gcagctcata tgcaggcagc      360
gcccattggg tgttcggcgg agggaccaag ctgaccgtcc taggttctag aggtggtggt      420
ggtagcggcg gcggcggctc tggtggtggt ggatccctcg agatggccga ggtccagctg      480
gtgcagtctg ggctgaggt gaagaagcct ggggcctcag tgaaggtttc ctgcaaggca      540
tctggataca ccttcagcag gtactatata cactgggtgc gacaggcccc tggacaaggg      600
cttgagtgga tgggatggat gaaccctaac agtggtaaca caggctatgc acagaagttc      660
cagggcagag tcaccatgac caggaacacc tccataagca cagcctacat ggagctgagc      720
agcctgagat ctgaggacac ggccgtgtat tactgtgcgc gcggtcgtta ccatgttatc      780
gattactggg gtcaaggtac tctggtgacc gtctcctca                            819
```

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Tyr Thr Phe Asn Thr Tyr Tyr
1               5

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ile Asn Pro Asn Asn Gly Gly Thr
1               5

<210> SEQ ID NO 354
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ala Arg Ser Tyr Asp Tyr
1               5

<210> SEQ ID NO 355
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ser Ser Asn Ile Gly Ser Asn Tyr
1               5

<210> SEQ ID NO 356
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Arg Asn Asn
1

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ala Ala Trp Asp Asp Ser Leu Ser Gly Arg Val
1               5                   10

<210> SEQ ID NO 358
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Gln Leu Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asn Thr Tyr
            20                  25                  30

Tyr Leu His Trp Val Arg Gln Ala Pro Gly Gln Gly Leu Glu Trp Met
        35                  40                  45

Gly Arg Ile Asn Pro Asn Asn Gly Gly Thr Asn Tyr Ala Gln Lys Phe
    50                  55                  60

```
Gln Gly Arg Val Thr Met Thr Arg Asp Thr Ser Ile Asn Thr Ala Tyr
 65                  70                  75                  80

Met Glu Leu Ser Arg Leu Arg Ser Asp Thr Ala Val Tyr Tyr Cys
                 85                  90                  95

Ala Arg Ser Tyr Asp Tyr Trp Gly Gln Gly Thr Leu Val Thr Val Ser
            100                 105                 110

Ser
```

<210> SEQ ID NO 359
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

```
Met Lys Lys Thr Ala Ile Ala Ile Ala Val Ala Leu Ala Gly Phe Ala
 1               5                  10                  15

Thr Val Ala Gln Ala Ala Glu Leu Gln Ala Val Leu Thr Gln Pro Pro
                20                  25                  30

Ser Ala Ser Gly Thr Pro Gly Gln Arg Val Thr Ile Ser Cys Ser Gly
            35                  40                  45

Ser Ser Ser Asn Ile Gly Ser Asn Tyr Val Tyr Trp Tyr Gln Gln Leu
 50                  55                  60

Pro Gly Thr Ala Pro Lys Leu Leu Ile Tyr Arg Asn Asn Gln Arg Pro
 65                  70                  75                  80

Ser Gly Val Pro Asp Arg Phe Ser Gly Ser Lys Ser Gly Thr Ser Ala
                 85                  90                  95

Ser Leu Ala Ile Ser Gly Leu Arg Ser Glu Asp Glu Ala Asp Tyr Tyr
            100                 105                 110

Cys Ala Ala Trp Asp Asp Ser Leu Ser Gly Arg Val Phe Gly Thr Gly
            115                 120                 125

Thr Lys Val Thr Val Leu Gly
            130                 135
```

<210> SEQ ID NO 360
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

```
Met Lys Lys Thr Ala Ile Ala Ile Ala Val Ala Leu Ala Gly Phe Ala
 1               5                  10                  15

Thr Val Ala Gln Ala Ala Glu Leu Gln Ala Val Leu Thr Gln Pro Pro
                20                  25                  30

Ser Ala Ser Gly Thr Pro Gly Gln Arg Val Thr Ile Ser Cys Ser Gly
            35                  40                  45

Ser Ser Ser Asn Ile Gly Ser Asn Tyr Val Tyr Trp Tyr Gln Gln Leu
 50                  55                  60

Pro Gly Thr Ala Pro Lys Leu Leu Ile Tyr Arg Asn Asn Gln Arg Pro
 65                  70                  75                  80

Ser Gly Val Pro Asp Arg Phe Ser Gly Ser Lys Ser Gly Thr Ser Ala
                 85                  90                  95

Ser Leu Ala Ile Ser Gly Leu Arg Ser Glu Asp Glu Ala Asp Tyr Tyr
```

```
            100                 105                 110
Cys Ala Ala Trp Asp Asp Ser Leu Ser Gly Arg Val Phe Gly Thr Gly
            115                 120                 125

Thr Lys Val Thr Val Leu Gly Ser Arg Gly Gly Gly Ser Gly Gly
        130                 135                 140

Gly Gly Ser Gly Gly Gly Ser Leu Glu Met Ala Gln Leu Gln Leu
145                 150                 155                 160

Val Gln Ser Gly Ala Glu Val Lys Lys Pro Gly Ser Ser Val Lys Val
                165                 170                 175

Ser Cys Lys Ala Ser Gly Tyr Thr Phe Asn Thr Tyr Tyr Leu His Trp
            180                 185                 190

Val Arg Gln Ala Pro Gly Gln Gly Leu Glu Trp Met Gly Arg Ile Asn
            195                 200                 205

Pro Asn Asn Gly Gly Thr Asn Tyr Ala Gln Lys Phe Gln Gly Arg Val
            210                 215                 220

Thr Met Thr Arg Asp Thr Ser Ile Asn Thr Ala Tyr Met Glu Leu Ser
225                 230                 235                 240

Arg Leu Arg Ser Asp Asp Thr Ala Val Tyr Tyr Cys Ala Arg Ser Tyr
                245                 250                 255

Asp Tyr Trp Gly Gln Gly Thr Leu Val Thr Val Ser Ser
            260                 265
```

<210> SEQ ID NO 361
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 361

```
cagctgcagc tggtgcaatc tgggcctgag gtgaagaagc ctgggtcctc ggtgaaggtc      60
tcctgcaagg cttctggata caccttcaac acctactatc tgcactgggt acgacaggcc     120
cctggacaag gcttgagtg gatgggacgg atcaaccta caatggtgg cacaaactat        180
gcacagaagt tcagggcag ggtcaccatg accaggaca cgtccatcaa cacagcctac       240
atggagctga gcaggctgag atctgacgac acggccgtgt attactgtgc gcgctcttac     300
gattactggg gtcaaggtac tctggtgacc gtctcctca                            339
```

<210> SEQ ID NO 362
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 362

```
atgaaaaaga cagctatcgc gattgcagtg gcactggctg gtttcgctac cgtggcccag      60
gcggccgagc tccaggctgt gctgactcag ccaccctcag cgtctgggac ccccgggcag     120
agggtcacca tctcttgttc tggaagcagc tccaacatcg aagtaatta tgtatactgg      180
taccagcagc tcccaggaac ggcccccaaa ctcctcatct ataggaataa tcagcggccc     240
tcagggtcc ctgaccgatt ctctggctcc aagtctggca cctcagcctc cctggccatc      300
agtgggctcc ggtccgagga tgaggctgat tattactgtg cagcatggga tgacagcctg     360
agtggtcggg tcttcggaac tgggaccaag gtcaccgtcc taggt                     405
```

<210> SEQ ID NO 363
<211> LENGTH: 807
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 363
atgaaaaaga cagctatcgc gattgcagtg gcactggctg gtttcgctac cgtggcccag      60
gcggccgagc tccaggctgt gctgactcag ccaccctcag cgtctgggac ccccgggcag     120
agggtcacca tctcttgttc tggaagcagc tccaacatcg gaagtaatta tgtatactgg     180
taccagcagc tcccaggaac ggcccccaaa ctcctcatct ataggaataa tcagcggccc     240
tcaggggtcc ctgaccgatt ctctggctcc aagtctggca cctcagcctc cctggccatc     300
agtgggctcc ggtccgagga tgaggctgat tattactgtg cagcatggga tgacagcctg     360
agtggtcggg tcttcggaac tgggaccaag gtcaccgtcc taggttctag aggtggtggt     420
ggtagcggcg gcggcggctc tggtggtggt ggatccctcg agatggccca gctgcagctg     480
gtgcaatctg ggctgaggt gaagaagcct gggtcctcgg tgaaggtctc ctgcaaggct     540
tctggataca ccttcaacac ctactatctg cactgggtac gacaggcccc tggacaaggg     600
cttgagtgga tgggacggat caaccctaac aatggtggca aaactatgc acagaagttt     660 cagggcaggg tcaccatgac cagggacacg tccatcaaca gcctacat ggagctgagc      720 aggctgagat ctgacgacac ggccgtgtat tactgtgcgc gctcttacga ttactggggt     780
caaggtactc tggtgaccgt ctcctca                                         807

<210> SEQ ID NO 364
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 364
ggtggaggtg gatcaggtgg aggtggatct ggtggaggtg gatct                      45

<210> SEQ ID NO 365
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 365

Gly Gly Gly Gly Ser
1               5

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 366

Ser Gly Gly Ser Gly Gly Ser

```
1               5
```

```
<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Gly Gly Gly Ser Gly Gly Gly Ser
1               5

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Gly Gly Gly Ser Gly Gly Gly Gly Ser
1               5                   10

<210> SEQ ID NO 369
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gly Gly Gly Gly Ser Gly Gly Gly Gly Ser Gly Gly Gly Gly Gly Gly
1               5                   10                  15

Gly Ser

<210> SEQ ID NO 370
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Gly Gly Gly Ser Gly Gly Gly Gly Ser Gly Gly Gly Gly Ser Gly
1               5                   10                  15

Gly Gly Gly Ser
            20

<210> SEQ ID NO 371
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 372
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 373
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser
        35

<210> SEQ ID NO 374
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Glu Pro Lys Ser Cys Asp Lys Thr His Thr Cys Pro Pro Cys Pro
1               5                   10                  15

<210> SEQ ID NO 375
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 376
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

-continued

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 377
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Ser Gly Ser Gly Ser
1               5

<210> SEQ ID NO 378
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Ala Ala
1

<210> SEQ ID NO 379
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Thr Ser Gly Gln Ala Gly Gln His His His His His Gly Ala Tyr
1               5                   10                  15

Pro Tyr Asp Val Pro Asp Tyr Ala Ser
            20                  25

<210> SEQ ID NO 380
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
actagtggcc aggccggcca gcaccatcac catcaccatg gcgcataccc gtacgacgtt      60
ccggactacg cttct                                                      75

<210> SEQ ID NO 381
<211> LENGTH: 363
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 381

```
caggtgcagc tggtgcagtc tggggctgag gtgaagaagc ctgggtcctc ggtgaaggtc    60
tcctgcaagg cttctggagg caccttccgc agctatgcta tcacctgggt gcgacaggcc   120
cctggacaag ggcttgagtg gatgggaagg atcatcccta tgcttgatat aacaaactac   180
gcacagaagt tccagggcag agtcacgatt accgcggaca atccacgag cacagcctac   240
atggagctga gcagcctgag atctgaggac acggccgtgt attactgtgc gcgcacttac   300
tctcgttctc cgttccatat ggaagatttc tggggtcaag gtactctggt gaccgtctcc   360
tca                                                                 363
```

<210> SEQ ID NO 382
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Cys Leu Ser Ser Glu Arg Glu Arg Val Glu Asp Leu Phe Glu Tyr Glu
1               5                   10                  15
Cys Glu Leu Leu Thr Ser Glu Pro Ile Phe His Cys Arg Gln Glu Asp
            20                  25                  30
Cys

<210> SEQ ID NO 383
<211> LENGTH: 10
<212> TYPE: PRT
<213> ORGANISM: Homo sapiens

<400> SEQUENCE: 383

Cys Asp Ala Glu Gly Pro Trp Gly Ile Ile
1               5                   10

<210> SEQ ID NO 384
<211> LENGTH: 8
<212> TYPE: PRT
<213> ORGANISM: Homo sapiens

<400> SEQUENCE: 384

Met Phe Val Asn Met Thr Pro Cys
1               5

<210> SEQ ID NO 385
<211> LENGTH: 9
<212> TYPE: PRT
<213> ORGANISM: Homo sapiens

<400> SEQUENCE: 385

Pro Gln Phe Gln Arg Gln Pro Gln Trp
1               5

<210> SEQ ID NO 386
<211> LENGTH: 13
<212> TYPE: PRT
<213> ORGANISM: Homo sapiens

<400> SEQUENCE: 386

-continued

```
Cys Ile Glu Ser Thr Gly Asp Tyr Phe Leu Leu Cys Asp
1               5                   10

<210> SEQ ID NO 387
<211> LENGTH: 11
<212> TYPE: PRT
<213> ORGANISM: Homo sapiens

<400> SEQUENCE: 387

Asn Gln Gln Thr Ala Pro Val Arg Tyr Phe Leu
1               5                   10

<210> SEQ ID NO 388
<211> LENGTH: 8
<212> TYPE: PRT
<213> ORGANISM: Homo sapiens

<400> SEQUENCE: 388

Gly Asp Tyr Phe Leu Leu Cys Asp
1               5

<210> SEQ ID NO 389
<211> LENGTH: 11
<212> TYPE: PRT
<213> ORGANISM: Homo sapiens

<400> SEQUENCE: 389

Met Phe Val Asn Met Thr Pro Cys Gln Leu Asn
1               5                   10

<210> SEQ ID NO 390
<211> LENGTH: 11
<212> TYPE: PRT
<213> ORGANISM: Homo sapiens

<400> SEQUENCE: 390

Gly Asn Pro Gln Phe Gln Arg Gln Pro Gln Trp
1               5                   10

<210> SEQ ID NO 391
<211> LENGTH: 9
<212> TYPE: PRT
<213> ORGANISM: Homo sapiens

<400> SEQUENCE: 391

Leu Cys Asp Ala Glu Gly Pro Trp Gly
1               5

<210> SEQ ID NO 392
<211> LENGTH: 14
<212> TYPE: PRT
<213> ORGANISM: Homo sapiens

<400> SEQUENCE: 392

Gln Phe Gln Arg Gln Pro Gln Trp Asp Asp Pro Val Val Cys
1               5                   10

<210> SEQ ID NO 393
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393
```

```
Cys Met Asp Tyr Asp Phe Lys Val Lys Leu Ser Ser Glu Arg Glu Arg
1               5                   10                  15

Cys Trp Ala Ile Gly Cys Ile Phe Ala Glu Leu Leu Thr Ser Glu Pro
            20                  25                  30

Cys
```

<210> SEQ ID NO 394
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

```
Cys Met Asp Tyr Asp Phe Lys Val Lys Leu Ser Ser Glu Arg Glu Arg
1               5                   10                  15

Cys Cys Ile Phe Ala Glu Leu Leu Thr Ser Glu Pro Ile Phe His Cys
            20                  25                  30

Cys
```

<210> SEQ ID NO 395
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

```
Cys Met Asp Tyr Asp Phe Lys Val Lys Leu Ser Ser Glu Arg Glu Arg
1               5                   10                  15

Cys Glu Leu Leu Thr Ser Glu Pro Ile Phe His Cys Arg Gln Glu Asp
            20                  25                  30

Cys
```

<210> SEQ ID NO 396
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

```
Cys Met Asp Tyr Asp Phe Lys Val Lys Leu Ser Ser Glu Arg Glu Arg
1               5                   10                  15

Cys Ser Glu Pro Ile Phe His Cys Arg Gln Glu Asp Ile Lys Thr Ser
            20                  25                  30

Cys
```

<210> SEQ ID NO 397
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

```
Cys Phe Lys Val Lys Leu Ser Ser Glu Arg Glu Arg Val Glu Asp Leu
1               5                   10                  15
```

Cys Trp Ala Ile Gly Cys Ile Phe Ala Glu Leu Leu Thr Ser Glu Pro
            20                  25                  30

Cys

<210> SEQ ID NO 398
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Cys Phe Lys Val Lys Leu Ser Ser Glu Arg Glu Arg Val Glu Asp Leu
1               5                   10                  15

Cys Cys Ile Phe Ala Glu Leu Leu Thr Ser Glu Pro Ile Phe His Cys
            20                  25                  30

Cys

<210> SEQ ID NO 399
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Cys Phe Lys Val Lys Leu Ser Ser Glu Arg Glu Arg Val Glu Asp Leu
1               5                   10                  15

Cys Glu Leu Leu Thr Ser Glu Pro Ile Phe His Cys Arg Gln Glu Asp
            20                  25                  30

Cys

<210> SEQ ID NO 400
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Cys Phe Lys Val Lys Leu Ser Ser Glu Arg Glu Arg Val Glu Asp Leu
1               5                   10                  15

Cys Ser Glu Pro Ile Phe His Cys Arg Gln Glu Asp Ile Lys Thr Ser
            20                  25                  30

Cys

<210> SEQ ID NO 401
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Cys Leu Ser Ser Glu Arg Glu Arg Val Glu Asp Leu Phe Glu Tyr Glu
1               5                   10                  15

Cys Trp Ala Ile Gly Cys Ile Phe Ala Glu Leu Leu Thr Ser Glu Pro
            20                  25                  30

Cys

<210> SEQ ID NO 402
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Cys Leu Ser Ser Glu Arg Glu Arg Val Glu Asp Leu Phe Glu Tyr Glu
1               5                   10                  15

Cys Cys Ile Phe Ala Glu Leu Leu Thr Ser Glu Pro Ile Phe His Cys
            20                  25                  30

Cys

<210> SEQ ID NO 403
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Cys Leu Ser Ser Glu Arg Glu Arg Val Glu Asp Leu Phe Glu Tyr Glu
1               5                   10                  15

Cys Ser Glu Pro Ile Phe His Cys Arg Gln Glu Asp Ile Lys Thr Ser
            20                  25                  30

Cys

<210> SEQ ID NO 404
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Cys Arg Glu Arg Val Glu Asp Leu Phe Glu Tyr Glu Gly Cys Lys Val
1               5                   10                  15

Cys Trp Ala Ile Gly Cys Ile Phe Ala Glu Leu Leu Thr Ser Glu Pro
            20                  25                  30

Cys

<210> SEQ ID NO 405
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Cys Arg Glu Arg Val Glu Asp Leu Phe Glu Tyr Glu Gly Cys Lys Val
1               5                   10                  15

Cys Cys Ile Phe Ala Glu Leu Leu Thr Ser Glu Pro Ile Phe His Cys
            20                  25                  30

Cys

<210> SEQ ID NO 406
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Cys Arg Glu Arg Val Glu Asp Leu Phe Glu Tyr Glu Gly Cys Lys Val
1               5                   10                  15

Cys Glu Leu Leu Thr Ser Glu Pro Ile Phe His Cys Arg Gln Glu Asp
            20                  25                  30

Cys

<210> SEQ ID NO 407
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Cys Arg Glu Arg Val Glu Asp Leu Phe Glu Tyr Glu Gly Cys Lys Val
1               5                   10                  15

Cys Ser Glu Pro Ile Phe His Cys Arg Gln Glu Asp Ile Lys Thr Ser
            20                  25                  30

Cys

<210> SEQ ID NO 408
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Met Asp Tyr Asp Phe Lys Val Lys Leu Ser Ser Glu Arg Glu Arg
1               5                   10                  15

<210> SEQ ID NO 409
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Phe Lys Val Lys Leu Ser Ser Glu Arg Glu Arg Val Glu Asp Leu
1               5                   10                  15

<210> SEQ ID NO 410
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Leu Ser Ser Glu Arg Glu Arg Val Glu Asp Leu Phe Glu Tyr Glu
1               5                   10                  15

```
<210> SEQ ID NO 411
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Arg Glu Arg Val Glu Asp Leu Phe Glu Tyr Glu Gly Cys Lys Val
1               5                   10                  15

<210> SEQ ID NO 412
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Trp Ala Ile Gly Cys Ile Phe Ala Glu Leu Leu Thr Ser Glu Pro
1               5                   10                  15

<210> SEQ ID NO 413
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Cys Ile Phe Ala Glu Leu Leu Thr Ser Glu Pro Ile Phe His Cys
1               5                   10                  15

<210> SEQ ID NO 414
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Glu Leu Leu Thr Ser Glu Pro Ile Phe His Cys Arg Gln Glu Asp
1               5                   10                  15

<210> SEQ ID NO 415
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Ser Glu Pro Ile Phe His Cys Arg Gln Glu Asp Ile Lys Thr Ser
1               5                   10                  15
```

ANTIBODIES TARGETING G-PROTEIN COUPLED RECEPTOR AND METHODS OF USE

CROSS-REFERENCE TO RELATED APPLICATIONS

This application is a Continuation of International Application Serial No. PCT/US2015/064122, filed Dec. 4, 2015, which claims priority to U.S. Provisional Application Ser. No. 62/088,228, filed Dec. 5, 2014, the contents of each of which are incorporated by reference in their entirety, and to each of which priority is claimed.

SEQUENCE LISTING

The specification further incorporates by reference the Sequence Listing submitted herewith via EFS on Jun. 5, 2017. Pursuant to 37 C.F.R. § 1.52(e)(5), the Sequence Listing text file, identified as 0727340349CON_SL.txt, is 263,773 bytes and was created on Jun. 5, 2017. The Sequence Listing electronically filed herewith, does not extend beyond the scope of the specification and thus does not contain new matter.

FIELD OF THE INVENTION

The presently disclosed subject matter relates to human antibodies that bind to a G-protein coupled receptor (e.g., a G-protein coupled receptor family C group 5 member D (GPRC5D)), and methods of using the same.

BACKGROUND

G protein-coupled receptors, also known as seven-transmembrane domain receptors, 7TM receptors, heptahelical receptors, serpentine receptor, and G protein-linked receptors, constitute a large protein family of receptors that sense molecules outside the cell and activate inside signal transduction pathways and, ultimately, cellular responses. GPCRs can be categorized into six classes based on sequence homology and functional similarity: Class A (Rhodopsin-like), Class B (Secretin receptor family), Class C (Metabotropic glutamate/pheromone), Class D (Fungal mating pheromone receptors), Class E (Cyclic AMP receptors), and Class F (Frizzled/Smoothened).

G-protein coupled receptor family C group 5 member D (GPRC5D) is an orphan receptor with no known ligand or function in humans. It is a member of a family of retinoic acid-inducible G-protein-coupled receptors. It is overexpressed in multiple myeloma (MM) cells and is not expressed or expressed in a significantly lower level by any other cell type, benign or malignant, as shown in FIG. 1. Several groups have identified this gene as highly differentially expressed by gene expression profiling of primary MM cells when compared to normal tissue1 or other hematologic malignancies (Frigyesi, I., et al. Robust isolation of malignant plasma cells in multiple myeloma. Blood 123, 1336-1340 (2014); Cohen, Y., Gutwein, O., Garach-Jehoshua, O., Bar-Haim, A. & Kornberg, A. GPRC5D is a promising marker for monitoring the tumor load and to target multiple myeloma cells. Hematology (Amsterdam, Netherlands) 18, 348-351 (2013); Bam, R., et al. GPRC5D Is a Cell Surface Plasma Cell Marker Whose Expression Is High In Myeloma Cells and Reduced Following Coculture With Osteoclasts. Blood 122, 3099 (2013)). It has been shown that higher mRNA expression correlates with worse overall survival (Atamaniuk, J., et al. Overexpression of G protein-coupled receptor 5D in the bone marrow is associated with poor prognosis in patients with multiple myeloma. *European journal of clinical investigation* 42, 953-960 (2012)). Surface staining of Bone marrow aspirates from patients with MM demonstrate plasma cell specific staining (B am, R., et al. GPRC5D Is a Cell Surface Plasma Cell Marker Whose Expression Is High In Myeloma Cells and Reduced Following Coculture With Osteoclasts. Blood 122, 3099 (2013)). Given the significant role for GPRC5D in multiple myeloma, antibodies that recognize GPRC5D, and methods of using such agents, are desired.

SUMMARY

The presently disclosed subject matter provides human antibodies that bind to a G-protein coupled receptor (e.g., GPRC5D), and methods of using the same.

In certain embodiments, the presently disclosed subject matter provides an isolated antibody, or an antigen-binding fragment thereof, comprising a heavy chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, wherein the antibody or antigen-binding fragment thereof specifically binds to human GPRC5D.

In certain embodiments, the presently disclosed subject matter provides an isolated antibody, or an antigen-binding fragment thereof, comprising a light chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, wherein the antibody or antigen-binding fragment thereof specifically binds to human GPRC5D.

In certain embodiments, the presently disclosed subject matter provides an isolated antibody, or an antigen-binding fragment thereof, comprising (a) a heavy chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and (b) a light chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, wherein the antibody or antigen-binding fragment thereof specifically binds to human GPRC5D.

In certain embodiments, the presently disclosed subject matter provides an isolated antibody, or an antigen-binding fragment thereof, comprising a heavy chain variable region and a light chain variable region, wherein the heavy chain variable region and the light chain variable region are selected from the group consisting of: (i) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:1, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:2; (ii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:5, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:6; (iii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:9, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:10; (iv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:13, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:14; (v) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:17, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:18; (vi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:21, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:22; (vii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:25, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:26; (viii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:29, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:30; (ix) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:33, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:34; (x) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:37, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:38; (xi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:41, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:42; (xii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:45, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:46; (xiii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:49, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:50; (xiv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:53, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:54; (xv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:57, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:58; (xvi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:61, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:62; (xvii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:65, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:66; (xviii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:69, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:70; (xix) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:73, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:74; (xx) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:77, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:78; (xxi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:81, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:82; (xxii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:85, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:86; (xxiii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:89, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:90; (xxiv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:93, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:94; (xxv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:274, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:275; (xxvi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:286, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:287; (xxvii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:298, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:299; (xxviii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:310, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:311; (xxix) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:322, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:323; (xxx) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:334, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:335; (xxxi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:346, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:347; or (xxxii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:358, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:359, wherein the antibody or antigen-binding fragment thereof specifically binds to human GPRC5D.

In certain embodiments, the antibody or antigen-binding fragment comprises: (i) a heavy chain variable region comprising amino acids having a sequence set forth in SEQ ID NO:1, and a light chain variable region comprising amino acids having a sequence set forth in SEQ ID NO:2; (ii) a heavy chain variable region comprising amino acids having a sequence set forth in SEQ ID NO:5, and a light chain variable region comprising amino acids having a sequence set forth in SEQ ID NO:6; (iii) a heavy chain variable region comprising amino acids having a sequence set forth in SEQ ID NO:9, and a light chain variable region comprising amino acids having a sequence set forth in SEQ ID NO:10; (iv) a heavy chain variable region comprising amino acids having a sequence set forth in SEQ ID NO:13, and a light chain variable region comprising amino acids having a sequence set forth in SEQ ID NO:14; (v) a heavy chain variable region comprising amino acids having a sequence set forth in SEQ ID NO:17, and a light chain variable region comprising amino acids having a sequence set forth in SEQ ID NO:18; (vi) a heavy chain variable region comprising amino acids having a sequence set forth in SEQ ID NO:21, and a light chain variable region comprising amino acids having a sequence set forth in SEQ ID NO:22; (vii) a heavy chain variable region comprising amino acids having a sequence set forth in SEQ ID NO:25, and a light chain variable region comprising amino acids having a sequence set forth in SEQ ID NO:26; (viii) a heavy chain variable region comprising amino acids having a sequence set forth in SEQ ID NO:29, and a light chain variable region comprising amino acids having a sequence set forth in SEQ ID NO:30; (ix) a heavy chain variable region comprising amino acids having a sequence set forth in SEQ ID NO:33, and a light chain variable region comprising amino acids having a sequence set forth in SEQ ID NO:34; (x) a heavy chain variable region comprising amino acids having a sequence set forth in SEQ ID NO:37, and a light chain variable region comprising amino acids having a sequence set forth in SEQ ID NO:38; (xi) a heavy chain variable region comprising amino acids having a sequence set forth in SEQ ID NO:41, and a light chain variable region comprising amino acids having a sequence set forth in SEQ ID NO:42; (xii) a heavy chain variable region comprising amino acids having a sequence set forth in SEQ ID NO:45, and a light chain variable region comprising amino acids having a sequence set forth in SEQ ID NO:46; (xiii) a heavy chain variable region comprising amino acids having a sequence set forth in SEQ ID NO:49, and a light chain variable region comprising amino acids having a sequence set forth in SEQ ID NO:50; (xiv) a heavy chain variable region comprising amino acids having a sequence set forth in SEQ ID NO:53, and a light chain variable region comprising amino acids having a sequence set forth in SEQ ID NO:54; (xv) a heavy chain variable region comprising amino acids having a sequence set forth in SEQ ID NO:57, and a light chain variable region comprising amino acids having a sequence set forth in SEQ ID NO:58; (xvi) a heavy chain variable region comprising amino acids having a sequence set forth in SEQ ID NO:61, and a light chain variable region comprising amino acids having a sequence set forth in SEQ ID NO:62; (xvii) a heavy chain variable region comprising amino acids having a sequence set forth in SEQ ID NO:65, and a light chain variable region comprising amino acids having a sequence set forth in SEQ ID NO:66; (xviii) a heavy chain variable region comprising amino acids having a sequence set forth in SEQ ID NO:69, and a light chain variable region comprising amino acids having a sequence set forth in SEQ ID NO:70; (xix) a heavy chain variable region comprising amino acids having a sequence set forth in SEQ ID NO:73, and a light chain variable region comprising amino acids having a sequence set forth in SEQ ID NO:74; (xx) a heavy chain variable region comprising amino acids having a sequence set forth in SEQ ID NO:77, and a light chain variable region comprising amino acids having a sequence set forth in SEQ ID NO:78; (xxi) a heavy chain variable region comprising amino acids having a sequence set forth in SEQ ID NO:81, and a light chain variable region comprising amino acids having a sequence set forth in SEQ ID NO:82; (xxii) a heavy chain variable region comprising amino acids having a sequence set forth in SEQ ID NO:85, and a light chain variable region comprising amino acids having a sequence set forth in SEQ ID NO:86; (xxiii) a heavy chain variable region comprising amino acids having a sequence set forth in SEQ ID NO:89, and a light chain variable region comprising amino acids having a sequence set forth in SEQ ID NO:90; (xxiv) a heavy chain variable region comprising amino acids having a sequence set forth in SEQ ID NO:93, and a light chain variable region comprising amino acids having a sequence set forth in SEQ ID NO:94; (xxv) a heavy chain variable region comprising amino acids having a sequence set forth in SEQ ID NO:274, and a light chain variable region comprising amino acids having a set forth in SEQ ID NO:275; (xxvi) a heavy chain variable region comprising amino acids having a sequence set forth in SEQ ID NO:286, and a light chain variable region comprising amino acids having a sequence set forth in SEQ ID NO:287; (xxvii) a heavy chain variable region comprising amino acids having a sequence set forth in SEQ ID NO:298, and a light chain variable region comprising amino acids having a sequence set forth in SEQ ID NO:299; (xxviii) a heavy chain variable region comprising amino acids having a sequence set forth in SEQ ID NO:310, and a light chain variable region comprising amino acids having a sequence set forth in SEQ ID NO:311; (xxix) a heavy chain variable region comprising amino acids having a sequence set forth in SEQ ID NO:322, and a light chain variable region comprising amino acids having a sequence set forth in SEQ ID NO:323; (xxx) a heavy chain variable region comprising amino acids having a sequence set forth in SEQ ID NO:334, and a light chain variable region comprising amino acids having a sequence set forth in SEQ ID NO:335; (xxxi) a heavy chain variable region comprising amino acids having a sequence set forth in SEQ ID NO:346, and a light chain variable region comprising amino acids having a sequence set forth in SEQ ID NO:347; or (xxxii) a heavy chain variable region comprising amino acids having a sequence set forth in SEQ ID NO:358, and a light chain variable region comprising amino acids having a sequence set forth in SEQ ID NO:359.

In certain embodiments, the presently disclosed subject matter provides an isolated antibody, or an antigen-binding fragment thereof, comprising a heavy chain variable region comprising an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, and conservative modifications thereof, wherein the antibody or antigen-binding fragment thereof specifically binds to human GPRC5D.

In certain embodiments, the presently disclosed subject matter provides an isolated antibody, or an antigen-binding fragment thereof, comprising a light chain variable region comprising an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, and conservative modifications thereof, wherein the antibody or antigen-binding fragment thereof specifically binds to human GPRC5D.

In certain embodiments, the presently disclosed subject matter provides an isolated antibody, or an antigen-binding fragment thereof, comprising: a heavy chain variable region comprising an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, and conservative modifications thereof; and a light chain variable region comprising an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, and conservative modifications thereof, wherein the antibody or antigen-binding fragment thereof specifically binds to human GPRC5D.

The presently disclosed subject matter also provides an isolated antibody or antigen-binding fragment thereof comprising a heavy chain variable region that comprises CDR1, CDR2, and CDR3 domains; and a light chain variable region that comprises CDR1, CDR2, and CDR3 domains, wherein the heavy chain variable region and light chain variable region CDR3 domains are selected from the group consisting of:

(i) a heavy chain variable region CDR3 comprising amino acids having the sequence set forth in SEQ ID NO:126 and conservative modifications thereof; and a light chain variable region CDR3 comprising amino acids having the sequence set forth in SEQ ID NO: 129 and conservative modifications thereof;

(ii) a heavy chain variable region CDR3 comprising amino acids having the sequence set forth in SEQ ID NO: 132 and conservative modifications thereof; and a light chain variable region CDR3 comprising amino acids having the sequence set forth in SEQ ID NO: 135 and conservative modifications thereof;

(iii) a heavy chain variable region CDR3 comprising amino acids having the sequence set forth in SEQ ID NO: 138 and conservative modifications thereof; and a light chain variable region CDR3 comprising amino acids having the sequence set forth in SEQ ID NO:141 and conservative modifications thereof;

(iv) a heavy chain variable region CDR3 comprising amino acids having the sequence set forth in SEQ ID NO: 144 and conservative modifications thereof; and a light chain variable region CDR3 comprising amino acids having the sequence set forth in SEQ ID NO: 147 and conservative modifications thereof;

(v) a heavy chain variable region CDR3 comprising amino acids having the sequence set forth in SEQ ID NO:150 and conservative modifications thereof; and a light chain variable region CDR3 comprising amino acids having the sequence set forth in SEQ ID NO:153 and conservative modifications thereof;

(vi) a heavy chain variable region CDR3 comprising amino acids having the sequence set forth in SEQ ID NO: 156 and conservative modifications thereof; and a light chain variable region CDR3 comprising amino acids having the sequence set forth in SEQ ID NO: 159 and conservative modifications thereof;

(vii) a heavy chain variable region CDR3 comprising amino acids having the sequence set forth in SEQ ID NO: 162 and conservative modifications thereof; and a light chain variable region CDR3 comprising amino acids having the sequence set forth in SEQ ID NO: 165 and conservative modifications thereof;

(viii) a heavy chain variable region CDR3 comprising amino acids having the sequence set forth in SEQ ID NO: 168 and conservative modifications thereof; and a light chain variable region CDR3 comprising amino acids having the sequence set forth in SEQ ID NO:171 and conservative modifications thereof;

(ix) a heavy chain variable region CDR3 comprising amino acids having the sequence set forth in SEQ ID NO: 174 and conservative modifications thereof; and a light chain variable region CDR3 comprising amino acids having the sequence set forth in SEQ ID NO: 177 and conservative modifications thereof;

(x) a heavy chain variable region CDR3 comprising amino acids having the sequence set forth in SEQ ID NO:180 and conservative modifications thereof; and a light chain variable region CDR3 comprising amino acids having the sequence set forth in SEQ ID NO:183 and conservative modifications thereof;

(xi) a heavy chain variable region CDR3 comprising amino acids having the sequence set forth in SEQ ID NO: 186 and conservative modifications thereof; and a light chain variable region CDR3 comprising amino acids having the sequence set forth in SEQ ID NO: 189 and conservative modifications thereof;

(xii) a heavy chain variable region CDR3 comprising amino acids having the sequence set forth in SEQ ID NO: 192 and conservative modifications thereof; and a light chain variable region CDR3 comprising amino acids having the sequence set forth in SEQ ID NO:195 and conservative modifications thereof;

(xiii) a heavy chain variable region CDR3 comprising amino acids having the sequence set forth in SEQ ID NO: 198 and conservative modifications thereof; and a light chain variable region CDR3 comprising amino acids having the sequence set forth in SEQ ID NO: 201 and conservative modifications thereof;

(xiv) a heavy chain variable region CDR3 comprising amino acids having the sequence set forth in SEQ ID NO: 204 and conservative modifications thereof; and a light chain variable region CDR3 comprising amino acids having the sequence set forth in SEQ ID NO: 207 and conservative modifications thereof;

(xv) a heavy chain variable region CDR3 comprising amino acids having the sequence set forth in SEQ ID NO: 210 and conservative modifications thereof; and a light chain variable region CDR3 comprising amino acids having the sequence set forth in SEQ ID NO: 213 and conservative modifications thereof;

(xvi) a heavy chain variable region CDR3 comprising amino acids having the sequence set forth in SEQ ID NO: 216 and conservative modifications thereof; and a light chain variable region CDR3 comprising amino acids having the sequence set forth in SEQ ID NO: 219 and conservative modifications thereof;

(xvii) a heavy chain variable region CDR3 comprising amino acids having the sequence set forth in SEQ ID NO:222 and conservative modifications thereof; and a light chain variable region CDR3 comprising amino acids having the sequence set forth in SEQ ID NO:225 and conservative modifications thereof;

(xviii) a heavy chain variable region CDR3 comprising amino acids having the sequence set forth in SEQ ID NO: 228 and conservative modifications thereof; and a light chain variable region CDR3 comprising amino acids having the sequence set forth in SEQ ID NO: 231 and conservative modifications thereof;

(xix) a heavy chain variable region CDR3 comprising amino acids having the sequence set forth in SEQ ID NO: 234 and conservative modifications thereof; and a light chain variable region CDR3 comprising amino acids having the sequence set forth in SEQ ID NO:237 and conservative modifications thereof;

(xx) a heavy chain variable region CDR3 comprising amino acids having the sequence set forth in SEQ ID NO:240 and conservative modifications thereof; and a light chain variable region CDR3 comprising amino acids having the sequence set forth in SEQ ID NO: 243 and conservative modifications thereof;

(xxi) a heavy chain variable region CDR3 comprising amino acids having the sequence set forth in SEQ ID NO: 246 and conservative modifications thereof; and a light chain variable region CDR3 comprising amino acids having the sequence set forth in SEQ ID NO: 249 and conservative modifications thereof;

(xxii) a heavy chain variable region CDR3 comprising amino acids having the sequence set forth in SEQ ID NO: 252 and conservative modifications thereof; and a light chain variable region CDR3 comprising amino acids having the sequence set forth in SEQ ID NO: 255 and conservative modifications thereof;

(xxiii) a heavy chain variable region CDR3 comprising amino acids having the sequence set forth in SEQ ID NO: 258 and conservative modifications thereof; and a light chain variable region CDR3 comprising amino acids having the sequence set forth in SEQ ID NO: 261 and conservative modifications thereof;

(xxiv) a heavy chain variable region CDR3 comprising amino acids having the sequence set forth in SEQ ID NO: 264 and conservative modifications thereof; and a light chain variable region CDR3 comprising amino acids having the sequence set forth in SEQ ID NO: 267 and conservative modifications thereof;

(xxv) a heavy chain variable region CDR3 comprising amino acids having the sequence set forth in SEQ ID NO: 270 and conservative modifications thereof; and a light chain variable region CDR3 comprising amino acids having the sequence set forth in SEQ ID NO: 273 and conservative modifications thereof;

(xxvi) a heavy chain variable region CDR3 comprising amino acids having the sequence set forth in SEQ ID NO: 282 and conservative modifications thereof; and a light chain variable region CDR3 comprising amino acids having the sequence set forth in SEQ ID NO: 285 and conservative modifications thereof;

(xxvii) a heavy chain variable region CDR3 comprising amino acids having the sequence set forth in SEQ ID NO: 294 and conservative modifications thereof; and a light chain variable region CDR3 comprising amino acids having the sequence set forth in SEQ ID NO: 297 and conservative modifications thereof;

(xxviii) a heavy chain variable region CDR3 comprising amino acids having the sequence set forth in SEQ ID NO: 305 and conservative modifications thereof; and a light chain variable region CDR3 comprising amino acids having the sequence set forth in SEQ ID NO: 308 and conservative modifications thereof;

(xxix) a heavy chain variable region CDR3 comprising amino acids having the sequence set forth in SEQ ID NO: 318 and conservative modifications thereof; and a light chain variable region CDR3 comprising amino acids having the sequence set forth in SEQ ID NO: 321 and conservative modifications thereof;

(xxx) a heavy chain variable region CDR3 comprising amino acids having the sequence set forth in SEQ ID NO: 330 and conservative modifications thereof; and a light chain variable region CDR3 comprising amino acids having the sequence set forth in SEQ ID NO: 333 and conservative modifications thereof;

(xxxi) a heavy chain variable region CDR3 comprising amino acids having the sequence set forth in SEQ ID NO: 342 and conservative modifications thereof; and a light chain variable region CDR3 comprising amino acids having the sequence set forth in SEQ ID NO: 345 and conservative modifications thereof; and (xxxii) a heavy chain variable region CDR3 comprising amino acids having the sequence set forth in SEQ ID NO: 354 and conservative modifications thereof; and a light chain variable region CDR3 comprising amino acids having the sequence set forth in SEQ ID NO: 357 and conservative modifications thereof, wherein the antibody or antigen-binding portion thereof specifically binds to GPRC5D.

In certain embodiments, the heavy chain variable region and light chain variable region CDR2 domains the antibody or antigen-binding portion thereof are selected from the group consisting of:

(i) a heavy chain variable region CDR2 comprising amino acids having the sequence set forth in SEQ ID NO:125 and conservative modifications thereof; and a light chain variable region CDR2 comprising amino acids having the sequence set forth in SEQ ID NO: 128 and conservative modifications thereof;

(ii) a heavy chain variable region CDR2 comprising amino acids having the sequence set forth in SEQ ID NO: 131 and conservative modifications thereof; and a light chain variable region CDR2 comprising amino acids having the sequence set forth in SEQ ID NO: 134 and conservative modifications thereof;

(iii) a heavy chain variable region CDR2 comprising amino acids having the sequence set forth in SEQ ID NO: 137 and conservative modifications thereof; and a light chain variable region CDR2 comprising amino acids having the sequence set forth in SEQ ID NO: 140 and conservative modifications thereof;

(iv) a heavy chain variable region CDR2 comprising amino acids having the sequence set forth in SEQ ID NO: 143 and conservative modifications thereof; and a light chain variable region CDR2 comprising amino acids having the sequence set forth in SEQ ID NO: 146 and conservative modifications thereof;

(v) a heavy chain variable region CDR2 comprising amino acids having the sequence set forth in SEQ ID NO: 149 and conservative modifications thereof; and a light chain variable region CDR2 comprising amino acids having the sequence set forth in SEQ ID NO: 152 and conservative modifications thereof;

(vi) a heavy chain variable region CDR2 comprising amino acids having the sequence set forth in SEQ ID NO: 155 and conservative modifications thereof; and a light chain variable region CDR2 comprising amino acids having the sequence set forth in SEQ ID NO: 158 and conservative modifications thereof;

(vii) a heavy chain variable region CDR2 comprising amino acids having the sequence set forth in SEQ ID NO: 161 and conservative modifications thereof; and a light chain variable region CDR2 comprising amino acids having the sequence set forth in SEQ ID NO: 164 and conservative modifications thereof;

(viii) a heavy chain variable region CDR2 comprising amino acids having the sequence set forth in SEQ ID NO: 167 and conservative modifications thereof; and a light chain variable region CDR2 comprising amino acids having the sequence set forth in SEQ ID NO: 170 and conservative modifications thereof;

(ix) a heavy chain variable region CDR2 comprising amino acids having the sequence set forth in SEQ ID NO: 173 and conservative modifications thereof; and a light chain variable region CDR2 comprising amino acids having the sequence set forth in SEQ ID NO: 176 and conservative modifications thereof;

(x) a heavy chain variable region CDR2 comprising amino acids having the sequence set forth in SEQ ID NO:179 and conservative modifications thereof; and a light chain variable region CDR2 comprising amino acids having the sequence set forth in SEQ ID NO:182 and conservative modifications thereof;

(xi) a heavy chain variable region CDR2 comprising amino acids having the sequence set forth in SEQ ID NO: 185 and conservative modifications thereof; and a light chain variable region CDR2 comprising amino acids having the sequence set forth in SEQ ID NO: 188 and conservative modifications thereof;

(xii) a heavy chain variable region CDR2 comprising amino acids having the sequence set forth in SEQ ID NO:191 and conservative modifications thereof; and a light chain variable region CDR2 comprising amino acids having the sequence set forth in SEQ ID NO:194 and conservative modifications thereof;

(xiii) a heavy chain variable region CDR2 comprising amino acids having the sequence set forth in SEQ ID NO:197 and conservative modifications thereof; and a light chain variable region CDR2 comprising amino acids having the sequence set forth in SEQ ID NO:200 and conservative modifications thereof;

(xiv) a heavy chain variable region CDR2 comprising amino acids having the sequence set forth in SEQ ID NO: 203 and conservative modifications thereof; and a light chain variable region CDR2 comprising amino acids having the sequence set forth in SEQ ID NO: 206 and conservative modifications thereof;

(xv) a heavy chain variable region CDR2 comprising amino acids having the sequence set forth in SEQ ID NO: 209 and conservative modifications thereof; and a light chain variable region CDR2 comprising amino acids having the sequence set forth in SEQ ID NO: 212 and conservative modifications thereof;

(xvi) a heavy chain variable region CDR2 comprising amino acids having the sequence set forth in SEQ ID NO: 215 and conservative modifications thereof; and a light chain variable region CDR2 comprising amino acids having the sequence set forth in SEQ ID NO: 218 and conservative modifications thereof;

(xvii) a heavy chain variable region CDR2 comprising amino acids having the sequence set forth in SEQ ID NO: 221 and conservative modifications thereof; and a light chain variable region CDR2 comprising amino acids having the sequence set forth in SEQ ID NO: 224 and conservative modifications thereof;

(xviii) a heavy chain variable region CDR2 comprising amino acids having the sequence set forth in SEQ ID NO: 227 and conservative modifications thereof; and a light chain variable region CDR2 comprising amino acids having the sequence set forth in SEQ ID NO:230 and conservative modifications thereof;

(xix) a heavy chain variable region CDR2 comprising amino acids having the sequence set forth in SEQ ID NO:233 and conservative modifications thereof; and a light chain variable region CDR2 comprising amino acids having the sequence set forth in SEQ ID NO:236 and conservative modifications thereof;

(xx) a heavy chain variable region CDR2 comprising amino acids having the sequence set forth in SEQ ID NO:239 and conservative modifications thereof; and a light chain variable region CDR2 comprising amino acids having the sequence set forth in SEQ ID NO:242 and conservative modifications thereof;

(xxi) a heavy chain variable region CDR2 comprising amino acids having the sequence set forth in SEQ ID NO:245 and conservative modifications thereof; and a light chain variable region CDR2 comprising amino acids having the sequence set forth in SEQ ID NO:248 and conservative modifications thereof;

(xxii) a heavy chain variable region CDR2 comprising amino acids having the sequence set forth in SEQ ID NO:251 and conservative modifications thereof; and a light chain variable region CDR2 comprising amino acids having the sequence set forth in SEQ ID NO:254 and conservative modifications thereof;

(xxiii) a heavy chain variable region CDR2 comprising amino acids having the sequence set forth in SEQ ID NO:257 and conservative modifications thereof; and a light chain variable region CDR2 comprising amino acids having the sequence set forth in SEQ ID NO:260 and conservative modifications thereof;

(xxiv) a heavy chain variable region CDR2 comprising amino acids having the sequence set forth in SEQ ID NO:263 and conservative modifications thereof; and a light chain variable region CDR2 comprising amino acids having the sequence set forth in SEQ ID NO:266 and conservative modifications thereof;

(xxv) a heavy chain variable region CDR2 comprising amino acids having the sequence set forth in SEQ ID NO:269 and conservative modifications thereof; and a light chain variable region CDR2 comprising amino acids having the sequence set forth in SEQ ID NO:272 and conservative modifications thereof;

(xxvi) a heavy chain variable region CDR2 comprising amino acids having the sequence set forth in SEQ ID NO:281 and conservative modifications thereof; and a light chain variable region CDR2 comprising amino acids having the sequence set forth in SEQ ID NO:284 and conservative modifications thereof;

(xxvii) a heavy chain variable region CDR2 comprising amino acids having the sequence set forth in SEQ ID NO:293 and conservative modifications thereof; and a light chain variable region CDR2 comprising amino acids having the sequence set forth in SEQ ID NO:296 and conservative modifications thereof;

(xxviii) a heavy chain variable region CDR2 comprising amino acids having the sequence set forth in SEQ ID NO:304 and conservative modifications thereof; and a light chain variable region CDR2 comprising amino acids having the sequence set forth in SEQ ID NO:307 and conservative modifications thereof;

(xxix) a heavy chain variable region CDR2 comprising amino acids having the sequence set forth in SEQ ID NO:317 and conservative modifications thereof; and a light chain variable region CDR2 comprising amino acids having the sequence set forth in SEQ ID NO:320 and conservative modifications thereof;

(xxx) a heavy chain variable region CDR2 comprising amino acids having the sequence set forth in SEQ ID NO:329 and conservative modifications thereof; and a light chain variable region CDR2 comprising amino acids having the sequence set forth in SEQ ID NO:332 and conservative modifications thereof;

(xxxi) a heavy chain variable region CDR2 comprising amino acids having the sequence set forth in SEQ ID NO:341 and conservative modifications thereof; and a light chain variable region CDR2 comprising amino acids having the sequence set forth in SEQ ID NO:344 and conservative modifications thereof; and (xxxii) a heavy chain variable region CDR2 comprising amino acids having the sequence set forth in SEQ ID NO:353 and conservative modifications thereof; and a light chain variable region CDR2 comprising amino acids having the sequence set forth in SEQ ID NO:356 and conservative modifications thereof, wherein the antibody or antigen-binding portion thereof specifically binds to GPRC5D.

In certain embodiments, the heavy chain variable region and light chain variable region CDR1 domains of the antibody or antigen-binding portion thereof are selected from the group consisting of:

(i) a heavy chain variable region CDR1 comprising amino acids having the sequence set forth in SEQ ID NO:124 and conservative modifications thereof; and a light chain variable region CDR1 comprising amino acids having the sequence set forth in SEQ ID NO: 127 and conservative modifications thereof;

(ii) a heavy chain variable region CDR1 comprising amino acids having the sequence set forth in SEQ ID NO:130 and conservative modifications thereof; and a light chain variable region CDR1 comprising amino acids having the sequence set forth in SEQ ID NO:133 and conservative modifications thereof;

(iii) a heavy chain variable region CDR1 comprising amino acids having the sequence set forth in SEQ ID NO:136 and conservative modifications thereof; and a light chain variable region CDR1 comprising amino acids having the sequence set forth in SEQ ID NO:139 and conservative modifications thereof;

(iv) a heavy chain variable region CDR1 comprising amino acids having the sequence set forth in SEQ ID NO:142 and conservative modifications thereof; and a light chain variable region CDR1 comprising amino acids having the sequence set forth in SEQ ID NO:145 and conservative modifications thereof;

(v) a heavy chain variable region CDR1 comprising amino acids having the sequence set forth in SEQ ID NO:148 and conservative modifications thereof; and a light chain variable region CDR1 comprising amino acids having the sequence set forth in SEQ ID NO:151 and conservative modifications thereof;

(vi) a heavy chain variable region CDR1 comprising amino acids having the sequence set forth in SEQ ID NO:154 and conservative modifications thereof; and a light chain variable region CDR1 comprising amino acids having the sequence set forth in SEQ ID NO:157 and conservative modifications thereof;

(vii) a heavy chain variable region CDR1 comprising amino acids having the sequence set forth in SEQ ID NO:160 and conservative modifications thereof; and a light chain variable region CDR1 comprising amino acids having the sequence set forth in SEQ ID NO:163 and conservative modifications thereof;

(viii) a heavy chain variable region CDR1 comprising amino acids having the sequence set forth in SEQ ID NO:166 and conservative modifications thereof; and a light chain variable region CDR1 comprising amino acids having the sequence set forth in SEQ ID NO:169 and conservative modifications thereof;

(ix) a heavy chain variable region CDR1 comprising amino acids having the sequence set forth in SEQ ID NO:172 and conservative modifications thereof; and a light chain variable region CDR1 comprising amino acids having the sequence set forth in SEQ ID NO:175 and conservative modifications thereof;

(x) a heavy chain variable region CDR1 comprising amino acids having the sequence set forth in SEQ ID NO:178 and conservative modifications thereof; and a light chain variable region CDR1 comprising amino acids having the sequence set forth in SEQ ID NO:181 and conservative modifications thereof;

(xi) a heavy chain variable region CDR1 comprising amino acids having the sequence set forth in SEQ ID NO:184 and conservative modifications thereof; and a light chain variable region CDR1 comprising amino acids having the sequence set forth in SEQ ID NO:187 and conservative modifications thereof;

(xii) a heavy chain variable region CDR1 comprising amino acids having the sequence set forth in SEQ ID NO:190 and conservative modifications thereof; and a light chain variable region CDR1 comprising amino acids having the sequence set forth in SEQ ID NO:193 and conservative modifications thereof;

(xiii) a heavy chain variable region CDR1 comprising amino acids having the sequence set forth in SEQ ID NO:196 and conservative modifications thereof; and a light chain variable region CDR1 comprising amino acids having the sequence set forth in SEQ ID NO:199 and conservative modifications thereof;

(xiv) a heavy chain variable region CDR1 comprising amino acids having the sequence set forth in SEQ ID NO:202 and conservative modifications thereof; and a light chain variable region CDR1 comprising amino acids having the sequence set forth in SEQ ID NO:205 and conservative modifications thereof;

(xv) a heavy chain variable region CDR1 comprising amino acids having the sequence set forth in SEQ ID NO:208 and conservative modifications thereof; and a light chain variable region CDR1 comprising amino acids having the sequence set forth in SEQ ID NO:211 and conservative modifications thereof;

(xvi) a heavy chain variable region CDR1 comprising amino acids having the sequence set forth in SEQ ID NO:214 and conservative modifications thereof; and a light chain variable region CDR1 comprising amino acids having the sequence set forth in SEQ ID NO:217 and conservative modifications thereof;

(xvii) a heavy chain variable region CDR1 comprising amino acids having the sequence set forth in SEQ ID NO:220 and conservative modifications thereof; and a light chain variable region CDR1 comprising amino acids having the sequence set forth in SEQ ID NO:223 and conservative modifications thereof;

(xviii) a heavy chain variable region CDR1 comprising amino acids having the sequence set forth in SEQ ID NO:226 and conservative modifications thereof; and a light chain variable region CDR1 comprising amino acids having the sequence set forth in SEQ ID NO:229 and conservative modifications thereof;

(xix) a heavy chain variable region CDR1 comprising amino acids having the sequence set forth in SEQ ID NO:232 and conservative modifications thereof; and a light chain variable region CDR1 comprising amino acids having the sequence set forth in SEQ ID NO:235 and conservative modifications thereof;

(xx) a heavy chain variable region CDR1 comprising amino acids having the sequence set forth in SEQ ID NO:238 and conservative modifications thereof; and a light chain variable region CDR1 comprising amino acids having the sequence set forth in SEQ ID NO:241 and conservative modifications thereof;

(xxi) a heavy chain variable region CDR1 comprising amino acids having the sequence set forth in SEQ ID NO:244 and conservative modifications thereof; and a light chain variable region CDR1 comprising amino acids having the sequence set forth in SEQ ID NO:247 and conservative modifications thereof;

(xxii) a heavy chain variable region CDR1 comprising amino acids having the sequence set forth in SEQ ID NO:250 and conservative modifications thereof; and a light chain variable region CDR1 comprising amino acids having the sequence set forth in SEQ ID NO:253 and conservative modifications thereof;

(xxiii) a heavy chain variable region CDR1 comprising amino acids having the sequence set forth in SEQ ID NO:256 and conservative modifications thereof; and a light chain variable region CDR1 comprising amino acids having the sequence set forth in SEQ ID NO:259 and conservative modifications thereof;

(xxiv) a heavy chain variable region CDR1 comprising amino acids having the sequence set forth in SEQ ID NO:262 and conservative modifications thereof; and a light chain variable region CDR1 comprising amino acids having the sequence set forth in SEQ ID NO:265 and conservative modifications thereof;

(xxv) a heavy chain variable region CDR1 comprising amino acids having the sequence set forth in SEQ ID NO:268 and conservative modifications thereof; and a light chain variable region CDR1 comprising amino acids having the sequence set forth in SEQ ID NO:271 and conservative modifications thereof;

(xxvi) a heavy chain variable region CDR1 comprising amino acids having the sequence set forth in SEQ ID NO:280 and conservative modifications thereof; and a light chain variable region CDR1 comprising amino acids having the sequence set forth in SEQ ID NO:283 and conservative modifications thereof;

(xxvii) a heavy chain variable region CDR1 comprising amino acids having the sequence set forth in SEQ ID NO:292 and conservative modifications thereof; and a light chain variable region CDR1 comprising amino acids having the sequence set forth in SEQ ID NO:295 and conservative modifications thereof;

(xxviii) a heavy chain variable region CDR1 comprising amino acids having the sequence set forth in SEQ ID NO:303 and conservative modifications thereof; and a light chain variable region CDR1 comprising amino acids having the sequence set forth in SEQ ID NO:306 and conservative modifications thereof;

(xxix) a heavy chain variable region CDR1 comprising amino acids having the sequence set forth in SEQ ID NO:316 and conservative modifications thereof; and a light chain variable region CDR1 comprising amino acids having the sequence set forth in SEQ ID NO:319 and conservative modifications thereof;

(xxx) a heavy chain variable region CDR1 comprising amino acids having the sequence set forth in SEQ ID NO:328 and conservative modifications thereof; and a light chain variable region CDR1 comprising amino acids having the sequence set forth in SEQ ID NO:331 and conservative modifications thereof;

(xxxi) a heavy chain variable region CDR1 comprising amino acids having the sequence set forth in SEQ ID NO:340 and conservative modifications thereof; and a light chain variable region CDR1 comprising amino acids having the sequence set forth in SEQ ID NO:343 and conservative modifications thereof; and (xxxii) a heavy chain variable region CDR1 comprising amino acids having the sequence set forth in SEQ ID NO:352 and conservative modifications thereof; and a light chain variable region CDR1 comprising amino acids having the sequence set forth in SEQ ID NO:355 and conservative modifications thereof, wherein the antibody or antigen-binding portion thereof specifically binds to GPRC5D.

Furthermore, the presently disclosed subject matter provides an isolated antibody, or an antigen-binding portion thereof, comprising:

(i) a heavy chain variable region CDR1 comprising amino acids having the sequence set forth in SEQ ID NO: 124; a heavy chain variable region CDR2 comprising amino acids having the sequence set forth in SEQ ID NO: 125; and a heavy chain variable region CDR3 comprising amino acids having the sequence set forth in SEQ ID NO: 126;

(ii) a heavy chain variable region CDR1 comprising amino acids having the sequence set forth in SEQ ID NO: 130; a heavy chain variable region CDR2 comprising amino acids having the sequence set forth in SEQ ID NO: 131; and a heavy chain variable region CDR3 comprising amino acids having the sequence set forth in SEQ ID NO: 132;

(iii) a heavy chain variable region CDR1 comprising amino acids having the sequence set forth in SEQ ID NO: 136; a heavy chain variable region CDR2 comprising amino acids having the sequence set forth in SEQ ID NO: 137; and a heavy chain variable region CDR3 comprising amino acids having the sequence set forth in SEQ ID NO: 138;

(iv) a heavy chain variable region CDR1 comprising amino acids having the sequence set forth in SEQ ID NO: 142; a heavy chain variable region CDR2 comprising amino acids having the sequence set forth in SEQ ID NO: 143; and a heavy chain variable region CDR3 comprising amino acids having the sequence set forth in SEQ ID NO: 144;

(v) a heavy chain variable region CDR1 comprising amino acids having the sequence set forth in SEQ ID NO: 148; a heavy chain variable region CDR2 comprising amino acids having the sequence set forth in SEQ ID NO: 149; and a heavy chain variable region CDR3 comprising amino acids having the sequence set forth in SEQ ID NO: 150;

(vi) a heavy chain variable region CDR1 comprising amino acids having the sequence set forth in SEQ ID NO: 154; a heavy chain variable region CDR2 comprising amino acids having the sequence set forth in SEQ ID NO: 155; and a heavy chain variable region CDR3 comprising amino acids having the sequence set forth in SEQ ID NO: 156;

(vii) a heavy chain variable region CDR1 comprising amino acids having the sequence set forth in SEQ ID NO: 160; a heavy chain variable region CDR2 comprising amino acids having the sequence set forth in SEQ ID NO: 161; and a heavy chain variable region CDR3 comprising amino acids having the sequence set forth in SEQ ID NO: 162;

(viii) a heavy chain variable region CDR1 comprising amino acids having the sequence set forth in SEQ ID NO: 166; a heavy chain variable region CDR2 comprising amino acids having the sequence set forth in SEQ ID NO: 167; and a heavy chain variable region CDR3 comprising amino acids having the sequence set forth in SEQ ID NO: 168;

(ix) a heavy chain variable region CDR1 comprising amino acids having the sequence set forth in SEQ ID NO: 172; a heavy chain variable region CDR2 comprising amino acids having the sequence set forth in SEQ ID NO: 173; and a heavy chain variable region CDR3 comprising amino acids having the sequence set forth in SEQ ID NO: 174;

(x) a heavy chain variable region CDR1 comprising amino acids having the sequence set forth in SEQ ID NO: 178; a heavy chain variable region CDR2 comprising amino acids having the sequence set forth in SEQ ID NO: 179; and a heavy chain variable region CDR3 comprising amino acids having the sequence set forth in SEQ ID NO: 180;

(xi) a heavy chain variable region CDR1 comprising amino acids having the sequence set forth in SEQ ID NO: 184; a heavy chain variable region CDR2 comprising amino acids having the sequence set forth in SEQ ID NO: 185; and a heavy chain variable region CDR3 comprising amino acids having the sequence set forth in SEQ ID NO: 186;

(xii) a heavy chain variable region CDR1 comprising amino acids having the sequence set forth in SEQ ID NO: 190 a heavy chain variable region CDR2 comprising amino acids having the sequence set forth in SEQ ID NO: 191; and a heavy chain variable region CDR3 comprising amino acids having the sequence set forth in SEQ ID NO: 192;

(xiii) a heavy chain variable region CDR1 comprising amino acids having the sequence set forth in SEQ ID NO: 196; a heavy chain variable region CDR2 comprising amino acids having the sequence set forth in SEQ ID NO: 197; and a heavy chain variable region CDR3 comprising amino acids having the sequence set forth in SEQ ID NO: 198;

(xiv) a heavy chain variable region CDR1 comprising amino acids having the sequence set forth in SEQ ID NO: 202; a heavy chain variable region CDR2 comprising amino acids having the sequence set forth in SEQ ID NO: 203; and a heavy chain variable region CDR3 comprising amino acids having the sequence set forth in SEQ ID NO: 204;

(xv) a heavy chain variable region CDR1 comprising amino acids having the sequence set forth in SEQ ID NO: 208; a heavy chain variable region CDR2 comprising amino acids having the sequence set forth in SEQ ID NO: 209; and a heavy chain variable region CDR3 comprising amino acids having the sequence set forth in SEQ ID NO: 210;

(xvi) a heavy chain variable region CDR1 comprising amino acids having the sequence set forth in SEQ ID NO: 214; a heavy chain variable region CDR2 comprising amino acids having the sequence set forth in SEQ ID NO: 215; and a heavy chain variable region CDR3 comprising amino acids having the sequence set forth in SEQ ID NO: 216;

(xvii) a heavy chain variable region CDR1 comprising amino acids having the sequence set forth in SEQ ID NO: 220; a heavy chain variable region CDR2 comprising amino acids having the sequence set forth in SEQ ID NO: 221; and a heavy chain variable region CDR3 comprising amino acids having the sequence set forth in SEQ ID NO: 222;

(xviii) a heavy chain variable region CDR1 comprising amino acids having the sequence set forth in SEQ ID NO: 226; a heavy chain variable region CDR2 comprising amino acids having the sequence set forth in SEQ ID NO: 227; and a heavy chain variable region CDR3 comprising amino acids having the sequence set forth in SEQ ID NO: 228;

(xix) a heavy chain variable region CDR1 comprising amino acids having the sequence set forth in SEQ ID NO: 232; a heavy chain variable region CDR2 comprising amino acids having the sequence set forth in SEQ ID NO: 233; and a heavy chain variable region CDR3 comprising amino acids having the sequence set forth in SEQ ID NO: 234;

(xx) a heavy chain variable region CDR1 comprising amino acids having the sequence set forth in SEQ ID NO: 238; a heavy chain variable region CDR2 comprising amino acids having the sequence set forth in SEQ ID NO: 239; and a heavy chain variable region CDR3 comprising amino acids having the sequence set forth in SEQ ID NO: 240;

(xxi) a heavy chain variable region CDR1 comprising amino acids having the sequence set forth in SEQ ID NO: 244; a heavy chain variable region CDR2 comprising amino acids having the sequence set forth in SEQ ID NO: 245; and a heavy chain variable region CDR3 comprising amino acids having the sequence set forth in SEQ ID NO: 246;

(xxii) a heavy chain variable region CDR1 comprising amino acids having the sequence set forth in SEQ ID NO: 250; a heavy chain variable region CDR2 comprising amino acids having the sequence set forth in SEQ ID NO: 251; and a heavy chain variable region CDR3 comprising amino acids having the sequence set forth in SEQ ID NO: 252; and (xxiii) a heavy chain variable region CDR1 comprising amino acids having the sequence set forth in SEQ ID NO: 256; a heavy chain variable region CDR2 comprising amino acids having the sequence set forth in SEQ ID NO: 257; and a heavy chain variable region CDR3 comprising amino acids having the sequence set forth in SEQ ID NO: 258;

(xxiv) a heavy chain variable region CDR1 comprising amino acids having the sequence set forth in SEQ ID NO: 262; a heavy chain variable region CDR2 comprising amino acids having the sequence set forth in SEQ ID NO: 263; and a heavy chain variable region CDR3 comprising amino acids having the sequence set forth in SEQ ID NO: 264;

(xxv) a heavy chain variable region CDR1 comprising amino acids having the sequence set forth in SEQ ID NO: 268; a heavy chain variable region CDR2 comprising amino acids having the sequence set forth in SEQ ID NO: 269; and a heavy chain variable region CDR3 comprising amino acids having the sequence set forth in SEQ ID NO: 270;

(xxvi) a heavy chain variable region CDR1 comprising amino acids having the sequence set forth in SEQ ID NO: 280; a heavy chain variable region CDR2 comprising amino acids having the sequence set forth in SEQ ID NO: 281; and a heavy chain variable region CDR3 comprising amino acids having the sequence set forth in SEQ ID NO: 282;

(xxvii) a heavy chain variable region CDR1 comprising amino acids having the sequence set forth in SEQ ID NO: 292; a heavy chain variable region CDR2 comprising amino acids having the sequence set forth in SEQ ID NO: 293; and a heavy chain variable region CDR3 comprising amino acids having the sequence set forth in SEQ ID NO: 294;

(xxviii) a heavy chain variable region CDR1 comprising amino acids having the sequence set forth in SEQ ID NO: 303; a heavy chain variable region CDR2 comprising amino acids having the sequence set forth in SEQ ID NO: 304; and a heavy chain variable region CDR3 comprising amino acids having the sequence set forth in SEQ ID NO: 305;

(xxix) a heavy chain variable region CDR1 comprising amino acids having the sequence set forth in SEQ ID NO: 316; a heavy chain variable region CDR2 comprising amino acids having the sequence set forth in SEQ ID NO: 317; and a heavy chain variable region CDR3 comprising amino acids having the sequence set forth in SEQ ID NO: 318;

(xxx) a heavy chain variable region CDR1 comprising amino acids having the sequence set forth in SEQ ID NO: 328; a heavy chain variable region CDR2 comprising amino acids having the sequence set forth in SEQ ID NO: 329; and a heavy chain variable region CDR3 comprising amino acids having the sequence set forth in SEQ ID NO: 330;

(xxxi) a heavy chain variable region CDR1 comprising amino acids having the sequence set forth in SEQ ID NO: 340; a heavy chain variable region CDR2 comprising amino acids having the sequence set forth in SEQ ID NO: 341; and a heavy chain variable region CDR3 comprising amino acids having the sequence set forth in SEQ ID NO: 342; or (xxxii) a heavy chain variable region CDR1 comprising amino acids having the sequence set forth in SEQ ID NO: 352; a heavy chain variable region CDR2 comprising amino acids having the sequence set forth in SEQ ID NO: 353; and a heavy chain variable region CDR3 comprising amino acids having the sequence set forth in SEQ ID NO: 354;

wherein the antibody or antigen-binding portion thereof specifically binds to GPRC5D.

Additionally, the presently disclosed subject matter provides an isolated antibody, or an antigen-binding portion thereof, comprising:

(i) a light chain variable region CDR1 comprising amino acids having the sequence set forth in SEQ ID NO: 127; a light chain variable region CDR2 comprising amino acids having the sequence set forth in SEQ ID NO:129; and a light chain variable region CDR3 comprising amino acids having the sequence set forth in SEQ ID NO: 130;

(ii) a light chain variable region CDR1 comprising amino acids having the sequence set forth in SEQ ID NO: 133; a light chain variable region CDR2 comprising amino acids having the sequence set forth in SEQ ID NO:134; and a light chain variable region CDR3 comprising SEQ ID NO: 135;

(iii) a light chain variable region CDR1 comprising amino acids having the sequence set forth in SEQ ID NO: 139; a light chain variable region CDR2 comprising amino acids having the sequence set forth in SEQ ID NO:140; and a light chain variable region CDR3 comprising amino acids having the sequence set forth in SEQ ID NO: 141;

(iv) a light chain variable region CDR1 comprising amino acids having the sequence set forth in SEQ ID NO: 145; a light chain variable region CDR2 comprising SEQ ID NO:146; and a light chain variable region CDR3 comprising amino acids having the sequence set forth in SEQ ID NO: 147;

(v) a light chain variable region CDR1 comprising amino acids having the sequence set forth in SEQ ID NO: 151; a light chain variable region CDR2 comprising amino acids having the sequence set forth in SEQ ID NO:152; and a light chain variable region CDR3 comprising amino acids having the sequence set forth in SEQ ID NO: 153;

(vi) a light chain variable region CDR1 comprising amino acids having the sequence set forth in SEQ ID NO: 157; a light chain variable region CDR2 comprising amino acids having the sequence set forth in SEQ ID NO:158; and a light chain variable region CDR3 comprising amino acids having the sequence set forth in SEQ ID NO: 159;

(vii) a light chain variable region CDR1 comprising amino acids having the sequence set forth in SEQ ID NO: 163; a light chain variable region CDR2 comprising amino acids having the sequence set forth in SEQ ID NO:164; and a light chain variable region CDR3 comprising amino acids having the sequence set forth in SEQ ID NO: 165;

(viii) a light chain variable region CDR1 comprising amino acids having the sequence set forth in SEQ ID NO: 169; a light chain variable region CDR2 comprising amino acids having the sequence set forth in SEQ ID NO:170; and a light chain variable region CDR3 comprising SEQ ID NO: 171;

(ix) a light chain variable region CDR1 comprising amino acids having the sequence set forth in SEQ ID NO: 175; a light chain variable region CDR2 comprising amino acids having the sequence set forth in SEQ ID NO:176; and a light chain variable region CDR3 comprising amino acids having the sequence set forth in SEQ ID NO: 177;

(x) a light chain variable region CDR1 comprising amino acids having the sequence set forth in SEQ ID NO: 181; a light chain variable region CDR2 comprising amino acids having the sequence set forth in SEQ ID NO:182; and a light chain variable region CDR3 comprising amino acids having the sequence set forth in SEQ ID NO: 183;

(xi) a light chain variable region CDR1 comprising amino acids having the sequence set forth in SEQ ID NO: 187; a light chain variable region CDR2 comprising amino acids having the sequence set forth in SEQ ID NO:188; and a light chain variable region CDR3 comprising amino acids having the sequence set forth in SEQ ID NO: 189;

(xii) a light chain variable region CDR1 comprising amino acids having the sequence set forth in SEQ ID NO: 193; a light chain variable region CDR2 comprising amino acids having the sequence set forth in SEQ ID NO:194; and a light chain variable region CDR3 comprising amino acids having the sequence set forth in SEQ ID NO: 195;

(xiii) a light chain variable region CDR1 comprising amino acids having the sequence set forth in SEQ ID NO: 199; a light chain variable region CDR2 comprising amino acids having the sequence set forth in SEQ ID NO:200; and a light chain variable region CDR3 comprising amino acids having the sequence set forth in SEQ ID NO: 201;

(xiv) a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207;

(xv) a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213;

(xvi) a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219;

(xvii) a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225;

(xviii) a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231;

(xix) a light chain variable region CDR1 comprising amino acids having the sequence set forth in SEQ ID NO: 235; a light chain variable region CDR2 comprising amino acids having the sequence set forth in SEQ ID NO:236; and a light chain variable region CDR3 comprising amino acids having the sequence set forth in SEQ ID NO: 237;

(xx) a light chain variable region CDR1 comprising amino acids having the sequence set forth in SEQ ID NO: 241; a light chain variable region CDR2 comprising amino acids having the sequence set forth in SEQ ID NO:242; and a light chain variable region CDR3 comprising amino acids having the sequence set forth in SEQ ID NO: 243;

(xxi) a light chain variable region CDR1 comprising amino acids having the sequence set forth in SEQ ID NO: 247; a light chain variable region CDR2 comprising amino acids having the sequence set forth in SEQ ID NO:248; and a light chain variable region CDR3 comprising amino acids having the sequence set forth in SEQ ID NO: 249;

(xxii) a light chain variable region CDR1 comprising amino acids having the sequence set forth in SEQ ID NO: 253; a light chain variable region CDR2 comprising amino acids having the sequence set forth in SEQ ID NO:254; and a light chain variable region CDR3 comprising amino acids having the sequence set forth in SEQ ID NO: 255;

(xxiii) a light chain variable region CDR1 comprising amino acids having the sequence set forth in SEQ ID NO: 259; a light chain variable region CDR2 comprising amino acids having the sequence set forth in SEQ ID NO:250; and a light chain variable region CDR3 comprising amino acids having the sequence set forth in SEQ ID NO: 261; or (xxiv) a light chain variable region CDR1 comprising amino acids having the sequence set forth in SEQ ID NO: 265; a light chain variable region CDR2 comprising amino acids having the sequence set forth in SEQ ID NO:266; and a light chain variable region CDR3 comprising amino acids having the sequence set forth in SEQ ID NO: 267;

(xxv) a light chain variable region CDR1 comprising amino acids having the sequence set forth in SEQ ID NO: 271; a light chain variable region CDR2 comprising amino acids having the sequence set forth in SEQ ID NO:272; and a light chain variable region CDR3 comprising amino acids having the sequence set forth in SEQ ID NO: 273;

(xxvi) a light chain variable region CDR1 comprising amino acids having the sequence set forth in SEQ ID NO: 283; a light chain variable region CDR2 comprising amino acids having the sequence set forth in SEQ ID NO:284; and a light chain variable region CDR3 comprising amino acids having the sequence set forth in SEQ ID NO: 285;

(xxvii) a light chain variable region CDR1 comprising amino acids having the sequence set forth in SEQ ID NO: 295; a light chain variable region CDR2 comprising amino acids having the sequence set forth in SEQ ID NO:296; and a light chain variable region CDR3 comprising amino acids having the sequence set forth in SEQ ID NO: 297;

(xxviii) a light chain variable region CDR1 comprising amino acids having the sequence set forth in SEQ ID NO: 306; a light chain variable region CDR2 comprising amino acids having the sequence set forth in SEQ ID NO:307; and a light chain variable region CDR3 comprising amino acids having the sequence set forth in SEQ ID NO: 308;

(xxix) a light chain variable region CDR1 comprising amino acids having the sequence set forth in SEQ ID NO: 319; a light chain variable region CDR2 comprising amino acids having the sequence set forth in SEQ ID NO:320; and a light chain variable region CDR3 comprising amino acids having the sequence set forth in SEQ ID NO: 321;

(xxx) a light chain variable region CDR1 comprising amino acids having the sequence set forth in SEQ ID NO: 331; a light chain variable region CDR2 comprising amino acids having the sequence set forth in SEQ ID NO:332; and a light chain variable region CDR3 comprising amino acids having the sequence set forth in SEQ ID NO: 333;

(xxxi) a light chain variable region CDR1 comprising amino acids having the sequence set forth in SEQ ID NO: 343; a light chain variable region CDR2 comprising amino acids having the sequence set forth in SEQ ID NO:344; and a light chain variable region CDR3 comprising amino acids having the sequence set forth in SEQ ID NO: 345; or (xxxii) a light chain variable region CDR1 comprising amino acids having the sequence set forth in SEQ ID NO: 355; a light chain variable region CDR2 comprising amino acids having the sequence set forth in SEQ ID NO:356; and a light chain variable region CDR3 comprising amino acids having the sequence set forth in SEQ ID NO: 357, wherein the antibody or antigen-binding portion thereof specifically binds to GPRC5D.

The presently disclosed subject matter also provides an isolated antibody, or an antigen-binding portion thereof, comprising:

(i) a heavy chain variable region CDR1 comprising amino acids having the sequence set forth in SEQ ID NO: 124; a heavy chain variable region CDR2 comprising amino acids having the sequence set forth in SEQ ID NO: 125; a heavy chain variable region CDR3 comprising amino acids having the sequence set forth in SEQ ID NO: 126; a light chain variable region CDR1 comprising amino acids having the sequence set forth in SEQ ID NO: 127; a light chain variable region CDR2 comprising amino acids having the sequence set forth in SEQ ID NO:128; and a light chain variable region CDR3 comprising amino acids having the sequence set forth in SEQ ID NO: 129;

(ii) a heavy chain variable region CDR1 comprising amino acids having the sequence set forth in SEQ ID NO: 130; a heavy chain variable region CDR2 comprising amino acids having the sequence set forth in SEQ ID NO: 131; a heavy chain variable region CDR3 comprising amino acids having the sequence set forth in SEQ ID NO: 132; a light chain variable region CDR1 comprising amino acids having the sequence set forth in SEQ ID NO: 133; a light chain variable region CDR2 comprising amino acids having the sequence set forth in SEQ ID NO:134; and a light chain variable region CDR3 comprising amino acids having the sequence set forth in SEQ ID NO: 135;

(iii) a heavy chain variable region CDR1 comprising amino acids having the sequence set forth in SEQ ID NO: 136; a heavy chain variable region CDR2 comprising amino acids having the sequence set forth in SEQ ID NO: 137; a heavy chain variable region CDR3 comprising amino acids having the sequence set forth in SEQ ID NO: 138; a light chain variable region CDR1 comprising amino acids having the sequence set forth in SEQ ID NO: 139; a light chain variable region CDR2 comprising amino acids having the sequence set forth in SEQ ID NO:140; and a light chain variable region CDR3 comprising amino acids having the sequence set forth in SEQ ID NO: 141;

(iv) a heavy chain variable region CDR1 comprising amino acids having the sequence set forth in SEQ ID NO: 142; a heavy chain variable region CDR2 comprising amino acids having the sequence set forth in SEQ ID NO: 143; a heavy chain variable region CDR3 comprising amino acids having the sequence set forth in SEQ ID NO: 144; a light chain variable region CDR1 comprising amino acids having the sequence set forth in SEQ ID NO: 145; a light chain variable region CDR2 comprising amino acids having the sequence set forth in SEQ ID NO:146; and a light chain variable region CDR3 comprising amino acids having the sequence set forth in SEQ ID NO: 147;

(v) a heavy chain variable region CDR1 comprising amino acids having the sequence set forth in SEQ ID NO: 148; a heavy chain variable region CDR2 comprising amino acids having the sequence set forth in SEQ ID NO: 149; a heavy chain variable region CDR3 comprising amino acids having the sequence set forth in SEQ ID NO: 150; a light chain variable region CDR1 comprising amino acids having the sequence set forth in SEQ ID NO: 151; a light chain variable region CDR2 comprising amino acids having the sequence set forth in SEQ ID NO:152; and a light chain variable region CDR3 comprising amino acids having the sequence set forth in SEQ ID NO: 153;

(vi) a heavy chain variable region CDR1 comprising amino acids having the sequence set forth in SEQ ID NO: 154; a heavy chain variable region CDR2 comprising amino acids having the sequence set forth in SEQ ID NO: 155; a heavy chain variable region CDR3 comprising amino acids having the sequence set forth in SEQ ID NO: 156; a light chain variable region CDR1 comprising amino acids having the sequence set forth in SEQ ID NO: 157; a light chain variable region CDR2 comprising amino acids having the sequence set forth in SEQ ID NO:158; and a light chain variable region CDR3 comprising amino acids having the sequence set forth in SEQ ID NO: 159;

(vii) a heavy chain variable region CDR1 comprising amino acids having the sequence set forth in SEQ ID NO: 160; a heavy chain variable region CDR2 comprising amino acids having the sequence set forth in SEQ ID NO: 161; a heavy chain variable region CDR3 comprising amino acids having the sequence set forth in SEQ ID NO: 162; a light chain variable region CDR1 comprising amino acids having the sequence set forth in SEQ ID NO: 163; a light chain variable region CDR2 comprising amino acids having the sequence set forth in SEQ ID NO:164; and a light chain variable region CDR3 comprising amino acids having the sequence set forth in SEQ ID NO: 165;

(viii) a heavy chain variable region CDR1 comprising amino acids having the sequence set forth in SEQ ID NO: 166; a heavy chain variable region CDR2 comprising amino acids having the sequence set forth in SEQ ID NO: 167; a heavy chain variable region CDR3 comprising amino acids having the sequence set forth in SEQ ID NO: 168; a light chain variable region CDR1 comprising amino acids having the sequence set forth in SEQ ID NO: 169; a light chain variable region CDR2 comprising amino acids having the sequence set forth in SEQ ID NO:170; and a light chain variable region CDR3 comprising amino acids having the sequence set forth in SEQ ID NO: 171;

(ix) a heavy chain variable region CDR1 comprising amino acids having the sequence set forth in SEQ ID NO: 172; a heavy chain variable region CDR2 comprising amino acids having the sequence set forth in SEQ ID NO: 173; a heavy chain variable region CDR3 comprising amino acids having the sequence set forth in SEQ ID NO: 174; a light chain variable region CDR1 comprising amino acids having the sequence set forth in SEQ ID NO: 175; a light chain variable region CDR2 comprising amino acids having the sequence set forth in SEQ ID NO:176; and a light chain variable region CDR3 comprising amino acids having the sequence set forth in SEQ ID NO: 177;

(x) a heavy chain variable region CDR1 comprising amino acids having the sequence set forth in SEQ ID NO: 178; a heavy chain variable region CDR2 comprising amino acids having the sequence set forth in SEQ ID NO: 179; a heavy chain variable region CDR3 comprising amino acids having the sequence set forth in SEQ ID NO: 180; a light chain variable region CDR1 comprising amino acids having the sequence set forth in SEQ ID NO: 181; a light chain variable region CDR2 comprising amino acids having the sequence set forth in SEQ ID NO:182; and a light chain variable region CDR3 comprising amino acids having the sequence set forth in SEQ ID NO: 183;

(xi) a heavy chain variable region CDR1 comprising amino acids having the sequence set forth in SEQ ID NO: 184; a heavy chain variable region CDR2 comprising amino acids having the sequence set forth in SEQ ID NO: 185; a heavy chain variable region CDR3 comprising amino acids having the sequence set forth in SEQ ID NO: 186; a light chain variable region CDR1 comprising amino acids having the sequence set forth in SEQ ID NO: 187; a light chain variable region CDR2 comprising amino acids having the sequence set forth in SEQ ID NO:188; and a light chain variable region CDR3 comprising amino acids having the sequence set forth in SEQ ID NO: 189;

(xii) a heavy chain variable region CDR1 comprising amino acids having the sequence set forth in SEQ ID NO: 190; a heavy chain variable region CDR2 comprising amino acids having the sequence set forth in SEQ ID NO: 191; a heavy chain variable region CDR3 comprising amino acids having the sequence set forth in SEQ ID NO: 192; a light chain variable region CDR1 comprising amino acids having the sequence set forth in SEQ ID NO: 193; a light chain variable region CDR2 comprising amino acids having the sequence set forth in SEQ ID NO:194; and a light chain variable region CDR3 comprising amino acids having the sequence set forth in SEQ ID NO: 195;

(xiii) a heavy chain variable region CDR1 comprising amino acids having the sequence set forth in SEQ ID NO: 196; a heavy chain variable region CDR2 comprising amino acids having the sequence set forth in SEQ ID NO: 197; a heavy chain variable region CDR3 comprising amino acids having the sequence set forth in SEQ ID NO: 198; a light chain variable region CDR1 comprising amino acids having the sequence set forth in SEQ ID NO: 199; a light chain variable region CDR2 comprising amino acids having the sequence set forth in SEQ ID NO:200; and a light chain variable region CDR3 comprising amino acids having the sequence set forth in SEQ ID NO: 201;

(xiv) a heavy chain variable region CDR1 comprising amino acids having the sequence set forth in SEQ ID NO: 202; a heavy chain variable region CDR2 comprising amino acids having the sequence set forth in SEQ ID NO: 203; a heavy chain variable region CDR3 comprising amino acids having the sequence set forth in SEQ ID NO: 204; a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207;

(xv) a heavy chain variable region CDR1 comprising amino acids having the sequence set forth in SEQ ID NO: 208; a heavy chain variable region CDR2 comprising amino acids having the sequence set forth in SEQ ID NO: 209; a heavy chain variable region CDR3 comprising amino acids having the sequence set forth in SEQ ID NO: 210; a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213;

(xvi) a heavy chain variable region CDR1 comprising amino acids having the sequence set forth in SEQ ID NO: 214; a heavy chain variable region CDR2 comprising amino acids having the sequence set forth in SEQ ID NO: 215; a heavy chain variable region CDR3 comprising amino acids having the sequence set forth in SEQ ID NO: 216; a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219;

(xvii) a heavy chain variable region CDR1 comprising amino acids having the sequence set forth in SEQ ID NO: 220; a heavy chain variable region CDR2 comprising amino acids having the sequence set forth in SEQ ID NO: 221; a heavy chain variable region CDR3 comprising amino acids having the sequence set forth in SEQ ID NO: 222; a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225;

(xviii) a heavy chain variable region CDR1 comprising amino acids having the sequence set forth in SEQ ID NO: 226; a heavy chain variable region CDR2 comprising amino acids having the sequence set forth in SEQ ID NO: 227; a heavy chain variable region CDR3 comprising amino acids having the sequence set forth in SEQ ID NO: 228; a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231;

(xix) a heavy chain variable region CDR1 comprising amino acids having the sequence set forth in SEQ ID NO: 232; a heavy chain variable region CDR2 comprising amino acids having the sequence set forth in SEQ ID NO: 233; a heavy chain variable region CDR3 comprising amino acids having the sequence set forth in SEQ ID NO: 234; a light chain variable region CDR1 comprising amino acids having the sequence set forth in SEQ ID NO: 235; a light chain variable region CDR2 comprising amino acids having the sequence set forth in SEQ ID NO:236; and a light chain variable region CDR3 comprising amino acids having the sequence set forth in SEQ ID NO: 237;

(xx) a heavy chain variable region CDR1 comprising amino acids having the sequence set forth in SEQ ID NO: 238; a heavy chain variable region CDR2 comprising amino acids having the sequence set forth in SEQ ID NO: 239; a heavy chain variable region CDR3 comprising amino acids having the sequence set forth in SEQ ID NO: 240; a light chain variable region CDR1 comprising amino acids having the sequence set forth in SEQ ID NO: 241; a light chain variable region CDR2 comprising amino acids having the sequence set forth in SEQ ID NO:242; and a light chain variable region CDR3 comprising amino acids having the sequence set forth in SEQ ID NO: 243;

(xxi) a heavy chain variable region CDR1 comprising amino acids having the sequence set forth in SEQ ID NO: 244; a heavy chain variable region CDR2 comprising amino acids having the sequence set forth in SEQ ID NO: 245; a heavy chain variable region CDR3 comprising amino acids having the sequence set forth in SEQ ID NO: 246; a light chain variable region CDR1 comprising amino acids having the sequence set forth in SEQ ID NO: 247; a light chain variable region CDR2 comprising amino acids having the sequence set forth in SEQ ID NO:248; and a light chain variable region CDR3 comprising amino acids having the sequence set forth in SEQ ID NO: 249;

(xxii) a heavy chain variable region CDR1 comprising amino acids having the sequence set forth in SEQ ID NO: 250; a heavy chain variable region CDR2 comprising amino acids having the sequence set forth in SEQ ID NO: 251; a heavy chain variable region CDR3 comprising amino acids having the sequence set forth in SEQ ID NO: 252; a light chain variable region CDR1 comprising amino acids having the sequence set forth in SEQ ID NO: 253; a light chain variable region CDR2 comprising amino acids having the sequence set forth in SEQ ID NO:254; and a light chain variable region CDR3 comprising amino acids having the sequence set forth in SEQ ID NO: 255;

(xxiii) a heavy chain variable region CDR1 comprising amino acids having the sequence set forth in SEQ ID NO: 256; a heavy chain variable region CDR2 comprising amino acids having the sequence set forth in SEQ ID NO: 257; a heavy chain variable region CDR3 comprising amino acids having the sequence set forth in SEQ ID NO: 258; a light chain variable region CDR1 comprising amino acids having the sequence set forth in SEQ ID NO: 259; a light chain variable region CDR2 comprising amino acids having the sequence set forth in SEQ ID NO:260; and a light chain variable region CDR3 comprising amino acids having the sequence set forth in SEQ ID NO: 261;

(xxiv) a heavy chain variable region CDR1 comprising amino acids having the sequence set forth in SEQ ID NO: 262; a heavy chain variable region CDR2 comprising amino acids having the sequence set forth in SEQ ID NO: 263; a heavy chain variable region CDR3 comprising amino acids having the sequence set forth in SEQ ID NO: 264; a light chain variable region CDR1 comprising amino acids having the sequence set forth in SEQ ID NO: 265; a light chain variable region CDR2 comprising amino acids having the sequence set forth in SEQ ID NO:266; and a light chain variable region CDR3 comprising amino acids having the sequence set forth in SEQ ID NO: 267;

(xxv) a heavy chain variable region CDR1 comprising amino acids having the sequence set forth in SEQ ID NO: 268; a heavy chain variable region CDR2 comprising amino acids having the sequence set forth in SEQ ID NO: 269; a heavy chain variable region CDR3 comprising amino acids having the sequence set forth in SEQ ID NO: 270; a light chain variable region CDR1 comprising amino acids having the sequence set forth in SEQ ID NO: 271; a light chain variable region CDR2 comprising amino acids having the sequence set forth in SEQ ID NO:272; and (vi) a light chain variable region CDR3 comprising amino acids having the sequence set forth in SEQ ID NO: 273;

(xxvi) a heavy chain variable region CDR1 comprising amino acids having the sequence set forth in SEQ ID NO: 280; a heavy chain variable region CDR2 comprising amino acids having the sequence set forth in SEQ ID NO: 281; a heavy chain variable region CDR3 comprising amino acids having the sequence set forth in SEQ ID NO: 282; a light chain variable region CDR1 comprising amino acids having the sequence set forth in SEQ ID NO: 283; a light chain variable region CDR2 comprising amino acids having the sequence set forth in SEQ ID NO:284; and a light chain variable region CDR3 comprising amino acids having the sequence set forth in SEQ ID NO: 285;

(xxvii) a heavy chain variable region CDR1 comprising amino acids having the sequence set forth in SEQ ID NO: 292; a heavy chain variable region CDR2 comprising amino acids having the sequence set forth in SEQ ID NO: 293; a heavy chain variable region CDR3 comprising amino acids having the sequence set forth in SEQ ID NO: 294; a light chain variable region CDR1 comprising amino acids having the sequence set forth in SEQ ID NO: 295; a light chain variable region CDR2 comprising amino acids having the sequence set forth in SEQ ID NO:296; and a light chain variable region CDR3 comprising amino acids having the sequence set forth in SEQ ID NO: 297;

(xxviii) a heavy chain variable region CDR1 comprising amino acids having the sequence set forth in SEQ ID NO: 303; a heavy chain variable region CDR2 comprising amino acids having the sequence set forth in SEQ ID NO: 304; a heavy chain variable region CDR3 comprising amino acids having the sequence set forth in SEQ ID NO: 305; a light chain variable region CDR1 comprising amino acids having the sequence set forth in SEQ ID NO: 306; a light chain variable region CDR2 comprising amino acids having the sequence set forth in SEQ ID NO: 307; and a light chain variable region CDR3 comprising amino acids having the sequence set forth in SEQ ID NO: 308;

(xxix) a heavy chain variable region CDR1 comprising amino acids having the sequence set forth in SEQ ID NO: 316; a heavy chain variable region CDR2 comprising amino acids having the sequence set forth in SEQ ID NO: 317; a heavy chain variable region CDR3 comprising amino acids having the sequence set forth in SEQ ID NO: 318; a light chain variable region CDR1 comprising amino acids having the sequence set forth in SEQ ID NO: 319; a light chain variable region CDR2 comprising amino acids having the sequence set forth in SEQ ID NO: 320; and a light chain variable region CDR3 comprising amino acids having the sequence set forth in SEQ ID NO: 321;

(xxx) a heavy chain variable region CDR1 comprising amino acids having the sequence set forth in SEQ ID NO: 328; a heavy chain variable region CDR2 comprising amino acids having the sequence set forth in SEQ ID NO: 329; a heavy chain variable region CDR3 comprising amino acids having the sequence set forth in SEQ ID NO: 330; a light chain variable region CDR1 comprising amino acids having the sequence set forth in SEQ ID NO: 331; a light chain variable region CDR2 comprising amino acids having the sequence set forth in SEQ ID NO: 332; and a light chain variable region CDR3 comprising amino acids having the sequence set forth in SEQ ID NO: 333;

(xxxi) a heavy chain variable region CDR1 comprising amino acids having the sequence set forth in SEQ ID NO: 340; a heavy chain variable region CDR2 comprising amino acids having the sequence set forth in SEQ ID NO: 341; a heavy chain variable region CDR3 comprising amino acids having the sequence set forth in SEQ ID NO: 342; a light chain variable region CDR1 comprising amino acids having the sequence set forth in SEQ ID NO: 343; a light chain variable region CDR2 comprising amino acids having the sequence set forth in SEQ ID NO: 344; and a light chain variable region CDR3 comprising amino acids having the sequence set forth in SEQ ID NO: 345; or (xxxii) a heavy chain variable region CDR1 comprising amino acids having the sequence set forth in SEQ ID NO: 352; a heavy chain variable region CDR2 comprising amino acids having the sequence set forth in SEQ ID NO: 353; a heavy chain variable region CDR3 comprising amino acids having the sequence set forth in SEQ ID NO: 354; a light chain variable region CDR1 comprising amino acids having the sequence set forth in SEQ ID NO: 355; a light chain variable region CDR2 comprising amino acids having the sequence set forth in SEQ ID NO: 356; and a light chain variable region CDR3 comprising amino acids having the sequence set forth in SEQ ID NO: 357.

Furthermore, the presently disclosed subject matter provides an isolated antibody, or an antigen-binding portion thereof, which cross-competes for binding to human GPRC5D with any of the disclosed antibodies. In certain embodiments, the presently disclosed subject matter provides an isolated antibody, or an antigen-binding portion thereof, which binds to the same epitope on human GPRC5D with an isolated antibody, or an antigen-binding portion thereof of any of the antibodies disclosed herein.

In certain embodiments, the presently disclosed subject matter provides an isolated antibody, or an antigen-binding portion thereof, which cross-competes for binding to human GPRC5D with a reference antibody or reference antigen-binding portion thereof comprising: (i) a heavy chain variable region comprising amino acids having a sequence set forth in SEQ ID NO:1, and a light chain variable region comprising amino acids having a sequence set forth in SEQ ID NO:2; (ii) a heavy chain variable region comprising amino acids having a sequence set forth in SEQ ID NO:5, and a light chain variable region comprising amino acids having a sequence set forth in SEQ ID NO:6; (iii) a heavy chain variable region comprising amino acids having a sequence set forth in SEQ ID NO:9, and a light chain variable region comprising amino acids having a sequence set forth in SEQ ID NO:10; (iv) a heavy chain variable region comprising amino acids having a sequence set forth in SEQ ID NO:13, and a light chain variable region comprising amino acids having a sequence set forth in SEQ ID NO:14; (v) a heavy chain variable region comprising amino acids having a sequence set forth in SEQ ID NO:17, and a light chain variable region comprising amino acids having a sequence set forth in SEQ ID NO:18; (vi) a heavy chain variable region comprising amino acids having a sequence set forth in SEQ ID NO:21, and a light chain variable region comprising amino acids having a sequence set forth in SEQ ID NO:22; (vii) a heavy chain variable region comprising amino acids having a sequence set forth in SEQ ID NO:25, and a light chain variable region comprising amino acids having a sequence set forth in SEQ ID NO:26; (viii) a heavy chain variable region comprising amino acids having a sequence set forth in SEQ ID NO:29, and a light chain variable region comprising amino acids having a sequence set forth in SEQ ID NO:30; (ix) a heavy chain variable region comprising amino acids having a sequence set forth in SEQ ID NO:33, and a light chain variable region comprising amino acids having a sequence set forth in SEQ ID NO:34; (x) a heavy chain variable region comprising amino acids having a sequence set forth in SEQ ID NO:37, and a light chain variable region comprising amino acids having a sequence set forth in SEQ ID NO:38; (xi) a heavy chain variable region comprising amino acids having a sequence set forth in SEQ ID NO:41, and a light chain variable region comprising amino acids having a sequence set forth in SEQ ID NO:42; (xii) a heavy chain variable region comprising amino acids having a sequence set forth in SEQ ID NO:45, and a light chain variable region comprising amino acids having a sequence set forth in SEQ ID NO:46; (xiii) a heavy chain variable region comprising amino acids having a sequence set forth in SEQ ID NO:49, and a light chain variable region comprising amino acids having a sequence set forth in SEQ ID NO:50; (xiv) a heavy chain variable region comprising amino acids having a sequence set forth in SEQ ID NO:53, and a light chain variable region comprising amino acids having a sequence set forth in SEQ ID NO:54; (xv) a heavy chain variable region comprising amino acids having a sequence set forth in SEQ ID NO:57, and a light chain variable region comprising amino acids having a sequence set forth in SEQ ID NO:58; (xvi) a heavy chain variable region comprising amino acids having a sequence set forth in SEQ ID NO:61, and a light chain variable region comprising amino acids having a sequence set forth in SEQ ID NO:62; (xvii) a heavy chain variable region comprising amino acids having a sequence set forth in SEQ ID NO:65, and a light chain variable region comprising amino acids having a sequence set forth in SEQ ID NO:66; (xviii) a heavy chain variable region comprising amino acids having a sequence set forth in SEQ ID NO:69, and a light chain variable region comprising amino acids having a sequence set forth in SEQ ID NO:70; (xix) a heavy chain variable region comprising amino acids having a sequence set forth in SEQ ID NO:73, and a light chain variable region comprising amino acids having a sequence set forth in SEQ ID NO:74; (xx) a heavy chain variable region comprising amino acids having a sequence set forth in SEQ ID NO:77, and a light chain variable region comprising amino acids having a sequence set forth in SEQ ID NO:78; (xxi) a heavy chain variable region comprising amino acids having a sequence set forth in SEQ ID NO:81, and a light chain variable region comprising amino acids having a sequence set forth in SEQ ID NO:82; (xxii) a heavy chain variable region comprising amino acids having a sequence set forth in SEQ ID NO:85, and a light chain variable region comprising amino acids having a sequence set forth in SEQ ID NO:86; (xxiii) a heavy chain variable region comprising amino acids having a sequence set forth in SEQ ID NO:89, and a light chain variable region comprising amino acids having a sequence set forth in SEQ ID NO:90; (xxiv) a heavy chain variable region comprising amino acids having a sequence set forth in SEQ ID NO:93, and a light chain variable region comprising amino acids having a sequence set forth in SEQ ID NO:94; (xxv) a heavy chain variable region comprising amino acids having a sequence set forth in SEQ ID NO:274, and a light chain variable region comprising amino acids having a sequence set forth in SEQ ID NO:275; (xxvi) a heavy chain variable region comprising amino acids having a sequence set forth in SEQ ID NO:286, and a light chain variable region comprising amino acids having a sequence set forth in SEQ ID NO:287; (xxvii) a heavy chain variable region comprising amino acids having a sequence set forth in SEQ ID NO:298, and a light chain variable region comprising amino acids having a sequence set forth in SEQ ID NO:299; (xviii) a heavy chain variable region comprising amino acids having a sequence set forth in SEQ ID NO:310, and a light chain variable region comprising amino acids having a sequence set forth in SEQ ID NO:311; (xxi) a heavy chain variable region comprising amino acids having a sequence set forth in SEQ ID NO:322, and a light chain variable region comprising amino acids having a sequence set forth in SEQ ID NO:323; (xx) a heavy chain variable region comprising amino acids having a sequence set forth in SEQ ID NO:334, and a light chain variable region comprising amino acids having a sequence set forth in SEQ ID NO:335; (xxi) a heavy chain variable region comprising amino acids having a sequence set forth in SEQ ID NO:346, and a light chain variable region comprising amino acids having a sequence set forth in SEQ ID NO:347; or (xxii) a heavy chain variable region comprising amino acids having a sequence set forth in SEQ ID NO:358, and a light chain variable region comprising amino acids having a sequence set forth in SEQ ID NO:359.

In addition, the presently disclosed subject matter provides an isolated antibody, or an antigen-binding portion thereof, which binds to the same epitope on human GPRC5D as a reference antibody or reference antigen-binding portion thereof comprising: (i) a heavy chain variable region comprising amino acids having a sequence set forth in SEQ ID NO:1, and a light chain variable region comprising amino acids having a sequence set forth in SEQ ID NO:2; (ii) a heavy chain variable region comprising amino acids having a sequence set forth in SEQ ID NO:5, and a light chain variable region comprising amino acids having a sequence set forth in SEQ ID NO:6; (iii) a heavy chain variable region comprising amino acids having a sequence set forth in SEQ ID NO:9, and a light chain variable region comprising amino acids having a sequence set forth in SEQ ID NO:10; (iv) a heavy chain variable region comprising amino acids having a sequence set forth in SEQ ID NO:13, and a light chain variable region comprising amino acids having a sequence set forth in SEQ ID NO:14; (v) a heavy chain variable region comprising amino acids having a sequence set forth in SEQ ID NO:17, and a light chain variable region comprising amino acids having a sequence set forth in SEQ ID NO:18; (vi) a heavy chain variable region comprising amino acids having a sequence set forth in SEQ ID NO:21, and a light chain variable region comprising amino acids having a sequence set forth in SEQ ID NO:22; (vii) a heavy chain variable region comprising amino acids having a sequence set forth in SEQ ID NO:25, and a light chain variable region comprising amino acids having a sequence set forth in SEQ ID NO:26; (viii) a heavy chain variable region comprising amino acids having a sequence set forth in SEQ ID NO:29, and a light chain variable region comprising amino acids having a sequence set forth in SEQ ID NO:30; (ix) a heavy chain variable region comprising amino acids having a sequence set forth in SEQ ID NO:33, and a light chain variable region comprising amino acids having a sequence set forth in SEQ ID NO:34; (x) a heavy chain variable region comprising amino acids having a sequence set forth in SEQ ID NO:37, and a light chain variable region comprising amino acids having a sequence set forth in SEQ ID NO:38; (xi) a heavy chain variable region comprising amino acids having a sequence set forth in SEQ ID NO:41, and a light chain variable region comprising amino acids having a sequence set forth in SEQ ID NO:42; (xii) a heavy chain variable region comprising amino acids having a sequence set forth in SEQ ID NO:45, and a light chain variable region comprising amino acids having a sequence set forth in SEQ ID NO:46; (xiii) a heavy chain variable region comprising amino acids having a sequence set forth in SEQ ID NO:49, and a light chain variable region comprising amino acids having a sequence set forth in SEQ ID NO:50; (xiv) a heavy chain variable region comprising amino acids having a sequence set forth in SEQ ID NO:53, and a light chain variable region comprising amino acids having a sequence set forth in SEQ ID NO:54; (xv) a heavy chain variable region comprising amino acids having a sequence set forth in SEQ ID NO:57, and a light chain variable region comprising amino acids having a sequence set forth in SEQ ID NO:58; (xvi) a heavy chain variable region comprising amino acids having a sequence set forth in SEQ ID NO:61, and a light chain variable region comprising amino acids having a sequence set forth in SEQ ID NO:62; (xvii) a heavy chain variable region comprising amino acids having a sequence set forth in SEQ ID NO:65, and a light chain variable region comprising amino acids having a sequence set forth in SEQ ID NO:66; (xviii) a heavy chain variable region comprising amino acids having a sequence set forth in SEQ ID NO:69, and a light chain variable region comprising amino acids having a sequence set forth in SEQ ID NO:70; (xix) a heavy chain variable region comprising amino acids having a sequence set forth in SEQ ID NO:73, and a light chain variable region comprising amino acids having a sequence set forth in SEQ ID NO:74; (xx) a heavy chain variable region comprising amino acids having a sequence set forth in SEQ ID NO:77, and a light chain variable region comprising amino acids having a sequence set forth in SEQ ID NO:78; (xxi) a heavy chain variable region comprising amino acids having a sequence set forth in SEQ ID NO:81, and a light chain variable region comprising amino acids having a sequence set forth in SEQ ID NO:82; (xxii) a heavy chain variable region comprising amino acids having a sequence set forth in SEQ ID NO:85, and a light chain variable region comprising amino acids having a sequence set forth in SEQ ID NO:86; (xxiii) a heavy chain variable region comprising amino acids having a sequence set forth in SEQ ID NO:89, and a light chain variable region comprising amino acids having a sequence set forth in SEQ ID NO:90; (xxiv) a heavy chain variable region comprising amino acids having a sequence set forth in SEQ ID NO:93, and a light chain variable region comprising amino acids having a sequence set forth in SEQ ID NO:94; (xxv) a heavy chain variable region comprising amino acids having a sequence set forth in SEQ ID NO:274, and a light chain variable region comprising amino acids having a sequence set forth in SEQ ID NO:275; (xxvi) a heavy chain variable region comprising amino acids having a sequence set forth in SEQ ID NO:286, and a light chain variable region comprising amino acids having a sequence set forth in SEQ ID NO:287; (xxvii) a heavy chain variable region comprising amino acids having a sequence set forth in SEQ ID NO:298, and a light chain variable region comprising amino acids having a sequence set forth in SEQ ID NO:299; (xviii) a heavy chain variable region comprising amino acids having a sequence set forth in SEQ ID NO:310, and a light chain variable region comprising amino acids having a sequence set forth in SEQ ID NO:311; (xxi) a heavy chain variable region comprising amino acids having a sequence set forth in SEQ ID NO:322, and a light chain variable region comprising amino acids having a sequence set forth in SEQ ID NO:323; (xx) a heavy chain variable region comprising amino acids having a sequence set forth in SEQ ID NO:334, and a light chain variable region comprising amino acids having a sequence set forth in SEQ ID NO:335; (xxi) a heavy chain variable region comprising amino acids having a sequence set forth in SEQ ID NO:346, and a light chain variable region comprising amino acids having a sequence set forth in SEQ ID NO:347; or (xxii) a heavy chain variable region comprising amino acids having a sequence set forth in SEQ ID NO:358, and a light chain variable region comprising amino acids having a sequence set forth in SEQ ID NO:359.

In certain embodiments, the antibodies of the present disclosure bind to GPRC5D comprising the amino acid sequence set forth in SEQ ID NO:97. In certain embodiments, the antibodies of the present disclosure binds to human GPRC5D with a binding affinity ($K_d$) of from about $1 \times 10^{-9}$ M to about $1 \times 10^{-8}$ M.

In certain embodiments, the antibodies of the present disclosure binds to one, two, three or four epitope region selected from the group consisting of an epitope region in N-terminal region comprising amino acids 1-27 of SEQ ID NO:97, an epitope region in ECL1 region comprising amino acids 85-93 of SEQ ID NO:97, an epitope region in ECL2 region comprising amino acids 145-167 of SEQ ID NO:97, and an epitope region in ECL3 region comprising amino acids 226-239 of SEQ ID NO:97. In certain embodiments, the antibodies of the present disclosure bind to an epitope region comprising amino acids 16-23 of SEQ ID NO:97. In certain embodiments, the antibodies of the present disclosure bind to an epitope region comprising amino acids 15-23 of SEQ ID NO:97. In certain embodiments, the antibodies of the present disclosure bind to an epitope region comprising amino acids 16-25 of SEQ ID NO:97. In certain embodiments, the antibodies of the present disclosure bind to an epitope region comprising amino acids 10-17 of SEQ ID NO:97. In certain embodiments, the antibodies of the present disclosure bind to an epitope region comprising amino acids 5-17 of SEQ ID NO:97. In certain embodiments, the antibodies of the present disclosure bind to an epitope region comprising amino acids 85-95 of SEQ ID NO:97. In certain embodiments, the antibodies of the present disclosure bind to an epitope region comprising amino acids 157-164 of SEQ ID NO:97. In certain embodiments, the antibodies of the present disclosure bind to an epitope region comprising amino acids 157-167 of SEQ ID NO:97. In certain embodiments, the antibodies of the present disclosure bind to an epitope region comprising amino acids 230-237 of SEQ ID NO:97. In certain embodiments, the antibodies of the present disclosure bind to an epitope region comprising amino acids 229-237 of SEQ ID NO:97. In certain embodiments, the antibodies of the present disclosure bind to an epitope region comprising amino acids 230-243 of SEQ ID NO:97. In certain embodiments, the antibodies of the present disclosure bind to an epitope region comprising amino acids 227-237 of SEQ ID NO:97.

The presently disclosed subject matter also provides an isolated antibody, or antigen-binding fragment thereof, comprising an amino acid sequence selected from the group consisting of SEQ ID NOS: 100-123, 276, 288, 300, 312, 324, 336, 348 and 360.

In certain embodiments, the antibody or antigen-binding fragment thereof comprises a human variable region framework region. In certain embodiments, the antibody or antigen-binding fragment thereof is fully human or an antigen-binding fragment thereof. In certain embodiments, the antibody or antigen-binding fragment thereof is a chimeric antibody or an antigen-binding fragment thereof. In certain embodiments, the antibody or antigen-binding portion thereof is a humanized antibody or an antigen-binding fragment thereof. In certain embodiments, the antigen-binding fragment of the antibody is an Fab, Fab', F(ab')$_2$, Fv or single chain Fv (scFv).

The presently disclosed subject matter also provides a composition comprising the antibody or antigen-binding fragment thereof disclosed herein, and a pharmaceutically acceptable carrier.

In addition, the presently disclosed subject matter provides an immunoconjugate comprising the antibody or antigen-binding fragment thereof disclosed herein, linked to a therapeutic agent. In certain embodiments, the therapeutic agent is a drug, cytotoxin, or a radioactive isotope. The presently disclosed subject matter also provides a composition comprising such immunoconjugate and a pharmaceutically acceptable carrier.

Furthermore, the presently disclosed subject matter provides a bispecific molecule comprising the antibody or antigen-binding fragment thereof disclosed herein, linked to a second functional moiety. In certain embodiments, the second functional moiety has a different binding specificity than the antibody or antigen binding fragment thereof. In certain embodiments, the second functional moiety has a binding specificity for an immune cell. In certain embodiments, the second functional moiety has a binding specificity for CD3.

The presently disclosed subject matter also provides a composition comprising such bispecific molecule and a pharmaceutically acceptable carrier.

In addition, the presently disclosed subject matter provides an isolated nucleic acid that encodes the antibody or antigen-binding fragment thereof disclosed herein, an expression vector comprising such nucleic acid molecule, and a host cell comprising such expression vector.

Furthermore, the presently disclosed subject matter provides a method for detecting GPRC5D in a whole cell or tissue. In certain embodiments, the method comprises: contacting a cell or tissue with the antibody or antigen-binding fragment thereof disclosed herein, wherein said antibody or antigen-binding fragment thereof comprises a detectable label; and determining the amount of the labeled antibody or antigen-binding fragment thereof bound to said cell or tissue by measuring the amount of detectable label associated with said cell or tissue, wherein the amount of bound antibody or antigen-binding fragment thereof indicates the amount of GPRC5D in said cell or tissue.

Furthermore, the presently disclosed subject matter provides a method of treating a tumor in a subject. In certain embodiments, the method comprises: administering an effective amount of the antibody or antigen-binding fragment thereof disclosed herein to the subject, thereby inducing death of a tumor cell in the subject. In certain embodiments, the method reduces the number of the tumor cells. In certain embodiments, the method reduces the tumor size. In certain embodiments, the method eradicates the tumor in the subject. In certain embodiments, the subject is a human.

In addition, the presently disclosed subject matter provides use of the antibody or antigen-binding fragment disclosed herein for the treatment of a tumor, and the antibody or antigen-binding fragment thereof disclosed herein for use in treating a tumor in a subject.

Furthermore, the presently disclosed subject matter provides a kit for treating a tumor, comprising the antibody or antigen-binding fragment thereof disclosed herein. In certain embodiments, the kit further comprises written instructions for using the antibody or antigen-binding fragment thereof for treating a subject having a tumor.

In certain embodiments, the tumor is multiple myeloma or Waldenstrom's Macroglobulinemia. In certain embodiments, the tumor is multiple myeloma.

BRIEF DESCRIPTION OF THE FIGURES

The following Detailed Description, given by way of example, but not intended to limit the invention to specific embodiments described, may be understood in conjunction with the accompanying drawings.

FIGS. 5A-5D illustrates heat map technology. (i) Table of combined peptides, with two sub-sequences indicated as "Loop 1" and "Loop 2". (ii) Data from A displayed as a matrix. (iii) Color bar indication of the heat map representation. (iv) Heat map visualization of data from A.

DETAILED DESCRIPTION OF EMBODIMENTS OF THE INVENTION

Figure 1:
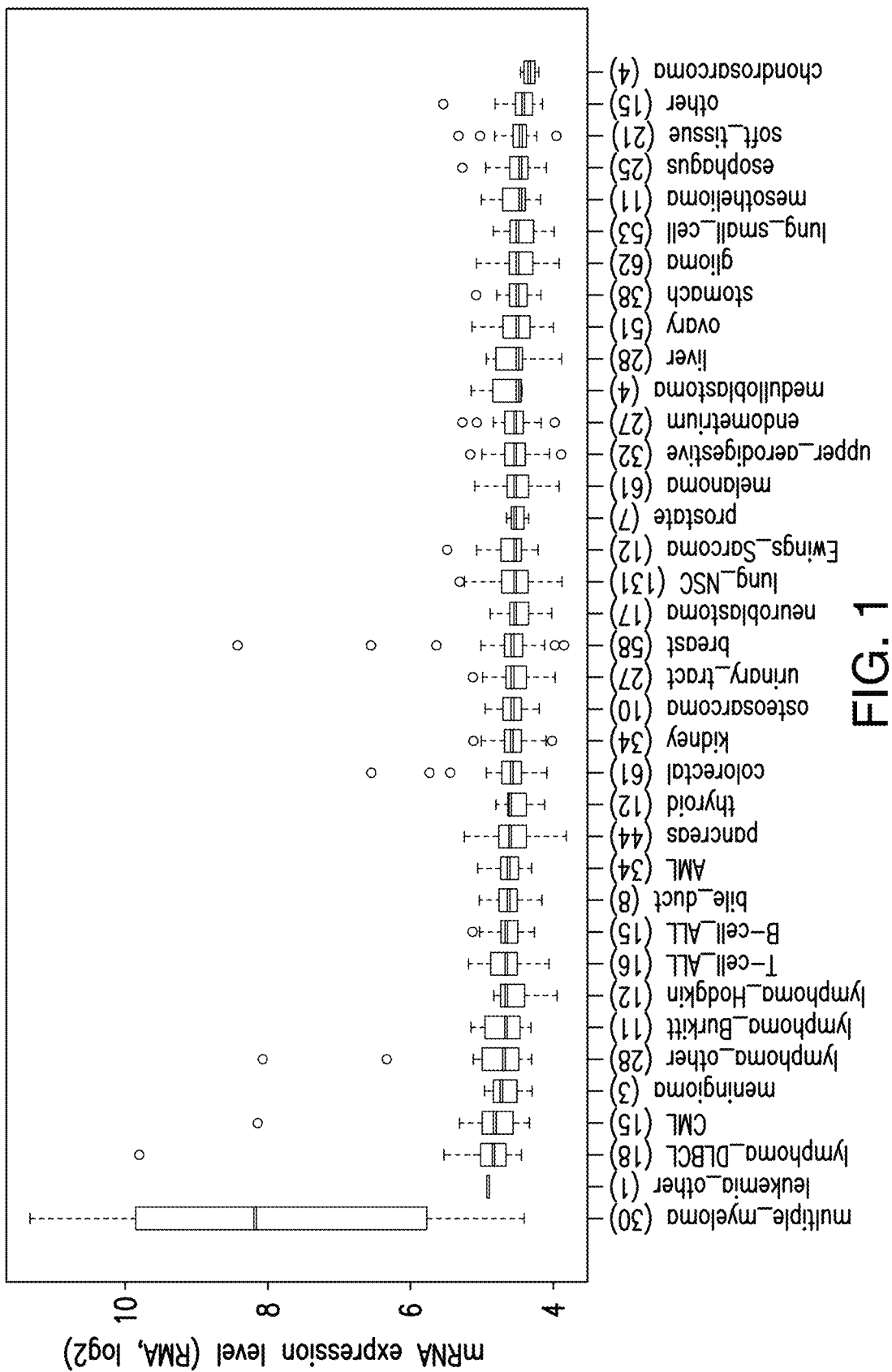
FIG. 1 depicts the human GPRC5D expression in various tissues.
Figure 1:
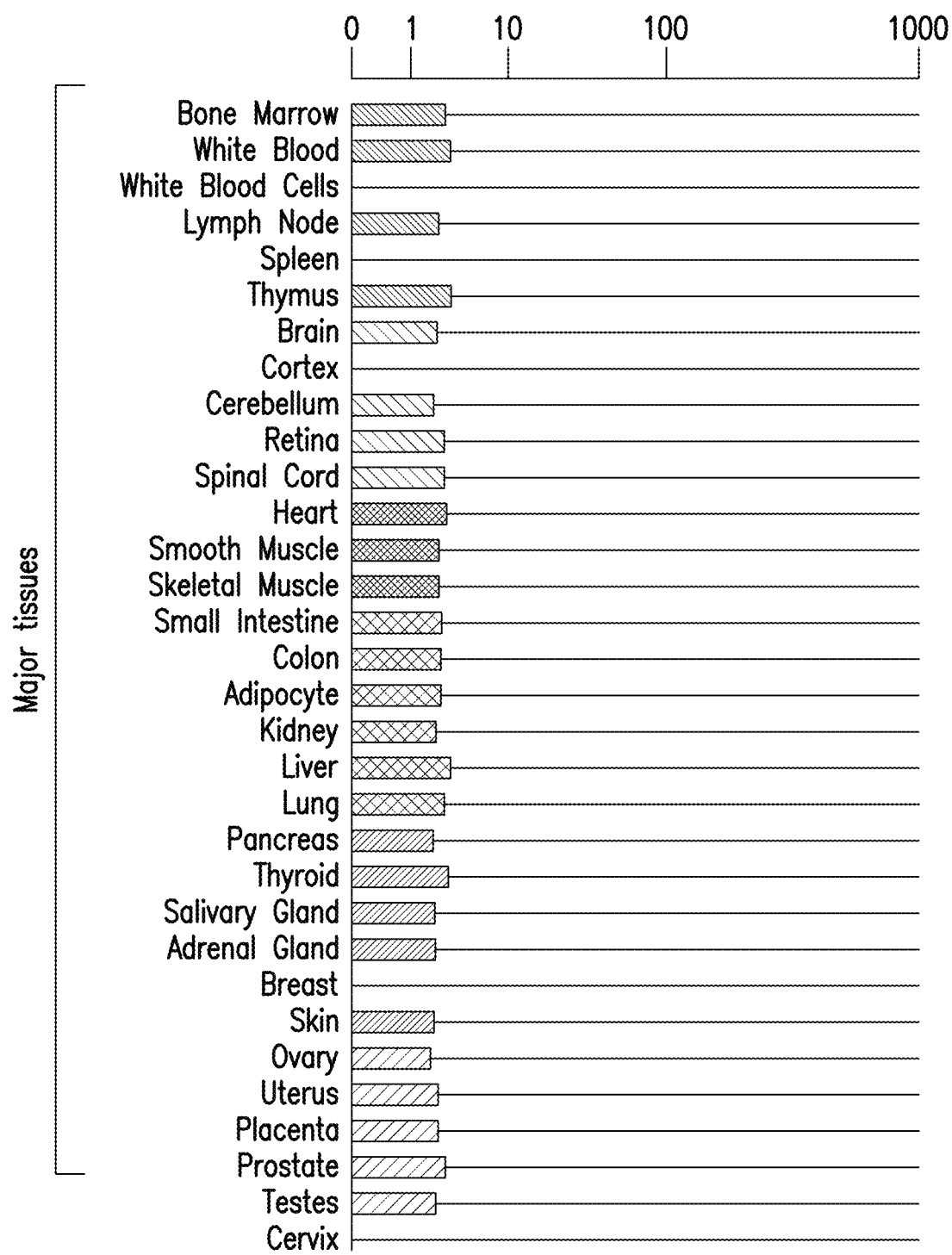
Figure 1:
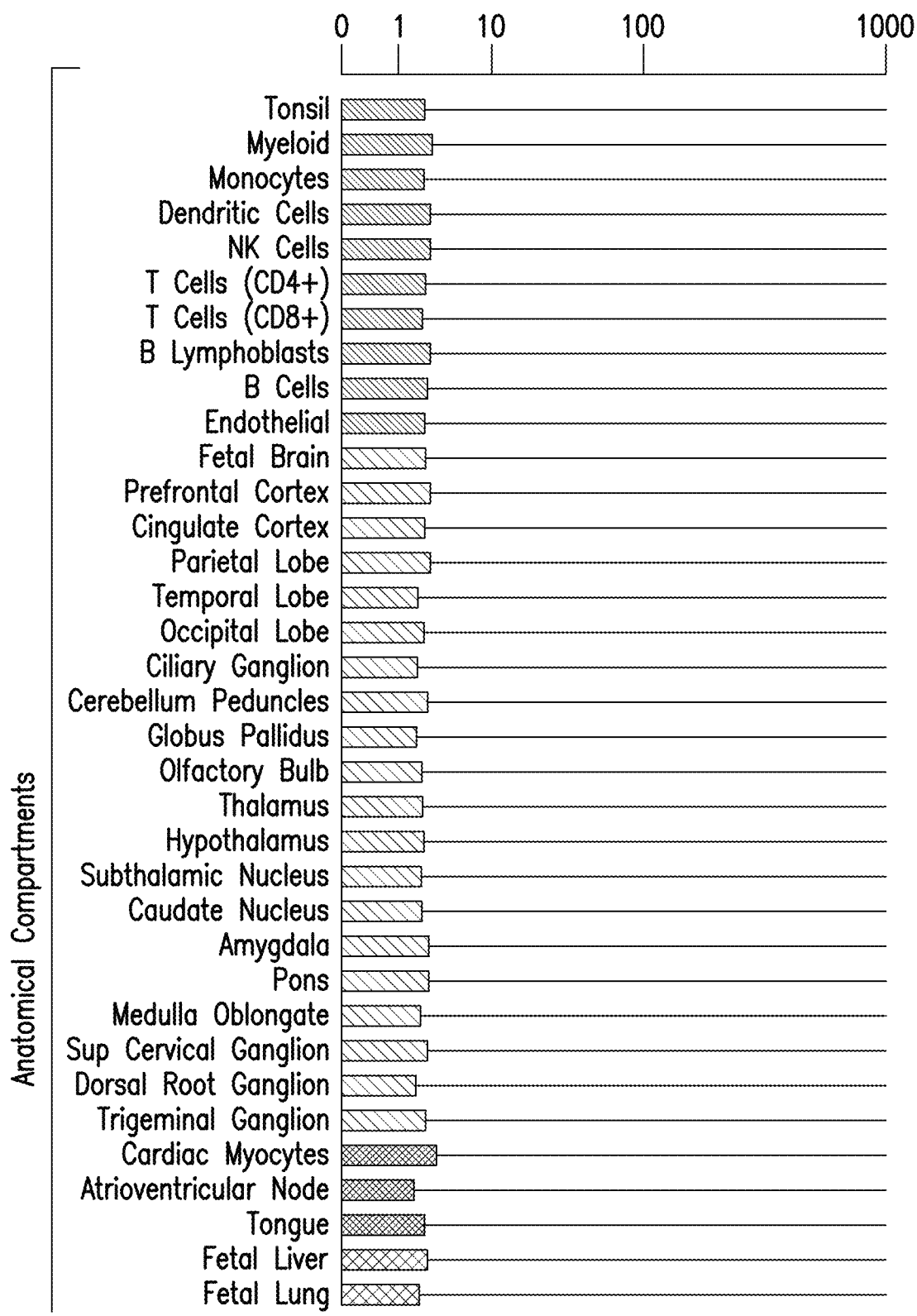
Figure 1:
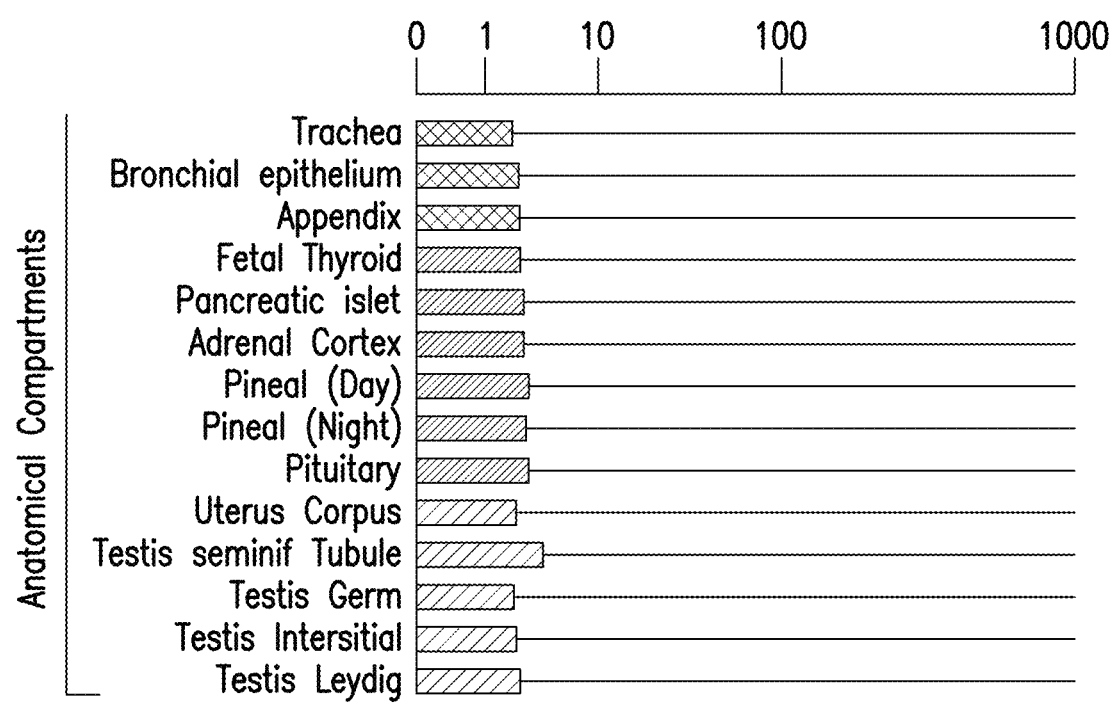

All publications, patents and other references cited herein are incorporated by reference in their entirety into the present disclosure.

In practicing the presently disclosed subject matter, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

Definitions

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

"Antibody" and "antibodies" as those terms are known in the art refer to antigen binding proteins of the immune system. The term "antibody" as referred to herein includes whole, full length antibodies having an antigen-binding region, and any fragment thereof in which the "antigen-binding portion" or "antigen-binding region" is retained, or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant (CH) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the presently disclosed subject matter may include amino acid residues not encoded by human germline immunoglobulin sequences (e.g., mutations introduced by random or site-specific mutagenesis in vitro or by somatic mutation in vivo).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline $V_H$ and $V_L$ sequences, may not naturally exist within the human antibody germline repertoire in vivo.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human GPRC5D" is intended to refer to an antibody that binds to human GPRC5D with a $K_D$ of $5 \times 10^{-7}$ M or less, $1 \times 10^{-7}$ M or less, $5 \times 10^{-8}$ M or less, $1 \times 10^{-8}$ M or less, $5 \times 10^{-8}$ M or less, $1 \times 10^{-9}$ M or less, $5 \times 10^{-10}$ M or less, or $1 \times 10^{-10}$ M or less.

An "antibody that competes for binding" or "antibody that cross-competes for binding" with a reference antibody for binding to an antigen, e.g., GRPC5D, refers to an antibody that blocks binding of the reference antibody to the antigen (e.g., GRPC5D) in a competition assay by 50% or more, and conversely, the reference antibody blocks binding of the antibody to the antigen (e.g., GRPC5D) in a competition assay by 50% or more. An exemplary competition assay is described in "Antibodies", Harlow and Lane (Cold Spring Harbor Press, Cold Spring Harbor, N.Y.).

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen (e.g., a GPRC5D polypeptide)."

The term "antigen-binding portion" or "antigen-binding region" of an antibody, as used herein, refers to that region or portion of the antibody that binds to the antigen and which confers antigen specificity to the antibody; fragments of antigen-binding proteins, for example, antibodies includes one or more fragments of an antibody that retain the ability to specifically bind to an antigen (e.g., a GPRC5D polypeptide). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

The terms "GPRC5D" and "G-protein coupled receptor family C group 5 member D" are used interchangeably, and include variants, isoforms, species homologs of human GPRC5D, and analogs having at least one common epitope with GPRC5D (e.g., human GPRC5D). An exemplary human GPRC5D sequence can be found under GenBank Protein Accession No: NP_061124.1.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. The linker can link the heavy chain variable region and the light chain variable region of the antibody or an antigen-binding fragment thereof. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker.

In certain embodiments, the linker comprises amino acids having the sequence set forth in SEQ ID NO:309 as provided below:

[SEQ ID NO: 309]
GGGGSGGGGSGGGGS.

In certain embodiments, the nucleic acid sequence encoding the amino acid sequence of SEQ ID NO:309 is set forth in SEQ ID NO:364, which is provided below:

[SEQ ID NO: 364]
GGTGGAGGTGGATCAGGTGGAGGTGGATCTGGTGGAGGTGGATCT.

In one non-limiting example, the linker comprises amino acids having the sequence set forth in SEQ ID NO:98 as provided below.

[SEQ ID NO: 98]
SRGGGGSGGGGSGGGGSLEMA

In certain embodiments, the nucleic acid sequence encoding the amino acid sequence of SEQ ID NO:98 is set forth in SEQ ID NO:99, which is provided below:

[SEQ ID NO: 99]
tctagaggtggtggtggtagcggcggcggcggctctggtggtggtggatc cctcgagatggcc In certain embodiments, the linker comprises amino acids having the following sequence GGGGS [SEQ ID NO:365].

In certain embodiments, the linker comprises amino acids having the following sequence SGGSGGS [SEQ ID NO:366].

In certain embodiments, the linker comprises amino acids having the following sequence GGGGSGGGS [SEQ ID NO:367].

In certain embodiments, the linker comprises amino acids having the following sequence GGGGSGGGGS [SEQ ID NO:368].

In certain embodiments, the linker comprises amino acids having the following sequence GGGGSGGGGSGGGGGGS [SEQ ID NO:369].

In certain embodiments, the linker comprises amino acids having the following sequence GGGGSGGGGSGGGGSGGGGS [SEQ ID NO:370].

In certain embodiments, the linker comprises amino acids having the following sequence GGGGSGGGGSGGGGSGGGGSGGGGS [SEQ ID NO:371].

In certain embodiments, the linker comprises amino acids having the following sequence GGGGSGGGGSGGGGSGGGGSGGGGSGGGGS [SEQ ID NO:372].

In certain embodiments, the linker comprises amino acids having the following sequence GGGGSGGGGSGGGGSGGGGSGGGGSGGGGSGGGGS [SEQ ID NO:373].

In certain embodiments, the linker comprises amino acids having the following sequence EPKSCDKTHTCPPCP [SEQ ID NO:374].

In certain embodiments, the linker comprises amino acids having the following sequence GGGGSGGGSEPKSCDKTHTCPPCP [SEQ ID NO:375].

In certain embodiments, the linker comprises amino acids having the following sequence ELKTPLGDTTHTCPRCPEPKSCDTPPPCPRCPEPKSCDTPPPCPRCPEPKSCDTPPPCPRCP [SEQ ID NO:376].

In certain embodiments, the linker comprises amino acids having the following sequence GSGSGS [SEQ ID NO:377].

In certain embodiments, the linker comprises amino acids having the following sequence AAA [SEQ ID NO:378].

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')$_2$" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise three heavy chain and three light chain CDRs or CDR regions in the variable region. CDRs provide the majority of contact residues for the binding of the antibody to the antigen or epitope.

An "isolated antibody" is one which has been separated from a component of its natural environment. In certain embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated nucleic acid encoding an antibody" (including references to a specific antibody, e.g. an anti-KLB antibody) refers to one or more nucleic acid molecules encoding antibody heavy and light chains (or fragments thereof), including such nucleic acid molecule(s) in a single vector separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "immunoconjugate" is an antibody conjugated to one or more heterologous molecule(s), including, but not limited to, a cytotoxic agent.

An "effective amount" of an agent, e.g., an anti-GPRC5D antibody or an antigen-binding fragment thereof, a pharmaceutical comprision comprising thereof, refers to an amount effective, at dosages and for periods of time necessary, to achieve the desired therapeutic or prophylactic result, e.g., treating a tumor (e.g., multiple myeloma).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the presently disclosed subject matter are used to delay development of a disease or to slow the progression of a disease, e.g., a tumor (multiple myeloma).

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As described herein, any concentration range, percentage range, ratio range or integer range is to be understood to include the value of any integer within the recited range and, when appropriate, fractions thereof (such as one tenth and one hundredth of an integer), unless otherwise indicated.

Anti-GPRC5D Antibodies

The antibodies of the presently disclosed subject matter are characterized by particular functional features or properties of the antibodies. For example, the antibodies bind specifically to GPRC5D (e.g., bind to human GPRC5D and may cross-react with GPRC5D from other species, such as mouse). In certain embodiments, an antibody of the presently disclosed subject matter binds to GPRC5D with high affinity, for example with a $K_d$ of $1 \times 10^{-7}$ M or less, e.g., about $1 \times 10^{-8}$ M or less, about $1 \times 10^{-9}$ M or less, or about $1 \times 10^{-10}$ M or less. In certain embodiments, a presently disclosed anti-GPRC5D antibody binds to GPRC5D (e.g., human GPRC5D) with a $K_d$ of from about $1 \times 10^{-10}$ M to about $1 \times 10^{-7}$ M, e.g., about from about $1 \times 10^{-10}$ M to about $1 \times 10^{-9}$ M, from $1 \times 10^{-9}$ M to about $1 \times 10^{-8}$ M, or from about $1 \times 10^{-8}$ M to about $1 \times 10^{-7}$ M. In certain embodiments, a presently disclosed anti-GPRC5D antibody binds to GPRC5D (e.g., human GPRC5D) with a $K_d$ of about $1 \times 10^{-8}$ M or less. In certain embodiments, a presently disclosed anti-GPRC5D antibody binds to GPRC5D (e.g., human GPRC5D) with a $K_d$ of from about $1 \times 10^{-9}$ M to about $1 \times 10^{-8}$ M. In certain embodiments, a presently disclosed anti-GPRC5D antibody binds to GPRC5D (e.g., human GPRC5D) with a $K_d$ of from about $1 \times 10^{-9}$ M to about $1.5 \times 10^{-9}$ M. In certain embodiments, a presently disclosed anti-GPRC5D antibody binds to GPRC5D (e.g., human GPRC5D) with a $K_d$ of about $1.2 \times 10^{-9}$ M. In certain embodiments, a presently disclosed anti-GPRC5D antibody binds to GPRC5D (e.g., human GPRC5D) with a $K_d$ of from about $4 \times 10^{-9}$ M to about $5 \times 10^{-9}$ M. In certain embodiments, a presently disclosed anti-GPRC5D antibody binds to GPRC5D (e.g., human GPRC5D) with a $K_d$ of about $5 \times 10^{-9}$ M. In certain embodiments, a presently disclosed anti-GPRC5D antibody binds to GPRC5D (e.g., human GPRC5D) with a $K_d$ of about $4.8 \times 10^{-9}$ M. In certain embodiments, a presently disclosed anti-GPRC5D antibody binds to GPRC5D (e.g., human GPRC5D) with a $K_d$ of from about $8 \times 10^{-9}$ M to about $9 \times 10^{-9}$ M. In certain embodiments, a presently disclosed anti-GPRC5D antibody binds to GPRC5D (e.g., human GPRC5D) with a $K_d$ of about $8 \times 10^{-9}$ M. In certain embodiments, a presently disclosed anti-GPRC5D antibody binds to GPRC5D (e.g., human GPRC5D) with a $K_d$ of about $8.1 \times 10^{-9}$ M.

The heavy and light chains of an antibody of the presently disclosed subject matter can be full-length (e.g., an antibody can include at least one (e.g., one or two) complete heavy chains, and at least one (e.g., one or two) complete light chains) or can include an antigen-binding portion (a Fab, F(ab')$_2$, Fv or a single chain Fv fragment ("scFv")). In certain embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

1. Single-Chain Variable Fragments (scFvs)

In certain embodiments, the presently disclosed subject matter includes antibodies that have the scFv sequence fused to one or more constant domains to form an antibody with an Fc region of a human immunoglobulin to yield a bivalent protein, increasing the overall avidity and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements, for targeted delivery of a therapeutic agent, to test for Fc-mediated cytotoxicity using immune effector cells and many other applications.

The results presented here highlight the specificity, sensitivity and utility of the antibodies of the invention in targeting a GRPC5D polypeptide.

The molecules of the invention are based on the identification and selection of single chain variable fragments (scFvs) using phage display, the amino acid sequence of which confers the molecules' specificity for a GRPC5D polypeptide of interest and forms the basis of all antigen binding proteins of the disclosure. The scFv, therefore, can be used to design a diverse array of "antibody" molecules, including, for example, full length antibodies, fragments thereof, such as Fab and F(ab')$_2$, minibodies, fusion proteins, including scFv-Fc fusions, multivalent antibodies, that is, antibodies that have more than one specificity for the same antigen or different antigens, for example, bispecific antibodies, tribodies, etc. (see Cuesta et al., Multivalent antibodies: when design surpasses evolution. Trends in Biotechnology 28:355-362 2010).

In certain embodiments, the antigen-binding protein is a full length antibody, the heavy and light chains of an antibody of the presently disclosed subject matter can be full-length (e.g., an antibody can include at least one, and preferably two, complete heavy chains, and at least one, and preferably two, complete light chains) or can include an antigen-binding portion (a Fab, F(ab')$_2$, Fv or a single chain Fv fragment ("scFv")). In certain embodiments, the antibody heavy chain constant region is chosen from, e.g., IgG1, IgG2, IgG3, IgG4, IgM, IgA1, IgA2, IgD, and IgE. In certain embodiments, the immunoglobulin isotype is selected from IgG1, IgG2, IgG3, and IgG4, more particularly, IgG1 (e.g., human IgG1). The choice of antibody isotype can depend on the immune effector function that the antibody is designed to elicit.

In constructing a recombinant immunoglobulin, appropriate amino acid sequences for constant regions of various immunoglobulin isotypes and methods for the production of a wide array of antibodies are known to those of skill in the art.

In certain embodiments, the antibody or other antigen binding protein is an anti-GPRC5D scFv or an antigen-binding fragment thereof having an antigen-binding region that comprises the amino acid sequence of SEQ ID NO: 100 and specifically binds to a GPRC5D polypeptide (e.g., a GPRC5D polypeptide having the amino acid sequence SEQ ID NO:97 which is provided below, or fragments thereof).

[SEQ ID NO: 97]
MYKDCIESTGDYFLLCDAEGPWGIILESLAILGIVVTILLLLAFLFLMRK

IQDCSQWNVLPTQLLFLLSVLGLFGLAFAFIIELNQQTAPVRYFLFGVLF

ALCFSCLLAHASNLVKLVRGCVSFSWTTILCIAIGCSLLQIIIATEYVTL

IMTRGMMFVNMTPCQLNVDFVVLLVYVLFLMALTFFVSKATFCGPCENWK

QHGRLIFITVLFSIIIWVVWISMLLRGNPQFQRQPQWDDPVVCIALVTNA

WVFLLLYIVPELCILYRSCRQECPLQGNACPVTAYQHSFQVENQELSRAR

DSDGAEEDVALTSYGTPIQPQTVDPTQECHPQAKLSPQQDAGGV

The N-terminal region of human GPRC5D has amino acids 1-27 of SEQ ID NO:97. The extracellular loop 1 (ECL1) region of human GPRC5D has amino acids 85-93 of SEQ ID NO:97. The extracellular loop 2 (ECL2) region of human GPRC5D has amino acids 145-167 of SEQ ID NO:97. The extracellular loop 3 (ECL3) region of human GPRC5D has amino acids 226-239 of SEQ ID NO:97.

In certain embodiments, the antibody or other antigen binding protein is an anti-GPRC5D scFv or an antigen-binding fragment thereof having an antigen-binding region that comprises the amino acid sequence of SEQ ID NO:100 and specifically binds to a GPRC5D polypeptide (e.g., a GPRC5D polypeptide having the amino acid sequence SEQ ID NO:97, or fragments thereof), which is designated as ET150-153 scFv (also referred to as "ET150-3 scFv").

In certain embodiments, the anti-GPRC5D scFv antibody comprises a heavy chain variable region comprising amino acids having the sequence set forth in SEQ ID NO:1 and a light chain variable region comprising amino acids having the sequence set forth in SEQ ID NO:2, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 1. In certain embodiments, the anti-GPRC5D scFv comprises a $V_H$ comprising amino acids having the sequence set forth in SEQ ID NO:1, as shown in Table 1. In certain embodiments, the anti-GPRC5D scFv comprises a $V_L$ comprising amino acids having the sequence set forth in SEQ ID NO:2, as shown in Table 1. In certain embodiments, the anti-GPRC5D scFv comprises a $V_H$ comprising amino acids having the sequence set forth in SEQ ID NO:1 and a $V_L$ comprising amino acids having the sequence set forth in SEQ ID NO:2, as shown in Table 1. In certain embodiments, the anti-GPRC5D scFv comprises a $V_H$ CDR1 comprising amino acids having the sequence set forth in SEQ ID NO:124 or conservative modifications thereof, a $V_H$ CDR2 comprising amino acids having the sequence set forth in SEQ ID NO:125 or conservative modifications thereof, and a $V_H$ CDR3 comprising amino acids having the sequence set forth in SEQ ID NO:126 or conservative modifications thereof, as shown in Table 1. In certain embodiments, the anti-GPRC5D scFv comprises a $V_L$ CDR1 comprising amino acids having the sequence set forth in SEQ ID NO:127 or conservative modifications thereof, a $V_L$ CDR2 comprising amino acids having the sequence set forth in SEQ ID NO:128 or conservative modifications thereof, and a $V_L$ CDR3 comprising amino acids having the sequence set forth in SEQ ID NO:129 or conservative modifications thereof, as shown in Table 1. In certain embodiments, the anti-GPRC5D scFv comprises a $V_H$ CDR1 comprising amino acids having the sequence set forth in SEQ ID NO:124 or conservative modifications thereof, a $V_H$ CDR2 comprising amino acids having the sequence set forth in SEQ ID NO:125 or conservative modifications thereof, a $V_H$ CDR3 comprising amino acids having the sequence set forth in SEQ ID NO:126 or conservative modifications thereof, a $V_L$ CDR1 comprising amino acids having the sequence set forth in SEQ ID NO:127 or conservative modifications thereof, a $V_L$ CDR2 comprising amino acids having the sequence set forth in SEQ ID NO:128 or conservative modifications thereof, and a $V_L$ CDR3 comprising amino acids having the sequence set forth in SEQ ID NO:129 or conservative modifications thereof, as shown in Table 1. In certain embodiments, the anti-GPRC5D scFv comprises a $V_H$ CDR1 comprising amino acids having the sequence set forth in SEQ ID NO:124, a $V_H$ CDR2 comprising amino acids having the sequence set forth in SEQ ID NO:125, a $V_H$ CDR3 comprising amino acids having the sequence set forth in SEQ ID NO:126, a $V_L$ CDR1 comprising amino acids having the sequence set forth in SEQ ID NO:127, a $V_L$ CDR2 comprising amino acids having the sequence set forth in SEQ ID NO:128, and a $V_L$ CDR3 comprising amino acids having the sequence set forth in SEQ ID NO:129.

TABLE 1

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 124] | GYTFTSYY [SEQ ID NO: 125] | ARGMYRSLLFYDP [SEQ ID NO: 126] |
| $V_L$ | RSNVGNYY [SEQ ID NO: 127] | DNN [SEQ ID NO: 128] | GTWDGSLSAHV [SEQ ID NO: 129] |

TABLE 1-continued

```
Full V_H    QVQLVQSGSELKKPGASVRVSCTASGYTFTSYYMHWVRQAPGQGLEW
            MGVINPNAGSTRYAQKFQGRVTMSTDTSTSTAYMDLSSLRSEDTAVYY
            CARGMYRSLLFYDPWGQGTLVTVSS [SEQ ID NO: 1]

DNA         Caggtgcagctggtgcagtctgggtctgagttgaagaagcctggggcctcagtcagagtctcctgcacggcttctg
            gatacaccttcaccagttactatatgcactgggtgcgacaggcccctggacaagggcttgagtggatgggagtaat
            caaccctaatgctggcagcacaagatacgcacagaaattccagggcagagtcaccatgagcactgacacgtcca
            cgagcacagcctacatggacctgagcagtctgagatctgaggacacggccgtgtattactgtgcgcgcggtatgta
            ccgttctctgctgttctacgatccgtggggtcaaggtactctggtgaccgtctcctca [SEQ ID NO: 3]

Full V_L    QSVLTQPPSVSAAPGQKVTIPCSGSRSNVGNYYVSWYQQLPGTAPKLLI
            YDNNKRPSGIPDRFSGSKSGTSATLGITGLQTGDEADYFCGTWDGSLSA
            HVFGTGTKVTVLG [SEQ ID NO: 2]

DNA         Cagtctgtgttgacgcagccgccctcagtgtctgcggcccaggacagaaggtcaccatcccctgctctggaagc
            cgttccaacgttgggaattattatgtgtcctggtaccagcaactcccaggaacagcccccaaactcctcatttatgac
            aataataagcgaccctcagggattcctgaccgattctctggctccaagtctggcacgtcagccaccctgggcatcac
            cggactccagactggggacgaggccgattatttctgcggaacatgggatggcagcctgagtgcccatgtcttcgga
            actgggaccaaggtcaccgtcctaggt [SEQ ID NO: 4]

scFv        QSVLTQPPSVSAAPGQKVTIPCSGSRSNVGNYYVSWYQQLPGTAPKLLI
            YDNNKRPSGIPDRFSGSKSGTSATLGITGLQTGDEADYFCGTWDGSLSA
            HVFGTGTKVTVLGSRGGGGSGGGGSGGGGSLEMAQVQLVQSGSELKK
            PGASVRVSCTASGYTFTSYYMHWVRQAPGQGLEWMGVINPNAGSTRY
            AQKFQGRVTMSTDTSTSTAYMDLSSLRSEDTAVYYCARGMYRSLLFYD
            PWGQGTLVTVSS [SEQ ID NO: 100]
```

In certain embodiments, the antibody or other antigen binding protein is an anti-GPRC5D scFv or an antigen-binding fragment thereof having an antigen-binding region that comprises the amino acid sequence of SEQ ID NO: 101 and specifically binds to a GPRC5D polypeptide (e.g., a GPRC5D polypeptide having the amino acid sequence SEQ ID NO:97, or fragments thereof), which is designated as ET150-166 scFv (also referred to as "ET150-16 scFv").

In certain embodiments, the anti-GPRC5D scFv antibody comprises a heavy chain variable region comprising amino acids having the sequence set forth in SEQ ID NO:5 and a light chain variable region comprising amino acids having the sequence set forth in SEQ ID NO:6, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 2. In certain embodiments, the anti-GPRC5D scFv comprises a $V_H$ comprising amino acids having the sequence set forth in SEQ ID NO:5, as shown in Table 2. In certain embodiments, the anti-GPRC5D scFv comprises a $V_L$ comprising amino acids having the sequence set forth in SEQ ID NO:6, as shown in Table 2. In certain embodiments, the anti-GPRC5D scFv comprises a $V_H$ comprising amino acids having the sequence set forth in SEQ ID NO:5 and a $V_L$ comprising amino acids having the sequence set forth in SEQ ID NO:6, as shown in Table 2. In certain embodiments, the anti-GPRC5D scFv comprises a $V_H$ CDR1 comprising amino acids having the sequence set forth in SEQ ID NO:130 or conservative modifications thereof, a $V_H$ CDR2 comprising amino acids having the sequence set forth in SEQ ID NO:131 or conservative modifications thereof, and a $V_H$ CDR3 comprising amino acids having the sequence set forth in SEQ ID NO:132 or conservative modifications thereof, as shown in Table 2. In certain embodiments, the anti-GPRC5D scFv comprises a $V_L$ CDR1 comprising amino acids having the sequence set forth in SEQ ID NO:133 or conservative modifications thereof, a $V_L$ CDR2 comprising amino acids having the sequence set forth in SEQ ID NO:134 or conservative modifications thereof, and a $V_L$ CDR3 comprising amino acids having the sequence set forth in SEQ ID NO:135 or conservative modifications thereof, as shown in Table 2. In certain embodiments, the anti-GPRC5D scFv comprises a $V_H$ CDR1 comprising amino acids having the sequence set forth in SEQ ID NO:130 or conservative modifications thereof, a $V_H$ CDR2 comprising amino acids having the sequence set forth in SEQ ID NO:131 or conservative modifications thereof, a $V_H$ CDR3 comprising amino acids having the sequence set forth in SEQ ID NO:132 or conservative modifications thereof, a $V_L$ CDR1 comprising amino acids having the sequence set forth in SEQ ID NO:133 or conservative modifications thereof, a $V_L$ CDR2 comprising amino acids having the sequence set forth in SEQ ID NO:134 or conservative modifications thereof, and a $V_L$ CDR3 comprising amino acids having the sequence set forth in SEQ ID NO:135 or conservative modifications thereof, as shown in Table 2. In certain embodiments, the anti-GPRC5D scFv comprises a $V_H$ CDR1 comprising amino acids having the sequence set forth in SEQ ID NO:130, a $V_H$ CDR2 comprising amino acids having the sequence set forth in SEQ ID NO:131, a $V_H$ CDR3 comprising amino acids having the sequence set forth in SEQ ID NO:132, a $V_L$ CDR1 comprising amino acids having the sequence set forth in SEQ ID NO:133, a $V_L$ CDR2 comprising amino acids having the sequence set forth in SEQ ID NO:134, and a $V_L$ CDR3 comprising amino acids having the sequence set forth in SEQ ID NO:135.

TABLE 2

| Antigen | A GPRC5D polypeptide having the amino acid sequence of SEQ ID NO: 97 | | |
|---------|---|---|---|
| CDRs | 1 | 2 | 3 |
| $V_H$ | GFTFSNYA [SEQ ID NO: 130] | ISGSGNT [SEQ ID NO: 131] | ARGSVRYTDI [SEQ ID NO: 132] |

TABLE 2-continued

| $V_L$ | SGAIAGAY [SEQ ID NO: 133] | DDN [SEQ ID NO: 134] | QSYDYDSSNVL [SEQ ID NO: 135] |
|---|---|---|---|
| Full $V_H$ | EVQLVESGGGLVQPGGSLRLSCAASGFTFSNYAMSWVRQAPGKGLE WVSAISGSGNTYYADSVKGRFTISRDNSKNTLYLQMNSLRAEDTAVY YCARGSVRYTDIWGQGTLVTVSS [SEQ ID NO: 5] | | |
| DNA | Gaggtgcagctggtggagtctgggggaggcttggtacagcctggggggtccctgagactctcctgtgcagc ctctggattcacctttagcaactatgccatgagttgggtccgccaggctccagggaagggactggagtgggtct cagctattagtggtagtggtaacacatactacgcagactccgtgaagggccggttcaccatctccagagacaat tccaagaacacgctgtatctgcaaatgaacagcctgagagccgaggacacggccgtatattactgtgcgcgcg gttctgttcgttacactgatatctggggtcaaggtactctggtgaccgtctcctca [SEQ ID NO: 7] | | |
| Full $V_L$ | NFMLTQPHSVSESPGKTVSISCTRTSGAIAGAYVQWFQQRPGSAPTTV IYDDNKRPSGVPDRFSGSIDKSSNSASLTISGLKTEDEADYYCQSYDY DSSNVLFGGGTKLTVLG [SEQ ID NO: 6] | | |
| DNA | Aattttatgctgactcagcccactcagtgtcggagtctccggggaagacggtaagcatctcctgcaccgca ccagtggcgccattgccggcgcctatgtgcagtggttccagcagcgcccgggcagtgcccccaccactgtga tctatgacgataacaaaagaccctctgggtccctgatcggttctctggttccatcgacaagtcctccaactctg cctccctcaccatctctggactgaagactgaggacgaggctgactattattgtcagtcttatgattatgatagcag caatgtgctattcggcggagggaccaagctgaccgtcctaggt [SEQ ID NO: 8] | | |
| scFv | NFMLTQPHSVSESPGKTVSISCTRTSGAIAGAYVQWFQQRPGSAPTTV IYDDNKRPSGVPDRFSGSIDKSSNSASLTISGLKTEDEADYYCQSYDY DSSNVLFGGGTKLTVLGSRGGGGSGGGGSGGGGSLEMAEVQLVESG GGLVQPGGSLRLSCAASGFTFSNYAMSWVRQAPGKGLEWVSAISGS GNTYYADSVKGRFTISRDNSKNTLYLQMNSLRAEDTAVYYCARGSV RYTDIWGQGTLVTVSS [SEQ ID NO: 101] | | |

In certain embodiments, the antibody or other antigen binding protein is an anti-GPRC5D scFv or an antigen-binding fragment thereof having an antigen-binding region that comprises the amino acid sequence of SEQ ID NO:102 and specifically binds to a GPRC5D polypeptide (e.g., a GPRC5D polypeptide having the amino acid sequence SEQ ID NO:97, or fragments thereof), which is designated as ET150-170 scFv (also referred to as "ET150-20 scFv").

In certain embodiments, the anti-GPRC5D scFv antibody comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 3. In certain embodiments, the anti-GPRC5D scFv comprises a $V_H$ comprising amino acids having the sequence set forth in SEQ ID NO:9, as shown in Table 3. In certain embodiments, the anti-GPRC5D scFv comprises a $V_L$ comprising amino acids having the sequence set forth in SEQ ID NO:10, as shown in Table 3. In certain embodiments, the anti-GPRC5D scFv comprises a $V_H$ comprising amino acids having the sequence set forth in SEQ ID NO:9 and a $V_L$ comprising amino acids having the sequence set forth in SEQ ID NO:10, as shown in Table 3. In certain embodiments, the anti-GPRC5D scFv comprises a $V_H$ CDR1 comprising amino acids having the sequence set forth in SEQ ID NO:136 or conservative modifications thereof, a $V_H$ CDR2 comprising amino acids having the sequence set forth in SEQ ID NO:137 or conservative modifications thereof, and a $V_H$ CDR3 comprising amino acids having the sequence set forth in SEQ ID NO:138 or conservative modifications thereof, as shown in Table 3. In certain embodiments, the anti-GPRC5D scFv comprises a $V_L$ CDR1 comprising amino acids having the sequence set forth in SEQ ID NO:139 or conservative modifications thereof, a $V_L$ CDR2 comprising amino acids having the sequence set forth in SEQ ID NO:140 or conservative modifications thereof, and a $V_L$ CDR3 comprising amino acids having the sequence set forth in SEQ ID NO:141 or conservative modifications thereof, as shown in Table 3. In certain embodiments, the anti-GPRC5D scFv comprises a $V_H$ CDR1 comprising amino acids having the sequence set forth in SEQ ID NO:136 or conservative modifications thereof, a $V_H$ CDR2 comprising amino acids having the sequence set forth in SEQ ID NO:137 or conservative modifications thereof, a $V_H$ CDR3 comprising amino acids having the sequence set forth in SEQ ID NO:138 or conservative modifications thereof, a $V_L$ CDR1 comprising amino acids having the sequence set forth in SEQ ID NO:139 or conservative modifications thereof, a $V_L$ CDR2 comprising amino acids having the sequence set forth in SEQ ID NO:140 or conservative modifications thereof, and a $V_L$ CDR3 comprising amino acids having the sequence set forth in SEQ ID NO:141 or conservative modifications thereof, as shown in Table 3. In certain embodiments, the anti-GPRC5D scFv comprises a $V_H$ CDR1 comprising amino acids having the sequence set forth in SEQ ID NO:136, a $V_H$ CDR2 comprising amino acids having the sequence set forth in SEQ ID NO:137, a $V_H$ CDR3 comprising amino acids having the sequence set forth in SEQ ID NO:138, a $V_L$ CDR1 comprising amino acids having the sequence set forth in SEQ ID NO:139, a $V_L$ CDR2 comprising amino acids having the sequence set forth in SEQ ID NO:140, and a $V_L$ CDR3 comprising amino acids having the sequence set forth in SEQ ID NO:141.

TABLE 3

| Antigen | A GPRC5D polypeptide having the amino acid sequence of SEQ ID NO: 97 | | |
|---|---|---|---|
| CDRs | 1 | 2 | 3 |
| $V_H$ | GFTFNNYW [SEQ ID NO: 136] | IKQDGSEK [SEQ ID NO: 137] | ARSMSTAV [SEQ ID NO: 138] |
| $V_L$ | QSISSY [SEQ ID NO: 139] | AAS [SEQ ID NO: 140] | QQSYSVPYT [SEQ ID NO: 141] |
| Full $V_H$ | EVQLVQSGGGLVQPGGSLRLSCATSGFTFNNYWMSWVRQAPGKGLE WVANIKQDGSEKYYADSVRGRFTISRDNAKNSLSLQLNNLRAEDTAV YYCARSMSTAWGYDEWGQGTLVTVSS [SEQ ID NO: 9] | | |
| DNA | Gaggtgcagctggtgcagtctgggggaggcttggtccagcctggggggtccctgagactctcctgtgcaacct ctggattcacctttaataactattggatgagttgggtccgccaggctccagggaaggggctggagtgggtggcc aacataaagcaagatggaagtgagaaatactacgcggactctgtgaggggccgattcaccatctccagagaca acgccaagaactcactgtctctgcaattgaacaacctgagagccgaggacacggccgtgtattactgtgcgcgc tctatgtctacttgcttggggttacgatgaatggggtcaaggtactctggtgaccgtctcctca [SEQ ID NO: 11] | | |
| Full $V_L$ | DIQLTQSPSSLSASVGDRVTITCRASQSISSYLNWYQQKPGKAPKLLIY AASSLQSGVPSRFSGSGSGTDFTLTISSLQPADFATYYCQQSYSVPYTF GQGTKLEIKR [SEQ ID NO: 10] | | |
| DNA | Gacatccagttgacccagtctccatcctccctgtctgcatctgtcggagacagagtcaccatcacttgccgggca agtcagagcattagcagctatttaaattggtatcaacagaaaccagggaaagcccctaagctcctgatctatgctg catccagtttgcaaagtggggtcccatcaaggttcagtggcagtggatctgggacagatttcactctcaccatcag cagtctgcaacctgcagatttgcaacttactactgtcaacagagttacagtgtcccgtacacttttggccagggga ccaagctggagatcaaacgt [SEQ ID NO: 12] | | |
| scFv | DIQLTQSPSSLSASVGDRVTITCRASQSISSYLNWYQQKPGKAPKLLIY AASSLQSGVPSRFSGSGSGTDFTLTISSLQPADFATYYCQQSYSVPYTF GQGTKLEIKRSRGGGGSGGGGSGGGGSLEMAEVQLVQSGGGLVQPG GSLRLSCATSGFTFNNYWMSWVRQAPGKGLEWVANIKQDGSEKYYA DSVRGRFTISRDNAKNSLSLQLNNLRAEDTAVYYCARSMSTAWGYDE WGQGTLVTVSS [SEQ ID NO: 102] | | |

In certain embodiments, the antibody or other antigen binding protein is an anti-GPRC5D scFv or an antigen-binding fragment thereof having an antigen-binding region that comprises the amino acid sequence of SEQ ID NO: 103 and specifically binds to a GPRC5D polypeptide (e.g., a GPRC5D polypeptide having the amino acid sequence SEQ ID NO:97, or fragments thereof), which is designated as ET150-171 scFv (also referred to as "ET150-21 scFv").

In certain embodiments, the anti-GPRC5D scFv antibody comprises a heavy chain variable region comprising amino acids having the sequence set forth in SEQ ID NO:13 and a light chain variable region comprising amino acids having the sequence set forth in SEQ ID NO:14, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 4. In certain embodiments, the anti-GPRC5D scFv comprises a $V_H$ comprising amino acids having the sequence set forth in SEQ ID NO:13, as shown in Table 4. In certain embodiments, the anti-GPRC5D scFv comprises a $V_L$ comprising amino acids having the sequence set forth in SEQ ID NO:14, as shown in Table 4. In certain embodiments, the anti-GPRC5D scFv comprises a $V_H$ comprising amino acids having the sequence set forth in SEQ ID NO:13 and a $V_L$ comprising amino acids having the sequence set forth in SEQ ID NO:14, as shown in Table 4. In certain embodiments, the anti-GPRC5D scFv comprises a $V_H$ CDR1 comprising amino acids having the sequence set forth in SEQ ID NO:142 or conservative modifications thereof, a $V_H$ CDR2 comprising amino acids having the sequence set forth in SEQ ID NO:143 or conservative modifications thereof, and a $V_H$ CDR3 comprising amino acids having the sequence set forth in SEQ ID NO:144 or conservative modifications thereof, as shown in Table 4. In certain embodiments, the anti-GPRC5D scFv comprises a $V_L$ CDR1 comprising amino acids having the sequence set forth in SEQ ID NO:145 or conservative modifications thereof, a $V_L$ CDR2 comprising amino acids having the sequence set forth in SEQ ID NO:146 or conservative modifications thereof, and a $V_L$ CDR3 comprising amino acids having the sequence set forth in SEQ ID NO:147 or conservative modifications thereof, as shown in Table 4. In certain embodiments, the anti-GPRC5D scFv comprises a $V_H$ CDR1 comprising amino acids having the sequence set forth in SEQ ID NO:142 or conservative modifications thereof, a $V_H$ CDR2 comprising amino acids having the sequence set forth in SEQ ID NO:143 or conservative modifications thereof, a $V_H$ CDR3 comprising amino acids having the sequence set forth in SEQ ID NO:144 or conservative modifications thereof, a $V_L$ CDR1 comprising amino acids having the sequence set forth in SEQ ID NO:145 or conservative modifications thereof, a $V_L$ CDR2 comprising amino acids having the sequence set forth in SEQ ID NO:146 or conservative modifications thereof, and a $V_L$ CDR3 comprising amino acids having the sequence set forth in SEQ ID NO:147 or conservative modifications thereof, as shown in Table 4. In certain embodiments, the anti-GPRC5D scFv comprises a $V_H$ CDR1 comprising amino acids having the sequence set forth in SEQ ID NO:142, a $V_H$ CDR2 comprising amino acids having the sequence set forth in SEQ ID NO:143, a $V_H$ CDR3 comprising amino acids having the sequence set forth in SEQ ID NO:144, a $V_L$ CDR1 comprising amino acids having the sequence set forth in SEQ ID NO:145, a V_L CDR2 comprising amino acids having the sequence set forth in SEQ ID NO:146, and a V_L CDR3 comprising amino acids having the sequence set forth in SEQ ID NO:147.

having the sequence set forth in SEQ ID NO:18, as shown in Table 5. In certain embodiments, the anti-GPRC5D scFv comprises a V_H CDR1 comprising amino acids having the sequence set forth in SEQ ID NO:148 or conservative

TABLE 4

| Antigen | A GPRC5D polypeptide having the amino acid sequence of SEQ ID NO: 97 | | |
|---|---|---|---|
| CDRs | 1 | 2 | 3 |
| V_H | GYTFTSYY [SEQ ID NO: 142] | INPSGGST [SEQ ID NO: 143] | ARGSSRWGGWTGDY [SEQ ID NO: 144] |
| V_L | SSDVGGYNF [SEQ ID NO: 145] | DVS [SEQ ID NO: 146] | SSYTSTRTVIFAGGTKVTVL [SEQ ID NO: 147] |
| Full V_H | QVQLVQSGAEVKKPGASVKVSCKASGYTFTSYYMHWVRQAPGQGLEW MGIINPSGGSTRYAQKFQGRVTMTRDTSTSTVYMELSSLRSEDTAVYYC ARGSSRWGGWTGDYWGQGTLVTVSS [SEQ ID NO: 13] | | |
| DNA | Caggtgcagctggtgcagtctggggctgaggtgaagaagcctggggcctcagtgaaggtttcctgcaaggcatct ggatacacctttaccagctactatatgcactgggtgcgacaggcccctggacaagggcttgagtggatgggaataat caaccctagtggtggtagcacaaggtacgcacagaagttccagggcagagtcaccatgaccagggacacgtcaac gagcacagtctacatggagctgagcagcctgagatctgaggacacggccgtgtattactgtgcgcgcggttcttctc gctggggtggttggactggtgattactggggtcaaggtactctggtgaccgtctcctca [SEQ ID NO: 15] | | |
| Full V_L | QSALTQPASVSGSPGQSITISCTGTSSDVGGYNFVSWYQQHPGKAPKVMI YDVSKRPSGISNRFSGSKSGNTASLTISGLQVEDEAEYYCSSYTSTRTVIF AGGTKVTVLG [SEQ ID NO: 14] | | |
| DNA | Caatctgccctgactcagcctgcctccgtgtctgggtctcctggacagtcgatcaccatctcctgcactggaaccagc agtgacgttggtggttataactttgtctcctggtaccaacagcacccaggcaaagccccaaagtcatgatttatgatg tcagtaagcggccctcagggatttctaatcgcttctctggctccaagtctggcaacacggcctcctgaccatctctgg gctccaggttgaggacgaggctgaatattactgcagctcatatacaagcactagaactgtgatattcgccggaggga ccaaggtcaccgtcctaggt [SEQ ID NO: 16] | | |
| scFv | QSALTQPASVSGSPGQSITISCTGTSSDVGGYNFVSWYQQHPGKAPKVMI YDVSKRPSGISNRFSGSKSGNTASLTISGLQVEDEAEYYCSSYTSTRTVIF AGGTKVTVLG SRGGGGSGGGGSGGGGSLEMAQVQLVQSGAEVKKPGASVKVSCKASG YTFTSYYMHWVRQAPGQGLEWMGIINPSGGSTRYAQKFQGRVTMTRDT STSTVYMELSSLRSEDTAVYYCARGSSRWGGWTGDYWGQGTLVTVSS [SEQ ID NO: 103] | | |

In certain embodiments, the antibody or other antigen binding protein is an anti-GPRC5D scFv or an antigen-binding fragment thereof having an antigen-binding region that comprises the amino acid sequence of SEQ ID NO: 104 and specifically binds to a GPRC5D polypeptide (e.g., a GPRC5D polypeptide having the amino acid sequence SEQ ID NO:97, or fragments thereof), which is designated as ET150-175 scFv (also referred to as "ET150-25 scFv").

In certain embodiments, the anti-GPRC5D scFv antibody comprises a heavy chain variable region comprising amino acids having the sequence set forth in SEQ ID NO:17 and a light chain variable region comprising amino acids having the sequence set forth in SEQ ID NO:18, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 5. In certain embodiments, the anti-GPRC5D scFv comprises a V_H comprising amino acids having the sequence set forth in SEQ ID NO:17, as shown in Table 5. In certain embodiments, the anti-GPRC5D scFv comprises a V_L comprising amino acids having the sequence set forth in SEQ ID NO:18, as shown in Table 5. In certain embodiments, the anti-GPRC5D scFv comprises a V_H comprising amino acids having the sequence set forth in SEQ ID NO:17 and a V_L comprising amino acids modifications thereof, a V_H CDR2 comprising amino acids having the sequence set forth in SEQ ID NO:149 or conservative modifications thereof, and a V_H CDR3 comprising amino acids having the sequence set forth in0 SEQ ID NO:150 or conservative modifications thereof, as shown in Table 5. In certain embodiments, the anti-GPRC5D scFv comprises a V_L CDR1 comprising amino acids having the sequence set forth in SEQ ID NO:151 or conservative modifications thereof, a V_L CDR2 comprising amino acids having the sequence set forth in SEQ ID NO:152 or conservative modifications thereof, and a V_L CDR3 comprising amino acids having the sequence set forth in SEQ ID NO:153 or conservative modifications thereof, as shown in Table 5. In certain embodiments, the anti-GPRC5D scFv comprises a V_H CDR1 comprising amino acids having the sequence set forth in SEQ ID NO:148 or conservative modifications thereof, a V_H CDR2 comprising amino acids having the sequence set forth in SEQ ID NO:149 or conservative modifications thereof, a V_H CDR3 comprising amino acids having the sequence set forth in SEQ ID NO:150 or conservative modifications thereof, a V_L CDR1 comprising amino acids having the sequence set forth in SEQ ID NO:151 or conservative modifications thereof, a V_L CDR2 comprising amino acids having the sequence set forth in SEQ ID NO:152 or conservative modifications thereof, and a V_L CDR3 comprising amino acids having the sequence set forth in SEQ ID NO:153 or conservative modifications thereof, as shown in Table 5. In certain embodiments, the anti-GPRC5D scFv comprises a $V_H$ CDR1 comprising amino acids having the sequence set forth in SEQ ID NO:148, a $V_H$ CDR2 comprising amino acids having the sequence set forth in SEQ ID NO:149, a $V_H$ CDR3 comprising amino acids having the sequence set forth in SEQ ID NO:150, a $V_L$ CDR1 comprising amino acids having the sequence set forth in SEQ ID NO:151, a $V_L$ CDR2 comprising amino acids having the sequence set forth in SEQ ID NO:152, and a $V_L$ CDR3 comprising amino acids having the sequence set forth in SEQ ID NO:153.

anti-GPRC5D scFv comprises a $V_L$ comprising amino acids having the sequence set forth in SEQ ID NO:22, as shown in Table 6. In certain embodiments, the anti-GPRC5D scFv comprises a $V_H$ comprising amino acids having the sequence set forth in SEQ ID NO:21 and a $V_L$ comprising amino acids having the sequence set forth in SEQ ID NO:22, as shown in Table 6. In certain embodiments, the anti-GPRC5D scFv comprises a $V_H$ CDR1 comprising amino acids having the sequence set forth in SEQ ID NO:154 or conservative modifications thereof, a $V_H$ CDR2 comprising amino acids

TABLE 5

| Antigen | A GPRC5D polypeptide having the amino acid sequence of SEQ ID NO: 97 | | |
|---|---|---|---|
| CDRs | 1 | 2 | 3 |
| $V_H$ | GSTFSSYA [SEQ ID NO: 148] | ISGRGRST [SEQ ID NO: 149] | ARYYKSKDH [SEQ ID NO: 150] |
| $V_L$ | RSNIGTNY [SEQ ID NO: 151] | RNH [SEQ ID NO: 152] | AAWDDNLSGVV [SEQ ID NO: 153] |
| Full $V_H$ | EVQLVETGGGLVQPGGSLRLSCAASGSTFSSYAMSWVRQAPGKGLE WVSAISGRGRSTYYADSVKGRFTISRDNSKNTLYLQMNSLRAEDTAV YYCARYYKSSKDHWGQGTLVTVSS [SEQ ID NO: 17] | | |
| DNA | Gaggtgcagctggtggagactgggggaggcttggtacagcctggggggtccctgagactctcctgtgcagcc tctggatccacctttagcagctatgccatgagctgggtccgccaggctccagggaaggggctggagtgggtctc agctattagtggtcgtggtcgtagcacatactacgcagactccgtgaaggccggttcaccatctccagagaca attccaagaacacgctgtatctgcaaatgaacagcctgagagccgaggacacggccgtatattactgtgcgcgc tactacaaatcttctaaagatcattggggtcaaggtactctggtgaccgtctcctca [SEQ ID NO: 19] | | |
| Full $V_L$ | QSVLTQPPSLSGAPGQRVTISCSGSRSNIGTNYVSWXQQLPGTAPKLLI YRNHQWPSGVPDRFTGSKSGTSASLAISGLRSEDEADYYCAAWDDNL SGVVFGGGTKLTVLG [SEQ ID NO: 18] | | |
| DNA | Cagtctgtgttgacgcagccgccctcactgtctggggccccagggcagagggtcaccatctcttgttccggaag caggtccaacatcggaactaattatgtatcctggnaccagcaactcccaggaacggcccccaaactcctcatcta taggaatcatcagtggccctcaggggtccctgaccgattcactggctccaagtctggcacctcagcctccctggc catcagtgggctccggtccgaggatgaggctgattactactgtgcagcatgggatgacaatttgagtggtgtggt gttcggcggagggaccaagctgaccgtcctaggt [SEQ ID NO: 20] | | |
| scFv | QSVLTQPPSLSGAPGQRVTISCSGSRSNIGTNYVSWXQQLPGTAPKLLI YRNHQWPSGVPDRFTGSKSGTSASLAISGLRSEDEADYYCAAWDDNL SGVVFGGGTKLTVLGSRGGGGSGGGGSGGGGSLEMAEVQLVETGGG LVQPGGSLRLSCAASGSTFSSYAMSWVRQAPGKGLEWVSAISGRGRS TYYADSVKGRFTISRDNSKNTLYLQMNSLRAEDTAVYYCARYYKSSK DHWGQGTLVTVSS [SEQ ID NO: 104] | | |

In certain embodiments, the antibody or other antigen binding protein is an anti-GPRC5D scFv or an antigen-binding fragment thereof having an antigen-binding region that comprises the amino acid sequence of SEQ ID NO: 105 and specifically binds to a GPRC5D polypeptide (e.g., a GPRC5D polypeptide having the amino acid sequence SEQ ID NO:97, or fragments thereof), which is designated as ET150-154 scFv (also referred to as "ET150-4 scFv").

In certain embodiments, the anti-GPRC5D scFv antibody comprises a heavy chain variable region comprising amino acids having the sequence set forth in SEQ ID NO:21 and a light chain variable region comprising amino acids having the sequence set forth in SEQ ID NO:22, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 6. In certain embodiments, the anti-GPRC5D scFv comprises a $V_H$ comprising amino acids having the sequence set forth in SEQ ID NO:21, as shown in Table 6. In certain embodiments, the having the sequence set forth in SEQ ID NO:155 or conservative modifications thereof, and a $V_H$ CDR3 comprising amino acids having the sequence set forth in SEQ ID NO:156 or conservative modifications thereof, as shown in Table 6. In certain embodiments, the anti-GPRC5D scFv comprises a $V_L$ CDR1 comprising amino acids having the sequence set forth in SEQ ID NO:157 or conservative modifications thereof, a $V_L$ CDR2 comprising amino acids having the sequence set forth in SEQ ID NO:158 or conservative modifications thereof, and a $V_L$ CDR3 comprising amino acids having the sequence set forth in SEQ ID NO:159 or conservative modifications thereof, as shown in Table 6. In certain embodiments, the anti-GPRC5D scFv comprises a $V_H$ CDR1 comprising amino acids having the sequence set forth in SEQ ID NO:154 or conservative modifications thereof, a $V_H$ CDR2 comprising amino acids having the sequence set forth in SEQ ID NO:155 or conservative modifications thereof, a $V_H$ CDR3 comprising amino acids having the sequence set forth in SEQ ID NO:156 or conservative modifications thereof, a $V_L$ CDR1 comprising amino acids having the sequence set forth in SEQ ID NO:157 or conservative modifications thereof, a $V_L$ CDR2 comprising amino acids having the sequence set forth in SEQ ID NO:158 or conservative modifications thereof, and a V$_L$ CDR3 comprising amino acids having the sequence set forth in SEQ ID NO:159 or conservative modifications thereof, as shown in Table 6. In certain embodiments, the anti-GPRC5D scFv comprises a V$_H$ CDR1 comprising amino acids having the sequence set forth in SEQ ID NO:154, a V$_H$ CDR2 comprising amino acids having the sequence set forth in SEQ ID NO:155, a V$_H$ CDR3 comprising amino acids having the sequence set forth in SEQ ID NO:156, a V$_L$ CDR1 comprising amino acids having the sequence set forth in SEQ ID NO:157, a V$_L$ CDR2 comprising amino acids having the sequence set forth in SEQ ID NO:158, and a V$_L$ CDR3 comprising amino acids having the sequence set forth in SEQ ID NO:159.

scFv-Fc fusion protein or full length human IgG with V$_H$ and V$_L$ regions or CDRs selected from Table 7. In certain embodiments, the anti-GPRC5D scFv comprises a V$_H$ comprising amino acids having the sequence set forth in SEQ ID NO:25, as shown in Table 7. In certain embodiments, the anti-GPRC5D scFv comprises a V$_L$ comprising amino acids having the sequence set forth in SEQ ID NO:26, as shown in Table 7. In certain embodiments, the anti-GPRC5D scFv comprises a V$_H$ comprising amino acids having the sequence set forth in SEQ ID NO:25 and a V$_L$ comprising amino acids having the sequence set forth in SEQ ID NO:26, as shown in Table 7. In certain embodiments, the anti-GPRC5D scFv comprises a V$_H$ CDR1 comprising amino acids having the sequence set forth in SEQ ID NO:160 or conservative

TABLE 6

| Antigen | A GPRC5D polypeptide having the amino acid sequence of SEQ ID NO: 97 | | |
|---|---|---|---|
| CDRs | 1 | 2 | 3 |
| V$_H$ | AYTFTDYY [SEQ ID NO: 154] | INPKSGRT [SEQ ID NO: 155] | ARVYGYSRWSGFDL [SEQ ID NO: 156] |
| V$_L$ | SSNIGSNY [SEQ ID NO: 157] | RNN [SEQ ID NO: 158] | AAWDDSLSGYV [SEQ ID NO: 159] |
| Full V$_H$ | QVQLVQSGAEVQRPGASVRVSCKAIAYTFTDYYIHWVRQAPGQGP EWMGWINPKSGRTQYAPKFQDRVTLARETPISTASMELRGLTSDDT AVYYCARVYGYSRWSGFDLWGQGTLVTVSS [SEQ ID NO: 21] | | |
| DNA | Caggtccagctggtgcagtctggggctgaggtgcagaggcctggggcctcagtgagggtctcctgcaag gctattgcgtacaccttcaccgactactatatccactgggtgcaggcccctggacaggggcctgagtgg atggggtggatcaaccctaaaagtggtcgcacacagtatgcaccgaagtttcaagacagggtcaccctggc cagggagacgcccatcagcacagcctccatggagctgcgcggactgacatctgacgacacggccgtgtat tactgtgcgcgcgtttacggttactctcgttggtctggtttcgatctgtggggtcaaggtactctggtgaccgtc tcctca [SEQ ID NO: 23] | | |
| Full V$_L$ | QAVLTQPPSASGTPGQRVTISCSGSSSNIGSNYVYWYQQLPGTAPKL LIYRNNQRPSGVPDRFSGSKSGTSASLAISGLRSEDEADYYCAAWD DSLSGYVFGTGTKVTVLG [SEQ ID NO: 22] | | |
| DNA | Caggctgtgctgactcagccaccctcagcgtctggaccccgggcagagggtcaccatctcttgttctgg aagcagctccaacatcggaagtaattatgtatactggtaccagcagctcccaggaacggcccccaaactcct catctataggaataatcagcggccctcaggggtccctgaccgattctctggctccaagtctggcacctcagc ctccctggccatcagtgggctccggtccgaggatgaggctgattattactgtgcagcatgggatgacagcct gagtggttatgtcttcggaactgggaccaaggtcaccgtcctaggt [SEQ ID NO: 24] | | |
| scFv | QAVLTQPPSASGTPGQRVTISCSGSSSNIGSNYVYWYQQLPGTAPKL LIYRNNQRPSGVPDRFSGSKSGTSASLAISGLRSEDEADYYCAAWD DSLSGYVFGTGTKVTVLGSRGGGGSGGGGSGGGGSLEMAQVQLV QSGAEVQRPGASVRVSCKAIAYTFTDYYIHWVRQAPGQGPEWMG WINPKSGRTQYAPKFQDRVTLARETPISTASMELRGLTSDDTAVYY CARVYGYSRWSGFDLWGQGTLVTVSS [SEQ ID NO: 105] | | |

In certain embodiments, the antibody or other antigen binding protein is an anti-GPRC5D scFv or an antigen-binding fragment thereof having an antigen-binding region that comprises the amino acid sequence of SEQ ID NO: 106 and specifically binds to a GPRC5D polypeptide (e.g., a GPRC5D polypeptide having the amino acid sequence SEQ ID NO:97, or fragments thereof), which is designated as ET150-156 scFv (also referred to as "ET150-6 scFv").

In certain embodiments, the anti-GPRC5D scFv antibody comprises a heavy chain variable region comprising amino acids having the sequence set forth in SEQ ID NO:25 and a light chain variable region comprising amino acids having the sequence set forth in SEQ ID NO:26, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an modifications thereof, a V$_H$ CDR2 comprising amino acids having the sequence set forth in SEQ ID NO:161 or conservative modifications thereof, and a V$_H$ CDR3 comprising amino acids having the sequence set forth in SEQ ID NO:162 or conservative modifications thereof, as shown in Table 7. In certain embodiments, the anti-GPRC5D scFv comprises a V$_L$ CDR1 comprising amino acids having the sequence set forth in SEQ ID NO:163 or conservative modifications thereof, a V$_L$ CDR2 comprising amino acids having the sequence set forth in SEQ ID NO:164 or conservative modifications thereof, and a V$_L$ CDR3 comprising amino acids having the sequence set forth in SEQ ID NO:165 or conservative modifications thereof, as shown in Table 7. In certain embodiments, the anti-GPRC5D scFv comprises a V$_H$CDR1 comprising amino acids having the sequence set forth in SEQ ID NO:160 or conservative modifications thereof, a V$_H$ CDR2 comprising amino acids having the sequence set forth in SEQ ID NO:161 or conservative modifications thereof, a V<sub>H</sub> CDR3 comprising amino acids having the sequence set forth in SEQ ID NO:162 or conservative modifications thereof, a V<sub>L</sub> CDR1 comprising amino acids having the sequence set forth in SEQ ID NO:163 or conservative modifications thereof, a V<sub>L</sub> CDR2 comprising amino acids having the sequence set forth in SEQ ID NO:164 or conservative modifications thereof, and a V<sub>L</sub> CDR3 comprising amino acids having the sequence set forth in SEQ ID NO:165 or conservative modifications thereof, as shown in Table 7. In certain embodiments, the anti-GPRC5D scFv comprises a V<sub>H</sub> CDR1 comprising amino acids having the sequence set forth in SEQ ID NO:160, a V<sub>H</sub> CDR2 comprising amino acids having the sequence set forth in SEQ ID NO:161, a V<sub>H</sub> CDR3 comprising amino acids having the sequence set forth in SEQ ID NO:162, a V<sub>L</sub> CDR1 comprising amino acids having the sequence set forth in SEQ ID NO:163, a V<sub>L</sub> CDR2 comprising amino acids having the sequence set forth in SEQ ID NO:164, and a V<sub>L</sub> CDR3 comprising amino acids having the sequence set forth in SEQ ID NO:165.

a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V<sub>H</sub> and V<sub>L</sub> regions or CDRs selected from Table 8. In certain embodiments, the anti-GPRC5D scFv comprises a V<sub>H</sub> comprising amino acids having the sequence set forth in SEQ ID NO:29, as shown in Table 8. In certain embodiments, the anti-GPRC5D scFv comprises a V<sub>L</sub> comprising amino acids having the sequence set forth in SEQ ID NO:30, as shown in Table 8. In certain embodiments, the anti-GPRC5D scFv comprises a V<sub>H</sub> comprising amino acids having the sequence set forth in SEQ ID NO:29 and a V<sub>L</sub> comprising amino acids having the sequence set forth in SEQ ID NO:30, as shown in Table 8. In certain embodiments, the anti-GPRC5D scFv comprises a V<sub>H</sub> CDR1 comprising amino acids having the sequence set forth in SEQ ID NO:166 or conservative modifications thereof, a V<sub>H</sub> CDR2 comprising amino acids

TABLE 7

| Antigen | A GPRC5D polypeptide having the amino acid sequence of SEQ ID NO: 97 | | |
|---|---|---|---|
| CDRs | 1 | 2 | 3 |
| V<sub>H</sub> | GYTFTTYY [SEQ ID NO: 160] | INPNGGGT [SEQ ID NO: 161] | ARGHKVYKSHPTGGYDR [SEQ ID NO: 162] |
| V<sub>L</sub> | SRDVGGYNY [SEQ ID NO: 163] | EVS [SEQ ID NO: 164] | SSYTSSSTLD [SEQ ID NO: 165] |
| Full V<sub>H</sub> | QVQLVQSGAEVKQPGASVKVSCQASGYTFTTYYMHWVRQAPGQGLE WMGIINPNGGGTFYAQKFQDRVTMTRDTSTGTVYMELSSLRSDDTAVY YCARGHKVYKSHPTGGYDRWGQGTLVTVSS [SEQ ID NO: 25] | | |
| DNA | Caggtgcagctggtgcaatctggggctgaggtgaagcagcctggggcctcagtgaaggtttcctgccaggcatct ggatacaccttcaccacttattatatgcactgggtgcgacaggcccctggacaagggcttgagtggatgggaataat caaccctaatggtggtggcacattctacgcacagaagttccaggacagagtcaccatgaccagggacacgtccac gggcacagtctacatggaactgagcagcctgagatctgacgacactgccgtgtattactgtgcgcgcggtcataaa gtttacaaatctcatccgactggtggttacgatcgttggggtcaaggtactctggtgaccgtctcctca [SEQ ID NO: 27] | | |
| Full V<sub>L</sub> | QSALTQPASVSGSPGQSITISCTGTSRDVGGYNYVSWYQQYPGKAPKLM IYEVSKRPSGVSNRFSGSKSGNTASLTISGLQAEDEADYYCSSYTSSSTLD FGTGTKVTVLG [SEQ ID NO: 26] | | |
| DNA | Caatctgccctgactcagcctgcctccgtgtctgggtctcctggacagtcgatcaccatctcctgcactggaaccag ccgtgacgttggtggttataactatgtctcctggtaccaacagtacccaggcaaagccccaaactcatgatttatga ggtcagtaagcggccctcaggggtttctaatcgcttctctggctccaagtctggcaacacggcctccctgaccatct ctgggctccaggctgaggacgaggctgattattactgcagctcatataccagtagcagcactttagacttcggaact gggaccaaggtcaccgtcctaggt [SEQ ID NO: 28] | | |
| scFv | QSALTQPASVSGSPGQSITISCTGTSRDVGGYNYVSWYQQYPGKAPKLM IYEVSKRPSGVSNRFSGSKSGNTASLTISGLQAEDEADYYCSSYTSSSTLD FGTGTKVTVLGSRGGGGSGGGGSGGGGSLEMAQVQLVQSGAEVKQPG ASVKVSCQASGYTFTTYYMHWVRQAPGQGLEWMGIINPNGGGTFYAQ KFQDRVTMTRDTSTGTVYMELSSLRSDDTAVYYCARGHKVYKSHPTG GYDRWGQGTLVTVSS [SEQ ID NO: 106] | | |

In certain embodiments, the antibody or other antigen binding protein is an anti-GPRC5D scFv or an antigen-binding fragment thereof having an antigen-binding region that comprises the amino acid sequence of SEQ ID NO: 107 and specifically binds to a GPRC5D polypeptide (e.g., a GPRC5D polypeptide having the amino acid sequence SEQ ID NO:97, or fragments thereof), which is designated as ET150-157 scFv (also referred to as "ET150-7 scFv").

In certain embodiments, the anti-GPRC5D scFv antibody comprises a heavy chain variable region comprising amino acids having the sequence set forth in SEQ ID NO:29 and a light chain variable region comprising amino acids having the sequence set forth in SEQ ID NO:30, optionally with (iii) having the sequence set forth in SEQ ID NO:167 or conservative modifications thereof, and a V<sub>H</sub> CDR3 comprising amino acids having the sequence set forth in SEQ ID NO:168 or conservative modifications thereof, as shown in Table 8. In certain embodiments, the anti-GPRC5D scFv comprises a V<sub>L</sub> CDR1 comprising amino acids having the sequence set forth in SEQ ID NO:169 or conservative modifications thereof, a V<sub>L</sub> CDR2 comprising amino acids having the sequence set forth in SEQ ID NO:170 or conservative modifications thereof, and a V<sub>L</sub> CDR3 comprising amino acids having the sequence set forth in SEQ ID NO:171 or conservative modifications thereof, as shown in Table 8. In certain embodiments, the anti-GPRC5D scFv comprises a V_H CDR1 comprising amino acids having the sequence set forth in SEQ ID NO:166 or conservative modifications thereof, a V_H CDR2 comprising amino acids having the sequence set forth in SEQ ID NO:167 or conservative modifications thereof, a V_H CDR3 comprising amino acids having the sequence set forth in SEQ ID NO:168 or conservative modifications thereof, a V_L CDR1 comprising amino acids having the sequence set forth in SEQ ID NO:169 or conservative modifications thereof, a V_L CDR2 comprising amino acids having the sequence set forth in SEQ ID NO:170 or conservative modifications thereof, and a V_L CDR3 comprising amino acids having the sequence set forth in SEQ ID NO:171 or conservative modifications thereof, as shown in Table 8. In certain embodiments, the anti-GPRC5D scFv comprises a V_H CDR1 comprising amino acids having the sequence set forth in SEQ ID NO:166, a V_H CDR2 comprising amino acids having the sequence set forth in SEQ ID NO:167, a V_H CDR3 comprising amino acids having the sequence set forth in SEQ ID NO:168, a V_L CDR1 comprising amino acids having the sequence set forth in SEQ ID NO:169, a V_L CDR2 comprising amino acids having the sequence set forth in SEQ ID NO:170, and a V_L CDR3 comprising amino acids having the sequence set forth in SEQ ID NO:171.

In certain embodiments, the anti-GPRC5D scFv antibody comprises a heavy chain variable region comprising amino acids having the sequence set forth in SEQ ID NO:33 and a light chain variable region comprising amino acids having the sequence set forth in SEQ ID NO:34, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 9. In certain embodiments, the anti-GPRC5D scFv comprises a V_H comprising amino acids having the sequence set forth in SEQ ID NO:33, as shown in Table 9. In certain embodiments, the anti-GPRC5D scFv comprises a V_L comprising amino acids having the sequence set forth in SEQ ID NO:34, as shown in Table 9. In certain embodiments, the anti-GPRC5D scFv comprises a V_H comprising amino acids having the sequence set forth in SEQ ID NO:33 and a V_L comprising amino acids having the sequence set forth in SEQ ID NO:34, as shown in Table 9. In certain embodiments, the anti-GPRC5D scFv comprises a V_H CDR1 comprising amino acids having the sequence set forth in SEQ ID NO:172 or conservative

TABLE 8

| Antigen | A GPRC5D polypeptide having the amino acid sequence of SEQ ID NO: 97 | | |
|---|---|---|---|
| CDRs | 1 | 2 | 3 |
| V_H | GGTFSSYA [SEQ ID NO: 166] | IIPIFGTA [SEQ ID NO: 167] | ARSHVAWSLLDY [SEQ ID NO: 168] |
| V_L | SSNIGSNY [SEQ ID NO: 169] | RNN [SEQ ID NO: 170] | AAWDDSLSGVV [SEQ ID NO: 171] |
| Full V_H | EVQLVQSGAEVKKPGSSVKVSCKASGGTFSSYAISWVRQAPGQGLEWMGGIIPIFGTAKYAQKFQGRVTITADESTSTAYMELSSLRSEDTAVYYCARSHVAWSLLDYWGQGTLVTVSS [SEQ ID NO: 29] | | |
| DNA | Gaggtccagctggtgcagtctggggctgaggtgaagaagcctgggtcctcggtgaaggtctcctgcaaggcttctggaggcacctttcagcagctatgctatcagctgggtgcgacaggcccctggacaagggcttgagtggatgggagggattatccctatctttggtacagcaaaatatgcacagaagttccagggcagagtcacgattaccgcggacgaatccacgagcacagcctacatggagctgagcagcctgagatctgaggacacggccgtgtattactgtgcgcgctctcatgttgcttggtctctgctggattactggggtcaaggtactctggtgaccgtctcctca [SEQ ID NO: 31] | | |
| Full V_L | SYELTQPPSASGTPGQRVTISCSGSSSNIGSNYVSWYQQLPGTAPKWYRNNQRPSGVPDRFSGSKSGTSASLAISGLRSEDEADYYCAAWDDSLSGVVFGGGTKLTVLG [SEQ ID NO: 30] | | |
| DNA | Tcctatgagctgactcagccaccctcagcgtctgggaccccgggcagagggtcaccatctcttgttctggaagcagctccaacatcggaagtaattatgtatcctggtaccagcagctcccaggaacggcccccaaactcctcatctataggaataatcagcggccctcaggggtccctgaccgattctctggctccaagtctggcacctcagcctccctggccatcagtgggctccggtccgaggatgaggctgattattactgtgcagcatgggatgacagcctgagtggtgtggttattcggcggagggaccaagctgaccgtcctaggt [SEQ ID NO: 32] | | |
| scFv | SYELTQPPSASGTPGQRVTISCSGSSSNIGSNYVSWYQQLPGTAPKWYRNNQRPSGVPDRFSGSKSGTSASLAISGLRSEDEADYYCAAWDDSLSGVVFGGGTKLTVLGSRGGGSGGGGSGGGGSLEMAEVQLVQSGAEVKKPGSSVKVSCKASGGTFSSYAISWVRQAPGQGLEWMGGIIPIFGTAKYAQKFQGRVTITADESTSTAYMELSSLRSEDTAVYYCARSHVAWSLLDYWGQGTLVTVSS [SEQ ID NO: 107] | | |

In certain embodiments, the antibody or other antigen binding protein is an anti-GPRC5D scFv or an antigen-binding fragment thereof having an antigen-binding region that comprises the amino acid sequence of SEQ ID NO: 108 and specifically binds to a GPRC5D polypeptide (e.g., a GPRC5D polypeptide having the amino acid sequence SEQ ID NO:97, or fragments thereof), which is designated as ET150-159 scFv (also referred to as "ET150-9 scFv").

modifications thereof, a V_H CDR2 comprising amino acids having the sequence set forth in SEQ ID NO:173 or conservative modifications thereof, and a V_H CDR3 comprising amino acids having the sequence set forth in SEQ ID NO:174 or conservative modifications thereof, as shown in Table 9. In certain embodiments, the anti-GPRC5D scFv comprises a V_L CDR1 comprising amino acids having the sequence set forth in SEQ ID NO:175 or conservative modifications thereof, a V_L CDR2 comprising amino acids having the sequence set forth in SEQ ID NO:176 or conservative modifications thereof, and a $V_L$ CDR3 comprising amino acids having the sequence set forth in SEQ ID NO:177 or conservative modifications thereof, as shown in Table 9. In certain embodiments, the anti-GPRC5D scFv comprises a $V_H$ CDR1 comprising amino acids having the sequence set forth in SEQ ID NO:172 or conservative modifications thereof, a $V_H$ CDR2 comprising amino acids having the sequence set forth in SEQ ID NO:173 or conservative modifications thereof, a $V_H$ CDR3 comprising amino acids having the sequence set forth in SEQ ID NO:174 or conservative modifications thereof, a $V_L$ CDR1 comprising amino acids having the sequence set forth in SEQ ID NO:175 or conservative modifications thereof, a $V_L$ CDR2 comprising amino acids having the sequence set forth in SEQ ID NO:176 or conservative modifications thereof, and a $V_L$ CDR3 comprising amino acids having the sequence set forth in SEQ ID NO:177 or conservative modifications thereof, as shown in Table 9. In certain embodiments, the anti-GPRC5D scFv comprises a $V_H$ CDR1 comprising amino acids having the sequence set forth in SEQ ID NO:172, a $V_H$ CDR2 comprising amino acids having the sequence set forth in SEQ ID NO:173, a $V_H$ CDR3 comprising amino acids having the sequence set forth in SEQ ID NO:174, a $V_L$ CDR1 comprising amino acids having the sequence set forth in SEQ ID NO:175, a $V_L$ CDR2 comprising amino acids having the sequence set forth in SEQ ID NO:176, and a $V_L$ CDR3 comprising amino acids having the sequence set forth in SEQ ID NO:177.

GPRC5D polypeptide having the amino acid sequence SEQ ID NO:97, or fragments thereof), which is designated as ET150-160 scFv (also referred to as "ET150-10 scFv").

In certain embodiments, the anti-GPRC5D scFv antibody comprises a heavy chain variable region comprising amino acids having the sequence set forth in SEQ ID NO:37 and a light chain variable region comprising amino acids having the sequence set forth in SEQ ID NO:38, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 10. In certain embodiments, the anti-GPRC5D scFv comprises a $V_H$ comprising amino acids having the sequence set forth in SEQ ID NO:37, as shown in Table 10. In certain embodiments, the anti-GPRC5D scFv comprises a $V_L$ comprising amino acids having the sequence set forth in SEQ ID NO:38, as shown in Table 10. In certain embodiments, the anti-GPRC5D scFv comprises a $V_H$ comprising amino acids having the sequence set forth in SEQ ID NO:37 and a $V_L$ comprising amino acids having the sequence set forth in SEQ ID NO:38, as shown in Table 10. In certain embodiments, the anti-GPRC5D scFv comprises a $V_H$ CDR1 comprising amino acids having the sequence set forth in SEQ ID NO:178 or conservative

TABLE 9

| Antigen | A GPRC5D polypeptide having the amino acid sequence of SEQ ID NO: 97 | | |
|---|---|---|---|
| CDRs | 1 | 2 | 3 |
| $V_H$ | GGTFSSYA [SEQ ID NO: 172] | MNPNSGNT [SEQ ID NO: 173] | ARYQSYKGSQSD S [SEQ ID NO: 174] |
| $V_L$ | SSNIGSNY [SEQ ID NO: 175] | RNN [SEQ ID NO: 176] | AAWDDSLSGWV [SEQ ID NO: 177] |
| Full $V_H$ | QVQLVQSGAEVKKPGSSVKVSCKASGGTFSSYAISWVRQAPGQGL EWMGWMNPNSGNTGYAQKFQGRVTMTRNTSISTAYMELSSLRSE DTAVYYCARYQSYKGSQSDSWGQGTLVTVSS [SEQ ID NO: 33] | | |
| DNA | Caggtgcagctggtgcagtctggggctgaggtgaagaagcctgggtcctcagtgaaggtctcctgcaag gcttctggaggcaccttcagcagctatgctatcagctgggtgcgacaggcccctggacaagggcttgagt ggatgggatggatgaaccctaacagtggtaacacaggctatgcacagaagttccagggcagagtcaccat gaccaggaacacctccataagcacagcctacatggagctgagcagcctgagatctgaggacacggccgt gtattactgtgcgcgctaccagtcttacaaaggttctcagtctgattcttggggtcaaggtactctggtgaccg tctcctca [SEQ ID NO: 35] | | |
| Full $V_L$ | QSVLTQPPSASGTPGQRVTISCSGSSSNIGSNYVYWYQQLPGTAPK LLIYRNNQRPSGVPDRFSGSKSGTSASLAISGLRSEDEADYYCAAW DDSLSGWVFGGGTKLTVLG [SEQ ID NO: 34] | | |
| DNA | Cagtctgtgttgacgcagccaccctcagcgtctggaccccggcagagggtcaccatctcttgttctg gaagcagctccaacatcggaagtaattatgtatactggtaccagcagctcccaggaacggcccccaaact cctcatctataggaataatcagcggccctcaggggtccctgaccgattctctggctccaagtctggcacctc agcctcccctggccatcagtgggctccggtccgaggatgaggctgattattactgtgcagcatgggatgaca gcctgagtggttgggtgttcggcggagggaccaagctgaccgtcctaggt [SEQ ID NO: 36] | | |
| scFv | QSVLTQPPSASGTPGQRVTISCSGSSSNIGSNYVYWYQQLPGTAPK LLIYRNNQRPSGVPDRFSGSKSGTSASLAISGLRSEDEADYYCAAW DDSLSGWVFGGGTKLTVLGSRGGGGSGGGGSGGGGSLEMAQVQL VQSGAEVKKPGSSVKVSCKASGGTFSSYAISWVRQAPGQGLEWM GWMNPNSGNTGYAQKFQGRVTMTRNTSISTAYMELSSLRSEDTA VYYCARYQSYKGSQSDSWGQGTLVTVSS [SEQ ID NO: 108] | | |

In certain embodiments, the antibody or other antigen binding protein is an anti-GPRC5D scFv or an antigen-binding fragment thereof having an antigen-binding region that comprises the amino acid sequence of SEQ ID NO: 109 and specifically binds to a GPRC5D polypeptide (e.g., a modifications thereof, a $V_H$ CDR2 comprising amino acids having the sequence set forth in SEQ ID NO:179 or conservative modifications thereof, and a $V_H$ CDR3 comprising amino acids having the sequence set forth in SEQ ID NO:180 or conservative modifications thereof, as shown in Table 10. In certain embodiments, the anti-GPRC5D scFv comprises a $V_L$ CDR1 comprising amino acids having the sequence set forth in SEQ ID NO:181 or conservative modifications thereof, a $V_L$ CDR2 comprising amino acids having the sequence set forth in SEQ ID NO:182 or conservative modifications thereof, and a $V_L$ CDR3 comprising amino acids having the sequence set forth in SEQ ID NO:183 or conservative modifications thereof, as shown in Table 10. In certain embodiments, the anti-GPRC5D scFv comprises a $V_H$ CDR1 comprising amino acids having the sequence set forth in SEQ ID NO:178 or conservative modifications thereof, a $V_H$ CDR2 comprising amino acids having the sequence set forth in SEQ ID NO:179 or conservative modifications thereof, a $V_H$ CDR3 comprising amino acids having the sequence set forth in SEQ ID NO:180 or conservative modifications thereof, a $V_L$ CDR1 comprising amino acids having the sequence set forth in SEQ ID NO:181 or conservative modifications thereof, a $V_L$ CDR2 comprising amino acids having the sequence set forth in SEQ ID NO:182 or conservative modifications thereof, and a $V_L$ CDR3 comprising amino acids having the sequence set forth in SEQ ID NO:183 or conservative modifications thereof, as shown in Table 10. In certain embodiments, the anti-GPRC5D scFv comprises a $V_H$ CDR1 comprising amino acids having the sequence set forth in SEQ ID NO:178, a $V_H$ CDR2 comprising amino acids having the sequence set forth in SEQ ID NO:179, a $V_H$ CDR3 comprising amino acids having the sequence set forth in SEQ ID NO:180, a $V_L$ CDR1 comprising amino acids having the sequence set forth in SEQ ID NO:181, a $V_L$ CDR2 comprising amino acids having the sequence set forth in SEQ ID NO:182, and a $V_L$ CDR3 comprising amino acids having the sequence set forth in SEQ ID NO:183.

TABLE 10

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 178] | INPSGGST [SEQ ID NO: 179] | ARGGSKKWSGEKW RRENFDY [SEQ ID NO: 180] |
| VL | SSDVGGYNY [SEQ ID NO: 181] | DVS [SEQ ID NO: 182] | SSYTRSSTEV [SEQ ID NO: 183] |
| Full $V_H$ | EVQLVQSGAEVKKPGASVKVSCKASGYTFTSYYMHWVRQAPGQG LEWMGIINPSGGSTSYAQKFQGRVTMTRDTSTSTVYMELSSLRSED TAVYYCARGGSKKWSGEKWRRENFDYWGQGTLVTVSS [SEQ ID NO: 37] | | |
| DNA | Gaggtccagctggtacagtctggggctgaggtgaagaagcctggggcctcagtgaaggtttcctgcaagg catctggatacaccttcaccagctactatatgcactggtgcgacaggcccctggacaagggcttgagtgga tgggaataatcaaccctagtggtggtagcacaagctacgcacagaagttccagggcagagtcaccatgacc agggacacgtccacgagcacagtctcatggagctgagcagcctgagatctgaggacacggccgtgtatt actgtgcgcgcggtggttctaaaaaatggtctggtgaaaaatggcgtcgtgaaaacttcgattactggggtca aggtactctggtgaccgtctcctca [SEQ ID NO: 39] | | |
| Full $V_L$ | QSALTQPASVSGSPGQSITISCTGTSSDVGGYNYVSWYQQHPGKAP KLMIYDVSKRPSGVSNRFSGSKSGNTASLTISGLQAEDEADYYCSSY TRSSTEVFGGGTKLTVLG [SEQ ID NO: 38] | | |
| DNA | Caatctgccctgactcagcctgcctccgtgtctgggtctcctggacagtcgatcaccatctcctgcactggaa ccagcagtgacgttggtggttataactatgtctcctggtaccaacagcacccaggcaaagcccccaaactca tgatttatgatgtcagtaagcggccctcaggggtttctaatcgcttctctggctccaagtctggcaacacggcc tccctgaccatctctgggctccaggctgaggacgaggctgattattactgcagctcatatacaagaagcagc actgaggtattcggcggagggaccaagctgaccgtcctaggt [SEQ ID NO: 40] | | |
| scFv | QSALTQPASVSGSPGQSITISCTGTSSDVGGYNYVSWYQQHPGKAP KLMIYDVSKRPSGVSNRFSGSKSGNTASLTISGLQAEDEADYYCSSY TRSSTEVFGGGTKLTVLGSRGGGGSGGGGSGGGGSLEMAEVQLVQ SGAEVKKPGASVKVSCKASGYTFTSYYMHWVRQAPGQGLEWMGI INPSGGSTSYAQKFQGRVTMTRDTSTSTVYMELSSLRSEDTAVYYC ARGGSKKWSGEKWRRENFDYWGQGTLVTVSS [SEQ ID NO: 109] | | |

In certain embodiments, the antibody or other antigen binding protein is an anti-GPRC5D scFv or an antigen-binding fragment thereof having an antigen-binding region that comprises the amino acid sequence of SEQ ID NO: 110 and specifically binds to a GPRC5D polypeptide (e.g., a GPRC5D polypeptide having the amino acid sequence SEQ ID NO:97, or fragments thereof), which is designated as ET150-161 scFv (also referred to as "ET150-11 scFv").

In certain embodiments, the anti-GPRC5D scFv antibody comprises a heavy chain variable region comprising amino acids having the sequence set forth in SEQ ID NO:41 and a light chain variable region comprising amino acids having the sequence set forth in SEQ ID NO:42, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 11. In certain embodiments, the anti-GPRC5D scFv comprises a $V_H$ comprising amino acids having the sequence set forth in SEQ ID NO:41, as shown in Table 11. In certain embodiments, the anti-GPRC5D scFv comprises a $V_L$ comprising amino acids having the sequence set forth in SEQ ID NO:42, as shown in Table 11. In certain embodiments, the anti-GPRC5D scFv comprises a V_H comprising amino acids having the sequence set forth in SEQ ID NO:41 and a V_L comprising amino acids having the sequence set forth in SEQ ID NO:42, as shown in Table 11. In certain embodiments, the anti-GPRC5D scFv comprises a V_H CDR1 comprising amino acids having the sequence set forth in SEQ ID NO:184 or conservative modifications thereof, a V_H CDR2 comprising amino acids having the sequence set forth in SEQ ID NO: 185 or conservative modifications thereof, and a V_H CDR3 comprising amino acids having the sequence set forth in SEQ ID NO: 186 or conservative modifications thereof, as shown in Table 11. In certain embodiments, the anti-GPRC5D scFv thereof, as shown in Table 11. In certain embodiments, the anti-GPRC5D scFv comprises a V_H CDR1 comprising amino acids having the sequence set forth in SEQ ID NO: 184, a V_H CDR2 comprising amino acids having the sequence set forth in SEQ ID NO: 185, a V_H CDR3 comprising amino acids having the sequence set forth in SEQ ID NO: 186, a V_L CDR1 comprising amino acids having the sequence set forth in SEQ ID NO: 187, a V_L CDR2 comprising amino acids having the sequence set forth in SEQ ID NO: 188, and a V_L CDR3 comprising amino acids having the sequence set forth in SEQ ID NO: 189.

TABLE 11

| Antigen | A GPRC5D polypeptide having the amino acid sequence of SEQ ID NO: 97 | | |
|---|---|---|---|
| CDRs | 1 | 2 | 3 |
| V_H | EYTFTRHI [SEQ ID NO: 184] | INPGNGNT [SEQ ID NO: 185] | ARLPDQ [SEQ ID NO: 186] |
| V_L | SSNIGSNT [SEQ ID NO: 187] | RNN [SEQ ID NO: 188] | AAWDDSLSGL [SEQ ID NO: 189] |
| Full V_H | QMQLVQSGAEVKKPGASVKVSCKASEYTFTRHILHWVRQAPGQSLEWMGWINPGNGNTKYSQKFQVRVTFTRDTSASTVYMELSSLRSEDTAVYYCARLPDQWGQGTLVTVSS [SEQ ID NO: 41] | | |
| DNA | Cagatgcagctggtgcagtctggggctgaggtgaagaagcctggggcctcagtgaaggtttcctgcaaggcttctgaatacaccttcactaggcatattctacattgggtgcgccaggctcccggacaaagccttgagtggatgggatggatcaacccaggcaatggtaatacaaaatattcacagaagttccaggtcagagtcacctttaccagggacacatccgcgagcacagtctatatggagctgagcagcctgagatctgaagacacggccgtgtattactgtgcgcgcctgccggatcagtgggtcaaggtactctggtgaccgtctcctca [SEQ ID NO: 43] | | |
| Full V_L | SYVLTQPPSASGTPGQRVTISCSGSSSNIGSNTVNWYQQLPGTAPKLLIYRNNQRPSGVPDRFSGSKSGTSASLAISGLRSEDEADYYCAAWDDSLSGLFGTGTKVTVLG [SEQ ID NO: 42] | | |
| DNA | Tcctatgtgctgactcagccaccctcagcgtctgggaccccgggcagagggtcaccatctcttgttctggaagcagctccaacatcggaagtaatactgtaaactggtaccagcagctcccaggaacggcccccaaactcctcatctataggaataatcagcggccctcaggggtccctgaccgattctctggctccaagtctggcacctcagcctccctggccatcagtgggctccggtccgaggatgaggctgattattactgtgcagcatgggatgacagcctgagtggtctcttcggaactgggaccaaggtcaccgtcctaggt [SEQ ID NO: 44] | | |
| scFv | SYVLTQPPSASGTPGQRVTISCSGSSSNIGSNTVNWYQQLPGTAPKLLIYRNNQRPSGVPDRFSGSKSGTSASLAISGLRSEDEADYYCAAWDDSLSGLFGTGTKVTVLGSRGGGGSGGGGSGGGGSLEMAQMQLVQSGAEVKKPGASVKVSCKASEYTFTRHILHWVRQAPGQSLEWMGWINPGNGNTKYSQKFQVRVTFTRDTSASTVYMELSSLRSEDTAVYYCARLPDQWGQGTLVTVSS [SEQ ID NO: 110] | | | comprises a V_L CDR1 comprising amino acids having the sequence set forth in SEQ ID NO: 187 or conservative modifications thereof, a V_L CDR2 comprising amino acids having the sequence set forth in SEQ ID NO: 188 or conservative modifications thereof, and a V_L CDR3 comprising amino acids having the sequence set forth in SEQ ID NO: 189 or conservative modifications thereof, as shown in Table 11. In certain embodiments, the anti-GPRC5D scFv comprises a V_H CDR1 comprising amino acids having the sequence set forth in SEQ ID NO: 184 or conservative modifications thereof, a V_H CDR2 comprising amino acids having the sequence set forth in SEQ ID NO: 185 or conservative modifications thereof, a V_H CDR3 comprising amino acids having the sequence set forth in SEQ ID NO: 186 or conservative modifications thereof, a V_L CDR1 comprising amino acids having the sequence set forth in SEQ ID NO: 187 or conservative modifications thereof, a V_L CDR2 comprising amino acids having the sequence set forth in SEQ ID NO: 188 or conservative modifications thereof, and a V_L CDR3 comprising amino acids having the sequence set forth in SEQ ID NO: 189 or conservative modifications In certain embodiments, the antibody or other antigen binding protein is an anti-GPRC5D scFv or an antigen-binding fragment thereof having an antigen-binding region that comprises the amino acid sequence of SEQ ID NO: 111 and specifically binds to a GPRC5D polypeptide (e.g., a GPRC5D polypeptide having the amino acid sequence SEQ ID NO:97, or fragments thereof), which is designated as ET150-162 scFv (also referred to as "ET150-12 scFv").

In certain embodiments, the anti-GPRC5D scFv antibody comprises a heavy chain variable region comprising amino acids having the sequence set forth in SEQ ID NO:45 and a light chain variable region comprising amino acids having the sequence set forth in SEQ ID NO:46, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 12. In certain embodiments, the anti-GPRC5D scFv comprises a V_H comprising amino acids having the sequence set forth in SEQ ID NO:45, as shown in Table 12. In certain embodiments, the anti-GPRC5D scFv comprises a $V_L$ comprising amino acids having the sequence set forth in SEQ ID NO:46, as shown in Table 12. In certain embodiments, the anti-GPRC5D scFv comprises a $V_H$ comprising amino acids having the sequence set forth in SEQ ID NO:45 and a $V_L$ comprising amino acids having the sequence set forth in SEQ ID NO:46, as shown in Table 12. In certain embodiments, the anti-GPRC5D scFv comprises a $V_H$ CDR1 comprising amino acids having the sequence set forth in SEQ ID NO:190 or conservative modifications thereof, a $V_H$ CDR2 comprising amino acids having the sequence set forth in SEQ ID NO: 191 or conservative modifications thereof, and a $V_H$ CDR3 comprising amino acids having the sequence set forth in SEQ ID NO: 192 or conservative modifications thereof, as shown in Table 12. In certain embodiments, the anti-GPRC5D scFv comprises a $V_L$ CDR1 comprising amino acids having the sequence set forth in SEQ ID NO: 193 or conservative modifications thereof, a $V_L$ CDR2 comprising amino acids having the sequence set forth in SEQ ID NO: 194 or conservative modifications thereof, and a $V_L$ CDR3 comprising amino acids having the sequence set forth in SEQ ID NO: 195 or conservative modifications thereof, as shown in Table 12. In certain embodiments, the anti-GPRC5D scFv comprises a $V_H$ CDR1 comprising amino acids having the sequence set forth in SEQ ID NO: 190, a $V_H$ CDR2 comprising amino acids having the sequence set forth in SEQ ID NO: 191, a $V_H$ CDR3 comprising amino acids having the sequence set forth in SEQ ID NO: 192, a $V_L$ CDR1 comprising amino acids having the sequence set forth in SEQ ID NO: 193, a $V_L$ CDR2 comprising amino acids having the sequence set forth in SEQ ID NO: 194, and a $V_L$ CDR3 comprising amino acids having the sequence set forth in SEQ ID NO: 195.

TABLE 12

| Antigen | A GPRC5D polypeptide having the amino acid sequence of SEQ ID NO: 97 | | |
|---|---|---|---|
| CDRs | 1 | 2 | 3 |
| $V_H$ | GFTFGDYG [SEQ ID NO: 190] | INWNGGST [SEQ ID NO: 191] | ARSKQDY [SEQ ID NO: 192] |
| $V_L$ | SRDAGGYNY [SEQ ID NO: 193] | EVT [SEQ ID NO: 194] | SSYGGSNNFRV [SEQ ID NO: 195] |
| Full $V_H$ | EVQLVESGGGVVRPGGSLRLSCAASGFTFGDYGMSWVRQAPGKG LEWVSGINWNGGSTGYADSVKGRFTISRDNAKNSLYLQMNSLRA EDTAVYYCARSKQDYWGQGTLVTVSS [SEQ ID NO: 45] | | |
| DNA | Gaggtgcagctggtggagtctgggggaggtgtggtacggcctgggggtccctgagactctcctgtgca gcctctggattcacctttggtgattatggcatgagctgggtccgccaagctccagggaaggggctggagtg ggtctctggtattaattggaatggtggtagcacaggttatgcagactctgtgaagggccgattcaccatctcc agagacaacgccaagaactccctgtatctgcaaatgaacagtctgagagccgaggacacggccgtatatt actgtgcgcgctctaaacaggattactggggtcaaggtactctggtgaccgtctcctca [SEQ ID NO: 47] | | |
| Full $V_L$ | QSALTQPPSASGSPGQSVTISCTGTSRDAGGYNYFSWYQQHPGKA PKWYEVTKRPSGVPDRFSGSKSGKTASLTVSGLQADDEAVYYCS SYGGSNNFRVFGGGTKLTVLG [SEQ ID NO: 46] | | |
| DNA | Cagtctgccctgactcagcctccctccgcgtccgggtctcctggacagtcagtcaccatctcctgcactgg aaccagcagggacgctggtggttataattatttctcctggtaccaacaacacccaggcaaagcccccaaac tcctgatttatgaggtcactaagcggccctcaggggtccctgatcgcttctctggctccaagtctggcaaga cggcctccctgaccgtctctgggctccaggctgacgatgaggctgtatattactgcagctcatatggaggc agcaacaactttcgggtgttcggcggagggaccaagctgaccgtcctaggt [SEQ ID NO: 48] | | |
| scFv | QSALTQPPSASGSPGQSVTISCTGTSRDAGGYNYFSWYQQHPGKA PKWYEVTKRPSGVPDRFSGSKSGKTASLTVSGLQADDEAVYYCS SYGGSNNFRVFGGGTKLTVLGSRGGGGSGGGGSGGGGSLEMAEV QLVESGGGVVRPGGSLRLSCAASGFTFGDYGMSWVRQAPGKGLE WVSGINWNGGSTGYADSVKGRFTISRDNAKNSLYLQMNSLRAED TAVYYCARSKQDYWGQGTLVTVSS [SEQ ID NO: 111] | | |

In certain embodiments, the antibody or other antigen binding protein is an anti-GPRC5D scFv or an antigen-binding fragment thereof having an antigen-binding region that comprises the amino acid sequence of SEQ ID NO: 112 and specifically binds to a GPRC5D polypeptide (e.g., a GPRC5D polypeptide having the amino acid sequence SEQ ID NO:97, or fragments thereof), which is designated as ET150-163 scFv (also referred to as "ET150-13 scFv").

In certain embodiments, the anti-GPRC5D scFv antibody comprises a heavy chain variable region comprising amino acids having the sequence set forth in SEQ ID NO:49 and a light chain variable region comprising amino acids having the sequence set forth in SEQ ID NO:50, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 13. In certain embodiments, the anti-GPRC5D scFv comprises a $V_H$ comprising amino acids having the sequence set forth in SEQ ID NO:49, as shown in Table 13. In certain embodiments, the anti-GPRC5D scFv comprises a $V_L$ comprising amino acids having the sequence set forth in SEQ ID NO:50, as shown in Table 13. In certain embodiments, the anti-GPRC5D scFv comprises a $V_H$ comprising amino acids having the sequence set forth in SEQ ID NO:49 and a $V_L$ comprising amino acids having the sequence set forth in SEQ ID NO:50, as shown in Table 13. In certain embodiments, the anti-GPRC5D scFv comprises a $V_H$ CDR1 comprising amino acids having the sequence set forth in SEQ ID NO:196 or conservative modifications thereof, a $V_H$ CDR2 comprising amino acids having the sequence set forth in SEQ ID NO: 197 or conservative modifications thereof, and a $V_H$ CDR3 comprising amino acids having the sequence set forth in SEQ ID NO: 198 or conservative modifications thereof, as shown in modifications thereof, a $V_H$ CDR2 comprising amino acids having the sequence set forth in SEQ ID NO: 197 or conservative modifications thereof, a $V_H$ CDR3 comprising amino acids having the sequence set forth in SEQ ID NO: 198 or conservative modifications thereof, a $V_L$ CDR1 comprising amino acids having the sequence set forth in SEQ ID NO: 199 or conservative modifications thereof, a $V_L$ CDR2 comprising amino acids having the sequence set forth in SEQ ID NO:200 or conservative modifications thereof, and a $V_L$ CDR3 comprising amino acids having the sequence set forth in SEQ ID NO:201 or conservative modifications thereof, as shown in Table 13. In certain embodiments, the anti-GPRC5D scFv comprises a $V_H$ CDR1 comprising amino acids having the sequence set forth in SEQ ID NO: 196, a $V_H$ CDR2 comprising amino acids having the sequence set forth in SEQ ID NO: 197, a $V_H$ CDR3 comprising amino acids having the sequence set forth in SEQ ID NO: 198, a $V_L$ CDR1 comprising amino acids having the sequence set forth in SEQ ID NO: 199, a $V_L$ CDR2 comprising amino acids having the sequence set forth in SEQ ID NO:200, and a $V_L$ CDR3 comprising amino acids having the sequence set forth in SEQ ID NO:201.

TABLE 13

| Antigen | A GPRC5D polypeptide having the amino acid sequence of SEQ ID NO: 97 | | |
|---|---|---|---|
| CDRs | 1 | 2 | 3 |
| $V_H$ | GFSFSGTA [SEQ ID NO: 196] | ISSTGRST [SEQ ID NO: 197] | ARVSFDY [SEQ ID NO: 198] |
| $V_L$ | SSNIGAGYD [SEQ ID NO: 199] | GNS [SEQ ID NO: 200] | QSYDSSLSGSYV [SEQ ID NO: 201] |
| Full $V_H$ | EVQLVETGGNLVQPGASLRLSCAASGFSFSGTAMHWVRQAPGKGLE WVSTISSTGRSTYYRDSVKGRFTISRDNSKNTLYLQMNSLRGEDTAV YYCARVSFDYWGQGTLVTVSS [SEQ ID NO: 49] | | |
| DNA | Gaggtgcagctggtggagactggggggaaacttggtacagccgggggcgtccctgagactctcctgtgcagc ctctggattcagctttagtggcactgccatgcactgggtccgccaggctccagggaaggggctggaatgggtc tcgactattagtagtactgggcgtagcacatactacagagactccgtgaagggccggttcaccatctccagaga caattccaagaacacgctgtatctgcaaatgaacagcctgagaggcgaggacacggccgtatattactgtgcg cgcgtttctttcgattactgggtcaaggtactctggtgaccgtctcctca [SEQ ID NO: 51] | | |
| Full $V_L$ | QSVVTQPPSVSGAPGQRVTISCTGSSSNIGAGYDVHWYQQLPGTAPK LLIYGNSNRPSGVPDRFSGSKSGTSASLAITGLQAEDEADYYCQSYDS SLSGSYVFGTGTKLTVLG [SEQ ID NO: 50] | | |
| DNA | Cagtctgtcgtgacgcagccgcccctcagtgtctggggccccagggcagagggtcaccatctcctgcactggg agcagctccaacatcggggcaggttatgatgtacactggtaccagcagcttccaggaacagcccccaaactcc tcatctatggtaacagcaatcggccctcaggggtccctgaccgattctctggctccaagtctggcacctcagcct ccctggccatcactgggctccaggctgaggatgaggctgattattactgccagtcctatgacagcagcctgagt ggctcctacgtcttcggaactgggaccaagctgaccgtcctaggt [SEQ ID NO: 52] | | |
| scFv | QSVVTQPPSVSGAPGQRVTISCTGSSSNIGAGYDVHWYQQLPGTAPK LLIYGNSNRPSGVPDRFSGSKSGTSASLAITGLQAEDEADYYCQSYDS SLSGSYVFGTGTKLTVLGSRGGGGSGGGGSGGGGSLEMAEVQLVET GGNLVQPGASLRLSCAASGFSFSGTAMHWVRQAPGKGLEWVSTISST GRSTYYRDSVKGRFTISRDNSKNTLYLQMNSLRGEDTAVYYCARVSF DYWGQGTLVTVSS [SEQ ID NO: 112] | | |

Table 13. In certain embodiments, the anti-GPRC5D scFv comprises a $V_L$ CDR1 comprising amino acids having the sequence set forth in SEQ ID NO: 199 or conservative modifications thereof, a $V_L$ CDR2 comprising amino acids having the sequence set forth in SEQ ID NO:200 or conservative modifications thereof, and a $V_L$ CDR3 comprising amino acids having the sequence set forth in SEQ ID NO:201 or conservative modifications thereof, as shown in Table 13. In certain embodiments, the anti-GPRC5D scFv comprises a $V_H$ CDR1 comprising amino acids having the sequence set forth in SEQ ID NO: 196 or conservative In certain embodiments, the antibody or other antigen binding protein is an anti-GPRC5D scFv or an antigen-binding fragment thereof having an antigen-binding region that comprises the amino acid sequence of SEQ ID NO: 113 and specifically binds to a GPRC5D polypeptide (e.g., a GPRC5D polypeptide having the amino acid sequence SEQ ID NO:97, or fragments thereof), which is designated as ET150-151 scFv (also referred to as "ET150-1 scFv").

In certain embodiments, the anti-GPRC5D scFv antibody comprises a heavy chain variable region comprising amino acids having the sequence set forth in SEQ ID NO:53 and a light chain variable region comprising amino acids having the sequence set forth in SEQ ID NO:54, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 14. In certain embodiments, the anti-GPRC5D scFv comprises a $V_H$ comprising amino acids having the sequence set forth in SEQ ID NO:53, as shown in Table 14. In certain embodiments, the anti-GPRC5D scFv comprises a $V_L$ comprising amino acids having the sequence set forth in SEQ ID NO:54, as shown in Table 14. In certain embodiments, the anti-GPRC5D scFv comprises a $V_H$ comprising amino acids having the sequence set forth in SEQ ID NO:53 and a $V_L$ comprising amino acids having the sequence set forth in SEQ ID NO:54, as shown in Table 14. In certain embodiments, the anti-GPRC5D scFv comprises a $V_H$ CDR1 comprising amino acids having the sequence set forth in SEQ ID NO:202 or conservative modifications thereof, a $V_H$ CDR2 comprising amino acids having the sequence set forth in SEQ ID NO:203 or conservative modifications thereof, and a $V_H$ CDR3 comprising amino acids having the sequence set forth in SEQ ID NO: 204 or conservative modifications thereof, as shown in Table 14. In certain embodiments, the anti-GPRC5D scFv comprises a $V_L$ CDR1 comprising amino acids having the sequence set forth in SEQ ID NO: 205 or conservative modifications thereof, a $V_L$ CDR2 comprising amino acids having the sequence set forth in SEQ ID NO: 206 or conservative modifications thereof, and a $V_L$ CDR3 comprising amino acids having the sequence set forth in SEQ ID NO: 207 or conservative modifications thereof, as shown in Table 14. In certain embodiments, the anti-GPRC5D scFv comprises a $V_H$ CDR1 comprising amino acids having the sequence set forth in SEQ ID NO: 202 or conservative modifications thereof, a $V_H$ CDR2 comprising amino acids having the sequence set forth in SEQ ID NO: 203 or conservative modifications thereof, a $V_H$ CDR3 comprising amino acids having the sequence set forth in SEQ ID NO: 204 or conservative modifications thereof, a $V_L$ CDR1 comprising amino acids having the sequence set forth in SEQ ID NO: 205 or conservative modifications thereof, a $V_L$ CDR2 comprising amino acids having the sequence set forth in SEQ ID NO: 206 or conservative modifications thereof, and a $V_L$ CDR3 comprising amino acids having the sequence set forth in SEQ ID NO: 207 or conservative modifications thereof, as shown in Table 14. In certain embodiments, the anti-GPRC5D scFv comprises a $V_H$ CDR1 comprising amino acids having the sequence set forth in SEQ ID NO: 202, a $V_H$ CDR2 comprising amino acids having the sequence set forth in SEQ ID NO: 203, a $V_H$ CDR3 comprising amino acids having the sequence set forth in SEQ ID NO: 204, a $V_L$ CDR1 comprising amino acids having the sequence set forth in SEQ ID NO: 205, a $V_L$ CDR2 comprising amino acids having the sequence set forth in SEQ ID NO: 206, and a $V_L$ CDR3 comprising amino acids having the sequence set forth in SEQ ID NO: 207.

TABLE 14

| Antigen | A GPRC5D polypeptide having the amino acid sequence of SEQ ID NO: 97 | | |
|---|---|---|---|
| CDRs | 1 | 2 | 3 |
| $V_H$ | GFTFSSYA [SEQ ID NO: 202] | ISGRGRST [SEQ ID NO: 203] | ARYYHAGAFDL [SEQ ID NO: 204] |
| $V_L$ | SSDVGGYNY [SEQ ID NO: 205] | DVS [SEQ ID NO: 206] | SSYTSSSTLV [SEQ ID NO: 207] |
| Full $V_H$ | EVQLVESGGAFVQPGGSLRLSCAASGFTFSSYAMTWVRQAPGKGL EWVSTISGRGRSTFYADSVKGRFTISRDNSKNTLYLQMNSLRAEDT AVYYCARYYHAGAFDLWGQGTLVTVSS [SEQ ID NO: 53] | | |
| DNA | Gaggtgcagctggtggagtctgggggagcctttgtacagcctggggggtccctgagactctcctgtgcag cctctggattcacctttagcagctatgccatgacctggctccgccaggctccagggaagggcctggaatg ggtctcgactattagtggtcgtggtcgtagcacattctacgcagactccgtgaagggccggtttaccatctcc agagacaattccaagaacacgctatatctgcaaatgaacagtctgagagccgaggacacggccgtatatt actgtgcgcgctactaccatgctggtgctttcgatctgtggggtcaaggtactctggtgaccgtctcctca [SEQ ID NO: 55] | | |
| Full $V_L$ | QSVVTQPASVSGSPGQSITISCTGTSSDVGGYNYVSWYQQHPGKA PKLMIYDVSKRPSGVSNRFSGSKSGNTASLTISGLQAEDEADYYCS SYTSSSTLVFGGGTKLTVLG [SEQ ID NO: 54] | | |
| DNA | Cagtctgtcgtgacgcagcctgcctccgtgtctgggtctcctggacagtcgatcaccatctcctgcactgg aaccagcagtgacgttggtggttataactatgtctcctggtaccaacagcacccaggcaaagcccccaaac tcatgatttatgatgtcagtaagcggccctcaggggtttctaatcgcttctctggctccaagtctggcaacac ggcctccctgaccatctctgggctccaggctgaggacgaggctgattattactgcagctcatatacaagca gcagcactttggtattcggcggagggaccaagctgaccgtcctaggt [SEQ ID NO: 56] | | |
| scFv | QSVVTQPASVSGSPGQSITISCTGTSSDVGGYNYVSWYQQHPGKA PKLMIYDVSKRPSGVSNRFSGSKSGNTASLTISGLQAEDEADYYCS SYTSSSTLVFGGGTKLTVLGSRGGGGSGGGGSGGGGSLEMAEVQL VESGGAFVQPGGSLRLSCAASGFTFSSYAMTWVRQAPGKGLEWV STISGRGRSTFYADSVKGRFTISRDNSKNTLYLQMNSLRAEDTAVY YCARYYHAGAFDLWGQGTLVTVSS [SEQ ID NO: 113] | | | prises a $V_L$ CDR1 comprising amino acids having the sequence set forth in SEQ ID NO: 205 or conservative modifications thereof, a $V_L$ CDR2 comprising amino acids having the sequence set forth in SEQ ID NO: 206 or conservative modifications thereof, and a $V_L$ CDR3 com- In certain embodiments, the antibody or other antigen binding protein is an anti-GPRC5D scFv or an antigen-binding fragment thereof having an antigen-binding region that comprises the amino acid sequence of SEQ ID NO: 114 and specifically binds to a GPRC5D polypeptide (e.g., a GPRC5D polypeptide having the amino acid sequence SEQ ID NO:97, or fragments thereof), which is designated as ET150-152 scFv (also referred to as "ET150-2 scFv").

In certain embodiments, the anti-GPRC5D scFv antibody comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 15. In certain embodiments, the anti-GPRC5D scFv comprises a $V_H$ comprising amino acids having the sequence set forth in SEQ ID NO:57, as shown in Table 15. In certain embodiments, the anti-GPRC5D scFv comprises a $V_L$ comprising amino acids having the sequence set forth in SEQ ID NO:58, as shown in Table 15. In certain embodiments, the anti-GPRC5D scFv comprises a $V_H$ comprising amino acids having the sequence set forth in SEQ ID NO:57 and a $V_L$ comprising amino acids having the sequence set forth in SEQ ID NO:58, as shown in Table 15. In certain embodiments, the anti-GPRC5D scFv comprises a $V_H$ CDR1 comprising amino acids having the sequence set forth in SEQ ID NO:208 or conservative modifications thereof, a $V_H$ CDR2 comprising amino acids having the sequence set forth in SEQ ID NO: 209 or conservative modifications thereof, and a $V_H$ CDR3 comprising amino acids having the sequence set forth in SEQ ID NO: 210 or conservative modifications thereof, as shown in Table 15. In certain embodiments, the anti-GPRC5D scFv comprises a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof, as shown in Table 15. In certain embodiments, the anti-GPRC5D scFv comprises a $V_H$ CDR1 comprising amino acids having the sequence set forth in SEQ ID NO: 208 or conservative modifications thereof, a $V_H$ CDR2 comprising amino acids having the sequence set forth in SEQ ID NO: 209 or conservative modifications thereof, a $V_H$ CDR3 comprising amino acids having the sequence set forth in SEQ ID NO: 210 or conservative modifications thereof, a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof, as shown in Table 15. In certain embodiments, the anti-GPRC5D scFv comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213.

TABLE 15

| Antigen | A GPRC5D polypeptide having the amino acid sequence of SEQ ID NO: 97 | | |
|---------|------|------|------|
| CDRs | 1 | 2 | 3 |
| $V_H$ | GYTFNRYA [SEQ ID NO: 208] | ISAYNGNS [SEQ ID NO: 209] | ARMAYDS [SEQ ID NO: 210] |
| $V_L$ | SNDVGAYKY [SEQ ID NO: 211] | DVF [SEQ ID NO: 212] | FSLTSSNTYV [SEQ ID NO: 213] |
| Full $V_H$ | QMQLVQSGAEVKKPGASVKVCKASGYTFNRYAITWVRQAPGQGLE WMGWISAYNGNSHYAQKLQGRVTMTTDTSTGTAYMELRRLRSDDT AVYYCARMAYDSWGQGTLVTVSS [SEQ ID NO: 57] | | |
| DNA | Cagatgcagctggtgcagtctggagctgaggtgaagaagcctggggcctcagtgaaggtctcctgcaaggctt ctggttacacctttaacagatatgctatcacctgggtgcgacaggcccctggacaaggccttgagtggatgggat ggatcagcgcttacaatggtaattcacactatgcacagaagctccagggcagagtcaccatgaccacagacac atccacgggcacagcctatatggagctgaggaggctgagatctgacgacacggccgtgtattactgtgcgcgc atggcttacgattcttggggtcaaggtactctggtgaccgtctcctca [SEQ ID NO: 59] | | |
| Full $V_L$ | QSVLTQPASVSGSPGQSLTISCTGTSNDVGAYKYVSWYQQYPGKAPK LILYDVFKRPSGVSNRFSGSKSDNTASLTISGLQAEDEADYYCFSLTSS NTYVFGTGTKVTVLG [SEQ ID NO: 58] | | |
| DNA | Cagtctgtgttgacgcagcctgcctccgtgtctgggtctcctggacagtcgctcaccatctcctgcactggaacc agcaatgacgttggtgcttataagtatgtctcctggtatcaacagtaccaggcaaagcccccaaactcatacttta tgatgtctttaagcggccctcagggtctctaatcgcttctctggctccaagtctgacaacacggcctccctgacc atctctgggctccaggctgaggacgaggctgattattactgcttctcacttacaagcagtaacacttatgtcttcgg aactgggaccaaggtcaccgtcctaggt [SEQ ID NO: 60] | | |
| scFv | QSVLTQPASVSGSPGQSLTISCTGTSNDVGAYKYVSWYQQYPGKAPK ULYDVFKRPSGVSNRFSGSKSDNTASLTISGLQAEDEADYYCFSLTSS NTYVFGTGTKVTVLGSRGGGGSGGGGSGGGGSLEMAQMQLVQSGAE VKKPGASVKVSCKASGYTFNRYAITWVRQAPGQGLEWMGWISAYNG NSHYAQKLQGRVTMTTDTSTGTAYMELRRLRSDDTAVYYCARMAY DSWGQGTLVTVSS [SEQ ID NO: 114] | | |

In certain embodiments, the antibody or other antigen binding protein is an anti-GPRC5D scFv or an antigen-binding fragment thereof having an antigen-binding region that comprises the amino acid sequence of SEQ ID NO: 115 and specifically binds to a GPRC5D polypeptide (e.g., a GPRC5D polypeptide having the amino acid sequence SEQ ID NO:97, or fragments thereof), which is designated as ET150-155 scFv (also referred to as "ET150-5 scFv").

In certain embodiments, the anti-GPRC5D scFv antibody comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 16. In certain embodiments, the anti-GPRC5D scFv comprises a $V_H$ comprising amino acids having the sequence set forth in SEQ ID NO:61, as shown in Table 16. In certain embodiments, the anti-GPRC5D scFv comprises a $V_L$ comprising amino acids having the sequence set forth in SEQ ID NO:62, as shown in Table 16. In certain embodiments, the anti-GPRC5D scFv comprises a $V_H$ comprising amino acids having the sequence set forth in SEQ ID NO:61 and a $V_L$ comprising amino acids having the sequence set forth in SEQ ID NO:62, as shown in Table 16. In certain embodiments, the anti-GPRC5D scFv comprises a $V_H$ CDR1 comprising amino acids having the sequence set forth in SEQ ID NO:214 or conservative modifications thereof, a $V_H$ CDR2 comprising amino acids having the sequence set forth in SEQ ID NO: 215 or conservative modifications thereof, and a $V_H$ CDR3 comprising amino acids having the sequence set forth in SEQ ID NO: 216 or conservative modifications thereof, as shown in Table 16. In certain embodiments, the anti-GPRC5D scFv comprises a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof, as shown in Table 16. In certain embodiments, the anti-GPRC5D scFv comprises a $V_H$ CDR1 comprising amino acids having the sequence set forth in SEQ ID NO: 214 or conservative modifications thereof, a $V_H$ CDR2 comprising amino acids having the sequence set forth in SEQ ID NO: 215 or conservative modifications thereof, a $V_H$ CDR3 comprising amino acids having the sequence set forth in SEQ ID NO: 216 or conservative modifications thereof, a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof, as shown in Table 16. In certain embodiments, the anti-GPRC5D scFv comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218, and a $V_L$ CDR3 comprising amino acids having the sequence set forth in SEQ ID NO: 219.

TABLE 16

| Antigen | A GPRC5D polypeptide having the amino acid sequence of SEQ ID NO: 97 | | |
|---|---|---|---|
| CDRs | 1 | 2 | 3 |
| $V_H$ | GFTFSDYY [SEQ ID NO: 214] | ISSSGSTI [SEQ ID NO: 215] | ARGYGKAYDQ [SEQ ID NO: 216] |
| $V_L$ | RSNVGGNY [SEQ ID NO: 217] | RSN [SEQ ID NO: 218] | ATWDDSLSGFV [SEQ ID NO: 219] |
| Full $V_H$ | EVQLVESGGGLVKPGGSLRLSCAASGFTFSDYYMSWIRQAPGKGLEW VSYISSSGSTIYYADSVKGRFTISRDNAKNSLYLQMNSLRAEDTAVYY CARGYGKAYDQWGQGTLVTVSS [SEQ ID NO: 61] | | |
| DNA | Gaggtgcagctggtggagtctgggggaggcttggtcaagcctggagggtccctgagactctcctgtgcagcct ctggattcaccttcagtgactactacatgagctggatccgccaggctccagggaaggggctggagtgggtttcat acattagtagtagtggtagtaccatatactacgcagactctgtgaagggccgattcaccatctccagggacaacg ccaagaactcactgtatctgcaaatgaacagcctgagagccgaggacacggccgtatattactgtgcgcgcggt tacggtaaagcttacgatcagtggggtcaaggtactctggtgaccgtctcctca [SEQ ID NO: 63] | | |
| Full $V_L$ | QSVLTQPPSASGTPGQRVTISCSGSRSNVGGNYVFWYQQVPGATPKLL IYRSNQRPSGVPDRFAGSKSGSSASLAISGLRSEDEADYYCATWDDSL SGFVFGTGTKVTVLG [SEQ ID NO: 62] | | |
| DNA | Cagtctgtgttgactcagccaccctcagcgtctgggaccccggacagagggtcaccatctcttgttctggaag caggtccaacgtaggaggtaattatgtattttggtaccagcaagtcccggagcgaccccaaactcctcatctat aggagtaatcagcggcctcgggggtccctgaccgattcgctggctccaagtctggctcctcagcctccctggc catcagtggactccggtccgaggatgaggctgattattactgtgcaacatgggatgacagcctgagtggttttgtc ttcggaactgggaccaaggtcaccgtcctaggt [SEQ ID NO: 64] | | |
| scFv | QSVLTQPPSASGTPGQRVTISCSGSRSNVGGNYVFWYQQVPGATPKLL IYRSNQRPSGVPDRFAGSKSGSSASLAISGLRSEDEADYYCATWDDSL SGFVFGTGTKVTVLGRGGGGSGGGGSGGGGSLEMAEVQLVESGGG LVKPGGSLRLSCAASGFTFSDYYMSWIRQAPGKGLEWVSYISSSGSTIY | | |

TABLE 16-continued

| Antigen | A GPRC5D polypeptide having the amino acid sequence of SEQ ID NO: 97 | | |
|---|---|---|---|
| CDRs | 1 | 2 | 3 |
| | YADSVKGRFTISRDNAKNSLYLQMNSLRAEDTAVYYCARGYGKAYD QWGQGTLVTVSS [SEQ ID NO: 115] | | |

In certain embodiments, the antibody or other antigen binding protein is an anti-GPRC5D scFv or an antigen-binding fragment thereof having an antigen-binding region that comprises the amino acid sequence of SEQ ID NO: 116 and specifically binds to a GPRC5D polypeptide (e.g., a GPRC5D polypeptide having the amino acid sequence SEQ ID NO:97, or fragments thereof), which is designated as ET150-158 scFv (also referred to as "ET150-8 scFv").

In certain embodiments, the anti-GPRC5D scFv antibody comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 17. In certain embodiments, the anti-GPRC5D scFv comprises a $V_H$ comprising amino acids having the sequence set forth in SEQ ID NO:65, as shown in Table 17. In certain embodiments, the anti-GPRC5D scFv comprises a $V_L$ comprising amino acids having the sequence set forth in SEQ ID NO:66, as shown in Table 17. In certain embodiments, the anti-GPRC5D scFv comprises a $V_H$ comprising amino acids having the sequence set forth in SEQ ID NO:65 and a $V_L$ comprising amino acids having the sequence set forth in SEQ ID NO:66, as shown in Table 17. In certain embodiments, the anti-GPRC5D scFv comprises a $V_H$ CDR1 comprising amino acids having the sequence set forth in SEQ ID NO:220 or conservative modifications thereof, a $V_H$ CDR2 comprising amino acids having the sequence set forth in SEQ ID NO: 221 or conservative modifications thereof, and a $V_H$ CDR3 comprising amino acids having the sequence set forth in SEQ ID NO: 222 or conservative modifications thereof, as shown in Table 17. In certain embodiments, the anti-GPRC5D scFv comprises a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof, as shown in Table 17. In certain embodiments, the anti-GPRC5D scFv comprises a $V_H$ CDR1 comprising amino acids having the sequence set forth in SEQ ID NO: 220 or conservative modifications thereof, a $V_H$ CDR2 comprising amino acids having the sequence set forth in SEQ ID NO: 221 or conservative modifications thereof, a $V_H$ CDR3 comprising amino acids having the sequence set forth in SEQ ID NO: 222 or conservative modifications thereof, a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof, as shown in Table 17. In certain embodiments, the anti-GPRC5D scFv comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a $V_L$ CDR3 comprising amino acids having the sequence set forth in SEQ ID NO: 225.

TABLE 17

| Antigen | A GPRC5D polypeptide having the amino acid sequence of SEQ ID NO: 97 | | |
|---|---|---|---|
| CDRs | 1 | 2 | 3 |
| $V_H$ | GFTFRSHS [SEQ ID NO: 220] | ISSDSTYT [SEQ ID NO: 221] | ARSGGQWKYYDY [SEQ ID NO: 222] |
| $V_L$ | SLRSYY [SEQ ID NO: 223] | GKN [SEQ ID NO: 224] | NSRDSSGNPPVV [SEQ ID NO: 225] |
| Full $V_H$ | QVQLVESGGGLVHPGGSLRLSCAASGFTFRSHSMNWVRQAPGKGLE WVSSISSDSTYTYYADSVKGRFTISRDNAKNSLYLQMNSLRAEDTAV YYCARSGGQWKYYDYWGQGTLVTVSS [SEQ ID NO: 65] | | |
| DNA | Caggtgcagctggtggagtctggggggaggcctggtccaccctgggggtccctgagactctcctgtgcagcct ctggattcaccttcagaagccatagcatgaactgggtccgccaggctccagggaaggggctggagtgggtctc atccattagtagtgatagtacttacacatactacgcagactcagtgaagggccgattcaccatctccagagacaac gccaagaactcactgtatctgcaaatgaacagcctgagagccgaggacacggccgtatattactgtgcgcgctc tggtggtcagtggaaatactacgattactggggtcaaggtactctggtgaccgtctcctca [SEQ ID NO: 67] | | |
| Full $V_L$ | SSELTQDPAVSVALGQTVRITCQGDSLRSYYASWYQQKPGQAPVLVIY GKNNRPSGIPDRFSGSSSGNTASLTITGAQAEDEADYYCNSRDSSGNPP VVFGGGTKLTVLG [SEQ ID NO: 66] | | |

TABLE 17-continued

| Antigen | A GPRC5D polypeptide having the amino acid sequence of SEQ ID NO: 97 |
|---|---|
| CDRs | 1      2      3 |
| DNA | Tcttctgagctgactcaggaccctgctgtgtctgtggccttgggacagacagtcaggatcacatgccaaggaga cagcctcagaagctattatgcaagctggtaccagcagaagccaggacaggcccctgtacttgtcatctatggtaa aaacaaccggccctcagggatcccagaccgattctctggctccagctcaggaaacacagcttccttgaccatca ctggggctcaggcggaagatgaggctgactattactgtaactcccgggacagcagtggtaacccccctgtggta ttcggcggagggaccaagctgaccgtcctaggt [SEQ ID NO: 68] |
| scFv | SSELTQDPAVSVALGQTVRITCQGDSLRSYYASWYQQKPGQAPVLVIY GKNNRPSGIPDRFSGSSSGNTASLTITGAQAEDEADYYCNSRDSSGNPP VVFGGGTKLTVLGSRGGGGSGGGGSGGGGSLEMAQVQLVESGGGLV HPGGSLRLSCAASGFTFRSHSMNWVRQAPGKGLEWVSSISSDSTYTY YADSVKGRFTISRDNAKNSLYLQMNSLRAEDTAVYYCARSGGQWKY YDYWGQGTLVTVSS [SEQ ID NO: 116] |

In certain embodiments, the antibody or other antigen binding protein is an anti-GPRC5D scFv or an antigen-binding fragment thereof having an antigen-binding region that comprises the amino acid sequence of SEQ ID NO: 117 and specifically binds to a GPRC5D polypeptide (e.g., a GPRC5D polypeptide having the amino acid sequence SEQ ID NO:97, or fragments thereof), which is designated as ET150-168 scFv (also referred to as "ET150-18 scFv").

In certain embodiments, the anti-GPRC5D scFv antibody comprises a heavy chain variable region comprising amino acids having the sequence set forth in SEQ ID NO:69 and a light chain variable region comprising amino acids having the sequence set forth in SEQ ID NO:70, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 18. In certain embodiments, the anti-GPRC5D scFv comprises a $V_H$ comprising amino acids having the sequence set forth in SEQ ID NO:69, as shown in Table 18. In certain embodiments, the anti-GPRC5D scFv comprises a $V_L$ comprising amino acids having the sequence set forth in SEQ ID NO:70, as shown in Table 18. In certain embodiments, the anti-GPRC5D scFv comprises a $V_H$ comprising amino acids having the sequence set forth in SEQ ID NO:69 and a $V_L$ comprising amino acids having the sequence set forth in SEQ ID NO:70, as shown in Table 18. In certain embodiments, the anti-GPRC5D scFv comprises a $V_H$ CDR1 comprising amino acids having the sequence set forth in SEQ ID NO:226 or conservative modifications thereof, a $V_H$ CDR2 comprising amino acids having the sequence set forth in SEQ ID NO: 227 or conservative modifications thereof, and a $V_H$ CDR3 comprising amino acids having the sequence set forth in SEQ ID NO: 228 or conservative modifications thereof, as shown in Table 18. In certain embodiments, the anti-GPRC5D scFv comprises a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof, as shown in Table 18. In certain embodiments, the anti-GPRC5D scFv comprises a $V_H$ CDR1 comprising amino acids having the sequence set forth in SEQ ID NO: 226 or conservative modifications thereof, a $V_H$ CDR2 comprising amino acids having the sequence set forth in SEQ ID NO: 227 or conservative modifications thereof, a $V_H$ CDR3 comprising amino acids having the sequence set forth in SEQ ID NO: 228 or conservative modifications thereof, a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof, as shown in Table 18. In certain embodiments, the anti-GPRC5D scFv comprises a $V_H$ CDR1 comprising amino acids having the sequence set forth in SEQ ID NO: 226, a $V_H$ CDR2 comprising amino acids having the sequence set forth in SEQ ID NO: 227, a $V_H$ CDR3 comprising amino acids having the sequence set forth in SEQ ID NO: 228, a $V_L$ CDR1 comprising amino acids having the sequence set forth in SEQ ID NO: 229, a $V_L$ CDR2 comprising amino acids having the sequence set forth in SEQ ID NO: 230, and a $V_L$ CDR3 comprising amino acids having the sequence set forth in SEQ ID NO: 231.

TABLE 18

| Antigen | A GPRC5D polypeptide having the amino acid sequence of SEQ ID NO: 97 | | |
|---|---|---|---|
| CDRs | 1 | 2 | 3 |
| $V_H$ | GFTFSNYA [SEQ ID NO: 226] | INGRGSST [SEQ ID NO: 227] | ARYISRGLGDS [SEQ ID NO: 228] |
| $V_L$ | NSNIERNY [SEQ ID NO: 229] | DND [SEQ ID NO: 230] | GTWDSSLRGWV [SEQ ID NO: 231] |
| Full $V_H$ | EVQLVESGGGLIQPGGSLRLSCAASGFTFSNYAMNWVRQAPGKGLEW VSTINGRGSSTIYADSVKGRFTISRDNSKNTLYLQMNSLRAEDTATYY CARYISRGLGDSWGQGTLVTV [SEQ ID NO: 69] | | |

TABLE 18-continued

| Antigen | A GPRC5D polypeptide having the amino acid sequence of SEQ ID NO: 97 | | |
|---|---|---|---|
| CDRs | 1 | 2 | 3 |
| DNA | Gaggtgcagctggtggagtccggggggaggcttgatacagcctgggggtccctgagactctcctgtgcagcc tctggattcacctttagcaactatgccatgaactgggtccgccaggctccagggaaggggctggagtgggtctc aactattaatggtcgtggtagtagtacaatctacgcagactccgtgaagggccggttcaccatctccagagacaa ttccaagaacacgctgtatctgcaaatgaacagcctgagagccgaggaccacagccacgtattactgtgcgcgct acatctctcgtggtctgggtgattcttggggtcaaggtactctggtgaccgtctcctca [SEQ ID NO: 71] | | |
| Full V$_L$ | QSVVTQPPSMSAAPGQQVTISCSGGNSNIERNYVSWYLQLPGTAPKLV IFDNDRRPSGIPDRFSGSKSGTSATLGITGLQTGDEADYYCGTWDSSLR GWVFGGGTKLTVLG [SEQ ID NO: 70] | | |
| DNA | Cagtctgtcgtgacgcagccgccctcaatgtctgcggccccaggacagcaagtcaccatctcctgctctggag gcaactccaacattgagagaaattatgtatcctggtacctccagctccctggaacagccccccaaactcgtcattttt gacaatgataggcgaccctcagggattcctgaccgattctctggctccaagtctggcacgtcagccaccctggg catcaccggactccagactggggacgaggccgattattactgcggaacatgggatagcagcctgagaggttgg gtgttcggcggagggaccaagctgaccgtcctaggt [SEQ ID NO: 72] | | |
| scFv | QSVVTQPPSMSAAPGQQVTISCSGGNSNIERNYVSWYLQLPGTAPKLV IFDNDRRPSGIPDRFSGSKSGTSATLGITGLQTGDEADYYCGTWDSSLR GWVFGGGTKLTVLGSRGGGGSGGGGSGGGGSLEMAEVQLVESGGGL IQPGGSLRLSCAASGFTFSNYAMNWVRQAPGKGLEWVSTINGRGSSTI YADSVKGRFTISRDNSKNTLYLQMNSLRAEDTATYYCARYISRGLGDS WGQGTLVTV [SEQ ID NO: 117] | | |

In certain embodiments, the antibody or other antigen binding protein is an anti-GPRC5D scFv or an antigen-binding fragment thereof having an antigen-binding region that comprises the amino acid sequence of SEQ ID NO: 118 and specifically binds to a GPRC5D polypeptide (e.g., a GPRC5D polypeptide having the amino acid sequence SEQ ID NO:97, or fragments thereof), which is designated as ET150-164 scFv (also referred to as "ET150-14 scFv").

In certain embodiments, the anti-GPRC5D scFv antibody comprises a heavy chain variable region comprising amino acids having the sequence set forth in SEQ ID NO:73 and a light chain variable region comprising amino acids having the sequence set forth in SEQ ID NO:74, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V$_H$ and V$_L$ regions or CDRs selected from Table 19. In certain embodiments, the anti-GPRC5D scFv comprises a V$_H$ comprising amino acids having the sequence set forth in SEQ ID NO:73, as shown in Table 19. In certain embodiments, the anti-GPRC5D scFv comprises a V$_L$ comprising amino acids having the sequence set forth in SEQ ID NO:74, as shown in Table 19. In certain embodiments, the anti-GPRC5D scFv comprises a V$_H$ comprising amino acids having the sequence set forth in SEQ ID NO:73 and a V$_L$ comprising amino acids having the sequence set forth in SEQ ID NO:74, as shown in Table 19. In certain embodiments, the anti-GPRC5D scFv comprises a V$_H$ CDR1 comprising amino acids having the sequence set forth in SEQ ID NO:232 or conservative modifications thereof, a V$_H$ CDR2 comprising amino acids having the sequence set forth in SEQ ID NO: 233 or conservative modifications thereof, and a V$_H$ CDR3 comprising amino acids having the sequence set forth in SEQ ID NO: 234 or conservative modifications thereof, as shown in Table 19. In certain embodiments, the anti-GPRC5D scFv comprises a V$_L$ CDR1 comprising amino acids having the sequence set forth in SEQ ID NO: 235 or conservative modifications thereof, a V$_L$ CDR2 comprising amino acids having the sequence set forth in SEQ ID NO: 236 or conservative modifications thereof, and a V$_L$ CDR3 comprising amino acids having the sequence set forth in SEQ ID NO: 237 or conservative modifications thereof, as shown in Table 19. In certain embodiments, the anti-GPRC5D scFv comprises a V$_H$ CDR1 comprising amino acids having the sequence set forth in SEQ ID NO: 232 or conservative modifications thereof, a V$_H$ CDR2 comprising amino acids having the sequence set forth in SEQ ID NO: 233 or conservative modifications thereof, a V$_H$ CDR3 comprising amino acids having the sequence set forth in SEQ ID NO: 234 or conservative modifications thereof, a V$_L$ CDR1 comprising amino acids having the sequence set forth in SEQ ID NO: 235 or conservative modifications thereof, a V$_L$ CDR2 comprising amino acids having the sequence set forth in SEQ ID NO: 236 or conservative modifications thereof, and a V$_L$ CDR3 comprising amino acids having the sequence set forth in SEQ ID NO: 237 or conservative modifications thereof, as shown in Table 19. In certain embodiments, the anti-GPRC5D scFv comprises a V$_H$ CDR1 comprising amino acids having the sequence set forth in SEQ ID NO: 232, a V$_H$ CDR2 comprising amino acids having the sequence set forth in SEQ ID NO: 233, a V$_H$ CDR3 comprising amino acids having the sequence set forth in SEQ ID NO: 234, a V$_L$ CDR1 comprising amino acids having the sequence set forth in SEQ ID NO: 235, a V$_L$ CDR2 comprising amino acids having the sequence set forth in SEQ ID NO: 236, and a V$_L$ CDR3 comprising amino acids having the sequence set forth in SEQ ID NO: 237.

TABLE 19

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 232] | INPSGGST [SEQ ID NO: 233] | ARAGMGMDT [SEQ ID NO: 234] |
| $V_L$ | SSDVGGYNY [SEQ ID NO: 235] | EVS [SEQ ID NO: 236] | SSYAGSNTLV [SEQ ID NO: 237] |
| Full $V_H$ | QMQLVQSGAEVKKPGASVKVSCKASGYTFTSYYMHWVRQAPGQGL EWMGIINPSGGSTSYAQKFQGRVTMTRDTSTSTVYMELSSLRSEDTAV YYCARAGMGMDTWGQGTLVTVSS [SEQ ID NO: 73] | | |
| DNA | Cagatgcagctggtgcagtctggggctgaggtgaagaagcctggggcctcagtgaaggtttcctgcaaggcat ctggatacaccttcaccagctactatatgcactgggtgcgacaggcccctggacaagggcttgagtggatggga ataatcaaccctagtggtggtagcacaagctacgcacagaagttccagggcagagtcaccatgaccagggaca cgtccacgagcacagtctacatggagctgagcagcctgagatctgaggacacggccgtgtattactgtgcgcg cgctggtatgggtatggatacttggggtcaaggtactctggtgaccgtctcctca [SEQ ID NO: 75] | | |
| Full $V_L$ | QSALTQPPSASGSPGQSVTISCTGTSSDVGGYNYVSWYQQHPGKAPKL MIYEVSKRPSGVPDRFSGSKSGNTASLTVSGLQAEDEADYYCSSYAGS NTLVFGGGTKLTVLG [SEQ ID NO: 74] | | |
| DNA | Cagtctgccctgactcagcctccctccgcgtccgggtctcctggacagtcagtcaccatctcctgcactggaac cagcagtgacgttggtggttataactatgtctcctggtaccaacagcacccaggcaaagcccccaaactcatgat ttatgaggtcagtaagcggccctcaggggtccctgatcgcttctctggctccaagtctggcaacacggcctcct gaccgtctctgggctccaggctgaggatgaggctgattattactgcagctcatatgcaggcagcaacaccttggt gttcggcggagggaccaagctgaccgtcctaggt [SEQ ID NO: 76] | | |
| scFv | QSALTQPPSASGSPGQSVTISCTGTSSDVGGYNYVSWYQQHPGKAPKL MIYEVSKRPSGVPDRFSGSKSGNTASLTVSGLQAEDEADYYCSSYAGS NTLVFGGGTKLTVLGSRGGGGSGGGGSGGGGSLEMAQMQLVQSGAE VKKPGASVKVSCKASGYTFTSYYMHWVRQAPGQGLEWMGIINPSGG STSYAQKFQGRVTMTRDTSTSTVYMELSSLRSEDTAVYYCARAGMG MDTWGQGTLVTVSS [SEQ ID NO: 118] | | |

In certain embodiments, the antibody or other antigen binding protein is an anti-GPRC5D scFv or an antigen-binding fragment thereof having an antigen-binding region that comprises the amino acid sequence of SEQ ID NO: 119 and specifically binds to a GPRC5D polypeptide (e.g., a GPRC5D polypeptide having the amino acid sequence SEQ ID NO:97, or fragments thereof), which is designated as ET150-165 scFv (also referred to as "ET150-15 scFv").

In certain embodiments, the anti-GPRC5D scFv antibody comprises a heavy chain variable region comprising amino acids having the sequence set forth in SEQ ID NO:77 and a light chain variable region comprising amino acids having the sequence set forth in SEQ ID NO:78, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 20. In certain embodiments, the anti-GPRC5D scFv comprises a $V_H$ comprising amino acids having the sequence set forth in SEQ ID NO:77, as shown in Table 20. In certain embodiments, the anti-GPRC5D scFv comprises a $V_L$ comprising amino acids having the sequence set forth in SEQ ID NO:78, as shown in Table 20. In certain embodiments, the anti-GPRC5D scFv comprises a $V_H$ comprising amino acids having the sequence set forth in SEQ ID NO:77 and a $V_L$ comprising amino acids having the sequence set forth in SEQ ID NO:78, as shown in Table 20. In certain embodiments, the anti-GPRC5D scFv comprises a $V_H$ CDR1 comprising amino acids having the sequence set forth in SEQ ID NO:238 or conservative modifications thereof, a $V_H$ CDR2 comprising amino acids having the sequence set forth in SEQ ID NO: 239 or conservative modifications thereof, and a $V_H$ CDR3 comprising amino acids having the sequence set forth in SEQ ID NO: 240 or conservative modifications thereof, as shown in Table 20. In certain embodiments, the anti-GPRC5D scFv comprises a $V_L$ CDR1 comprising amino acids having the sequence set forth in SEQ ID NO: 241 or conservative modifications thereof, a $V_L$ CDR2 comprising amino acids having the sequence set forth in SEQ ID NO: 242 or conservative modifications thereof, and a $V_L$ CDR3 comprising amino acids having the sequence set forth in SEQ ID NO: 243 or conservative modifications thereof, as shown in Table 20. In certain embodiments, the anti-GPRC5D scFv comprises a $V_H$ CDR1 comprising amino acids having the sequence set forth in SEQ ID NO: 238 or conservative modifications thereof, a $V_H$ CDR2 comprising amino acids having the sequence set forth in SEQ ID NO: 239 or conservative modifications thereof, a $V_H$ CDR3 comprising amino acids having the sequence set forth in SEQ ID NO: 240 or conservative modifications thereof, a $V_L$ CDR1 comprising amino acids having the sequence set forth in SEQ ID NO: 241 or conservative modifications thereof, a $V_L$ CDR2 comprising amino acids having the sequence set forth in SEQ ID NO: 242 or conservative modifications thereof, and a $V_L$ CDR3 comprising amino acids having the sequence set forth in SEQ ID NO: 243 or conservative modifications thereof, as shown in Table 20. In certain embodiments, the anti-GPRC5D scFv comprises a $V_H$ CDR1 comprising amino acids having the sequence set forth in SEQ ID NO: 238, a $V_H$ CDR2 comprising amino acids having the sequence set forth in SEQ ID NO: 239, a $V_H$ CDR3 comprising amino acids having the sequence set forth in SEQ ID NO: 240, a $V_L$ CDR1 comprising amino acids having the sequence set forth in SEQ ID NO: 241, a $V_L$ CDR2 comprising amino acids having the sequence set forth in SEQ ID NO: 242, and a $V_L$ CDR3 comprising amino acids having the sequence set forth in SEQ ID NO: 243.

TABLE 20

| Antigen | A GPRC5D polypeptide having the amino acid sequence of SEQ ID NO: 97 | | |
|---|---|---|---|
| CDRs | 1 | 2 | 3 |
| $V_H$ | GYTFTAYS [SEQ ID NO: 238] | INPSSGGA [SEQ ID NO: 239] | ARNVGGQADD [SEQ ID NO: 240] |
| $V_L$ | SSDIGGYNY [SEQ ID NO: 241] | EVN [SEQ ID NO: 242] | ASFAGRKTLV [SEQ ID NO: 243] |
| Full $V_H$ | QVQLVQSGAEVKKPGASVKVSCRASGYTFTAYSLHWVRQAPGQGLE WMGWINIPSSGGAVYAQKFQGRVTMTRDTSISTAYMELSGLRSDDTA VYYCARNVGGQADDWGQGTLVTVSS [SEQ ID NO: 77] | | |
| DNA | Caggtgcagctggtgcagtctggggctgaggtgaagaagcctggggcctcagtgaaggtctcctgcagggct tctggatacaccttcaccgcctactctttacactgggtgcgacaggcccctggacaagggcttgagtggatggga tggatcaaccctagcagtggtggcgcagtttatgcacagaaatttcagggtagggtcaccatgaccagggacac gtccatcagcacagcctacatggagctgagtggcctgagatctgacgacacggccgtgtattactgtgcgcgca acgttggtggtcaggctgatgactggggtcaaggtactctggtgaccgtctcctca [SEQ ID NO: 79] | | |
| Full $V_L$ | QSALTQPPSASGSPGQSVTISCTGTSSDIGGYNYVSWYQQHPGKAPKL MIYEVNKRPSGVPDRFSGSKSGNTASLTVSGLQAEDEADYYCASFAG RKTLVFGGGTKLTVLG [SEQ ID NO: 78] | | |
| DNA | Caatctgccctgactcagcctccctccgcgtccgggtctcctggacagtcagtcaccatctcctgcactggaacc agcagtgacattggtggttataactatgtctcctggtaccaacagcacccaggcaaagcccccaaactcatgattt atgaggtcaataagcggccctcaggggtccctgatcgcttctcggggctccaagtctggcaacacggcctcctg accgtctctgggctccaggctgaggatgaggctgattattactgcgcctcatttgcgggcaggaagacattggtc ttcggcggagggaccaagctgaccgtcctaggt [SEQ ID NO: 80] | | |
| scFv | QSALTQPPSASGSPGQSVTISCTGTSSDIGGYNYVSWYQQHPGKAPKL MIYEVNKRPSGVPDRFSGSKSGNTASLTVSGLQAEDEADYYCASFAG RKTLVFGGGTKLTVLGSRGGGGSGGGGSGGGGSLEMAQVQLVQSGA EVKKPGASVKVSCRASGYTFTAYSLHWVRQAPGQGLEWMGWINPSS GGAVYAQKFQGRVTMTRDTSISTAYMELSGLRSDDTAVYYCARNVG GQADDWGQGTLVTVSS [SEQ ID NO: 119] | | |

In certain embodiments, the antibody or other antigen binding protein is an anti-GPRC5D scFv or an antigen-binding fragment thereof having an antigen-binding region that comprises the amino acid sequence of SEQ ID NO: 120 and specifically binds to a GPRC5D polypeptide (e.g., a GPRC5D polypeptide having the amino acid sequence SEQ ID NO:97, or fragments thereof), which is designated as ET150-167 scFv (also referred to as "ET150-17 scFv").

In certain embodiments, the anti-GPRC5D scFv antibody comprises a heavy chain variable region comprising amino acids having the sequence set forth in SEQ ID NO:81 and a light chain variable region comprising amino acids having the sequence set forth in SEQ ID NO:82, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 21. In certain embodiments, the anti-GPRC5D scFv comprises a $V_H$ comprising amino acids having the sequence set forth in SEQ ID NO:81, as shown in Table 21. In certain embodiments, the anti-GPRC5D scFv comprises a $V_L$ comprising amino acids having the sequence set forth in SEQ ID NO:82, as shown in Table 21. In certain embodiments, the anti-GPRC5D scFv comprises a $V_H$ comprising amino acids having the sequence set forth in SEQ ID NO:81 and a $V_L$ comprising amino acids having the sequence set forth in SEQ ID NO:82, as shown in Table 21. In certain embodiments, the anti-GPRC5D scFv comprises a $V_H$ CDR1 comprising amino acids having the sequence set forth in SEQ ID NO: 244 or conservative modifications thereof, a $V_H$ CDR2 comprising amino acids having the sequence set forth in SEQ ID NO: 245 or conservative modifications thereof, and a $V_H$ CDR3 comprising amino acids having the sequence set forth in SEQ ID NO: 246 or conservative modifications thereof, as shown in Table 21. In certain embodiments, the anti-GPRC5D scFv comprises a $V_L$ CDR1 comprising amino acids having the sequence set forth in SEQ ID NO: 247 or conservative modifications thereof, a $V_L$ CDR2 comprising amino acids having the sequence set forth in SEQ ID NO: 248 or conservative modifications thereof, and a $V_L$ CDR3 comprising amino acids having the sequence set forth in SEQ ID NO: 249 or conservative modifications thereof, as shown in Table 21. In certain embodiments, the anti-GPRC5D scFv comprises a $V_H$ CDR1 comprising amino acids having the sequence set forth in SEQ ID NO: 244 or conservative modifications thereof, a $V_H$ CDR2 comprising amino acids having the sequence set forth in SEQ ID NO: 245 or conservative modifications thereof, a $V_H$ CDR3 comprising amino acids having the sequence set forth in SEQ ID NO: 246 or conservative modifications thereof, a $V_L$ CDR1 comprising amino acids having the sequence set forth in SEQ ID NO: 247 or conservative modifications thereof, a $V_L$ CDR2 comprising amino acids having the sequence set forth in SEQ ID NO: 248 or conservative modifications thereof, and a $V_L$ CDR3 comprising amino acids having the sequence set forth in SEQ ID NO: 249 or conservative modifications thereof, as shown in Table 21. In certain embodiments, the anti-GPRC5D scFv comprises a $V_H$ CDR1 comprising amino acids having the sequence set forth in SEQ ID NO: 244, a $V_H$ CDR2 comprising amino acids having the sequence set forth in SEQ ID NO: 245, a $V_H$ CDR3 comprising amino acids having the sequence set forth in SEQ ID NO: 246, a $V_L$ CDR1 comprising amino acids having the sequence set forth in SEQ ID NO: 247, a $V_L$ CDR2 comprising amino acids having the sequence set forth in SEQ ID NO: 248, and a $V_L$ CDR3 comprising amino acids having the sequence set forth in SEQ ID NO: 249.

TABLE 21

| Antigen | A GPRC5D polypeptide having the amino acid sequence of SEQ ID NO: 97 | | |
|---|---|---|---|
| CDRs | 1 | 2 | 3 |
| $V_H$ | GYTFTAYS [SEQ ID NO: 244] | INPSSGGA [SEQ ID NO: 245] | ARNVGGHADD [SEQ ID NO: 246] |
| $V_L$ | STDIGGYNY [SEQ ID NO: 247] | EVN [SEQ ID NO: 248] | ASFAGRKTLV [SEQ ID NO: 249] |
| Full $V_H$ | QVQLVQSGAEVKKPGASVKVSCRASGYTFTAYSLHWVRQAPGQGLE WMGWINIPSSGGAVYAQKFQGRVTMTRDTSISTAYMELSGLRSDDTA VYYCARNVGGHADDWGQGTLVTVSS [SEQ ID NO: 81] | | |
| DNA | Caggtgcagctggtgcagtctggggctgaggtgaaaaagcctggggcctcagtgaaagtctcctgcagggctt ctggatacaccttcaccgcctactctttacactgggtgcgacaggcccctggacaagggcttgagtggatgggat ggatcaaccctagcagtggtggcgcagtttatgcacagaaatttcagggtagggtcaccatgaccagggacac gtccatcagcacagcctacatggagctgagtggcctgagatctgacgacacggccgtgtattactgtgcgcgca acgttggtggtcacgctgatgactggggtcaaggtactctggtgaccgtctcctca [SEQ ID NO: 83] | | |
| Full $V_L$ | QSALTQPPSASGSPGQSVTISCTGTSTDIGGYNYVSWYQHHPSKAPKL MIYEVNKRPSGVPDRFSGSKSGNTASLTVSGLQAEDEADYYCASFAG RKTLVFGGGTKLTVLG [SEQ ID NO: 82] | | |
| DNA | Caatctgccctgactcagcctccctccgcgtccgggtctcctggacagtcagtcaccatctcctgcactggaacc agcactgacattggtggttataactatgtctcctggtaccaacaccacccaagcaaagccccccaaactcatgattt atgaggtcaataagcggccctcaggggtccctgatcgcttctcgggctccaagtctggcaacacggcctccctg accgtctctgggctccaggctgaggatgaggctgattattactgcgcctcatttgcgggcaggaagacattggtc ttcggcggagggaccaagctgaccgtcctaggt [SEQ ID NO: 84] | | |
| scFv | QSALTQPPSASGSPGQSVTISCTGTSTDIGGYNYVSWYQHHPSKAPKL MIYEVNKRPSGVPDRFSGSKSGNTASLTVSGLQAEDEADYYCASFAG RKTLVFGGGTKLTVLGSRGGGGSGGGGSGGGGSLEMAQVQLVQSGA EVKKPGASVKVSCRASGYTFTAYSLHWVRQAPGQGLEWMGWINPSS GGAVYAQKFQGRVTMTRDTSISTAYMELSGLRSDDTAVYYCARNVG GHADDWGQGTLVTVSS [SEQ ID NO: 120] | | |

In certain embodiments, the antibody or other antigen binding protein is an anti-GPRC5D scFv or an antigen-binding fragment thereof having an antigen-binding region that comprises the amino acid sequence of SEQ ID NO: 121 and specifically binds to a GPRC5D polypeptide (e.g., a GPRC5D polypeptide having the amino acid sequence SEQ ID NO:97, or fragments thereof), which is designated as ET150-169 scFv (also referred to as "ET150-19 scFv").

In certain embodiments, the anti-GPRC5D scFv antibody comprises a heavy chain variable region comprising amino acids having the sequence set forth in SEQ ID NO:85 and a light chain variable region comprising amino acids having the sequence set forth in SEQ ID NO:86, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 22. In certain embodiments, the anti-GPRC5D scFv comprises a $V_H$ comprising amino acids having the sequence set forth in SEQ ID NO:85, as shown in Table 22. In certain embodiments, the anti-GPRC5D scFv comprises a $V_L$ comprising amino acids having the sequence set forth in SEQ ID NO:86, as shown in Table 22. In certain embodiments, the anti-GPRC5D scFv comprises a $V_H$ comprising amino acids having the sequence set forth in SEQ ID NO:85 and a $V_L$ comprising amino acids having the sequence set forth in SEQ ID NO:86, as shown in Table 22. In certain embodiments, the anti-GPRC5D scFv comprises a $V_H$ CDR1 comprising amino acids having the sequence set forth in SEQ ID NO:250 or conservative modifications thereof, a $V_H$ CDR2 comprising amino acids having the sequence set forth in SEQ ID NO: 251 or conservative modifications thereof, and a $V_H$ CDR3 comprising amino acids having the sequence set forth in SEQ ID NO: 252 or conservative modifications thereof, as shown in Table 22. In certain embodiments, the anti-GPRC5D scFv comprises a $V_L$ CDR1 comprising amino acids having the sequence set forth in SEQ ID NO: 253 or conservative modifications thereof, a $V_L$ CDR2 comprising amino acids having the sequence set forth in SEQ ID NO: 254 or conservative modifications thereof, and a $V_L$ CDR3 comprising amino acids having the sequence set forth in SEQ ID NO: 255 or conservative modifications thereof, as shown in Table 22. In certain embodiments, the anti-GPRC5D scFv comprises a $V_H$ CDR1 comprising amino acids having the sequence set forth in SEQ ID NO: 250 or conservative modifications thereof, a $V_H$ CDR2 comprising amino acids having the sequence set forth in SEQ ID NO: 251 or conservative modifications thereof, a $V_H$ CDR3 comprising amino acids having the sequence set forth in SEQ ID NO: 252 or conservative modifications thereof, a $V_L$ CDR1 comprising amino acids having the sequence set forth in SEQ ID NO: 253 or conservative modifications thereof, a $V_L$ CDR2 comprising amino acids having the sequence set forth in SEQ ID NO: 254 or conservative modifications thereof, and a $V_L$ CDR3 comprising amino acids having the sequence set forth in SEQ ID NO: 255 or conservative modifications thereof, as shown in Table 22. In certain embodiments, the anti-GPRC5D scFv comprises a $V_H$ CDR1 comprising amino acids having the sequence set forth in SEQ ID NO: 250, a $V_H$ CDR2 comprising amino acids having the sequence set forth in SEQ ID NO: 251, a $V_H$ CDR3 comprising amino acids having the sequence set forth in SEQ ID NO: 252, a $V_L$ CDR1 comprising amino acids having the sequence set forth in SEQ ID NO: 253, a $V_L$ CDR2 comprising amino acids having the sequence set forth in SEQ ID NO: 254, and a $V_L$ CDR3 comprising amino acids having the sequence set forth in SEQ ID NO: 255.

prising amino acids having the sequence set forth in SEQ ID NO:89, as shown in Table 23. In certain embodiments, the anti-GPRC5D scFv comprises a $V_L$ comprising amino acids having the sequence set forth in SEQ ID NO:90, as shown in Table 23. In certain embodiments, the anti-GPRC5D scFv comprises a $V_H$ comprising amino acids having the sequence set forth in SEQ ID NO:89 and a $V_L$ comprising amino acids having the sequence set forth in SEQ ID NO:90, as shown in Table 23. In certain embodiments, the anti-GPRC5D scFv comprises a $V_H$ CDR1 comprising amino acids having the

TABLE 22

| Antigen | A GPRC5D polypeptide having the amino acid sequence of SEQ ID NO: 97 | | |
|---|---|---|---|
| CDRs | 1 | 2 | 3 |
| $V_H$ | GFTFNTYG [SEQ ID NO: 250] | ISANNGHT [SEQ ID NO: 251] | ARGGYHHQMQRYYK ATSVYSDY [SEQ ID NO: 252] |
| $V_L$ | SSNIGNNY [SEQ ID NO: 253] | DNN [SEQ ID NO: 254] | GTWDSSLSGVV [SEQ ID NO: 255] |
| Full $V_H$ | QVQLVQSGGEVKKPGASVKVSCKASGFTFNTYGISWVRQAPGQGLE WMGWISANNGHTKSAQRFQDRVAMATDTSTSTAYMELRSLKFDDTA VYYCARGGYHHQMQRYYKATSVYSDYWGQGTLVTVSS [SEQ ID NO: 85] | | |
| DNA | Caggtccagctggtgcagtctggaggtgaggtgaagaagcctgggcctcagtgaaggtctcctgcaaggctt ctggtttcaccttaacacctatggcatcagttgggtgcgacaggcccctggacaagggcttgagtggatgggat ggatcagcgctaacaatggtcacacaaagtctgcacagaggttccaggacagagtcgccatggccacagaca catccacgagcacggcctacatggagctgaggagcctgaaatttgacgacacggccgtgtattactgtgcgcgc ggtggttaccatcatcagatgcagcggtactacaaagctacttctgtttactctgattactggggtcaaggtactctg gtgaccgtctcctca [SEQ ID NO: 87] | | |
| Full $V_L$ | QSVVTQPPSVSAAPGQKVTISCSGSSSNIGNNYVSWYQQLPGTAPKLLI YDNNKRPSGIPDRFSGSKSGTSATLGITGLQTGDEADYYCGTWDSSLS GVVFGGGTKLTVLG [SEQ ID NO: 86] | | |
| DNA | Cagtctgtcgtgacgcagccgcccctcagtgtctgcggccccaggacagaaggtcaccatctcctgctctggaa gcagctccaacattgggaataattatgtatcctggtaccagcaactcccaggaacagccccaaactcctcattta tgacaataataagcgaccctcagggattcctgaccgattctctggctccaagtctggcacgtctgccaccctggg catcaccggactccagactggggacgaggccgattattactgcgaacatgggatagcagcctgagtggtgtg gtattcggcggagggaccaagctgaccgtcctaggt [SEQ ID NO: 88] | | |
| scFv | QSVVTQPPSVSAAPGQKVTISCSGSSSNIGNNYVSWYQQLPGTAPKLLI YDNNKRPSGIPDRFSGSKSGTSATLGITGLQTGDEADYYCGTWDSSLS GVVFGGGTKLTVLGSRGGGGSGGGGSGGGGSLEMAQVQLVQGGEV KKPGASVKVSCKASGFTFNTYGISWVRQAPGQGLEWMGWISANNGH TKSAQRFQDRVAMATDTSTSTAYMELRSLKFDDTAVYYCARGGYHH QMQRYYKATSVYSDYWGQGTLVTVSS [SEQ ID NO: 121] | | |

In certain embodiments, the antibody or other antigen binding protein is an anti-GPRC5D scFv or an antigen-binding fragment thereof having an antigen-binding region that comprises the amino acid sequence of SEQ ID NO: 122 and specifically binds to a GPRC5D polypeptide (e.g., a GPRC5D polypeptide having the amino acid sequence SEQ ID NO:97, or fragments thereof), which is designated as ET150-172 scFv (also referred to as "ET150-22 scFv").

In certain embodiments, the anti-GPRC5D scFv antibody comprises a heavy chain variable region comprising amino acids having the sequence set forth in SEQ ID NO:89 and a light chain variable region comprising amino acids having the sequence set forth in SEQ ID NO:90, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 23. In certain embodiments, the anti-GPRC5D scFv comprises a $V_H$ com-sequence set forth in SEQ ID NO:256 or conservative modifications thereof, a $V_H$ CDR2 comprising amino acids having the sequence set forth in SEQ ID NO: 257 or conservative modifications thereof, and a $V_H$ CDR3 comprising amino acids having the sequence set forth in SEQ ID NO: 258 or conservative modifications thereof, as shown in Table 23. In certain embodiments, the anti-GPRC5D scFv comprises a $V_L$ CDR1 comprising amino acids having the sequence set forth in SEQ ID NO: 259 or conservative modifications thereof, a $V_L$ CDR2 comprising amino acids having the sequence set forth in SEQ ID NO: 260 or conservative modifications thereof, and a $V_L$ CDR3 comprising amino acids having the sequence set forth in SEQ ID NO: 261 or conservative modifications thereof, as shown in Table 23. In certain embodiments, the anti-GPRC5D scFv comprises a $V_H$ CDR1 comprising amino acids having the sequence set forth in SEQ ID NO: 256 or conservative modifications thereof, a $V_H$ CDR2 comprising amino acids having the sequence set forth in SEQ ID NO: 257 or conservative modifications thereof, a $V_H$ CDR3 comprising amino acids having the sequence set forth in SEQ ID NO:

258 or conservative modifications thereof, a $V_L$ CDR1 comprising amino acids having the sequence set forth in SEQ ID NO: 259 or conservative modifications thereof, a $V_L$ CDR2 comprising amino acids having the sequence set forth in SEQ ID NO: 260 or conservative modifications thereof, and a $V_L$ CDR3 comprising amino acids having the sequence set forth in SEQ ID NO: 261 or conservative modifications thereof, as shown in Table 23. In certain embodiments, the anti-GPRC5D scFv comprises a $V_H$ CDR1 comprising amino acids having the sequence set forth in SEQ ID NO: 256, a $V_H$ CDR2 comprising amino acids having the sequence set forth in SEQ ID NO: 257, a $V_H$ CDR3 comprising amino acids having the sequence set forth in SEQ ID NO: 258, a $V_L$ CDR1 comprising amino acids having the sequence set forth in SEQ ID NO: 259, a $V_L$ CDR2 comprising amino acids having the sequence set forth in SEQ ID NO: 260, and a $V_L$ CDR3 comprising amino acids having the sequence set forth in SEQ ID NO: 261.

region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 24. In certain embodiments, the anti-GPRC5D scFv comprises a $V_H$ comprising amino acids having the sequence set forth in SEQ ID NO:93, as shown in Table 24. In certain embodiments, the anti-GPRC5D scFv comprises a $V_L$ comprising amino acids having the sequence set forth in SEQ ID NO:94, as shown in Table 24. In certain embodiments, the anti-GPRC5D scFv comprises a $V_H$ comprising amino acids having the sequence set forth in SEQ ID NO:93 and a $V_L$ comprising amino acids having the sequence set forth in SEQ ID NO:94, as shown in Table 24. In certain embodiments, the anti-GPRC5D scFv comprises a $V_H$ CDR1 comprising amino acids having the sequence set forth in SEQ ID NO:262 or conservative modifications thereof, a $V_H$ CDR2 comprising amino acids

TABLE 23

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 256] | INPSGGSS [SEQ ID NO: 257] | ARAGMGMDT [SEQ ID NO: 258] |
| $V_L$ | SSDVGGYNY [SEQ ID NO: 259] | EVS [SEQ ID NO: 260] | SSYAGSNTLV [SEQ ID NO: 261] |
| Full $V_H$ | QMQLVQSGAEVKKPGASVKVSCKASGYTFTSYYMHWVRQAPGQGL EWMGIINPSGGSSSYAQKFQGRVTMTRDTSTSTVYMELSSLRSEDTAV YYCARAGMGMDTWGQGTLVTVSS [SEQ ID NO: 89] | | |
| DNA | Cagatgcagctggtgcagtctggggctgaggtgaagaagcctggggcctcagtgaaggtttcctgcaaggcat ctggatacaccttcaccagctactatatgcactgggtgcgacaggcccctggacaagggcttgagtggatggga ataatcaaccctagtggtggtagctcaagctacgcacagaagttccagggcagagtcaccatgaccagggaca cgtccacgagcacagtctacatggagctgagcagcctgagatctgaggacacggccgtgtattactgtgcgcg cgctggtatgggtatggatacttggggtcaaggtactctggtgaccgtctcctca [SEQ ID NO: 91] | | |
| Full $V_L$ | QSALTQPPSASGSPGQSVTISCTGTSSDVGGYNYVSWYQQHPGKAPKL MIYEVSKRPSGVPDRFSGSKSGNTASLTVSGLQAEDEADYYCSSYAGS NTLVFGGGTKLTVLG [SEQ ID NO: 90] | | |
| DNA | Cagtctgccctgactcagcctccctccgcgtccgggtctcctggacagtcagtcaccatctcctgcactggaac cagcagtgacgttggtggttataactatgtctcctggtaccaacagcacccaggcaaagcccccaaactcatgat ttatgaggtcagtaagcggccctcaggggtccctgatcgcttctctggctccaagtctggcaacacggcctccct gaccgtctctgggctccaggctgaggatgaggctgattattactgcagctcatatgcaggcagcaacaccttggt gttcggcggagggaccaagctgaccgtcctaggt [SEQ ID NO: 92] | | |
| scFv | QSALTQPPSASGSPGQSVTISCTGTSSDVGGYNYVSWYQQHPGKAPKL MIYEVSKRPSGVPDRFSGSKSGNTASLTVSGLQAEDEADYYCSSYAGS NTLVFGGGTKLTVLGSRGGGGSGGGGSGGGGSLEMAQMQLVQSGAE VKKPGASVKVSCKASGYTFTSYYMHWVRQAPGQGLEWMGIINPSGG SSSYAQKFQGRVTMTRDTSTSTVYMELSSLRSEDTAVYYCARAGMG MDTWGQGTLVTVSS [SEQ ID NO: 122] | | |

In certain embodiments, the antibody or other antigen binding protein is an anti-GPRC5D scFv or an antigen-binding fragment thereof having an antigen-binding region that comprises the amino acid sequence of SEQ ID NO: 123 and specifically binds to a GPRC5D polypeptide (e.g., a GPRC5D polypeptide having the amino acid sequence SEQ ID NO:97, or fragments thereof), which is designated as ET150-173 scFv (also referred to as "ET150-23 scFv").

In certain embodiments, the anti-GPRC5D scFv antibody comprises a heavy chain variable region comprising amino acids having the sequence set forth in SEQ ID NO:93 and a light chain variable region comprising amino acids having the sequence set forth in SEQ ID NO:94, optionally with (iii) a linker sequence, for example a linker peptide, between the heavy chain variable region and the light chain variable region. In certain embodiments, the linker comprises amino acids having the sequence set forth in SEQ ID NO: 263 or conservative modifications thereof, and a $V_H$ CDR3 comprising amino acids having the sequence set forth in SEQ ID NO: 264 or conservative modifications thereof, as shown in Table 24. In certain embodiments, the anti-GPRC5D scFv comprises a $V_L$ CDR1 comprising amino acids having the sequence set forth in SEQ ID NO: 265 or conservative modifications thereof, a $V_L$ CDR2 comprising amino acids having the sequence set forth in SEQ ID NO: 266 or conservative modifications thereof, and a $V_L$ CDR3 comprising amino acids having the sequence set forth in SEQ ID NO: 267 or conservative modifications thereof, as shown in Table 24. In certain embodiments, the anti-GPRC5D scFv comprises a $V_H$ CDR1 comprising amino acids having the sequence set forth in SEQ ID NO: 262 or conservative modifications thereof, a V_H CDR2 comprising amino acids having the sequence set forth in SEQ ID NO: 263 or conservative modifications thereof, a V_H CDR3 comprising amino acids having the sequence set forth in SEQ ID NO: 264 or conservative modifications thereof, a V_L CDR1 comprising amino acids having the sequence set forth in SEQ ID NO: 265 or conservative modifications thereof, a V_L CDR2 comprising amino acids having the sequence set forth in SEQ ID NO: 266 or conservative modifications thereof, and a V_L CDR3 comprising amino acids having the sequence set forth in SEQ ID NO: 267 or conservative modifications thereof, as shown in Table 24. In certain embodiments, the anti-GPRC5D scFv comprises a V_H CDR1 comprising amino acids having the sequence set forth in SEQ ID NO: 262, a V_H CDR2 comprising amino acids having the sequence set forth in SEQ ID NO: 263, a V_H CDR3 comprising amino acids having the sequence set forth in SEQ ID NO: 264, a V_L CDR1 comprising amino acids having the sequence set forth in SEQ ID NO: 265, a V_L CDR2 comprising amino acids having the sequence set forth in SEQ ID NO: 266, and a V_L CDR3 comprising amino acids having the sequence set forth in SEQ ID NO: 267.

a light chain variable region comprising amino acids having the sequence set forth in SEQ ID NO:275, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 25. In certain embodiments, the anti-GPRC5D scFv comprises a V_H comprising amino acids having the sequence set forth in SEQ ID NO:274, as shown in Table 25. In certain embodiments, the anti-GPRC5D scFv comprises a V_L comprising amino acids having the sequence set forth in SEQ ID NO:275, as shown in Table 25. In certain embodiments, the anti-GPRC5D scFv comprises a V_H comprising amino acids having the sequence set forth in SEQ ID NO:274 and a V_L comprising amino acids having the sequence set forth in SEQ ID NO:275, as shown in Table 25. In certain embodiments, the anti-GPRC5D scFv comprises a V_H CDR1 comprising amino acids having the sequence set forth in SEQ ID NO:268 or conservative modifications thereof, a V_H CDR2 comprising

TABLE 24

| Antigen | A GPRC5D polypeptide having the amino acid sequence of SEQ ID NO: 97 | | |
|---|---|---|---|
| CDRs | 1 | 2 | 3 |
| V_H | GYTFTSYY [SEQ ID NO: 262] | INPSGGST [SEQ ID NO: 263] | ARDVISGFDS [SEQ ID NO: 264] |
| V_L | SSDVGGYNY [SEQ ID NO: 265] | GVS [SEQ ID NO: 266] | SSYAGVNNLM [SEQ ID NO: 267] |
| Full V_H | QVQLVQSGAEVKKPGASVKVSCKASGYTFTSYYMHWVRQAPGQGLE WMGIINPSGGSTSYAQKFQGRVTMTRDTSTSTVYMELSSLRSEDTAV YYCARDVISGFDSWGQGTLVTVSS [SEQ ID NO: 93] | | |
| DNA | Caggtgcagctggtgcaatctggggctgaggtgaagaagcctggggcctcagtgaaggtttcctgcaaggcat ctggatacaccttcaccagctactatatgcactgggtgcgacaggcccctggacaagggcttgagtggatggga ataatcaaccctagtggtggtagcacaagctacgcacagaagttccagggcagagtcaccatgaccagggaca cgtccacgagcacagtctacatggagctgagcagcctgagatctgaggacactgccgtgtattactgtgcgcgc gacgttatctctggtttcgattcttggggtcaaggtactctggtgaccgtctcctca [SEQ ID NO: 95] | | |
| Full V_L | QSALTQPASVSGSPGQSITISCTGTSSDVGGYNYVSWYQQSPGKAPRL MIYGVSKRPSGVPDRFSGSKSGNTASLTVSGLQAEDEADYYCSSYAG VNNLMFGGGTKLTVLG [SEQ ID NO: 94] | | |
| DNA | Cagtctgccctgactcagcctgcctccgtgtctgggtctcctggacagtcgatcaccatctcctgcactggaacc agcagtgacgttggtggttataactatgtctcctggtaccaacaatccccaggcaaagcccccagactcatgattt atggggtcagtaagcggccctctggggtccctgatcgcttctctggctccaagtctggcaacacggcctccctga ccgtctctgggctccaggctgaagatgaggctgattattactgcagctcatatgcaggcgtcaacaatttaatgttc ggcggagggaccaagctgaccgtcctaggt [SEQ ID NO: 96] | | |
| scFv | QSALTQPASVSGSPGQSITISCTGTSSDVGGYNYVSWYQQSPGKAPRL MIYGVSKRPSGVPDRFSGSKSGNTASLTVSGLQAEDEADYYCSSYAG VNNLMFGGGTKLTVLGSRGGGGSGGGGSGGGGSLEMAQVQLVQSG AEVKKPGASVKVSCKASGYTFTSYYMHWVRQAPGQGLEWMGIINPS GGSTSYAQKFQGRVTMTRDTSTSTVYMELSSLRSEDTAVYYCARDVI SGFDSWGQGTLVTVSS [SEQ ID NO: 123] | | |

In certain embodiments, the antibody or other antigen binding protein is an anti-GPRC5D scFv or an antigen-binding fragment thereof having an antigen-binding region that comprises the amino acid sequence of SEQ ID NO:276 and specifically binds to a GPRC5D polypeptide (e.g., a GPRC5D polypeptide having the amino acid sequence SEQ ID NO:97, or fragments thereof), which is designated as ET150-024 scFv (also referred to as "ET150-174 scFv").

In certain embodiments, the anti-GPRC5D scFv antibody comprises a heavy chain variable region comprising amino acids having the sequence set forth in SEQ ID NO:274 and amino acids having the sequence set forth in SEQ ID NO:269 or conservative modifications thereof, and a V_H CDR3 comprising amino acids having the sequence set forth in SEQ ID NO:270 or conservative modifications thereof, as shown in Table 8. In certain embodiments, the anti-GPRC5D scFv comprises a V_L CDR1 comprising amino acids having the sequence set forth in SEQ ID NO:271 or conservative modifications thereof, a V_L CDR2 comprising amino acids having the sequence set forth in SEQ ID NO:272 or conservative modifications thereof, and a V_L CDR3 comprising amino acids having the sequence set forth in SEQ ID NO:273 or conservative modifications thereof, as shown in Table 25. In certain embodiments, the anti-GPRC5D scFv comprises a V$_H$ CDR1 comprising amino acids having the sequence set forth in SEQ ID NO:268 or conservative modifications thereof, a V$_H$ CDR2 comprising amino acids having the sequence set forth in SEQ ID NO:269 or conservative modifications thereof, a V$_H$ CDR3 comprising amino acids having the sequence set forth in SEQ ID NO:270 or conservative modifications thereof, a V$_L$ CDR1 comprising amino acids having the sequence set forth in SEQ ID NO:271 or conservative modifications thereof, a V$_L$ CDR2 comprising amino acids having the sequence set forth in SEQ ID NO:272 or conservative modifications thereof, and a V$_L$ CDR3 comprising amino acids having the sequence set forth in SEQ ID NO:273 or conservative modifications thereof, as shown in Table 25. In certain embodiments, the anti-GPRC5D scFv comprises a V$_H$ CDR1 comprising amino acids having the sequence set forth in SEQ ID NO:268, a V$_H$ CDR2 comprising amino acids having the sequence set forth in SEQ ID NO:269, a V$_H$ CDR3 comprising amino acids having the sequence set forth in SEQ ID NO:270, a V$_L$ CDR1 comprising amino acids having the sequence set forth in SEQ ID NO:271, a V$_L$ CDR2 comprising amino acids having the sequence set forth in SEQ ID NO:272, and a V$_L$ CDR3 comprising amino acids having the sequence set forth in SEQ ID NO:273.

TABLE 25

| Antigen | A GPRC5D polypeptide having the amino acid sequence of SEQ ID NO: 97 | | |
|---|---|---|---|
| CDRs | 1 | 2 | 3 |
| V$_H$ | GFTFGDYG [SEQ ID NO: 268] | INWNGGST [SEQ ID NO: 269] | ARSKQGY [SEQ ID NO: 270] |
| V$_L$ | SRDAGGYNY [SEQ ID NO: 271] | EVT [SEQ ID NO: 272] | SSYGGSNNFRV [SEQ ID NO: 273] |
| Full V$_H$ | EVQLVESGGGVVRPGGSLRLSCAASGFTFGDYGMSWVRQAPGKGLE WVSGINWNGGSTGYADSVKGRFTISRDNAKNSLYLQMNSLRAEDTA VYYCARSKQDYWGQGTLVTVSS [SEQ ID NO: 274] | | |
| DNA | GAGGTGCAGCTGGTGGAGTCTGGGGGAGGTGTGGTACGGCCTGGG GGGTCCCTGAGACTCTCCTGTGCAGCCTCTGGATTCACCTTTGGTG ATTATGGCATGAGCTGGGTCCGCCAAGCTCCAGGGAAGGGGCTGG AGTGGGTCTCTGGTATTAATTGGAATGGTGGTAGCACAGGTTATGC AGACTCTGTGAAGGGCCGATTCACCATCTCCAGAGACAACGCCAA GAACTCCCTGTATCTGCAAATGAACAGTCTGAGAGCCGAGGACAC GGCCGTATATTACTGTGCGCGCTCTAAACAGGATTACTGGGGTCAA GGTACTCTGGTGACCGTCTCCTCA [SEQ ID NO: 277] | | |
| Full V$_L$ | MKKTAIAIAVALAGFATVAQAAELQSALTQPPSASGSPGQSVTISCTGT SRDAGGYNYFSWYQQHPGKAPKLLIYEVTKRPSGVPDRFSGSKSGKT ASLTVSGLQADDEAVYYCSSYGGSNNFRVFGGGTKLTVLG [SEQ ID NO: 275] | | |
| DNA | ATGAAAAAGACAGCTATCGCGATTGCAGTGGCACTGGCTGGTTTC GCTACCGTGGCCCAGGCGGCCGAGCTCCAGTCTGCCCTGACTCAGC CTCCCTCCGCGTCCGGGTCTCCTGGACAGTCAGTCACCATCTCCTG CACTGGAACCAGCAGGGACGCTGGTGGTTATAATTATTTCTCCTGG TACCAACAACACCCAGGCAAAGCCCCCAAACTCCTGATTTATGAG GTCACTAAGCGGCCCTCAGGGGTCCCTGATCGCTTCTCTGGCTCCA AGTCTGGCAAGACGGCCTCCCTGACCGTCTCTGGGCTCCAGGCTGA CGATGAGGCTGTATATTACTGCAGCTCATATGGAGGCAGCAACAA CTTTCGGGTGTTCGGCGGAGGGACCAAGCTGACCGTCCTAGGT [SEQ ID NO: 278] | | |
| scFv | MKKTAIAIAVALAGFATVAQAAELQSALTQPPSASGSPGQSVTISCTGT SRDAGGYNYFSWYQQHPGKAPKLLIYEVTKRPSGVPDRFSGSKSGKT ASLTVSGLQADDEAVYYCSSYGGSNNFRVFGGGTKLTVLG<u>SRGGGGS GGGGSGGGGSLEMA</u>EVQLVESGGGVVRPGGSLRLSCAASGFTFGDY GMSWVRQAPGKGLEWVSGINWNGGSTGYADSVKGRFTISRDNAKNS LYLQMNSLRAEDTAVYYCARSKQDYWGQGTLVTVSS [SEQ ID NO: 276] | | |
| DNA | ATGAAAAAGACAGCTATCGCGATTGCAGTGGCACTGGCTGGTTTC GCTACCGTGGCCCAGGCGGCCGAGCTCCAGTCTGCCCTGACTCAGC CTCCCTCCGCGTCCGGGTCTCCTGGACAGTCAGTCACCATCTCCTG CACTGGAACCAGCAGGGACGCTGGTGGTTATAATTATTTCTCCTGG TACCAACAACACCCAGGCAAAGCCCCCAAACTCCTGATTTATGAG GTCACTAAGCGGCCCTCAGGGGTCCCTGATCGCTTCTCTGGCTCCA AGTCTGGCAAGACGGCCTCCCTGACCGTCTCTGGGCTCCAGGCTGA CGATGAGGCTGTATATTACTGCAGCTCATATGGAGGCAGCAACAA CTTTCGGGTGTTCGGCGGAGGGACCAAGCTGACCGTCCTAGGTTCT AGAGGTGGTGGTGGTAGCGGCGGCGGCGGCTCTGGTGGTGGTGGA TCCCTCGAGATGGCCGAGGTGCAGCTGGTGGAGTCTGGGGGAGGT GTGGTACGGCCTGGGGGGTCCCTGAGACTCTCCTGTGCAGCCTCTG GATTCACCTTTGGTGATTATGGCATGAGCTGGGTCCGCCAAGCTCC AGGGAAGGGGCTGGAGTGGGTCTCTGGTATTAATTGGAATGGTGG TAGCACAGGTTATGCAGACTCTGTGAAGGGCCGATTCACCATCTCC | | |

TABLE 25-continued

```
AGAGACAACGCCAAGAACTCCCTGTATCTGCAAATGAACAGTCTG
AGAGCCGAGGACACGGCCGTATATTACTGTGCGCGCTCTAAACAG
GATTACTGGGGTCAAGGTACTCTGGTGACCGTCTCCTCA
[SEQ ID NO: 279]
```

In certain embodiments, the antibody or other antigen binding protein is an anti-GPRC5D scFv or an antigen-binding fragment thereof having an antigen-binding region that comprises the amino acid sequence of SEQ ID NO: 288 and specifically binds to a GPRC5D polypeptide (e.g., a GPRC5D polypeptide having the amino acid sequence SEQ ID NO:97, or fragments thereof), which is designated as ET150-026 scFv (also referred to as "ET150-176 scFv").

In certain embodiments, the anti-GPRC5D scFv antibody comprises a heavy chain variable region comprising amino acids having the sequence set forth in SEQ ID NO:286 and a light chain variable region comprising amino acids having the sequence set forth in SEQ ID NO:287, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 26. In certain embodiments, the anti-GPRC5D scFv comprises a $V_H$ comprising amino acids having the sequence set forth in SEQ ID NO:286, as shown in Table 26. In certain embodiments, the anti-GPRC5D scFv comprises a $V_L$ comprising amino acids having the sequence set forth in SEQ ID NO:287, as shown in Table 26. In certain embodiments, the anti-GPRC5D scFv comprises a $V_H$ comprising amino acids having the sequence set forth in SEQ ID NO:286 and a $V_L$ comprising amino acids having the sequence set forth in SEQ ID NO:287, as shown in Table 26. In certain embodiments, the anti-GPRC5D scFv comprises a $V_H$ CDR1 comprising amino acids having the sequence set forth in SEQ ID NO:280 or conservative modifications thereof, a $V_H$ CDR2 comprising amino acids having the sequence set forth in SEQ ID NO:281 or conservative modifications thereof, and a $V_H$ CDR3 comprising amino acids having the sequence set forth in SEQ ID NO:282 or conservative modifications thereof, as shown in Table 26. In certain embodiments, the anti-GPRC5D scFv comprises a $V_L$ CDR1 comprising amino acids having the sequence set forth in SEQ ID NO:283 or conservative modifications thereof, a $V_L$ CDR2 comprising amino acids having the sequence set forth in SEQ ID NO:284 or conservative modifications thereof, and a $V_L$ CDR3 comprising amino acids having the sequence set forth in SEQ ID NO:285 or conservative modifications thereof, as shown in Table 26. In certain embodiments, the anti-GPRC5D scFv comprises a $V_H$ CDR1 comprising amino acids having the sequence set forth in SEQ ID NO:280 or conservative modifications thereof, a $V_H$ CDR2 comprising amino acids having the sequence set forth in SEQ ID NO:281 or conservative modifications thereof, a $V_H$ CDR3 comprising amino acids having the sequence set forth in SEQ ID NO:282 or conservative modifications thereof, a $V_L$ CDR1 comprising amino acids having the sequence set forth in SEQ ID NO:283 or conservative modifications thereof, a $V_L$ CDR2 comprising amino acids having the sequence set forth in SEQ ID NO:284 or conservative modifications thereof, and a $V_L$ CDR3 comprising amino acids having the sequence set forth in SEQ ID NO:285 or conservative modifications thereof, as shown in Table 26. In certain embodiments, the anti-GPRC5D scFv comprises a $V_H$ CDR1 comprising amino acids having the sequence set forth in SEQ ID NO:280, a $V_H$ CDR2 comprising amino acids having the sequence set forth in SEQ ID NO:281, a $V_H$ CDR3 comprising amino acids having the sequence set forth in SEQ ID NO:282, a $V_L$ CDR1 comprising amino acids having the sequence set forth in SEQ ID NO:283, a $V_L$ CDR2 comprising amino acids having the sequence set forth in SEQ ID NO:284, and a $V_L$ CDR3 comprising amino acids having the sequence set forth in SEQ ID NO:285.

TABLE 26

| Antigen | A GPRC5D polypeptide having the amino acid sequence of SEQ ID NO: 97 | | |
|---|---|---|---|
| CDRs | 1 | 2 | 3 |
| $V_H$ | GFTFSNYA [SEQ ID NO: 280] | ITNSGRST [SEQ ID NO: 281] | ARVTHRRYGSTFDS [SEQ ID NO: 282] |
| $V_L$ | SSNIGSNT [SEQ ID NO: 283] | SNN [SEQ ID NO: 284] | AAWDDSVNGYV [SEQ ID NO: 285] |
| Full $V_H$ | QLQLQESGGGSVQPGGSLRLSCAASGFTFSNYAMSWVRQAPGKGLE WVSAITNSGRSTYYADSVKGRFTISRDNSKNTLSLQMSSLRAEDTAVY YCARVTHRRYGSTFDSRGQGTLVTVSS [SEQ ID NO: 286] | | |
| DNA | CAGCTGCAGCTGCAGGAGTCGGGGGGAGGCTCGGTACAGCCGGGG GGGTCTCTGAGACTGTCCTGTGCAGCCTCTGGATTCACCTTTAGCA ACTATGCCATGAGCTGGGTCCGCCAGGCTCCAGGGAAGGGGCTGG AGTGGGTCTCAGCTATCACTAATAGTGGTCGTAGTACATACTACGC AGACTCCGTGAAGGGCCGGTTCACCATCTCCAGAGACAATTCCAA GAACACGCTGTCTTTGCAAATGAGCAGCCTGAGAGCCGAAGACAC GGCCGTGTATTACTGTGCGCGCGTTACTCATCGTCGTTACGGTTCT ACTTTCGATTCTCGGGGTCAAGGTACTCTGGTGACCGTCTCCTCA ACTAGTGGCCAGGCCGGCCAGC [SEQ ID NO: 289] | | |

TABLE 26-continued

```
Full      MKKTAIAIAVALAGFATVAQAAELSYELTQPPSASGTPGQRVSISCSGS
V_L       SSNIGSNTVNWYQQFPGTAPKLLIHSNNQRPSGVPDRFSGSKSGTSASL
          AISGPQSEDEADYYCAAWDDSVNGYVFGTGTKVTVLG
          [SEQ ID NO: 287]

DNA       ATGAAAAAGACAGCTATCGCGATTGCAGTGGCACTGGCTGGTTTC
          GCTACCGTGGCCCAGGCGGCCGAGCTCTCCTATGAGCTGACTCAGC
          CACCCTCAGCGTCTGGGACCCCCGGGCAGAGGGTCAGCATCTCTTG
          TTCTGGAAGCAGCTCCAACATCGGGAGTAATACTGTAAACTGGTAC
          CAACAGTTCCCCGGAACGGCCCCCAAACTCCTCATCCATAGTAATA
          ATCAGCGGCCCTCAGGGGTCCCTGACCGATTCTCTGGCTCCAAGTC
          TGGCACCTCAGCCTCCCTGGCCATCAGTGGGCCCCAGTCTGAGGAT
          GAGGCTGATTATTACTGTGCAGCTTGGGATGACAGTGTGAATGGTT
          ATGTCTTCGGAACTGGGACCAAGGTCACCGTCCTAGGT
          [SEQ ID NO: 290]

scFv      MKKTAIAIAVALAGFATVAQAAELSYELTQPPSASGTPGQRVSISCSGS
          SSNIGSNTVNWYQQFPGTAPKLLIHSNNQRPSGVPDRFSGSKSGTSASL
          AISGPQSEDEADYYCAAWDDSVNGYVFGTGTKVTVLGSRGGGGSGG
          GGSGGGGSLEMAQLQLQESGGGSVQPGGSLRLSCAASGFTFSNYAMS
          WVRQAPGKGLEWVSAITNSGRSTYYADSVKGRFTISRDNSKNTLSLQ
          MSSLRAEDTAVYYCARVTHRRYGSTFDSRGQGTLVTVSS
          [SEQ ID NO: 288]

DNA       ATGAAAAAGACAGCTATCGCGATTGCAGTGGCACTGGCTGGTTTC
          GCTACCGTGGCCCAGGCGGCCGAGCTCTCCTATGAGCTGACTCAGC
          CACCCTCAGCGTCTGGGACCCCCGGGCAGAGGGTCAGCATCTCTTG
          TTCTGGAAGCAGCTCCAACATCGGGAGTAATACTGTAAACTGGTAC
          CAACAGTTCCCCGGAACGGCCCCCAAACTCCTCATCCATAGTAATA
          ATCAGCGGCCCTCAGGGGTCCCTGACCGATTCTCTGGCTCCAAGTC
          TGGCACCTCAGCCTCCCTGGCCATCAGTGGGCCCCAGTCTGAGGAT
          GAGGCTGATTATTACTGTGCAGCTTGGGATGACAGTGTGAATGGTT
          ATGTCTTCGGAACTGGGACCAAGGTCACCGTCCTAGGTTCTAGAGG
          TGGTGGTGGTAGCGGCGGCGGCGGCTCTGGTGGTGGTGGATCCCTC
          GAGATGGCCCAGCTGCAGCTGCAGGAGTCGGGGGGAGGCTCGGTA
          CAGCCGGGGGGTCTCTGAGACTGTCCTGTGCAGCCTCTGGATTCA
          CCTTTAGCAACTATGCCATGAGCTGGGTCCGCCAGGCTCCAGGGAA
          GGGGCTGGAGTGGGTCTCAGCTATCACTAATAGTGGTCGTAGTACA
          TACTACGCAGACTCCGTGAAGGGCCGGTTCACCATCTCCAGAGAC
          AATTCCAAGAACACGCTGTCTTTGCAAATGAGCAGCCTGAGAGCC
          GAAGACACGGCCGTGTATTACTGTGCGCGCGTTACTCATCGTCGTT
          ACGGTTCTACTTTCGATTCTCGGGGTCAAGGTACTCTGGTGACCGT
          CTCCTCA [SEQ ID NO: 291]
```

In certain embodiments, the antibody or other antigen binding protein is an anti-GPRC5D scFv or an antigen-binding fragment thereof having an antigen-binding region that comprises the amino acid sequence of SEQ ID NO: 300 and specifically binds to a GPRC5D polypeptide (e.g., a GPRC5D polypeptide having the amino acid sequence SEQ ID NO:97, or fragments thereof), which is designated as ET150-028 scFv (also referred to as "ET150-178 scFv").

In certain embodiments, the anti-GPRC5D scFv antibody comprises a heavy chain variable region comprising amino acids having the sequence set forth in SEQ ID NO:298 and a light chain variable region comprising amino acids having the sequence set forth in SEQ ID NO:299, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 27. In certain embodiments, the anti-GPRC5D scFv comprises a $V_H$ comprising amino acids having the sequence set forth in SEQ ID NO:298, as shown in Table 27. In certain embodiments, the anti-GPRC5D scFv comprises a $V_L$ comprising amino acids having the sequence set forth in SEQ ID NO:299, as shown in Table 27. In certain embodiments, the anti-GPRC5D scFv comprises a $V_H$ comprising amino acids having the sequence set forth in SEQ ID NO:298 and a $V_L$ comprising amino acids having the sequence set forth in SEQ ID NO:299, as shown in Table 27. In certain embodiments, the anti-GPRC5D scFv comprises a $V_H$ CDR1 comprising amino acids having the sequence set forth in SEQ ID NO:292 or conservative modifications thereof, a $V_H$ CDR2 comprising amino acids having the sequence set forth in SEQ ID NO:293 or conservative modifications thereof, and a $V_H$ CDR3 comprising amino acids having the sequence set forth in SEQ ID NO:294 or conservative modifications thereof, as shown in Table 27. In certain embodiments, the anti-GPRC5D scFv comprises a $V_L$ CDR1 comprising amino acids having the sequence set forth in SEQ ID NO:295 or conservative modifications thereof, a $V_L$ CDR2 comprising amino acids having the sequence set forth in SEQ ID NO:296 or conservative modifications thereof, and a $V_L$ CDR3 comprising amino acids having the sequence set forth in SEQ ID NO:297 or conservative modifications thereof, as shown in Table 27. In certain embodiments, the anti-GPRC5D scFv comprises a $V_H$ CDR1 comprising amino acids having the sequence set forth in SEQ ID NO:292 or conservative modifications thereof, a $V_H$ CDR2 comprising amino acids having the sequence set forth in SEQ ID NO:293 or conservative modifications thereof, a $V_H$ CDR3 comprising amino acids having the sequence set forth in SEQ ID NO:294 or conservative modifications thereof, a $V_L$ CDR1 comprising amino acids having the sequence set forth in SEQ ID NO:295 or conservative modifications thereof, a $V_L$ CDR2 comprising amino acids having the sequence set forth in SEQ ID NO:296 or conservative modifications thereof, and a $V_L$ CDR3 comprising amino acids having the sequence set forth in SEQ ID NO:297 or conservative modifications thereof, as shown in Table 27. In certain embodiments, the anti-GPRC5D scFv comprises a $V_H$ CDR1 comprising amino acids having the sequence set forth in SEQ ID NO:292, a $V_H$ CDR2 comprising amino acids having the sequence set forth in SEQ ID NO:293, a $V_H$ CDR3 comprising amino acids having the sequence set forth in SEQ ID NO:294, a $V_L$ CDR1 comprising amino acids having the sequence set forth in SEQ ID NO:295, a $V_L$ CDR2 comprising amino acids having the sequence set forth in SEQ ID NO:296, and a $V_L$ CDR3 comprising amino acids having the sequence set forth in SEQ ID NO:297.

TABLE 27

| Antigen | A GPRC5D polypeptide having the amino acid sequence of SEQ ID NO: 97 | | |
|---|---|---|---|
| CDRs | 1 | 2 | 3 |
| $V_H$ | GGTFRSYA [SEQ ID NO: 292] | IIPMLDIT [SEQ ID NO: 293] | ARTYSRSPFHMEDF [SEQ ID NO: 294] |
| $V_L$ | SSNIGGNT [SEQ ID NO: 295] | RNN [SEQ ID NO: 296] | AAWDASRQGV [SEQ ID NO: 297] |
| Full $V_H$ | QVQLVQSGAEVKKPGSSVKVSCKASGGTFRSYAITWVRQAPGQGLE WMGRIIPMLDITNYAQKFQGRVTITADKSTSTAYMELSSLRSEDTAVY YCARTYSRSPFHMEDFWGQGTLVTVSS [SEQ ID NO: 298] | | |
| DNA | CAGGTGCAGCTGGTGCAGTCTGGGGCTGAGGTGAAGAAGCCTGGG TCCTCGGTGAAGGTCTCCTGCAAGGCTTCTGGAGGCACCTTCCGCA GCTATGCTATCACCTGGGTGCGACAGGCCCCTGGACAAGGGCTTG AGTGGATGGGAAGGATCATCCCTATGCTTGATATAACAAACTACG CACAGAAGTTCCAGGGCAGAGTCACGATTACCGCGGACAAATCCA CGAGCACAGCCTACATGGAGCTGAGCAGCCTGAGATCTGAGGACA CGGCCGTGTATTACTGTGCGCGCACTTACTCTCGTTCTCCGTTCCAT ATGGAAGATTTCTGGGGTCAAGGTACTCTGGTGACCGTCTCCTCA [SEQ ID NO: 300] | | |
| Full $V_L$ | MKKTAIAIAVALAGFATVAQAAELQPVLTQPPSASGTPGQRVTISCSG SSSNIGGNTVSWYQQVPGTAPRLLIFRNNQRPPGVPDRFSGSKSGTSAS LAISGLRSEDEADYYCAAWDASRQGVFGGGTKLTVLG [SEQ ID NO: 299] | | |
| DNA | ATGAAAAAGACAGCTATCGCGATTGCAGTGGCACTGGCTGGTTTC GCTACCGTGGCCCAGGCGGCCGAGCTCCAGCCTGTGCTGACTCAG CCACCCTCAGCGTCTGGGACCCCCGGGCAGAGGGTCACCATCTCTT GTTCTGGAAGCAGCTCCAATATCGGAGGTAACACTGTCAGCTGGTA CCAGCAGGTCCCAGGAACGGCCCCCAGACTCCTCATTTTTAGGAAT AATCAACGGCCCCCAGGGGTCCCTGACCGATTCTCTGGCTCCAAGT CTGGCACCTCAGCCTCCTGGCCATCAGTGGGCTCCGGTCTGAGGA TGAGGCTGATTATTACTGTGCAGCATGGGACGCCAGTCGACAAGG GGTGTTCGGCGGAGGGACCAAGCTGACCGTCCTAGGT [SEQ ID NO: 301] | | |
| scFv | MKKTAIAIAVALAGFATVAQAAELQPVLTQPPSASGTPGQRVTISCSG SSSNIGGNTVSWYQQVPGTAPRLLIFRNNQRPPGVPDRFSGSKSGTSAS LAISGLRSEDEADYYCAAWDASRQGVFGGGTKLTVLGSRGGGGSGG GGSGGGGSLEMAQVQLVQSGAEVKKPGSSVKVSCKASGGTFRSYAIT WVRQAPGQGLEWMGRIIPMLDITNYAQKFQGRVTITADKSTSTAYME LSSLRSEDTAVYYCARTYSRSPFHMEDFWGQGTLVTVSS [SEQ ID NO: 300] | | |
| DNA | ATGAAAAAGACAGCTATCGCGATTGCAGTGGCACTGGCTGGTTTC GCTACCGTGGCCCAGGCGGCCGAGCTCCAGCCTGTGCTGACTCAG CCACCCTCAGCGTCTGGGACCCCCGGGCAGAGGGTCACCATCTCTT GTTCTGGAAGCAGCTCCAATATCGGAGGTAACACTGTCAGCTGGTA CCAGCAGGTCCCAGGAACGGCCCCCAGACTCCTCATTTTTAGGAAT AATCAACGGCCCCCAGGGGTCCCTGACCGATTCTCTGGCTCCAAGT CTGGCACCTCAGCCTCCTGGCCATCAGTGGGCTCCGGTCTGAGGA TGAGGCTGATTATTACTGTGCAGCATGGGACGCCAGTCGACAAGG GGTGTTCGGCGGAGGGACCAAGCTGACCGTCCTAGGTTCTAGAGG TGGTGGTGGTAGCGGCGGCGGCGGCTCTGGTGGTGGTGGATCCCTC GAGATGGCCCAGGTGCAGCTGGTGCAGTCTGGGGCTGAGGTGAAG AAGCCTGGGTCCTCGGTGAAGGTCTCCTGCAAGGCTTCTGGAGGCA CCTTCCGCAGCTATGCTATCACCTGGGTGCGACAGGCCCCTGGACA AGGGCTTGAGTGGATGGGAAGGATCATCCCTATGCTTGATATAAC AAACTACGCACAGAAGTTCCAGGGCAGAGTCACGATTACCGCGGA CAAATCCACGAGCACAGCCTACATGGAGCTGAGCAGCCTGAGATC TGAGGACACGGCCGTGTATTACTGTGCGCGCACTTACTCTCGTTCT CCGTTCCATATGGAAGATTTCTGGGGTCAAGGTACTCTGGTGACCG TCTCCTCA [SEQ ID NO: 302] | | |

In certain embodiments, the antibody or other antigen binding protein is an anti-GPRC5D scFv or an antigen-binding fragment thereof having an antigen-binding region that comprises the amino acid sequence of SEQ ID NO:312 and specifically binds to a GPRC5D polypeptide (e.g., a GPRC5D polypeptide having the amino acid sequence SEQ ID NO:97, or fragments thereof), which is designated as ET150-029 scFv (also referred to as "ET150-179 scFv").

In certain embodiments, the anti-GPRC5D scFv antibody comprises a heavy chain variable region comprising amino acids having the sequence set forth in SEQ ID NO:310 and a light chain variable region comprising amino acids having the sequence set forth in SEQ ID NO:311, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 28. In certain embodiments, the anti-GPRC5D scFv comprises a $V_H$ comprising amino acids having the sequence set forth in SEQ ID NO:310, as shown in Table 28. In certain embodiments, the anti-GPRC5D scFv comprises a $V_L$ comprising amino acids having the sequence set forth in SEQ ID NO:311, as shown in Table 28. In certain embodiments, the anti-GPRC5D scFv comprises a $V_H$ comprising amino acids having the sequence set forth in SEQ ID NO:310 and a $V_L$ comprising amino acids having the sequence set forth in SEQ ID NO:311, as shown in Table 28. In certain embodiments, the anti-GPRC5D scFv comprises a $V_H$ CDR1 comprising amino acids having the sequence set forth in SEQ ID NO:303 or conservative modifications thereof, a $V_H$ CDR2 comprising amino acids having the sequence set forth in SEQ ID NO:304 or conservative modifications thereof, and a $V_H$ CDR3 comprising amino acids having the sequence set forth in SEQ ID NO:305 or conservative modifications thereof, as shown in Table 28. In certain embodiments, the anti-GPRC5D scFv comprises a $V_L$ CDR1 comprising amino acids having the sequence set forth in SEQ ID NO:306 or conservative modifications thereof, a $V_L$ CDR2 comprising amino acids having the sequence set forth in SEQ ID NO:307 or conservative modifications thereof, and a $V_L$ CDR3 comprising amino acids having the sequence set forth in SEQ ID NO:308 or conservative modifications thereof, as shown in Table 28. In certain embodiments, the anti-GPRC5D scFv comprises a $V_H$ CDR1 comprising amino acids having the sequence set forth in SEQ ID NO:303 or conservative modifications thereof, a $V_H$ CDR2 comprising amino acids having the sequence set forth in SEQ ID NO:304 or conservative modifications thereof, a $V_H$ CDR3 comprising amino acids having the sequence set forth in SEQ ID NO:305 or conservative modifications thereof, a $V_L$ CDR1 comprising amino acids having the sequence set forth in SEQ ID NO:306 or conservative modifications thereof, a $V_L$ CDR2 comprising amino acids having the sequence set forth in SEQ ID NO:307 or conservative modifications thereof, and a $V_L$ CDR3 comprising amino acids having the sequence set forth in SEQ ID NO:308 or conservative modifications thereof, as shown in Table 28. In certain embodiments, the anti-GPRC5D scFv comprises a $V_H$ CDR1 comprising amino acids having the sequence set forth in SEQ ID NO:303, a $V_H$ CDR2 comprising amino acids having the sequence set forth in SEQ ID NO:304, a $V_H$ CDR3 comprising amino acids having the sequence set forth in SEQ ID NO:305, a $V_L$ CDR1 comprising amino acids having the sequence set forth in SEQ ID NO:306, a $V_L$ CDR2 comprising amino acids having the sequence set forth in SEQ ID NO:307, and a $V_L$ CDR3 comprising amino acids having the sequence set forth in SEQ ID NO:308.

TABLE 28

| Antigen | A GPRC5D polypeptide having the amino acid sequence of SEQ ID NO: 97 | | |
|---|---|---|---|
| CDRs | 1 | 2 | 3 |
| $V_H$ | GFTFSSYA [SEQ ID NO: 303] | ISGSGGST [SEQ ID NO: 304] | ARKYQDV [SEQ ID NO: 305] |
| $V_L$ | SSNIGSNT [SEQ ID NO: 306] | RNN [SEQ ID NO: 307] | AAWDDSLSGRV [SEQ ID NO: 308] |
| Full $V_H$ | EVQLVESGGGLVQPGGSLRLSCAASGFTFSSYAMSWVRQAPGKGLE WVSAISGSGGSTYYADSVKGRFTISRDNAKNTLYLQMNSLRAEDTAV YYCARKYQDVWGQGTLVTVSS [SEQ ID NO: 310] | | |
| DNA | GAGGTGCAGCTGGTGGAGTCTGGGGGAGGCTTGGTACAGCCTGGG GGGTCCCTGAGACTCTCCTGTGCAGCCTCTGGATTCACCTTTAGCA GCTATGCCATGAGCTGGGTCCGCCAGGCTCCAGGGAAGGGGCTGG AGTGGGTCTCAGCTATTAGTGGTAGTGGTGGTAGCACATACTACGC AGACTCCGTGAAGGGCCGGTTCACCATCTCCAGAGACAATGCCAA GAACACGCTGTATCTGCAAATGAACAGCCTGAGAGCCGAGGACAC GGCCGTATATTACTGTGCGCGCAAATACCAGGATGTTTGGGGTCAA GGTACTCTGGTGACCGTCTCCTCA [SEQ ID NO: 313] | | |
| Full $V_L$ | MKKTAIAIAVALAGFATVAQAAELQSVLTQPPSASGTPGQRVTISCSG SSSNIGSNTVNWYQQLPGTAPKLLIYRNNQRPSGVPDRFSGSKSGTSAS LAISGLRSEDEADYYCAAWDDSLSGRVFGGGTKLTVLG [SEQ ID NO: 311] | | |
| DNA | ATGAAAAAGACAGCTATCGCGATTGCAGTGGCACTGGCTGGTTTC GCTACCGTGGCCCAGGCGGCCGAGCTCCAGTCTGTGCTGACGCAG CCGCCCTCAGCGTCTGGGACCCCCGGGCAGAGGGTCACCATCTCTT GTTCTGGAAGCAGCTCCAACATCGGAAGTAATACTGTAAACTGGT ACCAGCAGCTCCCAGGAACGGCCCCCAAACTCCTCATCTATAGGA ATAATCAGCGGCCCTCAGGGGTCCCTGACCGATTCTCTGGCTCCAA | | |

TABLE 28-continued

```
          GTCTGGCACCTCAGCCTCCCTGGCCATCAGTGGGCTCCGGTCCGAG
          GATGAGGCTGATTATTACTGTGCAGCATGGGATGACAGCCTGAGT
          GGTAGGGTGTTCGGCGGAGGGACCAAGCTGACCGTCCTAGGT
          [SEQ ID NO: 314]

scFv      MKKTAIAIAVALAGFATVAQAAELQSVLTQPPSASGTPGQRVTISCSG
          SSSNIGSNTVNWYQQLPGTAPKLLIYRNNQRPSGVPDRFSGSKSGTSAS
          LAISGLRSEDEADYYCAAWDDSLSGRVFGGGTKLTVLGSRGGGGSGG
          GGSGGGGSLEMAEVQLVESGGGLVQPGGSLRLSCAASGFTFSSYAMS
          WVRQAPGKGLEWVSAISGSGGSTYYADSVKGRFTISRDNAKNTLYLQ
          MNSLRAEDTAVYYCARKYQDVWGQGTLVTVSS
          [SEQ ID NO: 312]

DNA       ATGAAAAAGACAGCTATCGCGATTGCAGTGGCACTGGCTGGTTTC
          GCTACCGTGGCCCAGGCGGCCGAGCTCCAGTCTGTGCTGACGCAG
          CCGCCCTCAGCGTCTGGGACCCCCGGGCAGAGGGTCACCATCTCTT
          GTTCTGGAAGCAGCTCCAACATCGGAAGTAATACTGTAAACTGGT
          ACCAGCAGCTCCCAGGAACGGCCCCCAAACTCCTCATCTATAGGA
          ATAATCAGCGGCCCTCAGGGGTCCCTGACCGATTCTCTGGCTCCAA
          GTCTGGCACCTCAGCCTCCCTGGCCATCAGTGGGCTCCGGTCCGAG
          GATGAGGCTGATTATTACTGTGCAGCATGGGATGACAGCCTGAGT
          GGTAGGGTGTTCGGCGGAGGGACCAAGCTGACCGTCCTAGGTTCT
          AGAGGTGGTGGTGGTAGCGGCGGCGGCGGCTCTGGTGGTGGTGGA
          TCCCTCGAGATGGCCGAGGTGCAGCTGGTGGAGTCTGGGGGAGGC
          TTGGTACAGCCTGGGGGGTCCCTGAGACTCTCCTGTGCAGCCTCTG
          GATTCACCTTTAGCAGCTATGCCATGAGCTGGGTCCGCCAGGCTCC
          AGGGAAGGGGCTGGAGTGGGTCTCAGCTATTAGTGGTAGTGGTGG
          TAGCACATACTACGCAGACTCCGTGAAGGGCCGGTTCACCATCTCC
          AGAGACAATGCCAAGAACACGCTGTATCTGCAAATGAACAGCCTG
          AGAGCCGAGGACACGGCCGTATATTACTGTGCGCGCAAATACCAG
          GATGTTTGGGGTCAAGGTACTCTGGTGACCGTCTCCTCA
          [SEQ ID NO: 315]
```

In certain embodiments, the antibody or other antigen binding protein is an anti-GPRC5D scFv or an antigen-binding fragment thereof having an antigen-binding region that comprises the amino acid sequence of SEQ ID NO:324 and specifically binds to a GPRC5D polypeptide (e.g., a GPRC5D polypeptide having the amino acid sequence SEQ ID NO:97, or fragments thereof), which is designated as ET150-030 scFv (also referred to as "ET150-180 scFv").

In certain embodiments, the anti-GPRC5D scFv antibody comprises a heavy chain variable region comprising amino acids having the sequence set forth in SEQ ID NO:322 and a light chain variable region comprising amino acids having the sequence set forth in SEQ ID NO:323, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 29. In certain embodiments, the anti-GPRC5D scFv comprises a $V_H$ comprising amino acids having the sequence set forth in SEQ ID NO:322, as shown in Table 29. In certain embodiments, the anti-GPRC5D scFv comprises a $V_L$ comprising amino acids having the sequence set forth in SEQ ID NO:323, as shown in Table 29. In certain embodiments, the anti-GPRC5D scFv comprises a $V_H$ comprising amino acids having the sequence set forth in SEQ ID NO:322 and a $V_L$ comprising amino acids having the sequence set forth in SEQ ID NO:323, as shown in Table 29. In certain embodiments, the anti-GPRC5D scFv comprises a $V_H$ CDR1 comprising amino acids having the sequence set forth in SEQ ID NO:316 or conservative modifications thereof, a $V_H$ CDR2 comprising amino acids having the sequence set forth in SEQ ID NO:317 or conservative modifications thereof, and a $V_H$ CDR3 comprising amino acids having the sequence set forth in SEQ ID NO:318 or conservative modifications thereof, as shown in Table 29. In certain embodiments, the anti-GPRC5D scFv comprises a $V_L$ CDR1 comprising amino acids having the sequence set forth in SEQ ID NO:319 or conservative modifications thereof, a $V_L$ CDR2 comprising amino acids having the sequence set forth in SEQ ID NO:320 or conservative modifications thereof, and a $V_L$ CDR3 comprising amino acids having the sequence set forth in SEQ ID NO:321 or conservative modifications thereof, as shown in Table 29. In certain embodiments, the anti-GPRC5D scFv comprises a $V_H$ CDR1 comprising amino acids having the sequence set forth in SEQ ID NO:316 or conservative modifications thereof, a $V_H$ CDR2 comprising amino acids having the sequence set forth in SEQ ID NO:317 or conservative modifications thereof, a $V_H$ CDR3 comprising amino acids having the sequence set forth in SEQ ID NO:318 or conservative modifications thereof, a $V_L$ CDR1 comprising amino acids having the sequence set forth in SEQ ID NO:319 or conservative modifications thereof, a $V_L$ CDR2 comprising amino acids having the sequence set forth in SEQ ID NO:320 or conservative modifications thereof, and a $V_L$ CDR3 comprising amino acids having the sequence set forth in SEQ ID NO:321 or conservative modifications thereof, as shown in Table 29. In certain embodiments, the anti-GPRC5D scFv comprises a $V_H$ CDR1 comprising amino acids having the sequence set forth in SEQ ID NO:316, a $V_H$ CDR2 comprising amino acids having the sequence set forth in SEQ ID NO:317, a $V_H$ CDR3 comprising amino acids having the sequence set forth in SEQ ID NO:318, a $V_L$ CDR1 comprising amino acids having the sequence set forth in SEQ ID NO:319, a $V_L$ CDR2 comprising amino acids having the sequence set forth in SEQ ID NO:320, and a $V_L$ CDR3 comprising amino acids having the sequence set forth in SEQ ID NO:321.

TABLE 29

| Antigen | A GPRC5D polypeptide having the amino acid sequence of SEQ ID NO: 97 | | |
|---|---|---|---|
| CDRs | 1 | 2 | 3 |
| V_H | GFSFSGTA [SEQ ID NO: 316] | ISSTGRST [SEQ ID NO: 317] | ARPVSSMTLSIQSDG [SEQ ID NO: 318] |
| V_L | SSNIGAGYD [SEQ ID NO: 319] | GNS [SEQ ID NO: 320] | QSYDSSLRGYV [SEQ ID NO: 321] |
| Full V_H | QVQLVQSGGGVVQPGRSLRLSCAASGFSFSGTAMHWVRQAPGKGLEWVSTISSTGRSTYYRDSVKGRFTISRDNSKNTLYLQMNSLRGEDTAVYYCARPVSSMTLSIQSDGWGQGTLVTVSS [SEQ ID NO: 322] | | |
| DNA | CAGGTGCAGCTGGTGCAGTCTGGGGGAGGCGTGGTCCAGCCTGGGAGGTCCCTGAGACTCTCCTGTGCAGCCTCTGGATTCAGCTTTAGTGGCACTGCCATGCACTGGGTCCGCCAGGCTCCAGGGAAGGGGCTGGAATGGGTCTCGACTATTAGTAGTACTGGGCGTAGCACATACTACAGAGACTCCGTGAAGGGCCGGTTCACCATCTCCAGAGACAATTCCAAGAACACGCTGTATCTGCAAATGAACAGCCTGAGAGGCGAGGACACGGCCGTATATTACTGTGCGCGCCCGGTTTCTTCTATGACTCTGTCTATCCAGTCTGATGGTTGGGGTCAAGGTACTCTGGTGACCGTCTCCTCA [SEQ ID NO: 325] | | |
| Full V_L | MKKTAIAIAVALAGFATVAQAAELQSVLTQPPSVSGAPGQRVTISCTGSSSNIGAGYDVHWYQQLPGRAPKLLIYGNSNRPSGVPDRFSGSKSGTSASLAITGLQAEDEADYYCQSYDSSLRGYVFGTGTKVTVLG [SEQ ID NO: 323] | | |
| DNA | ATGAAAAAGACAGCTATCGCGATTGCAGTGGCACTGGCTGGTTTCGCTACCGTGGCCCAGGCGGCCGAGCTCCAGTCTGTGTTGACGCAGCCGCCCTCAGTGTCTGGGGCCCCAGGGCAGAGGGTCACCATCTCCTGCACTGGGAGCAGCTCCAACATCGGGGCAGGTTATGATGTACACTGGTACCAGCAGCTTCCAGGAAGAGCCCCCAAACTCCTCATCTATGGTAACAGCAATCGGCCCTCAGGGGTCCCTGACCGATTCTCTGGCTCCAAGTCTGGCACCTCAGCCTCCCTGGCCATCACTGGGCTCCAGGCTGAGGATGAGGCTGATTATTACTGCCAGTCCTATGACAGCAGCCTGAGAGGTTATGTCTTCGGAACTGGGACCAAGGTCACCGTCCTAGGT [SEQ ID NO: 326] | | |
| scFv | MKKTAIAIAVALAGFATVAQAAELQSVLTQPPSVSGAPGQRVTISCTGSSSNIGAGYDVHWYQQLPGRAPKLLIYGNSNRPSGVPDRFSGSKSGTSASLAITGLQAEDEADYYCQSYDSSLRGYVFGTGTKVTVLGSRGGGGSGGGGSGGGGSLEMAQVQLVQSGGGVVQPGRSLRLSCAASGFSFSGTAMHWVRQAPGKGLEWVSTISSTGRSTYYRDSVKGRFTISRDNSKNTLYLQMNSLRGEDTAVYYCARPVSSMTLSIQSDGWGQGTLVTVSS [SEQ ID NO: 324] | | |
| DNA | ATGAAAAAGACAGCTATCGCGATTGCAGTGGCACTGGCTGGTTTCGCTACCGTGGCCCAGGCGGCCGAGCTCCAGTCTGTGTTGACGCAGCCGCCCTCAGTGTCTGGGGCCCCAGGGCAGAGGGTCACCATCTCCTGCACTGGGAGCAGCTCCAACATCGGGGCAGGTTATGATGTACACTGGTACCAGCAGCTTCCAGGAAGAGCCCCCAAACTCCTCATCTATGGTAACAGCAATCGGCCCTCAGGGGTCCCTGACCGATTCTCTGGCTCCAAGTCTGGCACCTCAGCCTCCCTGGCCATCACTGGGCTCCAGGCTGAGGATGAGGCTGATTATTACTGCCAGTCCTATGACAGCAGCCTGAGAGGTTATGTCTTCGGAACTGGGACCAAGGTCACCGTCCTAGGTTCTAGAGGTGGTGGTGGTAGCGGCGGCGGCGGCTCTGGTGGTGGTGGATCCCTCGAGATGGCCCAGGTGCAGCTGGTGCAGTCTGGGGGAGGCGTGGTCCAGCCTGGGAGGTCCCTGAGACTCTCCTGTGCAGCCTCTGGATTCAGCTTTAGTGGCACTGCCATGCACTGGGTCCGCCAGGCTCCAGGGAAGGGGCTGGAATGGGTCTCGACTATTAGTAGTACTGGGCGTAGCACATACTACAGAGACTCCGTGAAGGGCCGGTTCACCATCTCCAGAGACAATTCCAAGAACACGCTGTATCTGCAAATGAACAGCCTGAGAGGCGAGGACACGGCCGTATATTACTGTGCGCGCCCGGTTTCTTCTATGACTCTGTCTATCCAGTCTGATGGTTGGGGTCAAGGTACTCTGGTGACCGTCTCCTCA [SEQ ID NO: 327] | | |

In certain embodiments, the antibody or other antigen binding protein is an anti-GPRC5D scFv or an antigen-binding fragment thereof having an antigen-binding region that comprises the amino acid sequence of SEQ ID NO:336 and specifically binds to a GPRC5D polypeptide (e.g., a GPRC5D polypeptide having the amino acid sequence SEQ ID NO:97, or fragments thereof), which is designated as ET150-031 scFv (also referred to as "ET150-181 scFv").

In certain embodiments, the anti-GPRC5D scFv antibody comprises a heavy chain variable region comprising amino acids having the sequence set forth in SEQ ID NO:334 and a light chain variable region comprising amino acids having the sequence set forth in SEQ ID NO:335, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 30. In certain embodiments, the anti-GPRC5D scFv comprises a $V_H$ comprising amino acids having the sequence set forth in SEQ ID NO:334, as shown in Table 30. In certain embodiments, the anti-GPRC5D scFv comprises a $V_L$ comprising amino acids having the sequence set forth in SEQ ID NO:335, as shown in Table 30. In certain embodiments, the anti-GPRC5D scFv comprises a $V_H$ comprising amino acids having the sequence set forth in SEQ ID NO:334 and a $V_L$ comprising amino acids having the sequence set forth in SEQ ID NO:335, as shown in Table 30. In certain embodiments, the anti-GPRC5D scFv comprises a $V_H$ CDR1 comprising amino acids having the sequence set forth in SEQ ID NO:328 or conservative modifications thereof, a $V_H$ CDR2 comprising amino acids having the sequence set forth in SEQ ID NO:329 or conservative modifications thereof, and a $V_H$ CDR3 comprising amino acids having the sequence set forth in SEQ ID NO:330 or conservative modifications thereof, as shown in Table 30. In certain embodiments, the anti-GPRC5D scFv comprises a $V_L$ CDR1 comprising amino acids having the sequence set forth in SEQ ID NO:331 or conservative modifications thereof, a $V_L$ CDR2 comprising amino acids having the sequence set forth in SEQ ID NO:332 or conservative modifications thereof, and a $V_L$ CDR3 comprising amino acids having the sequence set forth in SEQ ID NO:333 or conservative modifications thereof, as shown in Table 30. In certain embodiments, the anti-GPRC5D scFv comprises a $V_H$ CDR1 comprising amino acids having the sequence set forth in SEQ ID NO:328 or conservative modifications thereof, a $V_H$ CDR2 comprising amino acids having the sequence set forth in SEQ ID NO:329 or conservative modifications thereof, a $V_H$ CDR3 comprising amino acids having the sequence set forth in SEQ ID NO:330 or conservative modifications thereof, a $V_L$ CDR1 comprising amino acids having the sequence set forth in SEQ ID NO:331 or conservative modifications thereof, a $V_L$ CDR2 comprising amino acids having the sequence set forth in SEQ ID NO:332 or conservative modifications thereof, and a $V_L$ CDR3 comprising amino acids having the sequence set forth in SEQ ID NO:333 or conservative modifications thereof, as shown in Table 30. In certain embodiments, the anti-GPRC5D scFv comprises a $V_H$ CDR1 comprising amino acids having the sequence set forth in SEQ ID NO:328, a $V_H$ CDR2 comprising amino acids having the sequence set forth in SEQ ID NO:329, a $V_H$ CDR3 comprising amino acids having the sequence set forth in SEQ ID NO:330, a $V_L$ CDR1 comprising amino acids having the sequence set forth in SEQ ID NO:331, a $V_L$ CDR2 comprising amino acids having the sequence set forth in SEQ ID NO:332, and a $V_L$ CDR3 comprising amino acids having the sequence set forth in SEQ ID NO:333.

TABLE 30

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 328] | INPSGGST [SEQ ID NO: 329] | ARGQKYHSQYSRGG TGGGMTQDM [SEQ ID NO: 330] |
| $V_L$ | SSNIGNNY [SEQ ID NO: 331] | DNN [SEQ ID NO: 332] | GTWDSSLRNWV [SEQ ID NO: 333] |
| Full $V_H$ | QMQLVQSGAEVKKPGASVKVSCKASGYTFTSYYMHWVRQAPGQGL EWMGIINPSGGSTSYAQKFQGRVTMTRDTSTSTVYMELSSLRSEDTA VYYCARGQKYHSQYSRGGTGGGMTQDMWGQGTLVTVSS [SEQ ID NO: 334] | | |
| DNA | CAGATGCAGCTGGTGCAGTCTGGGGCTGAGGTGAAGAAGCCTGG GGCCTCAGTGAAGGTTTCCTGCAAGGCATCTGGATACACCTTCAC CAGCTACTATATGCACTGGGTGCGACAGGCCCCTGGACAAGGGCT TGAGTGGATGGGAATAATCAACCCTAGTGGTGGTAGCACAAGCTA CGCACAAAAGTTCCAGGGCAGAGTCACCATGACCAGGGACACGT CCACGAGCACAGTCTACATGGAGCTGAGCAGCCTGAGATCTGAGG ACACGGCCGTGTATTACTGTGCGCGCGGTCAGAAATACCATTCTC AGTACTCTCGTGGTGGTACTGGTGGTGGTATGACTCAGGATATGT GGGGTCAAGGTACTCTGGTGACCGTCTCCTCA [SEQ ID NO: 337] | | |
| Full $V_L$ | MKKTAIAIAVALAGFATVAQAAELQSVVTQPPSVSAAPGQRVTISCS GGSSNIGNNYVSWFQQLPRTAPKLLIYDNNKRPSGIPDRFSGSKSGTS AALDITVLQTGDEADYYCGTWDSSLRNWVFGGGTKLTVLG [SEQ ID NO: 335] | | |
| DNA | ATGAAAAAGACAGCTATCGCGATTGCAGTGGCACTGGCTGGTTTC GCTACCGTGGCCCAGGCGGCCGAGCTCCAGTCTGTCGTGACGCAG CCGCCCTCTGTGTCTGCGGCCCCAGGACAGAGGGTCACCATCTCC TGCTCTGGAGGTAGTTCCAACATTGGGAATAATTATGTTTCCTGGT TCCAACAACTCCCACGAACAGCCCCCAAACTCCTCATTTATGACA ATAATAAGCGACCCTCAGGGATTCCTGACCGATTCTCTGGCTCCA AGTCTGGCACGTCAGCCGCCCTGGACATCACCGTTCTCCAGACTG GGGACGAGGCCGATTATTACTGCGGAACTTGGGATAGCAGCCTGA GAAATTGGGTGTTCGGCGGAGGGACCAAGCTGACCGTCCTAGGT [SEQ ID NO: 338] | | |

TABLE 30-continued

```
scFv    MKKTAIAIAVALAGFATVAQAAELQSVVTQPPSVSAAPGQRVTISCS
        GGSSNIGNNYVSWFQQLPRTAPKLLIYDNNKRPSGIPDRFSGSKSGTS
        AALDITVLQTGDEADYYCGTWDSSLRNWVFGGGTKLTVLGSRGGG
        GSGGGGSGGGGSLEMAQMQLVQSGAEVKKPGASVKVSCKASGYTF
        TSYYMHWVRQAPGQGLEWMGIINPSGGSTSYAQKFQGRVTMTRDTS
        TSTVYMELSSLRSEDTAVYYCARGQKYHSQYSRGGTGGGMTQDMW
        GQGTLVTVSS [SEQ ID NO: 336]

DNA     ATGAAAAAGACAGCTATCGCGATTGCAGTGGCACTGGCTGGTTTC
        GCTACCGTGGCCCAGGCGGCCGAGCTCCAGTCTGTCGTGACGCAG
        CCGCCCTCTGTGTCTGCGGCCCCAGGACAGAGGGTCACCATCTCC
        TGCTCTGGAGGTAGTTCCAACATTGGGAATAATTATGTTTCCTGGT
        TCCAACAACTCCCACGAACAGCCCCCAAACTCCTCATTTATGACA
        ATAATAAGCGACCCTCAGGGATTCCTGACCGATTCTCTGGCTCCA
        AGTCTGGCACGTCAGCCGCCCTGGACATCACCGTTCTCCAGACTG
        GGGACGAGGCCGATTATTACTGCGGAACTTGGGATAGCAGCCTGA
        GAAATTGGGTGTTCGGCGGAGGGACCAAGCTGACCGTCCTAGGTT
        CTAGAGGTGGTGGTGGTAGCGGCGGCGGCGGCTCTGGTGGTGGTG
        GATCCCTCGAGATGGCCCAGATGCAGCTGGTGCAGTCTGGGGCTG
        AGGTGAAGAAGCCTGGGGCCTCAGTGAAGGTTTCCTGCAAGGCAT
        CTGGATACACCTTCACCAGCTACTATATGCACTGGGTGCGACAGG
        CCCCTGGACAAGGGCTTGAGTGGATGGGAATAATCAACCCTAGTG
        GTGGTAGCACAAGCTACGCACAAAAGTTCCAGGGCAGAGTCACC
        ATGACCAGGGACACGTCCACGAGCACAGTCTACATGGAGCTGAG
        CAGCCTGAGATCTGAGGACACGGCCGTGTATTACTGTGCGCGCGG
        TCAGAAATACCATTCTCAGTACTCTCGTGGTGGTACTGGTGGTGGT
        ATGACTCAGGATATGTGGGGTCAAGGTACTCTGGTGACCGTCTCC
        TCA [SEQ ID NO: 339]
```

In certain embodiments, the antibody or other antigen binding protein is an anti-GPRC5D scFv or an antigen-binding fragment thereof having an antigen-binding region that comprises the amino acid sequence of SEQ ID NO:348 and specifically binds to a GPRC5D polypeptide (e.g., a GPRC5D polypeptide having the amino acid sequence SEQ ID NO:97, or fragments thereof), which is designated as ET150-032 scFv (also referred to as "ET150-182 scFv").

In certain embodiments, the anti-GPRC5D scFv antibody comprises a heavy chain variable region comprising amino acids having the sequence set forth in SEQ ID NO:346 and a light chain variable region comprising amino acids having the sequence set forth in SEQ ID NO:347, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 31. In certain embodiments, the anti-GPRC5D scFv comprises a $V_H$ comprising amino acids having the sequence set forth in SEQ ID NO:346, as shown in Table 31. In certain embodiments, the anti-GPRC5D scFv comprises a $V_L$ comprising amino acids having the sequence set forth in SEQ ID NO:347, as shown in Table 31. In certain embodiments, the anti-GPRC5D scFv comprises a $V_H$ comprising amino acids having the sequence set forth in SEQ ID NO:346 and a $V_L$ comprising amino acids having the sequence set forth in SEQ ID NO:347, as shown in Table 31. In certain embodiments, the anti-GPRC5D scFv comprises a $V_H$ CDR1 comprising amino acids having the sequence set forth in SEQ ID NO:340 or conservative modifications thereof, a $V_H$ CDR2 comprising amino acids having the sequence set forth in SEQ ID NO:341 or conservative modifications thereof, and a $V_H$ CDR3 comprising amino acids having the sequence set forth in SEQ ID NO:342 or conservative modifications thereof, as shown in Table 31. In certain embodiments, the anti-GPRC5D scFv comprises a $V_L$ CDR1 comprising amino acids having the sequence set forth in SEQ ID NO:343 or conservative modifications thereof, a $V_L$ CDR2 comprising amino acids having the sequence set forth in SEQ ID NO:344 or conservative modifications thereof, and a $V_L$ CDR3 comprising amino acids having the sequence set forth in SEQ ID NO:345 or conservative modifications thereof, as shown in Table 31. In certain embodiments, the anti-GPRC5D scFv comprises a $V_H$ CDR1 comprising amino acids having the sequence set forth in SEQ ID NO:340 or conservative modifications thereof, a $V_H$ CDR2 comprising amino acids having the sequence set forth in SEQ ID NO:341 or conservative modifications thereof, a $V_H$ CDR3 comprising amino acids having the sequence set forth in SEQ ID NO:342 or conservative modifications thereof, a $V_L$ CDR1 comprising amino acids having the sequence set forth in SEQ ID NO:343 or conservative modifications thereof, a $V_L$ CDR2 comprising amino acids having the sequence set forth in SEQ ID NO:344 or conservative modifications thereof, and a $V_L$ CDR3 comprising amino acids having the sequence set forth in SEQ ID NO:345 or conservative modifications thereof, as shown in Table 31. In certain embodiments, the anti-GPRC5D scFv comprises a $V_H$ CDR1 comprising amino acids having the sequence set forth in SEQ ID NO:340, a $V_H$ CDR2 comprising amino acids having the sequence set forth in SEQ ID NO:341, a $V_H$ CDR3 comprising amino acids having the sequence set forth in SEQ ID NO:342, a $V_L$ CDR1 comprising amino acids having the sequence set forth in SEQ ID NO:343, a $V_L$ CDR2 comprising amino acids having the sequence set forth in SEQ ID NO:344, and a $V_L$ CDR3 comprising amino acids having the sequence set forth in SEQ ID NO:345.

TABLE 31

| Antigen | A GPRC5D polypeptide having the amino acid sequence of SEQ ID NO: 97 | | |
|---|---|---|---|
| CDRs | 1 | 2 | 3 |
| V_H | GYTFSRYY [SEQ ID NO: 340] | MNPNSGNT [SEQ ID NO: 341] | ARGRYHVIDY [SEQ ID NO: 342] |
| V_L | SSDVGGYNH [SEQ ID NO: 343] | EVT [SEQ ID NO: 344] | SSYAGSAHWV [SEQ ID NO: 345] |

Full V_H
EVQLVQSGAEVKKPGASVKVSCKASGYTFSRYYIHWVRQAPGQGLE
WMGWMNPNSGNTGYAQKFQGRVTMTRNTSISTAYMELSSLRSEDTA
VYYCARGRYHVIDYWGQGTLVTVSS [SEQ ID NO: 346]

DNA
GAGGTCCAGCTGGTGCAGTCTGGGGCTGAGGTGAAGAAGCCTGGG
GCCTCAGTGAAGGTTTCCTGCAAGGCATCTGGATACACCTTCAGCA
GGTACTATATACACTGGGTGCGACAGGCCCCTGGACAAGGGCTTG
AGTGGATGGGATGGATGAACCCTAACAGTGGTAACACAGGCTATG
CACAGAAGTTCCAGGGCAGAGTCACCATGACCAGGAACACCTCCA
TAAGCACAGCCTACATGGAGCTGAGCAGCCTGAGATCTGAGGACA
CGGCCGTGTATTACTGTGCGCGCGGTCGTTACCATGTTATCGATTA
CTGGGGTCAAGGTACTCTGGTGACCGTCTCCTCA
[SEQ ID NO: 349]

Full V_L
MKKTAIAIAVALAGFATVAQAAELQSVLTQPPSASGSPGQSLTISCTGT
SSDVGGYNHVSWYQQYPGKAPKLMIYEVTKRPSGVPDRFSGSKSGNT
ASLTVSGLQAEDEADYYCSSYAGSAHWVFGGGTKLTVLG
[SEQ ID NO: 347]

DNA
ATGAAAAAGACAGCTATCGCGATTGCAGTGGCACTGGCTGGTTTC
GCTACCGTGGCCCAGGCGGCCGAGCTCCAGTCTGTGTTGACTCAGC
CACCCTCCGCGTCCGGGTCTCCTGGACAGTCACTCACCATCTCCTG
CACTGGAACCAGCAGTGACGTTGGTGGTTATAACCATGTCTCCTGG
TACCAACAGTACCCAGGCAAAGCCCCCAAACTCATGATTTATGAG
GTCACTAAGCGGCCCTCAGGGGTCCCTGATCGCTTCTCTGGCTCCA
AGTCTGGCAACACGGCCTCCCTGACCGTCTCTGGGCTCCAGGCTGA
GGATGAGGCTGATTATTACTGCAGCTCATATGCAGGCAGCGCCCAT
TGGGTGTTCGGCGGAGGGACCAAGCTGACCGTCCTAGGT
[SEQ ID NO: 350]

scFv
MKKTAIAIAVALAGFATVAQAAELQSVLTQPPSASGSPGQSLTISCTGT
SSDVGGYNHVSWYQQYPGKAPKLMIYEVTKRPSGVPDRFSGSKSGNT
ASLTVSGLQAEDEADYYCSSYAGSAHWVFGGGTKLTVLGSRGGGGS
GGGGSGGGGSLEMAEVQLVQSGAEVKKPGASVKVSCKASGYTFSRY
YIHWVRQAPGQGLEWMGWMNPNSGNTGYAQKFQGRVTMTRNTSIS
TAYMELSSLRSEDTAVYYCARGRYHVIDYWGQGTLVTVSS
[SEQ ID NO: 348]

DNA
ATGAAAAAGACAGCTATCGCGATTGCAGTGGCACTGGCTGGTTTC
GCTACCGTGGCCCAGGCGGCCGAGCTCCAGTCTGTGTTGACTCAGC
CACCCTCCGCGTCCGGGTCTCCTGGACAGTCACTCACCATCTCCTG
CACTGGAACCAGCAGTGACGTTGGTGGTTATAACCATGTCTCCTGG
TACCAACAGTACCCAGGCAAAGCCCCCAAACTCATGATTTATGAG
GTCACTAAGCGGCCCTCAGGGGTCCCTGATCGCTTCTCTGGCTCCA
AGTCTGGCAACACGGCCTCCCTGACCGTCTCTGGGCTCCAGGCTGA
GGATGAGGCTGATTATTACTGCAGCTCATATGCAGGCAGCGCCCAT
TGGGTGTTCGGCGGAGGGACCAAGCTGACCGTCCTAGGTTCTAGA
GGTGGTGGTGGTAGCGGCGGCGGCGGCTCTGGTGGTGGTGGATCC
CTCGAGATGGCCGAGGTCCAGCTGGTGCAGTCTGGGGCTGAGGTG
AAGAAGCCTGGGGCCTCAGTGAAGGTTTCCTGCAAGGCATCTGGA
TACACCTTCAGCAGGTACTATATACACTGGGTGCGACAGGCCCCTG
GACAAGGGCTTGAGTGGATGGGATGGATGAACCCTAACAGTGGTA
ACACAGGCTATGCACAGAAGTTCCAGGGCAGAGTCACCATGACCA
GGAACACCTCCATAAGCACAGCCTACATGGAGCTGAGCAGCCTGA
GATCTGAGGACACGGCCGTGTATTACTGTGCGCGCGGTCGTTACCA
TGTTATCGATTACTGGGGTCAAGGTACTCTGGTGACCGTCTCCTCA
[SEQ ID NO: 351]

In certain embodiments, the antibody or other antigen binding protein is an anti-GPRC5D scFv or an antigen-binding fragment thereof having an antigen-binding region that comprises the amino acid sequence of SEQ ID NO:360 and specifically binds to a GPRC5D polypeptide (e.g., a GPRC5D polypeptide having the amino acid sequence SEQ ID NO:97, or fragments thereof), which is designated as ET150-033 scFv (also referred to as "ET150-183 scFv").

In certain embodiments, the anti-GPRC5D scFv antibody comprises a heavy chain variable region comprising amino acids having the sequence set forth in SEQ ID NO:358 and a light chain variable region comprising amino acids having the sequence set forth in SEQ ID NO:359, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 32. In certain embodiments, the anti-GPRC5D scFv comprises a $V_H$ comprising amino acids having the sequence set forth in SEQ ID NO:358, as shown in Table 32. In certain embodiments, the anti-GPRC5D scFv comprises a $V_L$ comprising amino acids having the sequence set forth in SEQ ID NO:359, as shown in Table 32. In certain embodiments, the anti-GPRC5D scFv comprises a $V_H$ comprising amino acids having the sequence set forth in SEQ ID NO:358 and a $V_L$ comprising amino acids having the sequence set forth in SEQ ID NO:359, as shown in Table 32. In certain embodiments, the anti-GPRC5D scFv comprises a $V_H$ CDR1 comprising amino acids having the sequence set forth in SEQ ID NO:352 or conservative modifications thereof, a $V_H$ CDR2 comprising amino acids having the sequence set forth in SEQ ID NO:353 or conservative modifications thereof, and a $V_H$ CDR3 comprising amino acids having the sequence set forth in SEQ ID NO:354 or conservative modifications thereof, as shown in Table 32. In certain embodiments, the anti-GPRC5D scFv comprises a $V_L$ CDR1 comprising amino acids having the sequence set forth in SEQ ID NO:355 or conservative modifications thereof, a $V_L$ CDR2 comprising amino acids having the sequence set forth in SEQ ID NO:356 or conservative modifications thereof, and a $V_L$ CDR3 comprising amino acids having the sequence set forth in SEQ ID NO:357 or conservative modifications thereof, as shown in Table 32. In certain embodiments, the anti-GPRC5D scFv comprises a $V_H$ CDR1 comprising amino acids having the sequence set forth in SEQ ID NO:352 or conservative modifications thereof, a $V_H$ CDR2 comprising amino acids having the sequence set forth in SEQ ID NO:353 or conservative modifications thereof, a $V_H$ CDR3 comprising amino acids having the sequence set forth in SEQ ID NO:354 or conservative modifications thereof, a $V_L$ CDR1 comprising amino acids having the sequence set forth in SEQ ID NO:355 or conservative modifications thereof, a $V_L$ CDR2 comprising amino acids having the sequence set forth in SEQ ID NO:356 or conservative modifications thereof, and a $V_L$ CDR3 comprising amino acids having the sequence set forth in SEQ ID NO:357 or conservative modifications thereof, as shown in Table 32. In certain embodiments, the anti-GPRC5D scFv comprises a $V_H$ CDR1 comprising amino acids having the sequence set forth in SEQ ID NO:352, a $V_H$ CDR2 comprising amino acids having the sequence set forth in SEQ ID NO:353, a $V_H$ CDR3 comprising amino acids having the sequence set forth in SEQ ID NO:354, a $V_L$ CDR1 comprising amino acids having the sequence set forth in SEQ ID NO:355, a $V_L$ CDR2 comprising amino acids having the sequence set forth in SEQ ID NO:356, and a $V_L$ CDR3 comprising amino acids having the sequence set forth in SEQ ID NO:357.

TABLE 32

| Antigen | A GPRC5D polypeptide having the amino acid sequence of SEQ ID NO: 97 | | |
|---|---|---|---|
| CDRs | 1 | 2 | 3 |
| $V_H$ | GYTFNTYY [SEQ ID NO: 352] | INPNNGGT [SEQ ID NO: 353] | ARSYDY [SEQ ID NO: 354] |
| $V_L$ | SSNIGSNY [SEQ ID NO: 355] | RNN [SEQ ID NO: 356] | AAWDDSLSGRV [SEQ ID NO: 357] |
| Full $V_H$ | QLQLVQSGAEVKKPGSSVKVSCKASGYTFNTYYLHWVRQAPGQGLE WMGRINPNNGGTNYAQKFQGRVTMTRDTSINTAYMELSRLRSDDTA VYYCARSYDYWGQGTLVTVSS [SEQ ID NO: 358] | | |
| DNA | CAGCTGCAGCTGGTGCAATCTGGGGCTGAGGTGAAGAAGCCTGGG TCCTCGGTGAAGGTCTCCTGCAAGGCTTCTGGATACACCTTCAACA CCTACTATCTGCACTGGGTACGACAGGCCCCTGGACAAGGGCTTGA GTGGATGGGACGGATCAACCCTAACAATGGTGGCACAAACTATGC ACAGAAGTTTCAGGGCAGGGTCACCATGACCAGGGACACGTCCAT CAACACAGCCTACATGGAGCTGAGCAGGCTGAGATCTGACGACAC GGCCGTGTATTACTGTGCGCGCTCTTACGATTACTGGGGTCAAGGT ACTCTGGTGACCGTCTCCTCA [SEQ ID NO: 361] | | |
| Full $V_L$ | MKKTAIAIAVALAGFATVAQAAELQAVLTQPPSASGTPGQRVTISCSG SSSNIGSNYVYWYQQLPGTAPKLLIYRNNQRPSGVPDRFSGSKSGTSA SLAISGLRSEDEADYYCAAWDDSLSGRVFGTGTKVTVLG [SEQ ID NO: 359] | | |
| DNA | ATGAAAAAGACAGCTATCGCGATTGCAGTGGCACTGGCTGGTTTC GCTACCGTGGCCCAGGCGGCCGAGCTCCAGGCTGTGCTGACTCAG CCACCCTCAGCGTCTGGGACCCCCGGGCAGAGGGTCACCATCTCTT GTTCTGGAAGCAGCTCCAACATCGGAAGTAATTATGTATACTGGTA CCAGCAGCTCCCAGGAACGGCCCCCAAACTCCTCATCTATAGGAA TAATCAGCGGCCCTCAGGGGTCCCTGACCGATTCTCTGGCTCCAAG TCTGGCACCTCAGCCTCCCTGGCCATCAGTGGGCTCCGGTCCGAGG ATGAGGCTGATTATTACTGTGCAGCATGGGATGACAGCCTGAGTG GTCGGGTCTTCGGAACTGGGACCAAGGTCACCGTCCTAGGT [SEQ ID NO: 362] | | |
| scFv | MKKTAIAIAVALAGFATVAQAAELQAVLTQPPSASGTPGQRVTISCSG SSSNIGSNYVYWYQQLPGTAPKLLIYRNNQRPSGVPDRFSGSKSGTSA SLAISGLRSEDEADYYCAAWDDSLSGRVFGTGTKVTVLGSRGGGGSG GGGSGGGGSLEMAQLQLVQSGAEVKKPGSSVKVSCKASGYTFNTYY LHWVRQAPGQGLEWMGRINPNNGGTNYAQKFQGRVTMTRDTSINTA | | |

TABLE 32-continued

```
        YMELSRLRSDDTAVYYCARSYDYWGQGTLVTVSS
        [SEQ ID NO: 360]

DNA     ATGAAAAAGACAGCTATCGCGATTGCAGTGGCACTGGCTGGTTTC
        GCTACCGTGGCCCAGGCGGCCGAGCTCCAGGCTGTGCTGACTCAG
        CCACCCTCAGCGTCTGGGACCCCCGGGCAGAGGGTCACCATCTCTT
        GTTCTGGAAGCAGCTCCAACATCGGAAGTAATTATGTATACTGGTA
        CCAGCAGCTCCCAGGAACGGCCCCCAAACTCCTCATCTATAGGAA
        TAATCAGCGGCCCTCAGGGGTCCCTGACCGATTCTCTGGCTCCAAG
        TCTGGCACCTCAGCCTCCCTGGCCATCAGTGGGCTCCGGTCCGAGG
        ATGAGGCTGATTATTACTGTGCAGCATGGGATGACAGCCTGAGTG
        GTCGGGTCTTCGGAACTGGGACCAAGGTCACCGTCCTAGGTTCTAG
        AGGTGGTGGTGGTAGCGGCGGCGGCGGCTCTGGTGGTGGTGGATC
        CCTCGAGATGGCCCAGCTGCAGCTGGTGCAATCTGGGGCTGAGGT
        GAAGAAGCCTGGGTCCTCGGTGAAGGTCTCCTGCAAGGCTTCTGG
        ATACACCTTCAACACCTACTATCTGCACTGGGTACGACAGGCCCCT
        GGACAAGGGCTTGAGTGGATGGGACGGATCAACCCTAACAATGGT
        GGCACAAACTATGCACAGAAGTTTCAGGGCAGGGTCACCATGACC
        AGGGACACGTCCATCAACACAGCCTACATGGAGCTGAGCAGGCTG
        AGATCTGACGACACGGCCGTGTATTACTGTGCGCGCTCTTACGATT
        ACTGGGGTCAAGGTACTCTGGTGACCGTCTCCTCA
        [SEQ ID NO: 363]
```

The presently disclosed subject matter further provides anti-GPRC5D scFv antibodies comprising a heavy chain variable region, a light chain variable region, a linker peptide between the heavy chain variable region and the light chain variable region, and an His-tag and an HA-tag. In certain embodiments, the amino acid sequence of the His-tag and HA-tag comprises the amino acid sequence of SEQ ID NO:379, which is provided below:

TSGQAGQHHHHHHGAYPYDVPDYAS    [SEQ ID NO: 379]

The nucleotide sequence encoding SEQ ID NO: 379 is SEQ ID NO: 380, which is provided below:

[SEQ ID NO: 380]
ACTAGTGGCCAGGCCGGCCAGCACCATCACCATCACCATGGCGCATACCC

GTACGACGTTCCGGACTACGCTTCT

2. Monoclonal Antibodies

The presently disclosed subject matter provides human antibodies (e.g., human monoclonal antibodies) that specifically bind to GPRC5D (e.g., human GPRC5D) and were isolated and structurally characterized as described in Example 2. The $V_H$ amino acid sequences of human anti-GPRC5D antibodies ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, respectively. The $V_L$ amino acid sequences of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, respectively.

Given that each of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies can bind to GPRC5D, the $V_H$ and $V_L$ sequences can be "mixed and matched" to create other anti-GPRC5D binding molecules. GPRC5D binding of such "mixed and matched" antibodies can be tested using the binding assays known in the art, including for example, ELISAs, Western blots, RIAs, Biacore analysis. Preferably, when $V_H$ and $V_L$ chains are mixed and matched, a $V_H$ sequence from a particular $V_H/V_L$ pairing is replaced with a structurally similar $V_H$ sequence. Likewise, a $V_L$ sequence from a particular $V_H/V_L$ pairing is replaced with a structurally similar $V_L$ sequence.

In certain embodiments, the presently disclosed subject matter provides an isolated antibody, or antigen-binding portion thereof comprising: (i) a heavy chain variable region comprising an amino acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and (ii) a light chain variable region comprising an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359; wherein the antibody specifically binds GPRC5D, e.g., human GPRC5D.

Preferred heavy and light chain combinations include:
(i) a heavy chain variable region comprising amino acids having a sequence set forth in SEQ ID NO:1, and a light chain variable region comprising amino acids having a sequence set forth in SEQ ID NO:2; or
(ii) a heavy chain variable region comprising amino acids having a sequence set forth in SEQ ID NO:5, and a light chain variable region comprising amino acids having a sequence set forth in SEQ ID NO:6;
(iii) a heavy chain variable region comprising amino acids having a sequence set forth in SEQ ID NO:9, and a light chain variable region comprising amino acids having a sequence set forth in SEQ ID NO:10;

(iv) a heavy chain variable region comprising amino acids having a sequence set forth in SEQ ID NO:13, and a light chain variable region comprising amino acids having a sequence set forth in SEQ ID NO:14;

(v) a heavy chain variable region comprising amino acids having a sequence set forth in SEQ ID NO:17, and a light chain variable region comprising amino acids having a sequence set forth in SEQ ID NO:18;

(vi) a heavy chain variable region comprising amino acids having a sequence set forth in SEQ ID NO:21, and a light chain variable region comprising amino acids having a sequence set forth in SEQ ID NO:22;

(vii) a heavy chain variable region comprising amino acids having a sequence set forth in SEQ ID NO:25, and a light chain variable region comprising amino acids having a sequence set forth in SEQ ID NO:26;

(viii) a heavy chain variable region comprising amino acids having a sequence set forth in SEQ ID NO:29, and a light chain variable region comprising amino acids having a sequence set forth in SEQ ID NO:30;

(ix) a heavy chain variable region comprising amino acids having a sequence set forth in SEQ ID NO:33, and a light chain variable region comprising amino acids having a sequence set forth in SEQ ID NO:34;

(x) a heavy chain variable region comprising amino acids having a sequence set forth in SEQ ID NO:37, and a light chain variable region comprising amino acids having a sequence set forth in SEQ ID NO:38;

(xi) a heavy chain variable region comprising amino acids having a sequence set forth in SEQ ID NO:41, and a light chain variable region comprising amino acids having a sequence set forth in SEQ ID NO:42;

(xii) a heavy chain variable region comprising amino acids having a sequence set forth in SEQ ID NO:45, and a light chain variable region comprising amino acids having a sequence set forth in SEQ ID NO:46;

(xiii) a heavy chain variable region comprising amino acids having a sequence set forth in SEQ ID NO:49, and a light chain variable region comprising amino acids having a sequence set forth in SEQ ID NO:50;

(xiv) a heavy chain variable region comprising amino acids having a sequence set forth in SEQ ID NO:53, and a light chain variable region comprising amino acids having a sequence set forth in SEQ ID NO:54;

(xv) a heavy chain variable region comprising amino acids having a sequence set forth in SEQ ID NO:57, and a light chain variable region comprising amino acids having a sequence set forth in SEQ ID NO:58;

(xvi) a heavy chain variable region comprising amino acids having a sequence set forth in SEQ ID NO:61, and a light chain variable region comprising amino acids having a sequence set forth in SEQ ID NO:62;

(xvii) a heavy chain variable region comprising amino acids having a sequence set forth in SEQ ID NO:65, and a light chain variable region comprising amino acids having a sequence set forth in SEQ ID NO:66;

(xviii) a heavy chain variable region comprising amino acids having a sequence set forth in SEQ ID NO:69, and a light chain variable region comprising amino acids having a sequence set forth in SEQ ID NO:70;

(xix) a heavy chain variable region comprising amino acids having a sequence set forth in SEQ ID NO:73, and a light chain variable region comprising amino acids having a sequence set forth in SEQ ID NO:74;

(xx) a heavy chain variable region comprising amino acids having a sequence set forth in SEQ ID NO:77, and a light chain variable region comprising amino acids having a sequence set forth in SEQ ID NO:78;

(xxi) a heavy chain variable region comprising amino acids having a sequence set forth in SEQ ID NO:81, and a light chain variable region comprising amino acids having a sequence set forth in SEQ ID NO:82;

(xxii) a heavy chain variable region comprising amino acids having a sequence set forth in SEQ ID NO:85, and a light chain variable region comprising amino acids having a sequence set forth in SEQ ID NO:86;

(xxiii) a heavy chain variable region comprising amino acids having a sequence set forth in SEQ ID NO:89, and a light chain variable region comprising amino acids having a sequence set forth in SEQ ID NO:90;

(x) a heavy chain variable region comprising amino acids having a sequence set forth in SEQ ID NO:93, and a light chain variable region comprising amino acids having a sequence set forth in SEQ ID NO:94.

(xvi) a heavy chain variable region comprising amino acids having a sequence set forth in SEQ ID NO:274, and a light chain variable region comprising amino acids having a sequence set forth in SEQ ID NO:275;

(xvii) a heavy chain variable region comprising amino acids having a sequence set forth in SEQ ID NO:286, and a light chain variable region comprising amino acids having a sequence set forth in SEQ ID NO:287;

(xviii) a heavy chain variable region comprising amino acids having a sequence set forth in SEQ ID NO:298, and a light chain variable region comprising amino acids having a sequence set forth in SEQ ID NO:299;

(xix) a heavy chain variable region comprising amino acids having a sequence set forth in SEQ ID NO:310, and a light chain variable region comprising amino acids having a sequence set forth in SEQ ID NO:311;

(xx) a heavy chain variable region comprising amino acids having a sequence set forth in SEQ ID NO:322, and a light chain variable region comprising amino acids having a sequence set forth in SEQ ID NO:323;

(xxi) a heavy chain variable region comprising amino acids having a sequence set forth in SEQ ID NO:334, and a light chain variable region comprising amino acids having a sequence set forth in SEQ ID NO:335;

(xxii) a heavy chain variable region comprising amino acids having a sequence set forth in SEQ ID NO:346, and a light chain variable region comprising amino acids having a sequence set forth in SEQ ID NO:347; or (xxiii) a heavy chain variable region comprising amino acids having a sequence set forth in SEQ ID NO:358, and a light chain variable region comprising amino acids having a sequence set forth in SEQ ID NO:359.

In certain embodiments, the presently disclosed subject matter provides antibodies that comprise the heavy chain and light chain CDR1s, CDR2s and CDR3s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies. The amino acid sequences of the $V_H$ CDR1s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 124, 130, 136, 142, 148, 154, 160, 166, 172, 178, 184, 190, 196, 202, 208, 214, 220, 226, 232, 238, 244, 250, 256, 262, 268, 280, 292, 303, 316, 328, 340 and 352, respectively. The amino acid sequences of the $V_H$ CDR2s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies are shown in SEQ ID NOs: 125, 131, 137, 143, 149, 155, 161, 167, 173, 179, 185, 191, 197, 203, 209, 215, 221, 227, 233, 239, 245, 251, 257, 263, 269, 281, 293, 304, 317, 329, 341 and 353, respectively. The amino acid sequences of the $V_H$ CDR3s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 126, 132, 138, 144, 150, 156, 162, 168, 174, 180, 186, 192, 198, 204, 210, 216, 222, 228, 234, 240, 246, 252, 258, 264, 270, 282, 294, 305, 318, 330, 342 and 354, respectively.

The amino acid sequences of the $V_L$ CDR1s of 1 ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 127, 133, 139, 145, 151, 157, 163, 169, 175, 181, 187, 193, 199, 205, 211, 217, 223, 229, 235, 241, 247, 253, 259, 265, 271, 283, 295, 306, 319, 331, 343 and 355, respectively. The amino acid sequences of the $V_L$ CDR2s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 128, 134, 140, 146, 152, 158, 164, 170, 176, 182, 188, 194, 200, 206, 212, 218, 224, 230, 236, 242, 248, 254, 260, 266, 272, 284, 296, 307, 320, 332, 344 and 356, respectively. The amino acid sequences of the $V_L$ CDR3s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 129, 135, 141, 147, 153, 159, 165, 171, 177, 183, 189, 195, 201, 207, 213, 219, 225, 231, 237, 243, 249, 255, 261, 267, 273, 285, 297, 308, 321, 333, 345 and 357, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to GPRC5D and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_L$ CDR1, CDR2, and CDR3) to create other anti-GPRC5D binding molecules. GPRC5D binding of such "mixed and matched" antibodies can be tested using the binding assays described above. When $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences of the antibodies disclosed herein ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033.

In certain embodiments, the presently disclosed subject matter provides an isolated antibody, or antigen-binding portion thereof comprising: (ix) a heavy chain variable region CDR1 comprising an amino acid sequence selected from the group consisting of SEQ ID NOs: 124, 130, 136, 142, 148, 154, 160, 166, 172, 178, 184, 190, 196, 202, 208, 214, 220, 226, 232, 238, 244, 250, 256, 262, 268, 280, 292, 303, 316, 328, 340 and 352; (ii) a heavy chain variable region CDR2 comprising an amino acid sequence selected from the group consisting of SEQ ID NOs: 125, 131, 137, 143, 149, 155, 161, 167, 173, 179, 185, 191, 197, 203, 209, 215, 221, 227, 233, 239, 245, 251, 257, 263, 269, 281, 293, 304, 317, 329, 341 and 353; (iii) a heavy chain variable region CDR3 comprising an amino acid sequence selected from the group consisting of SEQ ID NOs: 126, 132, 138, 144, 150, 156, 162, 168, 174, 180, 186, 192, 198, 204, 210, 216, 222, 228, 234, 240, 246, 252, 258, 264, 270, 282, 294, 305, 318, 330, 342 and 354; (iv) a light chain variable region CDR1 comprising an amino acid sequence selected from the group consisting of SEQ ID NOs: 127, 133, 139, 145, 151, 157, 163, 169, 175, 181, 187, 193, 199, 205, 211, 217, 223, 229, 235, 241, 247, 253, 259, 265, 271, 283, 295, 306, 319, 331, 343 and 355; (v) a light chain variable region CDR2 comprising an amino acid sequence selected from the group consisting of SEQ ID NOs: 128, 134, 140, 146, 152, 158, 164, 170, 176, 182, 188, 194, 200, 206, 212, 218, 224, 230, 236, 242, 248, 254, 260, 266, 272, 284, 296, 307, 320, 332, 344 and 356; and (f) a light chain variable region CDR3 comprising an amino acid sequence selected from the group consisting of SEQ ID NOs: 129, 135, 141, 147, 153, 159, 165, 171, 177, 183, 189, 195, 201, 207, 213, 219, 225, 231, 237, 243, 249, 255, 261, 267, 273, 285, 297, 308, 321, 333, 345 and 357; wherein the antibody specifically binds GPRC5D, e.g., human GPRC5D.

In certain embodiments, the antibody comprises:
(i) a heavy chain variable region CDR1 comprising amino acids having the sequence set forth in SEQ ID NO: 124;
(ii) a heavy chain variable region CDR2 comprising amino acids having the sequence set forth in SEQ ID NO: 125;

(iii) a heavy chain variable region CDR3 comprising amino acids having the sequence set forth in SEQ ID NO: 126;
(iv) a light chain variable region CDR1 comprising amino acids having the sequence set forth in SEQ ID NO: 127;
(v) a light chain variable region CDR2 comprising amino acids having the sequence set forth in SEQ ID NO:128; and
(vi) a light chain variable region CDR3 comprising amino acids having the sequence set forth in SEQ ID NO: 129.

In certain embodiments, the antibody comprises:
(i) a heavy chain variable region CDR1 comprising amino acids having the sequence set forth in SEQ ID NO: 130;
(ii) a heavy chain variable region CDR2 comprising amino acids having the sequence set forth in SEQ ID NO: 131;
(iii) a heavy chain variable region CDR3 comprising amino acids having the sequence set forth in SEQ ID NO: 132;
(iv) a light chain variable region CDR1 comprising amino acids having the sequence set forth in SEQ ID NO: 133;
(v) a light chain variable region CDR2 comprising amino acids having the sequence set forth in SEQ ID NO:134; and
(vi) a light chain variable region CDR3 comprising amino acids having the sequence set forth in SEQ ID NO: 135.

In certain embodiments, the antibody comprises:
(i) a heavy chain variable region CDR1 comprising amino acids having the sequence set forth in SEQ ID NO: 136;
(ii) a heavy chain variable region CDR2 comprising amino acids having the sequence set forth in SEQ ID NO: 137;
(iii) a heavy chain variable region CDR3 comprising amino acids having the sequence set forth in SEQ ID NO: 138;
(iv) a light chain variable region CDR1 comprising amino acids having the sequence set forth in SEQ ID NO: 139;
(v) a light chain variable region CDR2 comprising amino acids having the sequence set forth in SEQ ID NO:140; and
(vi) a light chain variable region CDR3 comprising amino acids having the sequence set forth in SEQ ID NO: 141.

In certain embodiments, the antibody comprises:
(i) a heavy chain variable region CDR1 comprising amino acids having the sequence set forth in SEQ ID NO: 142;
(ii) a heavy chain variable region CDR2 comprising amino acids having the sequence set forth in SEQ ID NO: 143;
(iii) a heavy chain variable region CDR3 comprising amino acids having the sequence set forth in SEQ ID NO: 144;
(iv) a light chain variable region CDR1 comprising amino acids having the sequence set forth in SEQ ID NO: 145;
(v) a light chain variable region CDR2 comprising amino acids having the sequence set forth in SEQ ID NO:146; and
(vi) a light chain variable region CDR3 comprising amino acids having the sequence set forth in SEQ ID NO: 147.

In certain embodiments, the antibody comprises:
(i) a heavy chain variable region CDR1 comprising amino acids having the sequence set forth in SEQ ID NO: 148;
(ii) a heavy chain variable region CDR2 comprising amino acids having the sequence set forth in SEQ ID NO: 149;
(iii) a heavy chain variable region CDR3 comprising amino acids having the sequence set forth in SEQ ID NO: 150;
(iv) a light chain variable region CDR1 comprising amino acids having the sequence set forth in SEQ ID NO: 151;
(v) a light chain variable region CDR2 comprising amino acids having the sequence set forth in SEQ ID NO:152; and
(vi) a light chain variable region CDR3 comprising amino acids having the sequence set forth in SEQ ID NO: 153.

In certain embodiments, the antibody comprises:
(i) a heavy chain variable region CDR1 comprising amino acids having the sequence set forth in SEQ ID NO: 154;
(ii) a heavy chain variable region CDR2 comprising amino acids having the sequence set forth in SEQ ID NO: 155;
(iii) a heavy chain variable region CDR3 comprising amino acids having the sequence set forth in SEQ ID NO: 156;
(iv) a light chain variable region CDR1 comprising amino acids having the sequence set forth in SEQ ID NO: 157;
(v) a light chain variable region CDR2 comprising amino acids having the sequence set forth in SEQ ID NO:158; and
(vi) a light chain variable region CDR3 comprising amino acids having the sequence set forth in SEQ ID NO: 159.

In certain embodiments, the antibody comprises:
(i) a heavy chain variable region CDR1 comprising amino acids having the sequence set forth in SEQ ID NO: 160;
(ii) a heavy chain variable region CDR2 comprising amino acids having the sequence set forth in SEQ ID NO: 161;
(iii) a heavy chain variable region CDR3 comprising amino acids having the sequence set forth in SEQ ID NO: 162;
(iv) a light chain variable region CDR1 comprising amino acids having the sequence set forth in SEQ ID NO: 163;
(v) a light chain variable region CDR2 comprising amino acids having the sequence set forth in SEQ ID NO:164; and
(vi) a light chain variable region CDR3 comprising amino acids having the sequence set forth in SEQ ID NO: 165.

In certain embodiments, the antibody comprises:
(i) a heavy chain variable region CDR1 comprising amino acids having the sequence set forth in SEQ ID NO: 166;
(ii) a heavy chain variable region CDR2 comprising amino acids having the sequence set forth in SEQ ID NO: 167;
(iii) a heavy chain variable region CDR3 comprising amino acids having the sequence set forth in SEQ ID NO: 168;
(iv) a light chain variable region CDR1 comprising amino acids having the sequence set forth in SEQ ID NO: 169;
(v) a light chain variable region CDR2 comprising amino acids having the sequence set forth in SEQ ID NO:170; and
(vi) a light chain variable region CDR3 comprising amino acids having the sequence set forth in SEQ ID NO: 171.

In certain embodiments, the antibody comprises:
(i) a heavy chain variable region CDR1 comprising amino acids having the sequence set forth in SEQ ID NO: 172;
(ii) a heavy chain variable region CDR2 comprising amino acids having the sequence set forth in SEQ ID NO: 173;
(iii) a heavy chain variable region CDR3 comprising amino acids having the sequence set forth in SEQ ID NO: 174;
(iv) a light chain variable region CDR1 comprising amino acids having the sequence set forth in SEQ ID NO: 175;
(v) a light chain variable region CDR2 comprising amino acids having the sequence set forth in SEQ ID NO:176; and
(vi) a light chain variable region CDR3 comprising amino acids having the sequence set forth in SEQ ID NO: 177.

In certain embodiments, the antibody comprises:
(i) a heavy chain variable region CDR1 comprising amino acids having the sequence set forth in SEQ ID NO: 178;
(ii) a heavy chain variable region CDR2 comprising amino acids having the sequence set forth in SEQ ID NO: 179;
(iii) a heavy chain variable region CDR3 comprising amino acids having the sequence set forth in SEQ ID NO: 180;
(iv) a light chain variable region CDR1 comprising amino acids having the sequence set forth in SEQ ID NO: 181;
(v) a light chain variable region CDR2 comprising amino acids having the sequence set forth in SEQ ID NO:182; and
(vi) a light chain variable region CDR3 comprising amino acids having the sequence set forth in SEQ ID NO: 183.

In certain embodiments, the antibody comprises:
(i) a heavy chain variable region CDR1 comprising amino acids having the sequence set forth in SEQ ID NO: 184;
(ii) a heavy chain variable region CDR2 comprising amino acids having the sequence set forth in SEQ ID NO: 185;
(iii) a heavy chain variable region CDR3 comprising amino acids having the sequence set forth in SEQ ID NO: 186;
(iv) a light chain variable region CDR1 comprising amino acids having the sequence set forth in SEQ ID NO: 187;

(v) a light chain variable region CDR2 comprising amino acids having the sequence set forth in SEQ ID NO:188; and
(vi) a light chain variable region CDR3 comprising amino acids having the sequence set forth in SEQ ID NO: 189.

In certain embodiments, the antibody comprises:
(i) a heavy chain variable region CDR1 comprising amino acids having the sequence set forth in SEQ ID NO: 190;
(ii) a heavy chain variable region CDR2 comprising amino acids having the sequence set forth in SEQ ID NO: 191;
(iii) a heavy chain variable region CDR3 comprising amino acids having the sequence set forth in SEQ ID NO: 192;
(iv) a light chain variable region CDR1 comprising amino acids having the sequence set forth in SEQ ID NO: 193;
(v) a light chain variable region CDR2 comprising amino acids having the sequence set forth in SEQ ID NO:194; and
(vi) a light chain variable region CDR3 comprising amino acids having the sequence set forth in SEQ ID NO: 195.

In certain embodiments, the antibody comprises:
(i) a heavy chain variable region CDR1 comprising amino acids having the sequence set forth in SEQ ID NO: 196;
(ii) a heavy chain variable region CDR2 comprising amino acids having the sequence set forth in SEQ ID NO: 197;
(iii) a heavy chain variable region CDR3 comprising amino acids having the sequence set forth in SEQ ID NO: 198;
(iv) a light chain variable region CDR1 comprising amino acids having the sequence set forth in SEQ ID NO: 199;
(xxii) a light chain variable region CDR2 comprising amino acids having the sequence set forth in SEQ ID NO:200; and
(vi) a light chain variable region CDR3 comprising amino acids having the sequence set forth in SEQ ID NO: 201.

In certain embodiments, the antibody comprises:
(i) a heavy chain variable region CDR1 comprising amino acids having the sequence set forth in SEQ ID NO: 202;
(ii) a heavy chain variable region CDR2 comprising amino acids having the sequence set forth in SEQ ID NO: 203;
(iii) a heavy chain variable region CDR3 comprising amino acids having the sequence set forth in SEQ ID NO: 204;
(iv) a light chain variable region CDR1 comprising amino acids having the sequence set forth in SEQ ID NO: 205;
(xxii) a light chain variable region CDR2 comprising amino acids having the sequence set forth in SEQ ID NO:206; and
(vi) a light chain variable region CDR3 comprising amino acids having the sequence set forth in SEQ ID NO: 207.

In certain embodiments, the antibody comprises:
(i) a heavy chain variable region CDR1 comprising amino acids having the sequence set forth in SEQ ID NO: 208;
(ii) a heavy chain variable region CDR2 comprising amino acids having the sequence set forth in SEQ ID NO: 209;
(iii) a heavy chain variable region CDR3 comprising amino acids having the sequence set forth in SEQ ID NO: 210;
(iv) a light chain variable region CDR1 comprising amino acids having the sequence set forth in SEQ ID NO: 211;
(xxii) a light chain variable region CDR2 comprising amino acids having the sequence set forth in SEQ ID NO:212; and
(vi) a light chain variable region CDR3 comprising amino acids having the sequence set forth in SEQ ID NO: 213.

In certain embodiments, the antibody comprises:
(i) a heavy chain variable region CDR1 comprising amino acids having the sequence set forth in SEQ ID NO: 214;
(ii) a heavy chain variable region CDR2 comprising amino acids having the sequence set forth in SEQ ID NO: 215;
(iii) a heavy chain variable region CDR3 comprising amino acids having the sequence set forth in SEQ ID NO: 216;
(iv) a light chain variable region CDR1 comprising amino acids having the sequence set forth in SEQ ID NO: 217;
(xxii) a light chain variable region CDR2 comprising amino acids having the sequence set forth in SEQ ID NO:218; and
(vi) a light chain variable region CDR3 comprising amino acids having the sequence set forth in SEQ ID NO: 219.

In certain embodiments, the antibody comprises:
(i) a heavy chain variable region CDR1 comprising amino acids having the sequence set forth in SEQ ID NO: 220;
(ii) a heavy chain variable region CDR2 comprising amino acids having the sequence set forth in SEQ ID NO: 221;
(iii) a heavy chain variable region CDR3 comprising amino acids having the sequence set forth in SEQ ID NO: 222;
(iv) a light chain variable region CDR1 comprising amino acids having the sequence set forth in SEQ ID NO: 223;
(xxii) a light chain variable region CDR2 comprising amino acids having the sequence set forth in SEQ ID NO:224; and
(vi) a light chain variable region CDR3 comprising amino acids having the sequence set forth in SEQ ID NO: 225.

In certain embodiments, the antibody comprises:
(i) a heavy chain variable region CDR1 comprising amino acids having the sequence set forth in SEQ ID NO: 226;
(ii) a heavy chain variable region CDR2 comprising amino acids having the sequence set forth in SEQ ID NO: 227;
(iii) a heavy chain variable region CDR3 comprising amino acids having the sequence set forth in SEQ ID NO: 228;
(iv) a light chain variable region CDR1 comprising amino acids having the sequence set forth in SEQ ID NO: 229;
(xxii) a light chain variable region CDR2 comprising amino acids having the sequence set forth in SEQ ID NO:230; and
(vi) a light chain variable region CDR3 comprising amino acids having the sequence set forth in SEQ ID NO: 231.

In certain embodiments, the antibody comprises:
(i) a heavy chain variable region CDR1 comprising amino acids having the sequence set forth in SEQ ID NO: 232;
(ii) a heavy chain variable region CDR2 comprising amino acids having the sequence set forth in SEQ ID NO: 233;
(iii) a heavy chain variable region CDR3 comprising amino acids having the sequence set forth in SEQ ID NO: 234;
(iv) a light chain variable region CDR1 comprising amino acids having the sequence set forth in SEQ ID NO: 235;
(xxii) a light chain variable region CDR2 comprising amino acids having the sequence set forth in SEQ ID NO:236; and
(vi) a light chain variable region CDR3 comprising amino acids having the sequence set forth in SEQ ID NO: 237.

In certain embodiments, the antibody comprises:
(i) a heavy chain variable region CDR1 comprising amino acids having the sequence set forth in SEQ ID NO: 238;
(ii) a heavy chain variable region CDR2 comprising amino acids having the sequence set forth in SEQ ID NO: 239;
(iii) a heavy chain variable region CDR3 comprising amino acids having the sequence set forth in SEQ ID NO: 240;
(iv) a light chain variable region CDR1 comprising amino acids having the sequence set forth in SEQ ID NO: 241;
(xxii) a light chain variable region CDR2 comprising amino acids having the sequence set forth in SEQ ID NO:242; and
(vi) a light chain variable region CDR3 comprising amino acids having the sequence set forth in SEQ ID NO: 243.

In certain embodiments, the antibody comprises:
(i) a heavy chain variable region CDR1 comprising amino acids having the sequence set forth in SEQ ID NO: 244;
(ii) a heavy chain variable region CDR2 comprising amino acids having the sequence set forth in SEQ ID NO: 245;
(iii) a heavy chain variable region CDR3 comprising amino acids having the sequence set forth in SEQ ID NO: 246;
(iv) a light chain variable region CDR1 comprising amino acids having the sequence set forth in SEQ ID NO: 247;
(xxii) a light chain variable region CDR2 comprising amino acids having the sequence set forth in SEQ ID NO:248; and
(vi) a light chain variable region CDR3 comprising amino acids having the sequence set forth in SEQ ID NO: 249.

In certain embodiments, the antibody comprises:
(i) a heavy chain variable region CDR1 comprising amino acids having the sequence set forth in SEQ ID NO: 250;
(ii) a heavy chain variable region CDR2 comprising amino acids having the sequence set forth in SEQ ID NO: 251;
(iii) a heavy chain variable region CDR3 comprising amino acids having the sequence set forth in SEQ ID NO: 252;
(iv) a light chain variable region CDR1 comprising amino acids having the sequence set forth in SEQ ID NO: 253;
(xxii) a light chain variable region CDR2 comprising amino acids having the sequence set forth in SEQ ID NO:254; and
(vi) a light chain variable region CDR3 comprising amino acids having the sequence set forth in SEQ ID NO: 255.

In certain embodiments, the antibody comprises:
(i) a heavy chain variable region CDR1 comprising amino acids having the sequence set forth in SEQ ID NO: 256;
(ii) a heavy chain variable region CDR2 comprising amino acids having the sequence set forth in SEQ ID NO: 257;
(iii) a heavy chain variable region CDR3 comprising amino acids having the sequence set forth in SEQ ID NO: 258;
(iv) a light chain variable region CDR1 comprising amino acids having the sequence set forth in SEQ ID NO: 259;
(xxii) a light chain variable region CDR2 comprising amino acids having the sequence set forth in SEQ ID NO:260; and
(vi) a light chain variable region CDR3 comprising amino acids having the sequence set forth in SEQ ID NO: 261.

In certain embodiments, the antibody comprises:
(i) a heavy chain variable region CDR1 comprising amino acids having the sequence set forth in SEQ ID NO: 262;
(ii) a heavy chain variable region CDR2 comprising amino acids having the sequence set forth in SEQ ID NO: 263;
(iii) a heavy chain variable region CDR3 comprising amino acids having the sequence set forth in SEQ ID NO: 264;
(iv) a light chain variable region CDR1 comprising amino acids having the sequence set forth in SEQ ID NO: 265;
(xxii) a light chain variable region CDR2 comprising amino acids having the sequence set forth in SEQ ID NO:266; and
(vi) a light chain variable region CDR3 comprising amino acids having the sequence set forth in SEQ ID NO: 267.

In certain embodiments, the antibody comprises:
(i) a heavy chain variable region CDR1 comprising amino acids having the sequence set forth in SEQ ID NO: 268;
(ii) a heavy chain variable region CDR2 comprising amino acids having the sequence set forth in SEQ ID NO: 269;
(iii) a heavy chain variable region CDR3 comprising amino acids having the sequence set forth in SEQ ID NO: 270;
(iv) a light chain variable region CDR1 comprising amino acids having the sequence set forth in SEQ ID NO: 271;
(xxii) a light chain variable region CDR2 comprising amino acids having the sequence set forth in SEQ ID NO:272; and
(vi) a light chain variable region CDR3 comprising amino acids having the sequence set forth in SEQ ID NO: 273.

In certain embodiments, the antibody comprises:
(i) a heavy chain variable region CDR1 comprising amino acids having the sequence set forth in SEQ ID NO: 280;
(ii) a heavy chain variable region CDR2 comprising amino acids having the sequence set forth in SEQ ID NO: 281;
(iii) a heavy chain variable region CDR3 comprising amino acids having the sequence set forth in SEQ ID NO: 282;
(iv) a light chain variable region CDR1 comprising amino acids having the sequence set forth in SEQ ID NO: 283;
(xxii) a light chain variable region CDR2 comprising amino acids having the sequence set forth in SEQ ID NO:284; and
(vi) a light chain variable region CDR3 comprising amino acids having the sequence set forth in SEQ ID NO: 285.

In certain embodiments, the antibody comprises:
(i) a heavy chain variable region CDR1 comprising amino acids having the sequence set forth in SEQ ID NO: 292;
(ii) a heavy chain variable region CDR2 comprising amino acids having the sequence set forth in SEQ ID NO: 293;
(iii) a heavy chain variable region CDR3 comprising amino acids having the sequence set forth in SEQ ID NO: 294;
(iv) a light chain variable region CDR1 comprising amino acids having the sequence set forth in SEQ ID NO: 295;
(xxii) a light chain variable region CDR2 comprising amino acids having the sequence set forth in SEQ ID NO:296; and
(vi) a light chain variable region CDR3 comprising amino acids having the sequence set forth in SEQ ID NO: 297.

In certain embodiments, the antibody comprises:
(i) a heavy chain variable region CDR1 comprising amino acids having the sequence set forth in SEQ ID NO: 303;
(ii) a heavy chain variable region CDR2 comprising amino acids having the sequence set forth in SEQ ID NO: 304;
(iii) a heavy chain variable region CDR3 comprising amino acids having the sequence set forth in SEQ ID NO: 305;
(iv) a light chain variable region CDR1 comprising amino acids having the sequence set forth in SEQ ID NO: 306;
(xxii) a light chain variable region CDR2 comprising amino acids having the sequence set forth in SEQ ID NO: 307; and
(vi) a light chain variable region CDR3 comprising amino acids having the sequence set forth in SEQ ID NO: 308.

In certain embodiments, the antibody comprises:
(i) a heavy chain variable region CDR1 comprising amino acids having the sequence set forth in SEQ ID NO: 316;
(ii) a heavy chain variable region CDR2 comprising amino acids having the sequence set forth in SEQ ID NO: 317;
(iii) a heavy chain variable region CDR3 comprising amino acids having the sequence set forth in SEQ ID NO: 318;
(iv) a light chain variable region CDR1 comprising amino acids having the sequence set forth in SEQ ID NO: 319;
(xxii) a light chain variable region CDR2 comprising amino acids having the sequence set forth in SEQ ID NO: 320; and
(vi) a light chain variable region CDR3 comprising amino acids having the sequence set forth in SEQ ID NO: 321.

In certain embodiments, the antibody comprises:
(i) a heavy chain variable region CDR1 comprising amino acids having the sequence set forth in SEQ ID NO: 328;
(ii) a heavy chain variable region CDR2 comprising amino acids having the sequence set forth in SEQ ID NO: 329;
(iii) a heavy chain variable region CDR3 comprising amino acids having the sequence set forth in SEQ ID NO: 330;
(iv) a light chain variable region CDR1 comprising amino acids having the sequence set forth in SEQ ID NO: 331;
(xxii) a light chain variable region CDR2 comprising amino acids having the sequence set forth in SEQ ID NO: 332; and
(vi) a light chain variable region CDR3 comprising amino acids having the sequence set forth in SEQ ID NO: 333.

In certain embodiments, the antibody comprises:
(i) a heavy chain variable region CDR1 comprising amino acids having the sequence set forth in SEQ ID NO: 340;
(ii) a heavy chain variable region CDR2 comprising amino acids having the sequence set forth in SEQ ID NO: 341;
(iii) a heavy chain variable region CDR3 comprising amino acids having the sequence set forth in SEQ ID NO: 342;
(iv) a light chain variable region CDR1 comprising amino acids having the sequence set forth in SEQ ID NO: 343;
(xxii) a light chain variable region CDR2 comprising amino acids having the sequence set forth in SEQ ID NO: 344; and
(vi) a light chain variable region CDR3 comprising amino acids having the sequence set forth in SEQ ID NO: 345.

In certain embodiments, the antibody comprises:
(i) a heavy chain variable region CDR1 comprising amino acids having the sequence set forth in SEQ ID NO: 352;

(ii) a heavy chain variable region CDR2 comprising amino acids having the sequence set forth in SEQ ID NO: 353;
(iii) a heavy chain variable region CDR3 comprising amino acids having the sequence set forth in SEQ ID NO: 354;
(iv) a light chain variable region CDR1 comprising amino acids having the sequence set forth in SEQ ID NO: 355;
(xxii) a light chain variable region CDR2 comprising amino acids having the sequence set forth in SEQ ID NO: 356; and
(vi) a light chain variable region CDR3 comprising amino acids having the sequence set forth in SEQ ID NO: 357.

The constant region/framework region of the anti-GPRC5D antibodies disclosed herein can be altered, for example, by amino acid substitution, to modify the properties of the antibody (e.g., to increase or decrease one or more of: antigen binding affinity, Fc receptor binding, antibody carbohydrate, for example, glycosylation, fucosylation etc, the number of cysteine residues, effector cell function, effector cell function, complement function or introduction of a conjugation site).

In certain embodiments, a presently disclosed anti-GPRC5D antibody is a fully-human antibody, e.g., any one of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033. Fully-human mAbs are preferred for therapeutic use in humans because murine antibodies cause an immunogenicity reaction, known as the HAMA (human anti-mouse antibodies) response (Azinovic I, et al. Survival benefit associated with human anti-mouse antibody (HAMA) in patients with B-cell malignancies. Cancer Immunol Immunother 2006; 55(12):1451-8; Tjandra J J, et al. Development of human anti-murine antibody (HAMA) response in patients. Immunol Cell Biol 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (Riechmann L, et al. Reshaping human antibodies for therapy. Nature 1988; 332 (6162): 332:323; Queen C, et al. A humanized antibody that binds to the interleukin 2 receptor. Proc Natl Acad Sci USA 1989; 86 (24): 10029-33) can be employed to reduce the immunogenicity of murine-derived antibodies (Gerd R, et al. Serological Analysis of Human Anti-Human Antibody Responses in Colon Cancer Patients Treated with Repeated Doses of Humanized Monoclonal Antibody A33. Cancer Res 2001; 61, 6851-6859).

The use of phage display libraries has made it possible to select large numbers of Ab repertoires for unique and rare Abs against very defined epitopes (for more details on phage display see McCafferty et al., Phage antibodies: filamentous phage displaying antibody variable domains. Nature, 348: 552-554.) The rapid identification of human Fab or single chain Fv (ScFV) fragments highly specific for tumor antigen-derived peptide-MHC complex molecules has thus become possible (19-22). Recently, immunotoxins, generated by fusing TCR-like Fab specific for melanoma Ag MART-1 26-35/A2 or gp100 280-288/A2 to a truncated form of *Pseudomonas* endotoxin, have been shown to inhibit human melanoma growth both in vitro and in vivo (Klechevsky E, et al. Antitumor activity of immunotoxins with T-cell receptor-like specificity against human melanoma xenografts. Cancer Res 2008; 68 (15): 6360-6367). In addition, by engineering full-length mAb using the Fab fragments, it is possible to directly generate a therapeutic human mAb, bypassing months of time-consuming work, normally needed for developing therapeutic mAbs. The presently disclosed subject matter involves the development of a fully human mAb that recognizes, for example, a human GPRC5D polypeptide (e.g., a polypeptide having the amino acid sequence set forth in SEQ ID NO:97) for cancer therapy.

3. Homologous Antibodies

In certain embodiments, an antibody of the presently disclosed subject matter comprises heavy and light chain variable regions comprising amino acid sequences that are homologous to the amino acid sequences of the antibodies described herein (e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies), and wherein the antibodies retain the desired functional properties of the anti-PGPRC5D antibodies of the presently disclosed subject matter.

For example, the presently disclosed subject matter provides an isolated antibody, or antigen-binding portion thereof, comprising a heavy chain variable region and a light chain variable region, wherein:
(a) the heavy chain variable region comprises an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and
(b) the light chain variable region comprises an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359; and the antibody binds to human GPRC5D with a $K_d$ of $1 \times 10^{-7}$ M or less.

In certain embodiments, the $V_H$ and/or $V_L$ amino acid sequences can be at least 80%, 81%, 82%, 83%, 84%, 85%, 86%, 87%, 88%, 89%, 90%, 91%, 92%, 93%, 94%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

4. Antibodies with Conservative Modifications

In certain embodiments, an antibody of the presently disclosed subject matter comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies), or conservative modifications thereof, and wherein the antibodies retain the desired functional properties of the anti-GPRC5D antibodies of the presently disclosed subject matter.

The presently disclosed subject matter provides an isolated antibody, or antigen-binding portion thereof, comprising a heavy chain variable region comprising CDR1, CDR2, and CDR3 sequences and a light chain variable region comprising CDR1, CDR2, and CDR3 sequences, wherein:
(a) the heavy chain variable region CDR3 sequence comprises an amino acid sequence selected from the group consisting of amino acid sequences of SEQ ID NOs: 126, 132, 138, 144, 150, 156, 162, 168, 174, 180, 186, 192, 198, 204, 210, 216, 222, 228, 234, 240, 246, 252, 258, 264, 270, 282, 294, 305, 318, 330, 342 and 354, and conservative modifications thereof;
(b) the light chain variable region CDR3 sequence comprises an amino acid sequence selected from the group consisting of amino acid sequence of SEQ ID NOs: 129, 135, 141, 147, 153, 159, 165, 171, 177, 183, 189, 195, 201, 207, 213, 219, 225, 231, 237, 243, 249, 255, 261, 267, 273, 285, 297, 308, 321, 333, 345 and 357, and 431, and conservative modifications thereof; and the antibody exhibits its binds to human GPRC5D with a $K_d$ of $1\times10^{-7}$ M or less.

In certain embodiments, the heavy chain variable region CDR2 sequence comprises an amino acid sequence selected from the group consisting of amino acid sequences of SEQ ID NOs: 125, 131, 137, 143, 149, 155, 161, 167, 173, 179, 185, 191, 197, 203, 209, 215, 221, 227, 233, 239, 245, 251, 257, 263, 269, 281, 293, 304, 317, 329, 341 and 353, and conservative modifications thereof; and the light chain variable region CDR2 sequence comprises an amino acid sequence selected from the group consisting of amino acid sequences of SEQ ID NOs: 128, 134, 140, 146, 152, 158, 164, 170, 176, 182, 188, 194, 200, 206, 212, 218, 224, 230, 236, 242, 248, 254, 260, 266, 272, 284, 296, 307, 320, 332, 344 and 356, and conservative modifications thereof.

In certain embodiments, the heavy chain variable region CDR1 sequence comprises an amino acid sequence selected from the group consisting of amino acid sequences of SEQ ID NOs: 124, 130, 136, 142, 148, 154, 160, 166, 172, 178, 184, 190, 196, 202, 208, 214, 220, 226, 232, 238, 244, 250, 256, 262, 268, 280, 292, 303, 316, 328, 340 and 352, and conservative modifications thereof; and the light chain variable region CDR1 sequence comprises an amino acid sequence selected from the group consisting of amino acid sequences of SEQ ID NOs: 127, 133, 139, 145, 151, 157, 163, 169, 175, 181, 187, 193, 199, 205, 211, 217, 223, 229, 235, 241, 247, 253, 259, 265, 271, 283, 295, 306, 319, 331, 343 and 355, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 33. Amino acid substitutions may be introduced into an antibody of interest and the products screened for a desired activity, e.g., retained/improved antigen binding, decreased immunogenicity, or improved ADCC or CDC. In certain embodiments, a sequence disclosed herein, e.g., a CDR sequence, a VH sequence or a VL sequence, can have up to about one, up to about two, up to about three, up to about four, up to about five, up to about six, up to about seven, up to about eight, up to about nine or up to about ten amino acid residues that are modified and/or substituted.

TABLE 33

| Original Residue | Exemplary conservative amino acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |

TABLE 33-continued

| Original Residue | Exemplary conservative amino acid Substitutions |
|---|---|
| Ile (I) | Leu; Val; Met; Ala; Phe |
| Leu (xii) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (xxiii) | Tyr; Phe |
| Tyr (Y) | Trp; Phe; Thr; Ser |
| Val (V) | Ile; Leu; Met; Phe; Ala |

Amino acids may be grouped according to common side-chain properties:
hydrophobic: Norleucine, Met, Ala, Val, Leu, Be;
neutral hydrophilic: Cys, Ser, Thr, Asn, Gln;
acidic: Asp, Glu;
basic: His, Lys, Arg;
residues that influence chain orientation: Gly, Pro;
aromatic: Trp, Tyr, Phe.

Non-conservative substitutions will entail exchanging a member of one of these classes for another class.

5. Anti-GPRC5D Antibodies that Cross-Compete for Binding to GPRC5D with Anti-GPRC5D Antibodies of the Invention The presently disclosed subject matter provides antibodies that cross-compete with any of the disclosed anti-GPRC5D antibodies for binding to GPRC5D (e.g., human GPRC5D). For example, and not by way of limitation, the cross-competing antibodies can bind to the same epitope region, e.g., same epitope, adjacent epitope, or overlapping as any of the anti-GPRC5D antibodies of the presently disclosed subject matter. In certain embodiments, the reference antibody for cross-competition studies can be any one of the anti-GPRC5D antibodies disclosed herein, e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies.

In certain embodiments, the cross-competing antibody binds to an epitope region comprising amino acids 14-22 of SEQ ID NO: 97. In certain embodiments, the cross-competing antibody binds to one, two, three, four, five, six, or seven epitope regions selected from the group consisting of amino acids 5-17, 10-17, 1-27, 15-23, 16-23, 16-25, 85-93, 85-95, 145-167, 157-164, 157-167, 226-239, 230-237, 229-237, 230-243 and 227-237 of SEQ ID NO: 97.

Such cross-competing antibodies can be identified based on their ability to cross-compete with any one of the presently disclosed anti-GPRC5D antibodies in standard GPRC5D binding assays. For example, Biacore analysis, ELISA assays or flow cytometry can be used to demonstrate cross-competition with the antibodies of the presently disclosed subject matter. The ability of a test antibody to inhibit the binding of, for example, any one of the presently disclosed GPRC5D antibodies (e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies) to human GPRC5D demonstrates that the test antibody can compete with any one of the presently disclosed anti-GPRC5D antibodies for binding to human GPRC5D and thus binds to the same epitope region on human GPRC5D as any one of the presently disclosed anti-GPRC5D antibodies. In certain embodiments, the cross-competing antibody binds to the same epitope on human GPRC5D as any one of the presently disclosed anti-GPRC5D antibodies.

6. Characterization of Antibody Binding to Antigen

Antibodies of the presently disclosed subject can be tested for binding to GPRC5D by, for example, standard ELISA. To determine if the selected anti-GPRC5D antibodies bind to unique epitopes, each antibody can be biotinylated using commercially available reagents (Pierce, Rockford, Ill.). Competition studies using unlabeled monoclonal antibodies and biotinylated monoclonal antibodies can be performed using GPRC5D coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. Anti-GPRC5D human IgGs can be further tested for reactivity with GPRC5D antigen by Western blotting.

In certain embodiments, $K_d$ is measured by a radiolabeled antigen binding assay (RIA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)).

In certain embodiments, $K_d$ is measured using a BIA-CORE® surface plasmon resonance assay. For example, an assay using a BIACORE®-2000 or a BIACORE®-3000 (BIAcore, Inc., Piscataway, N.J.).

Epitope Mapping

In certain embodiments, the antibody or an antigen-binding fragment thereof binds to a human GPRC5D polypeptide comprising the amino acid sequence set forth in SEQ ID NO: 97. In certain embodiments, the antibody or an antigen-binding fragment thereof binds to one, two, three or four of N-terminal region (amino acids 1-27 of SEQ ID NO:97), ECL1 region (amino acids 85-93 of SEQ ID NO:97), ECL2 region (amino acids 145-167 of SEQ ID NO:97), and ECL3 region (amino acids 226-239 of SEQ ID NO:97). In certain embodiments, an antibody or an antigen-binding fragment thereof of the presently disclosed subject matter binds to an epitope region in the N-terminal region, including, but not limited to, an epitope region comprising amino acids 16-23 of SEQ ID NO:97, and an epitope region comprising amino acids 10-17 of SEQ ID NO:97. In certain embodiments, the epitope region in the N-terminal region comprises amino acids 15-23 of SEQ ID NO:97. In certain embodiments, the epitope region in the N-terminal region comprises amino acids 16-25 of SEQ ID NO:97. In certain embodiments, the epitope region in the N-terminal region comprises amino acids 10-17 of SEQ ID NO:97. In certain embodiments, the epitope region in the N-terminal region comprises amino acids 5-17 of SEQ ID NO:97.

In certain embodiments, an antibody or an antigen-binding fragment thereof of the presently disclosed subject matter binds to an epitope region in the ECL1 region, including, but not limited to, an epitope region comprising amino acids 85-95 of SEQ ID NO:97.

In certain embodiments, an antibody or an antigen-binding fragment thereof of the presently disclosed subject matter binds to an epitope region in the ECL2 region, including, but not limited to, an epitope region comprising amino acids 157-164 of SEQ ID NO:97. In certain embodiments, the epitope region in the ECL2 region comprises amino acids 157-164 of SEQ ID NO:97. In certain embodiments, the epitope region in the ECL2 region comprises amino acids 157-167 of SEQ ID NO:97.

In certain embodiments, an antibody or an antigen-binding fragment thereof of the presently disclosed subject matter binds to an epitope region in the ECL3 region, including, but not limited to, an epitope region comprising amino acids 230-237 of SEQ ID NO:97. In certain embodiments, the epitope region in the ECL3 region comprises amino acids 229-237 of SEQ ID NO:97. In certain embodiments, the epitope region in the ECL3 region comprises amino acids 230-243 of SEQ ID NO:97. In certain embodiments, the epitope region in the ECL3 region comprises amino acids 227-237 of SEQ ID NO:97.

In certain embodiments, the antibody or an antigen-binding fragment thereof binds to an epitope region comprising amino acids 16-25 of SEQ ID NO:97, an epitope region comprising amino acids 157-164 of SEQ ID NO:97, and an epitope region comprising amino acids 229-237 of SEQ ID NO:97. For example, the antibody or an antigen-binding fragment thereof comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 15. In certain embodiments, the antibody or an antigen-binding fragment thereof comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:57. In certain embodiments, the antibody or an antigen-binding fragment thereof comprises a $V_H$ comprising amino acids having the sequence set forth in SEQ ID NO:57. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:58. In certain embodiments, the antibody or an antigen-binding fragment thereof comprises a $V_L$ comprising amino acids having the sequence set forth in SEQ ID NO:58. In certain embodiments, the antibody or an antigen-binding fragment thereof comprises a $V_H$ comprising amino acids having the sequence set forth in SEQ ID NO:57 and a $V_L$ comprising amino acids having the sequence set forth in SEQ ID NO:58. In certain embodiments, the antibody or an antigen-binding fragment thereof comprises a $V_H$ CDR1 comprising amino acids having the sequence set forth in SEQ ID NO:208 or conservative modifications thereof, a $V_H$ CDR2 comprising amino acids having the sequence set forth in SEQ ID NO: 209 or conservative modifications thereof, and a $V_H$ CDR3 comprising amino acids having the sequence set forth in SEQ ID NO: 210 or conservative modifications thereof. In certain embodiments, the antibody or an antigen-binding fragment thereof comprises a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof. In certain embodiments, the antibody or an antigen-binding fragment thereof comprises a $V_H$ CDR1 comprising amino acids having the sequence set forth in SEQ ID NO: 208 or conservative modifications thereof, a $V_H$ CDR2 comprising amino acids having the sequence set forth in SEQ ID NO: 209 or conservative modifications thereof, a $V_H$ CDR3 comprising amino acids having the sequence set forth in SEQ ID NO: 210 or conservative modifications thereof, a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof. In certain embodiments, the antibody or an antigen-binding fragment thereof comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213. In certain embodiments, the antibody or an antigen-binding fragment thereof is ET150-2 scFv (or ET150-152 scFv).

In certain embodiments, the antibody or an antigen-binding fragment thereof binds to an epitope region comprising amino acids 5-17 of SEQ ID NO:97, an epitope region comprising amino acids 85-95 of SEQ ID NO:97, and an epitope region comprising amino acids 157-164 of SEQ ID NO:97. For example, the antibody or an antigen-binding fragment thereof comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 16. In certain embodiments, the antibody or an antigen-binding fragment thereof comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:61. In certain embodiments, the antibody or an antigen-binding fragment thereof comprises a $V_H$ comprising amino acids having the sequence set forth in SEQ ID NO:61. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:62. In certain embodiments, the antibody or an antigen-binding fragment thereof comprises a $V_L$ comprising amino acids having the sequence set forth in SEQ ID NO:62. In certain embodiments, the antibody or an antigen-binding fragment thereof comprises a $V_H$ comprising amino acids having the sequence set forth in SEQ ID NO:61 and a $V_L$ comprising amino acids having the sequence set forth in SEQ ID NO:62. In certain embodiments certain embodiments, the antibody or an antigen-binding fragment thereof comprises a $V_H$ CDR1 comprising amino acids having the sequence set forth in SEQ ID NO:214 or conservative modifications thereof, a $V_H$ CDR2 comprising amino acids having the sequence set forth in SEQ ID NO: 215 or conservative modifications thereof, and a $V_H$ CDR3 comprising amino acids having the sequence set forth in SEQ ID NO: 216 or conservative modifications thereof. In certain embodiments, the antibody or an antigen-binding fragment thereof comprises a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof. In certain embodiments, the antibody or an antigen-binding fragment thereof comprises a $V_H$ CDR1 comprising amino acids having the sequence set forth in SEQ ID NO: 214 or conservative modifications thereof, a $V_H$ CDR2 comprising amino acids having the sequence set forth in SEQ ID NO: 215 or conservative modifications thereof, a $V_H$ CDR3 comprising amino acids having the sequence set forth in SEQ ID NO: 216 or conservative modifications thereof, a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof. In certain embodiments, the antibody or an antigen-binding fragment thereof comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218 and a $V_L$ CDR3 comprising amino acids having the sequence set forth in SEQ ID NO: 219. In certain embodiments, the antibody or an antigen-binding fragment thereof is ET150-155 scFv (or ET150-5 scFv).

In certain embodiments, the antibody or an antigen-binding fragment thereof binds to an epitope region comprising amino acids 15-23 of SEQ ID NO:97, and an epitope region comprising amino acids 230-243 of SEQ ID NO:97. For example, the antibody or an antigen-binding fragment thereof comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 17. In certain embodiments, the antibody or an antigen-binding fragment thereof comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:65. In certain embodiments, the antibody or an antigen-binding fragment thereof comprises a $V_H$ comprising amino acids having the sequence set forth in SEQ ID NO:65. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:66, as shown in Table 17. In certain embodiments, the antibody or an antigen-binding fragment thereof comprises a $V_L$ comprising amino acids having the sequence set forth in SEQ ID NO:66. In certain embodiments, the antibody or an antigen-binding fragment thereof comprises a $V_H$ comprising amino acids having the sequence set forth in SEQ ID NO:65 and a $V_L$ comprising amino acids having the sequence set forth in SEQ ID NO:66. In certain embodiments, the antibody or an antigen-binding fragment thereof comprises a $V_H$ CDR1 comprising amino acids having the sequence set forth in SEQ ID NO:220 or conservative modifications thereof, a $V_H$ CDR2 comprising amino acids having the sequence set forth in SEQ ID NO: 221 or conservative modifications thereof, and a $V_H$ CDR3 comprising amino acids having the sequence set forth in SEQ ID NO: 222 or conservative modifications thereof. In certain embodiments, the antibody or an antigen-binding fragment thereof comprises a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof. In certain embodiments, the antibody or an antigen-binding fragment thereof comprises a $V_H$ CDR1 comprising amino acids having the sequence set forth in SEQ ID NO: 220 or conservative modifications thereof, a $V_H$ CDR2 comprising amino acids having the sequence set forth in SEQ ID NO: 221 or conservative modifications thereof, a $V_H$ CDR3 comprising amino acids having the sequence set forth in SEQ ID NO: 222 or conservative modifications thereof, a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof. In certain embodiments, the antibody or an antigen-binding fragment thereof comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a V$_L$ CDR3 comprising amino acids having the sequence set forth in SEQ ID NO: 225. In certain embodiments, the antibody or an antigen-binding fragment thereof is ET150-8 scFv (or ET150-158 scFv).

In certain embodiments, the antibody or an antigen-binding fragment thereof binds to an epitope region comprising amino acids 10-17 of SEQ ID NO:97, an epitope region comprising amino acids 157-167 of SEQ ID NO:97, and an epitope region comprising amino acids 227-237 of SEQ ID NO:97. For example, the antibody or an antigen-binding fragment thereof comprises a heavy chain variable region comprising amino acids having the sequence set forth in SEQ ID NO:69 and a light chain variable region comprising amino acids having the sequence set forth in SEQ ID NO:70, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with V$_H$ and V$_L$ regions or CDRs selected from Table 18. In certain embodiments, the antibody or an antigen-binding fragment thereof comprises a V$_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:69. In certain embodiments, the antibody or an antigen-binding fragment thereof comprises a V$_H$ comprising amino acids having the sequence set forth in SEQ ID NO:69. In certain embodiments, the antibody or an antigen-binding fragment thereof comprises a V$_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:70. In certain embodiments, the antibody or an antigen-binding fragment thereof comprises a V$_L$ comprising amino acids having the sequence set forth in SEQ ID NO:70. In certain embodiments, the antibody or an antigen-binding fragment thereof comprises a V$_H$ comprising amino acids having the sequence set forth in SEQ ID NO:69 and a V$_L$ comprising amino acids having the sequence set forth in SEQ ID NO:70. In certain embodiments, the antibody or an antigen-binding fragment thereof comprises a V$_H$ CDR1 comprising amino acids having the sequence set forth in SEQ ID NO:226 or conservative modifications thereof, a V$_H$ CDR2 comprising amino acids having the sequence set forth in SEQ ID NO: 227 or conservative modifications thereof, and a V$_H$ CDR3 comprising amino acids having the sequence set forth in SEQ ID NO: 228 or conservative modifications thereof. In certain embodiments, the antibody or an antigen-binding fragment thereof comprises a V$_L$ CDR1 comprising amino acids having the sequence set forth in SEQ ID NO: 229 or conservative modifications thereof, a V$_L$ CDR2 comprising amino acids having the sequence set forth in SEQ ID NO: 230 or conservative modifications thereof, and a V$_L$ CDR3 comprising amino acids having the sequence set forth in SEQ ID NO: 231 or conservative modifications thereof. In certain embodiments, the antibody or an antigen-binding fragment thereof comprises a V$_H$ CDR1 comprising amino acids having the sequence set forth in SEQ ID NO: 226 or conservative modifications thereof, a V$_H$ CDR2 comprising amino acids having the sequence set forth in SEQ ID NO: 227 or conservative modifications thereof, a V$_H$ CDR3 comprising amino acids having the sequence set forth in SEQ ID NO: 228 or conservative modifications thereof, a V$_L$ CDR1 comprising amino acids having the sequence set forth in SEQ ID NO: 229 or conservative modifications thereof, a V$_L$ CDR2 comprising amino acids having the sequence set forth in SEQ ID NO: 230 or conservative modifications thereof, and a V$_L$ CDR3 comprising amino acids having the sequence set forth in SEQ ID NO: 231 or conservative modifications thereof. In certain embodiments, the antibody or an antigen-binding fragment thereof comprises a V$_H$ CDR1 comprising amino acids having the sequence set forth in SEQ ID NO: 226, a V$_H$ CDR2 comprising amino acids having the sequence set forth in SEQ ID NO: 227, a V$_H$ CDR3 comprising amino acids having the sequence set forth in SEQ ID NO: 228, a V$_L$ CDR1 comprising amino acids having the sequence set forth in SEQ ID NO: 229, a V$_L$ CDR2 comprising amino acids having the sequence set forth in SEQ ID NO: 230, and a V$_L$ CDR3 comprising amino acids having the sequence set forth in SEQ ID NO: 231. In certain embodiments, the antibody or an antigen-binding fragment thereof is ET150-18 scFv (or ET150-168 scFv).

7. Immunoconjugates

The presently disclosed subject provides an anti-GPRC5D antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol (such as ricin, diphtheria, gelonin), cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, calecheamicin, aureastatin, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an anti-GPRC5D antibody disclosed herein include duocarmycins, calicheamicins, maytansines and auristatins, and derivatives thereof. An example of a calicheamicin antibody conjugate is commercially available (MYLOTARG™ (Gemtuzumab ozogamicin); Wyeth-Ayerst).

Cytoxins can be conjugated to anti-GPRC5D antibody disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-GPRC5D antibodies of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}$Y, $^{131}$I, $^{225}$Ac, $^{213}$Bi, $^{213}$Ra and $^{227}$Th. Methods for preparing radioimmunconjugates are established in the art. Examples of radioimmunoconjugates are commercially available, including ZEVALIN™ (Ibritumomab tiuxetan) (IDEC Pharmaceuticals) and BEXXAR™ (Tositumomab) (Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor (TNF) or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

8. Bispecific Molecules

The presently disclosed subject matter provides bispecific molecules comprising an anti-GPRC5D antibody, or a fragment thereof, disclosed herein. An antibody of the presently disclosed subject matter, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-GPRC5D antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least a first binding specificity for GRPC5D and a second binding specificity for a second target epitope. The second target epitope can be a GPRC5D epitope, or a non-GPRC5D epitope, e.g., a different antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function. In certain embodiments, a bispecific antibody of the present disclosure comprises at least a first binding to GPRC5D and at least a second binding to an immune cell. For example, and not by way of limitation, a bispecific antibody of the present disclosure comprises at least a first binding to GPRC5D and at least a second binding to a receptor present on the surface of an immune cell, e.g., CD3.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In certain embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

9. Selecting a High Affinity ScFv Against a GPRC5D Polypeptide

The next step is to the selection of phage that bind to the target antigen of interest with high affinity, from phage in a human phage display library that either does not bind or that binds with lower affinity. This is accomplished by iterative binding of phage to the antigen, which is bound to a solid support, for example, beads or mammalian cells followed by removal of non-bound phage and by elution of specifically bound phage. In certain embodiments, antigens are first biotinylated for immobilization to, for example, streptavidin-conjugated Dynabeads M-280. The phage library is incubated with the cells, beads or other solid support and non binding phage is removed by washing. Clones that bind are selected and tested.

Once selected, positive scFv clones are tested for their binding to GPRC5D (human GPRC5D) on live 3T3 cell surfaces by flow cytometry. Briefly, phage clones are incubated with 3T3 cells over-expressing GPRC5D. The cells are washed and then with a mouse anti-M13 coat protein mAb. Cells are washed again and labeled with a FITC-goat anti-mouse Ig prior to flow cytometry.

In other embodiments, the anti-GPRC5D antibodies can comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

10. Engineering Full Length mAb Using the Selected ScFv Fragments

Phage display technology allows for the rapid selection and production of antigen-specific scFv and Fab fragments, which are useful in and of themselves, or which can be further developed to provide complete antibodies, antigen binding proteins or antigen binding fragments thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In certain embodiments, therefore, once scFv clones specific for GRPC5D were obtained from phage display libraries, a full length IgG mAb using the scFv fragments was produced.

To produce recombinant human monoclonal IgG in Chinese hamster ovary (CHO) cells, a full length IgG mAb can be engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions can be subcloned into mammalian expression vectors, with matching Lambda or Kappa light chain constant sequences and IgG1 subclass Fc (for example) (Lidija P, et al. An integrated vector system for the eukaryotic expression of antibodies or their fragments after selection from phage display libraries. Gene 1997; 187(1): 9-18; Lisa J H, et al. Crystallographic structure of an intact IgG1 monoclonal antibody. Journal of Molecular Biology 1998; 275 (5): 861-872). Kinetic binding analysis (Yasmina N A, et al. Probing the binding mechanism and affinity of tanezumab, a recombinant humanized anti-NGF monoclonal antibody, using a repertoire of biosensors. Protein Science 2008; 17(8): 1326-1335) can be used to confirm specific binding of full length IgG to GRPC5D, with a $K_D$ in nanomolar range.

Pharmaceutical Compositions and Methods of Treatment

Anti-GPRC5D antibodies of the presently disclosed subject matter can be administered for therapeutic treatments to a patient suffering from a tumor (e.g., multiple myeloma) in an amount sufficient to prevent, inhibit, or reduce the progression of the tumor. Progression includes, e.g., the growth, invasiveness, metastases and/or recurrence of the tumor. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

The identification of medical conditions treatable by anti-GPRC5D antibodies of the presently disclosed subject matter is well within the ability and knowledge of one skilled in the art. For example, human individuals who are either suffering from multiple myeloma or who are at risk of developing multiple myeloma are suitable for administration of the presently disclosed anti-GPRC5D antibodies. A clinician skilled in the art can readily determine, for example, by the use of clinical tests, physical examination and medical/family history, if an individual is a candidate for such treatment.

In certain embodiments, the presently disclosed subject matter provides a method of treating a tumor by administering a presently disclosed anti-GPRC5D antibody in combination with one or more other agents. For example, the presently disclosed subject matter provides a method of treating a tumor by administering a presently disclosed anti-GPRC5D antibody with an antineoplastic agent. The anti-GPRC5D antibody can be chemically or biosynthetically linked to one or more of the antineoplastic agents.

Non-limiting examples of suitable tumors include multiple myeloma and Waldenstrom's Macroglobulinemia. In certain embodiments, the tumor is multiple myeloma.

Any suitable method or route can be used to administer a presently disclosed anti-GPRC5D antibody, and optionally, to coadminister antineoplastic agents. Routes of administration include, for example, oral, intravenous, intraperitoneal, subcutaneous, or intramuscular administration. It should be emphasized, however, that the presently disclosed subject matter is not limited to any particular method or route of administration.

It is noted that presently disclosed anti-GPRC5D antibody can be administered as a conjugate, which binds specifically to the receptor and delivers a toxic, lethal payload following ligand-toxin internalization.

It is understood that anti-GPRC5D antibodies of the presently disclosed subject matter can be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The presently disclosed subject matter also provides use of antibodies and nucleic acids that encode them for treatment of a tumor (e.g., multiple myeloma), for diagnostic and prognostic applications as well as use as research tools for the detection of GPRC5D in cells and tissues. Pharmaceutical compositions comprising the disclosed antibodies and nucleic acids are encompassed by the presently disclosed subject matter. Vectors comprising the nucleic acids of the presently disclosed subject matter for antibody-based treatment by vectored immunotherapy are also contemplated by the presently disclosed subject matter. Vectors include expression vectors which enable the expression and secretion of antibodies, as well as vectors which are directed to cell surface expression of the antigen binding proteins, such as chimeric antigen receptors.

Cells comprising the nucleic acids, for example cells that have been transfected with the vectors of the invention are also encompassed by the presently disclosed subject matter.

Kits

The presently disclosed subject matter provides kits for the treatment or prevention of a tumor (e.g., multiple myeloma). In certain embodiments, the kit comprises a therapeutic composition containing an effective amount of an anti-GPRC5D antibody in unit dosage form. In certain embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the anti-GPRC5D antibody is provided together with instructions for administering the cell to a subject having or at risk of developing a tumor (e.g., multiple myeloma). The instructions will generally include information about the use of the composition for the treatment or prevention of a tumor (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Methods

Flow Cytometry Analysis.

For cell surface staining, cells can be incubated with appropriate mAbs for 30 minutes on ice, washed, and incubated with secondary antibody reagents when necessary. Flow cytometry data can be collected on a FACS Calibur (Becton Dickinson) and analyzed with FlowJo V8.7.1 and 9.4.8 software.

Selection and Characterization of scFv Specific for GPRC5D.

A human scFv antibody phage display library is used for the selection of mAb clones. In brief, biotinylated antigens can be first mixed with the human scFv phage library, then the antigen-scFv antibody complexes can be pulled down by streptavidin-conjugated Dynabeads M-280 through a magnetic rack. Bound clones can be then eluted and used to infect E. Coli XL1-Blue. The scFv phage clones expressed in the bacteria can be purified (Yasmina N A, et al. Probing the binding mechanism and affinity of tanezumab, a recombinant humanized anti-NGF monoclonal antibody, using a repertoire of biosensors. Protein Science 2008; 17(8): 1326-1335; Roberts W K, et al. Vaccination with CD20 peptides induces a biologically active, specific immune response in mice. Blood 2002: 99 (10): 3748-3755). Panning can be performed for 3-4 cycles to enrich scFv phage clones binding to GPRC5D specifically. Positive clones can be determined by flow cytometry method against biotinylated single chain GPRC5D. Positive clones can be further tested for their binding to GPRC5D on live cell surfaces by flow cytometry, using a GPRC5D$^+$ cell line, 3T3. The cells can be washed, and the staining can be performed in following steps.

The cells can be first stained with purified scFv phage clones, and followed by staining with a mouse anti-M13 mAb, and finally the goat anti-mouse Ig's conjugate to FITC. Each step of the staining can be done between 30-60 minutes on ice and the cells were washed twice between each step of the staining.

Engineering Full Length mAb Using the Selected ScFv Fragments.

Full-length human IgG of the selected phage clones can be produced in HEK293 and Chinese hamster ovary (CHO) cell lines, as described (Caron P C, Class K, Laird W, Co M S, Queen C, Scheinberg D A. Engineered humanized dimeric forms of IgG are more effective antibodies. J Exp Med 176:1 191-1 195 (1992). In brief, antibody variable regions can be subcloned into mammalian expression vectors, with matching human lambda or kappa light chain constant region and human IgG constant region sequences. Molecular weight of the purified full length IgG antibodies can be measured under both reducing and non-reducing conditions by electrophoresis.

Characterization of the Full-Length Human IgG for GPRC5D.

Initially, specificities of the fully human IgG mAbs for the GPRC5D can be determined by staining 3T3 cells transduced to overexpress GPRC5D, followed by secondary goat anti-human IgG mAb conjugate to PE or FITC. The fluorescence intensity can be measured by flow cytometry. The same method can be used to determine the binding of the mAbs to fresh tumor cells and cell lines.

Antibody-Dependent Cellular Cytotoxicity (ADCC).

Target cells used for ADCC can be 3T3 cells overexpressing GPRC5D. Anti-GPRC5D antibody or its control human IgG at various concentrations can be incubated with target cells and fresh PBMCs at different effector:target (E:T) ratio for 16 hrs. The supernatant can be harvested and the cytotoxicity can be measured by LDH release assay using Cytotox 96 nonradioactive kit from Promega following their instruction. Cytotoxicity can also be measured by standard 4 hours 51 Cr-release assay.

EXAMPLES

The following examples are put forth so as to provide those of ordinary skill in the art with a complete disclosure and description of how to make and use the antibodies, bispecific antibodies, compositions comprising thereof, screening, and therapeutic methods of the presently disclosed subject matter, and are not intended to limit the scope of what the inventors regard as their presently disclosed subject matter. It is understood that various other embodiments may be practiced, given the general description provided above.

Example 1—GPRC5D Expression in Various Tissues

Figure 2:
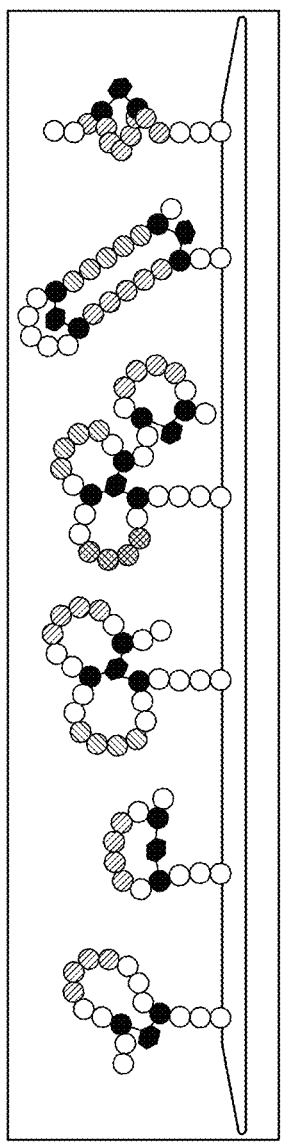
FIG. 2 illustrates the CLIPS technology. The CLIPS reaction takes place between bromo groups of the CLIPS scaffold and thiol sidechains of cysteines. The reaction is fast and specific under mild conditions. Using this elegant chemistry, native protein sequences are transformed into CLIPS constructs with a range of structures. From left to right: two different single T2 loops, T3 double loop, conjugated T2+T3 loops, stabilized beta sheet, and stabilized alpha helix (Timmerman et al., J. Mol. Recognit. 2007; 20: 283-29).
Figure 2:
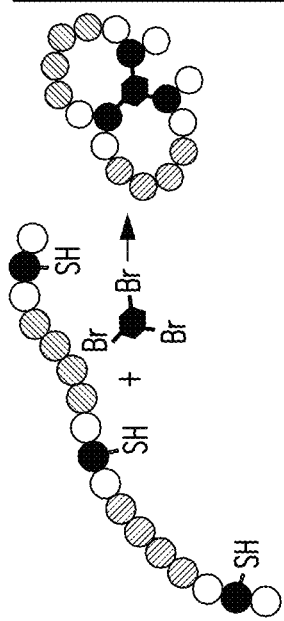

The expression of human GPRC5D was evaluated in various malignant and normal tissues by investigating gene expression profiles in databases such as the cancer cell line encyclopedia and BioGPS. As shown in FIG. 2, human GPRC5D was highly expressed in multiple myeloma, but not in other malignant tissues. Normal expression appeared limited to plasma cells. Potential GPRC5D targeted CAR T cell eradication of this normal cell type may not have significant adverse effects based on inventors' patient experience with CD19 targeted CAR T cells. Any lack of physiologic antibody production can be addressed with intravenous immunoglobulin treatment.

Example 2—Selection of ScFv Specific for GPRC5D Using a Fully Human Phage Display Library Phage display against GPRC5D was performed for 4 panning rounds to enrich the scFv phage clones binding to GPRC5D specifically. Four independent pannings with 12 different phage libraries were carried out against GPRC5D overexpressing 3T3 cells identifying 80 positive clones. Individual scFv phage clones positive for the GPRC5D were determined by ELISA and the clones that possessed unique DNA coding sequences were subjected to further characterization. To test if the ScFv bound to GPRC5D on live cells, the positive phage clones were tested for binding to a GPRC5D-positive cell line, 3T3. 72 positive clones were identified out of 80 clones screened FACS; the positive clone rate was 90%. After sequencing, 32 unique and GPRC5D-3T3 positive binding clones were found out of 72 sequenced positive clones; the unique clone rate was 45%.

Example 3—Epitope Mapping of Anti-GPRC5D Antibodies

Four anti-GPRC5D antibodies: ET150-2, ET150-5, ET150-8, and ET150-18 mIgG1. "mIgG1" used in all Examples represents that the variable region is fully human and the Fc part is mouse IgG1. See Table 34.

TABLE 34

| Name | Origin | Concentration | Location | Status |
| --- | --- | --- | --- | --- |
| ET150-18 mIgG1 | mouse Fc | 1.1 mg/ml | +4° C./22 | ok |
| ET150-2 mIgG1 | mouse Fc | 0.66 mg/ml | +4° C./22 | ok |

TABLE 34-continued

| Name | Origin | Concentration | Location | Status |
| --- | --- | --- | --- | --- |
| ET150-5 mIgG1 | mouse Fc | 1.9 mg/ml | +4° C./22 | ok |
| ET150-8 mIgG1 | mouse Fc | 2.9 mg/ml | +4° C./22 | ok |

The target protein is human GPRC5D having the amino acid sequence set forth in SEQ ID NO: 97. The N-terminal region of human GPRC5D has amino acids 1-27 of SEQ ID NO:97. The extracellular loop 1 (ECL1) region of human GPRC5D has amino acids 85-93 of SEQ ID NO:97. The extracellular loop 2 (ECL2) region of human GPRC5D has amino acids 145-167 of SEQ ID NO:97. The extracellular loop 3 (ECL3) region of human GPRC5D has amino acids 226-239 of SEQ ID NO:97.

Methods

The principles of clips technology. CLIPS technology structurally fixes peptides into defined three-dimensional structures. This results in functional mimics of even the most complex binding sites. CLIPS technology is now routinely used to shape peptide libraries into single, double or triple looped structures as well as sheet- and helix-like folds (FIG. 2).

Figure 3:
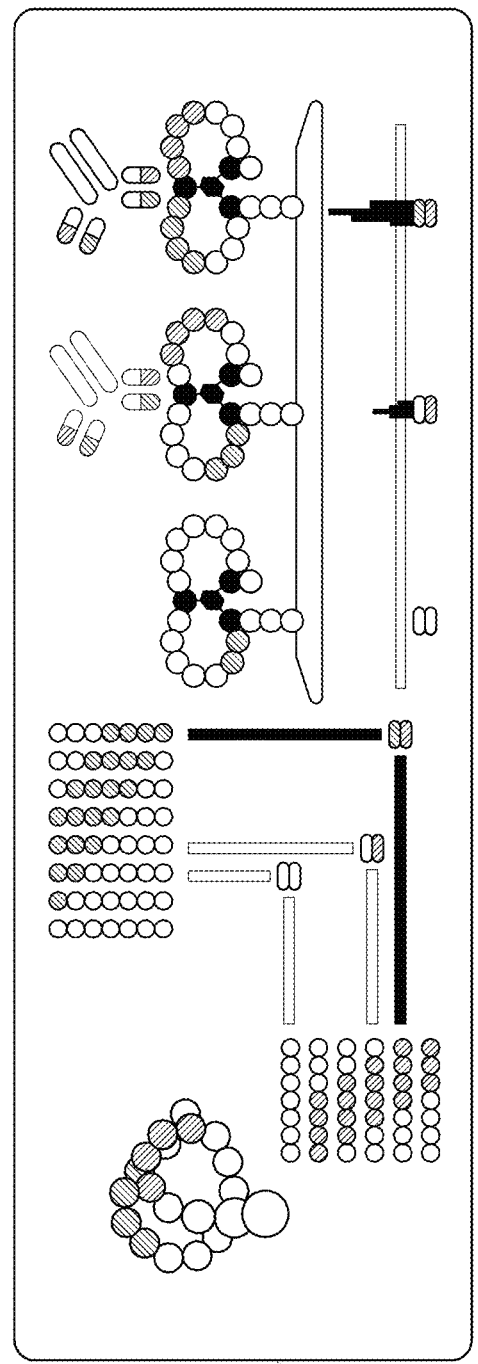
FIG. 3 illustrates combinatorial clips library screening. The target protein (left) containing a discontinuous conformational epitope is converted into a matrix library (middle). Combinatorial peptides are synthesized on a proprietary minicard and chemically converted into spatially defined CLIPS constructs (right).
Figure 3:

Combinatorial clips library screening in detail. CLIPS library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS constructs (FIG. 3). Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

Figure 4:
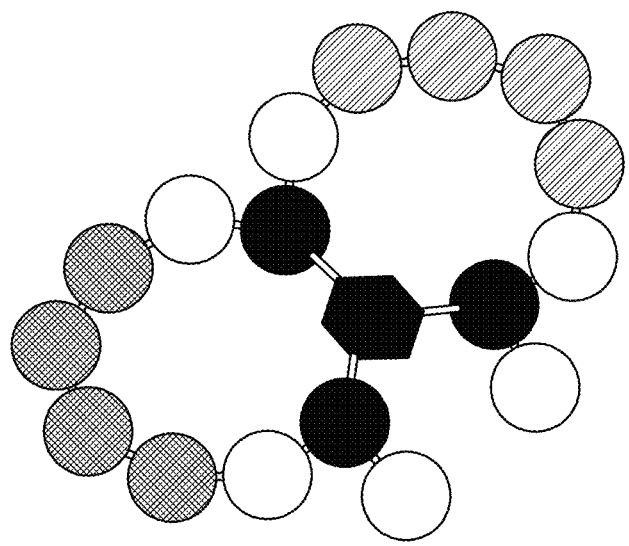
FIG. 4 depicts T3 looped CLIPS™ construct.
Figure 5B:
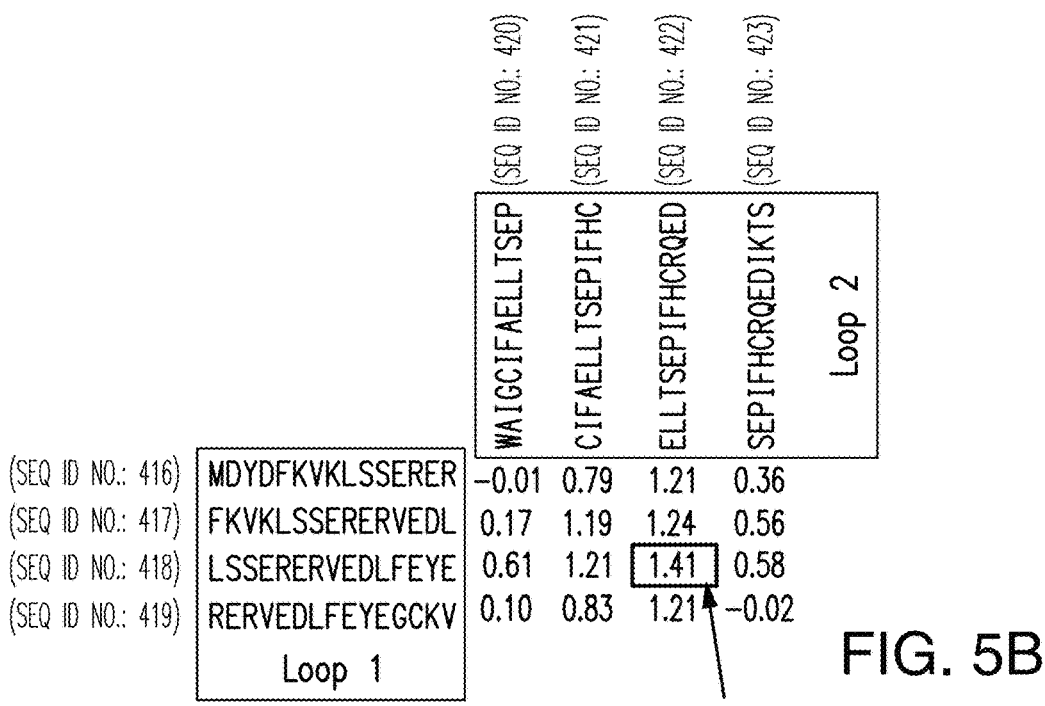
Figure 5C:
Figure 5D:
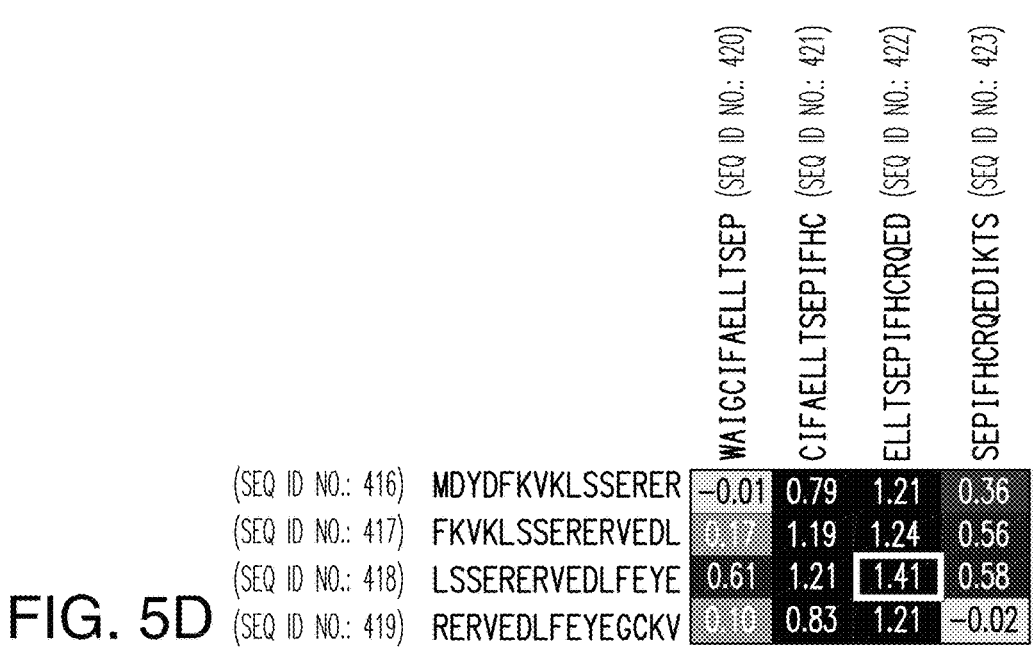

Heat map analysis. A heat map is a graphical representation of data where the values taken by a variable in a two-dimensional map are represented as colors. For double-looped CLIPS peptides, such a two-dimensional map can be derived from the independent sequences of the first and second loops. For example, the sequences of the 16 CLIPS peptides depicted in FIG. 5 are effectively permutations of 4 unique sub-sequences in loop 1 (colored in blue in FIG. 4) and 4 unique sub-sequences in loop 2 (colored in green in FIG. 4). Thus, the observed ELISA data (colored in red in FIG. 5A) can be plotted in a 4×4 matrix, where each X coordinate corresponds to the sequence of the first loop, and each Y coordinate corresponds to the sequence of the second loop. For instance, the ELISA value observed for CLIPS peptide CLSSERERVEDLFEYECELLTSEPIFHCRQEDC (indicated with an arrow in FIG. 4A) can be found at the third row, third column of FIG. 5B (indicated with an arrow and a red square). To further facilitate the visualization, ELISA values can be replaced with colors from a continuous gradient. In this case, extremely low values are colored in green, extremely high values are colored in red, and average values are colored in black (see FIG. 5C). For the aforementioned example, the average value is 0.71. When this color map is applied to the data matrix depicted in FIG. 5B, a color heat map is obtained (see FIG. 5D, the original data is still indicated for extra clarity).

Synthesis of peptides. To reconstruct epitopes of the target molecule a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was done using Pepscan's proprietary Chemically Linked Peptides on Scaffolds (CLIPS) technology. CLIPS technology allows to structure peptides into single loops, doubleloops, triple loops, sheet-like folds, helix-like folds and combinations thereof. CLIPS templates are coupled to cysteine residues. The side-chains of multiple cysteines in the peptides were coupled to one or two CLIPS templates. For example, a 0.5 mM solution of the P2 CLIPS (2,6-bis(bromomethyl)pyridine) was dissolved in ammonium bicarbonate (20 mM, pH 7.8)/acetonitrile (1:3 (v/v)). This solution was added onto the peptide arrays. The CLIPS template bound to side-chains of two cysteines as present in the solid-phase bound peptides of the peptide-arrays (455 wells plate with 3 µl wells). The peptide arrays were gently shaken in the solution for 30 to 60 minutes while completely covered in solution. Finally, the peptide arrays were washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

ELISA Screening. The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 2 µl/ml of 3 percent H2O2 were added. After one hour, the color development was measured. The color development was quantified with a charge coupled device (CCD)—camera and an image processing system.

Data processing. The values obtained from the CCD camera ranged from 0 to 3000 mAU, similar to a standard 96-well plate ELISA-reader. The results were quantified and stored into the Peplab database. Occasionally a well contained an air-bubble resulting in a false-positive value, the cards were manually inspected and any values caused by an air-bubble were scored as 0.

Synthesis quality control—To verify the quality of the synthesized peptides, a separate set of positive and negative control peptides was synthesized in parallel. These were screened with antibody 57.9 (ref. Posthumus et al., J. Virology, 1990, 64:3304-3309).

Results

Screening. Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affected binding. These details are summed up in Table 35. For the Pepscan Buffer and Preconditioning (SQ), the numbers indicate the relative amount of competing protein (a combination of horse serum and ovalbumin).

TABLE 35

| | Screening conditions | | |
|---|---|---|---|
| Label | Dilution | Sample buffer | Pre-conditioning |
| ET150-18 mIgG1 | 1 µg/ml | 1% SQ | 1% SQ |
| ET150-2 mIgG1 | 1 µg/ml | 10% SQ | 10% SQ |
| ET150-5 mIgG1 | 1 µg/ml | 10% SQ | 10% SQ |
| ET150-8 mIgG1 | 1 µg/ml | 10% SQ | 10% SQ |

Figure 6:
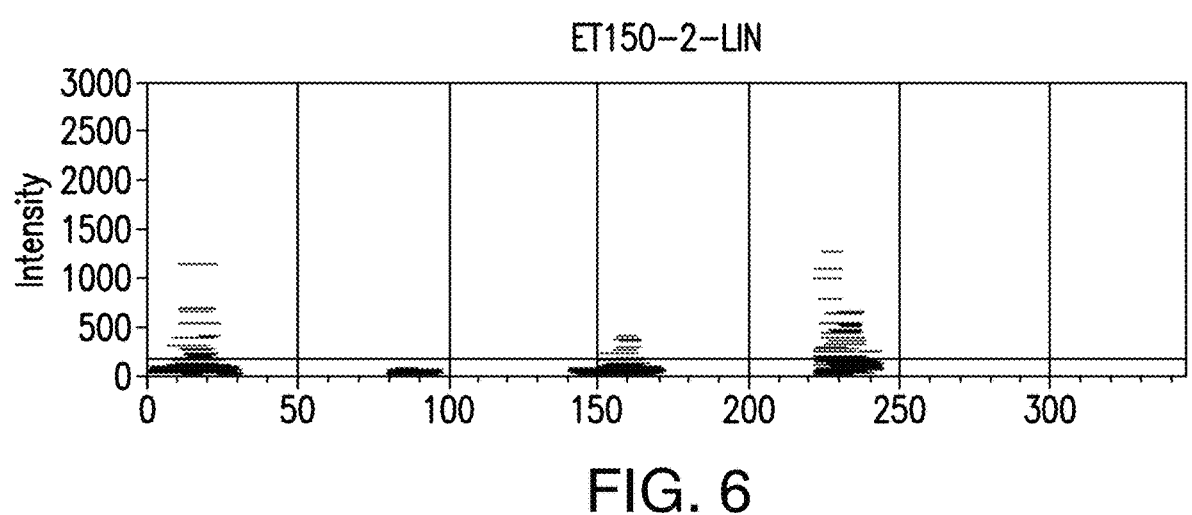
FIG. 6 shows intensity profiles recorded for ET150-2. Lines are drawn from the starting residue to the ending residue of a single peptide on the height at which the signal for that peptide is recorded.

Antibody ET150-2. When tested under moderate stringency conditions antibody ET150-2 avidly bound peptides from all sets (FIG. 6). Cumulative data analysis shows that the antibody recognize a discontinuous epitope composed of peptides stretches $_{16}$CDAEGPWGII$_{25}$ (N-term), $_{157}$MFVNMTPC$_{164}$ (ECL2) and $_{229}$PQFQRQPQW$_{237}$ (ECL3), where peptide stretches $_{16}$CDAEGPWGII$_{25}$ and $_{229}$PQFQRQPQW$_{237}$ alone suffice for binding.

Figure 7:
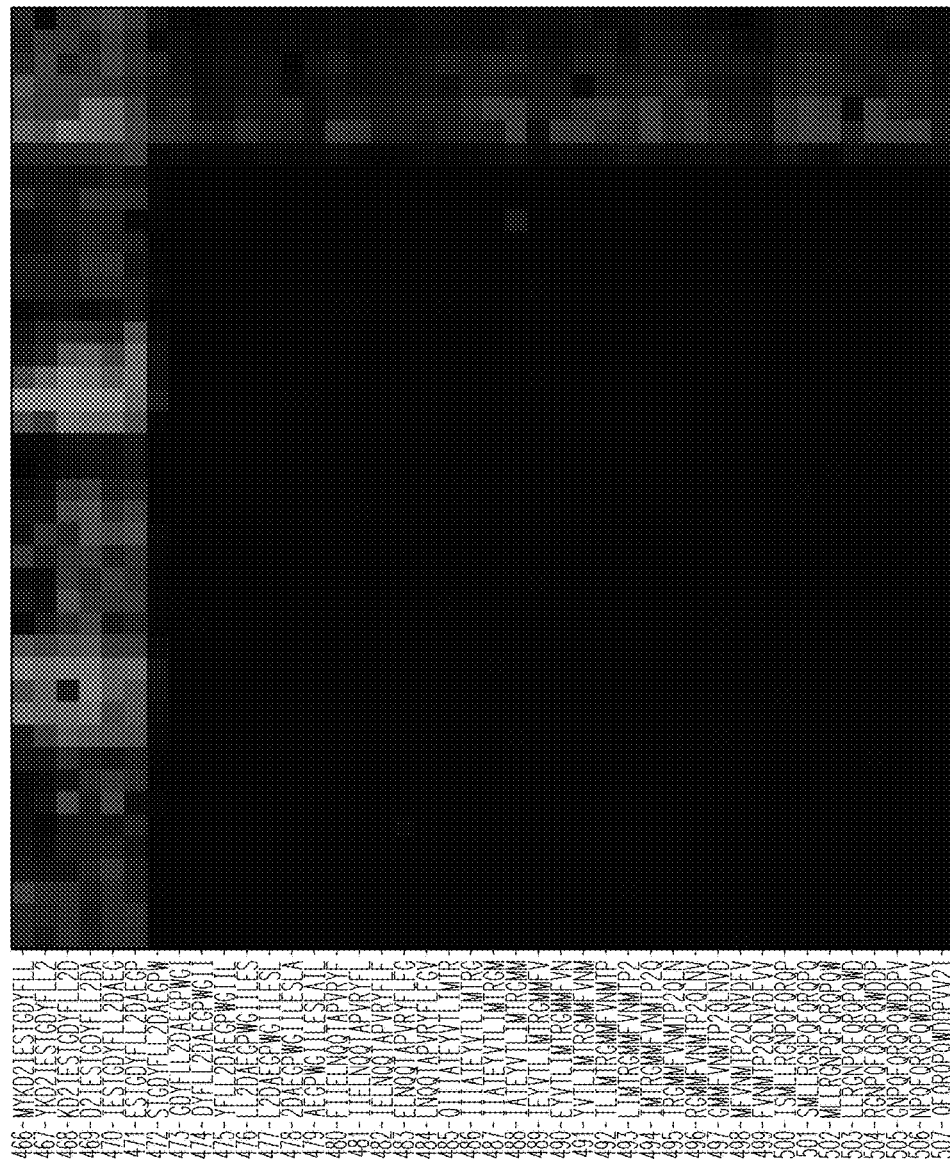
FIG. 7 shows heatmap analysis of data recorded for ET150-5 under high stringency conditions.

Antibody ET150-5. When tested under high stringency conditions antibody ET150-5 avidly bound peptides from all sets (FIG. 7). Cumulative data analysis shows that the antibody recognizes a discontinuous epitope composed of peptide stretches $_5$CIESTGDYFLLCD$_{17}$ (N-term), $_{85}$NQQTAPVRYFL$_{95}$ (ECL1) and $_{157}$MFVNMTPC$_{164}$ (ECL2), where peptide stretch $_5$CIESTGDYFLCD$_{17}$ alone suffices for binding.

Figure 8:
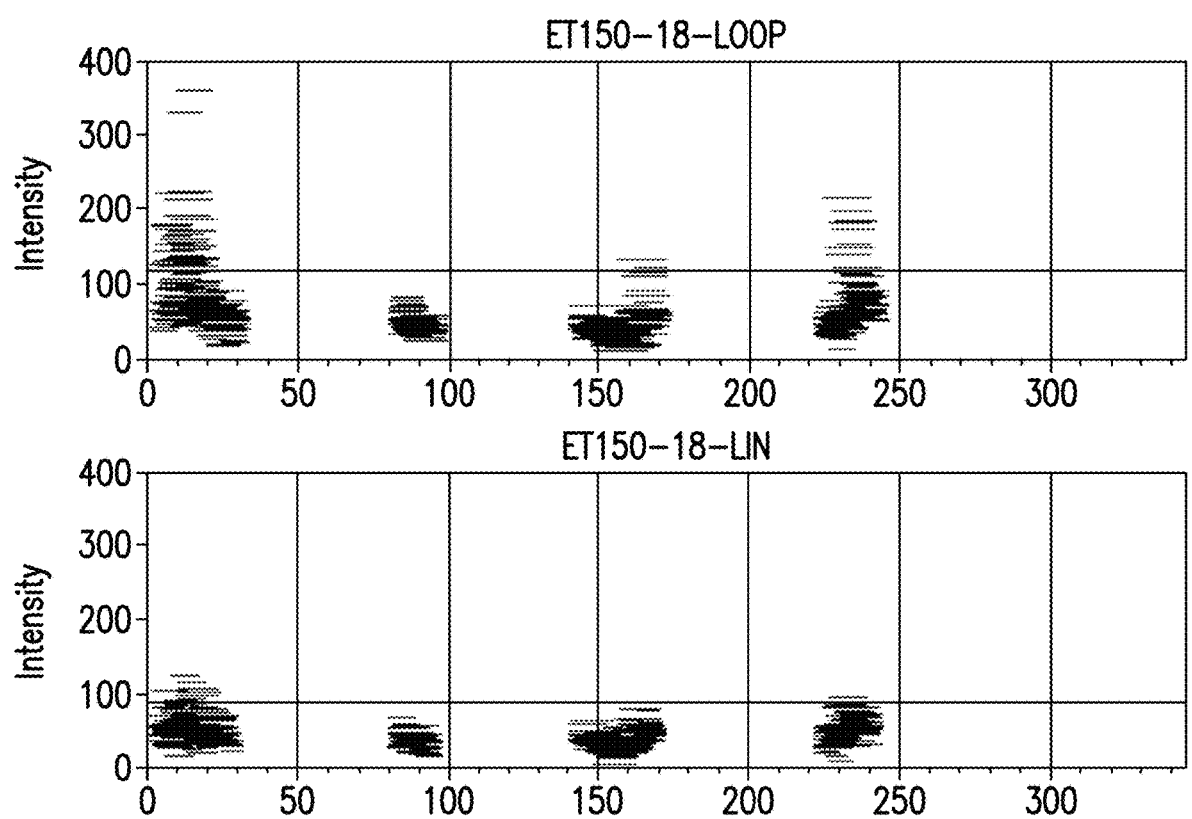
FIG. 8 shows intensity profiles recorded for ET150-18.

Antibody ET150-18. When tested under high stringency conditions antibody ET150-18 bound peptides from set 4 and set 7, containing structurally constrained peptides. No significant binding was recorded on sets containing linear peptides (FIG. 8). Cumulative data analysis shows that the antibody recognizes a discontinuous epitope composed of stretches $_{10}$GDYFLLCD$_{17}$ (N-term), $_{157}$MFVNMTPC-QLN$_{167}$ (ECL2) and $_{227}$GNPQFQRQPQW$_{237}$ (ECL3). Peptide stretches $_{10}$GDYFLLCD$_{17}$ and $_{227}$GNPQFQRQPQW$_{237}$ represent the epitope's core, as both peptide stretches separately suffice for binding.

Figure 9:
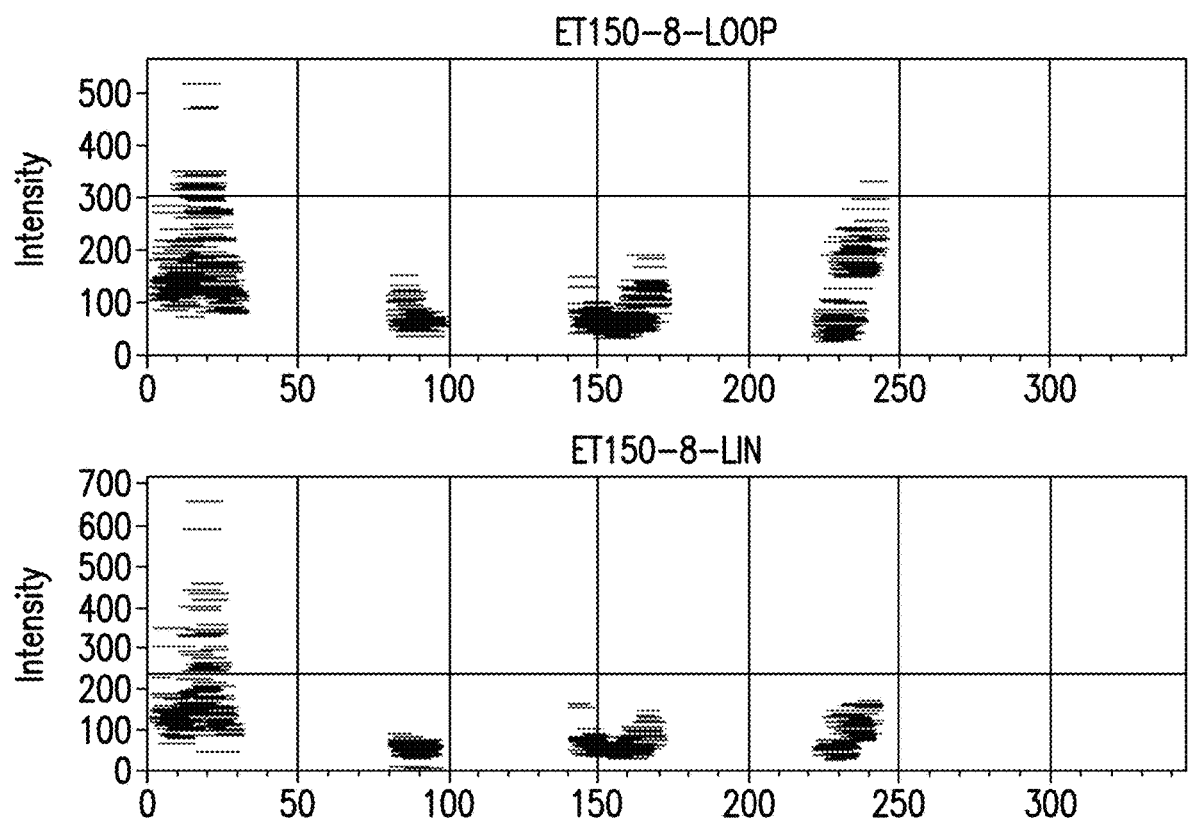
FIG. 9 shows intensity profiles recorded for ET150-8.

Antibody ET150-8. When tested under high stringency conditions antibody ET150-8 bound peptides from all sets, except for set 2 (FIG. 9). Cumulative data analysis shows that the antibody recognizes a discontinuous epitope composed of peptides stretches $_{15}$LCDAEGPWG$_{23}$ (N-term) and $_{230}$QFQRQPQWDDPVVC$_{243}$ (ECL3) where peptide stretch $_{15}$LCDAEGPWG$_{23}$ is the dominant part of the epitope, as it alone suffices for binding. Moreover, comparison of the results obtained on set 1 (linear) and set 4 (loop) shows that introduction of structural constrains to epitope mimics enhances binding of peptides, especially in case of peptides containing sequence $_{230}$QFQRQPQWDDPVVC$_{243}$.

Conclusions

All antibodies investigated recognized discontinuous epitopes, which were mapped using Pepscan arrays. Core tentative epitopes are listed in Table 36. All antibodies commonly recognized overlapping regions at the N-terminus of the protein in combination with regions from one or two ECLs. Two antibodies ET150-18 and ET150-8 showed a requirement for structural constraints to support antibody binding, suggesting that these two antibodies recognize not only discontinuous, but also conformational epitopes. Antibodies ET150-2 and ET150-5 did not show notable discrepancies in peptide binding between linear and looped peptides.

TABLE 36

List of epitopes

| Antibody | N-terminus | ECL1 | ECL2 | ECL3 |
|---|---|---|---|---|
| ET150-2 | $_{16}$CDAEGPWGII$_{25}$*) | — | $_{157}$MFVNMTPC$_{164}$ | $_{278}$PQFQRQPQW$_{387}$*) |
| ET150-5 | $_{5}$CIESTGDYFLLCD$_{17}$*) | $_{85}$NQQTAPVRYFL$_{95}$ | $_{157}$MFVNMTPC$_{164}$ | — |
| ET150-8 | $_{13}$LCDAEGPWG$_{23}$*) | — | — | $_{230}$QFQRQPQWDDPVVC$_{243}$ |
| ET150-18 | $_{10}$GDYFLLCD$_{27}$*) | — | $_{157}$MFVNMTPCQLN$_{167}$ | $_{227}$GNPQFQRQPQW$_{237}$*) |

*)dominant part

Figure 10:
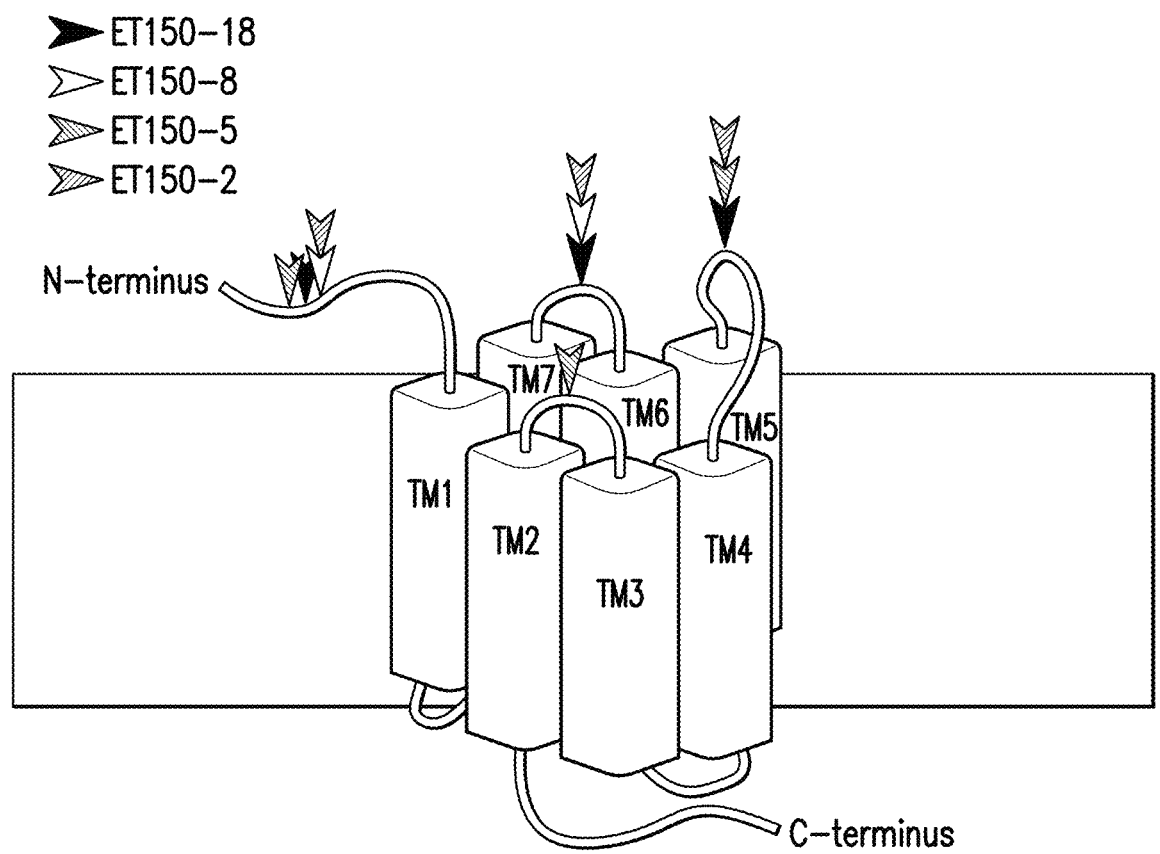
FIG. 10 depicts schematic drawing of a GPCR containing seven transmembrane helices (TM) and 3 extracellular regions (ECLs). Colored arrows binding sites for each antibody is depicted.

FIG. 10 is an illustration of the results of the study with respect to overall organization of GPCRs. As the N-terminus is highly flexible and unstructured, it likely transiently interacts with ECLs forming discontinuous immunodominant regions.

Figure 11:
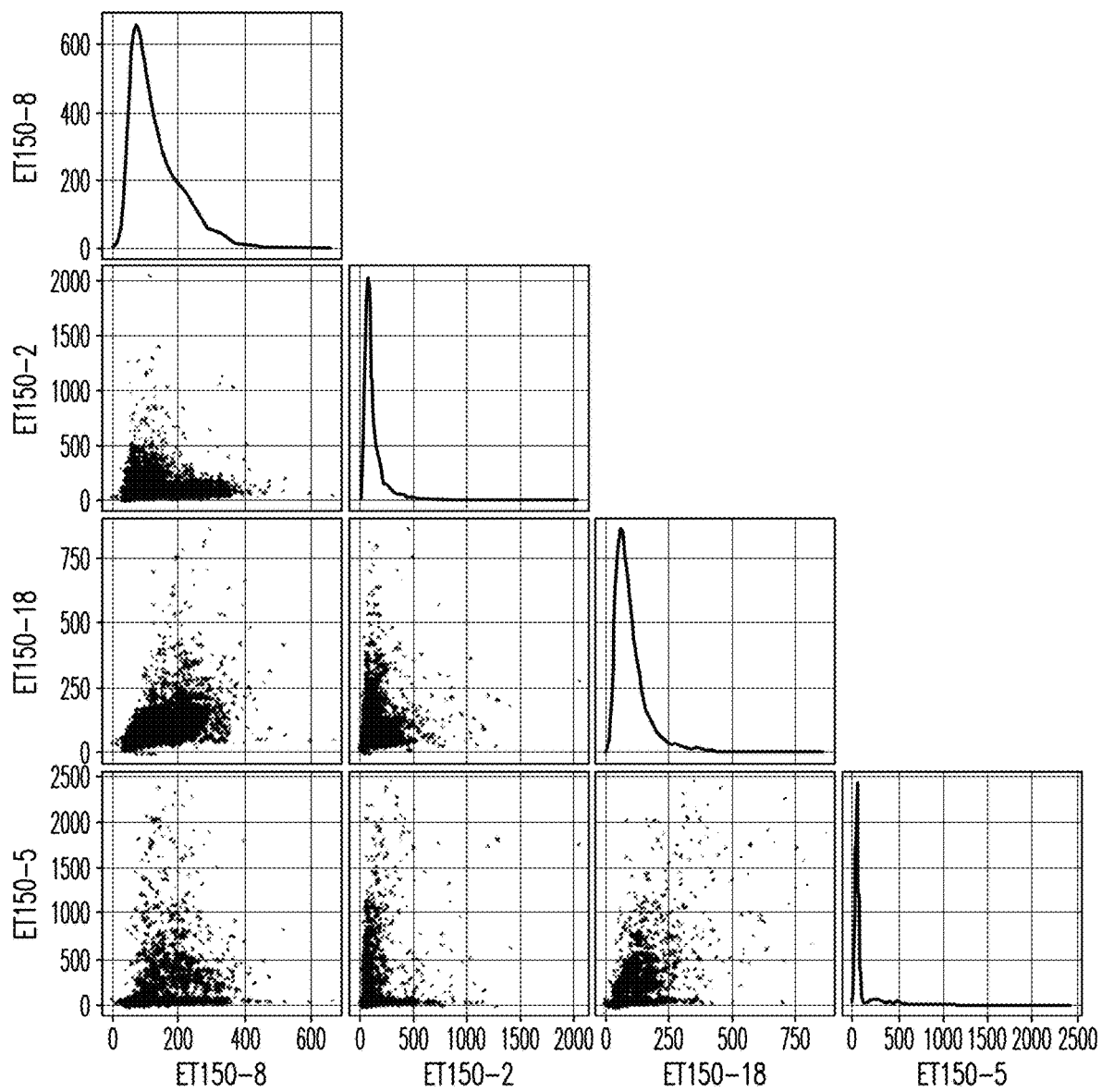
FIG. 11 depicts scatterplot analysis of all data recorded for each sample. On the diagonal is the statistical data distribution.

Differences and commonalities in peptide binding can be illustrated with a scatter plot analysis in FIG. 11. Data points in the top left and bottom right corners point to the differences in the binding. Despite significant epitope overlap, the fine specificities of epitopes of the individual antibodies differ to a large extent.

Example 4—Screening Data for Anti-GPRC5D Antibodies

Figure 12:
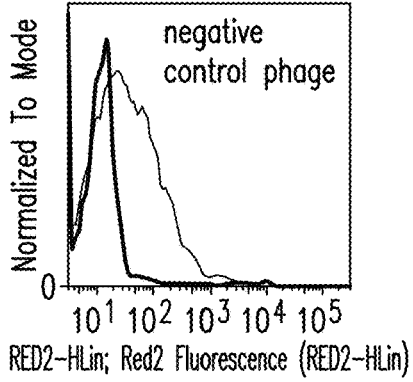
FIG. 12 depicts FACS analysis of anti-GPRC5D antibodies.
Figure 12:
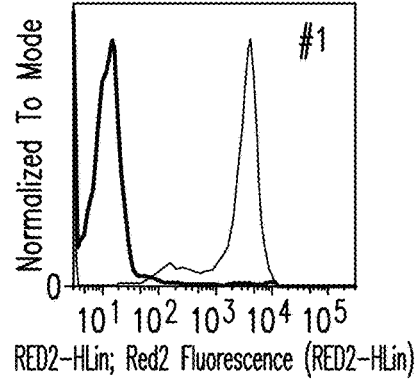
Figure 12:
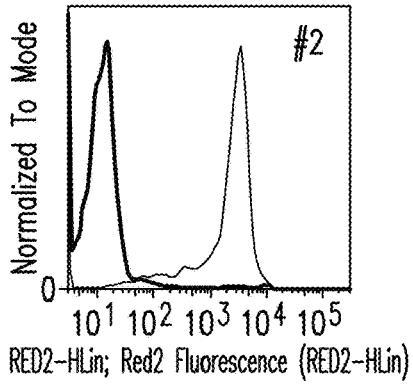
Figure 12:
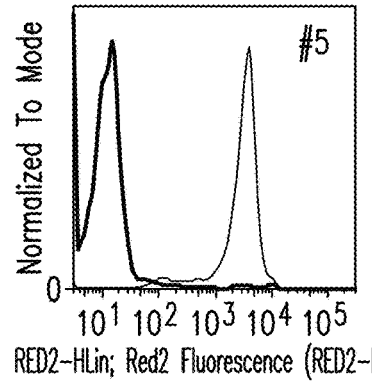
Figure 12:
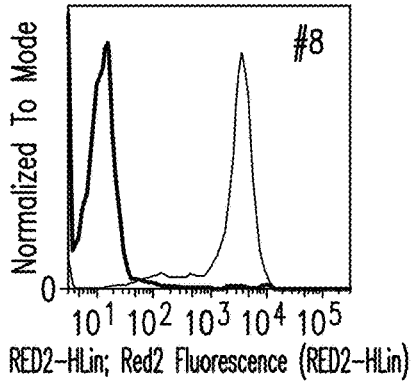
Figure 12:
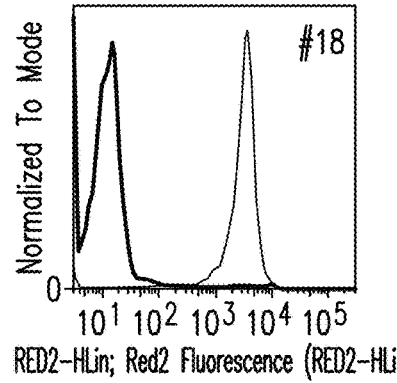

FACS Screening. FIG. 12 shows FACS analysis of the GPRC5D-specific phage antibody clones (ET150-1, ET150-2, ET150-5, ET150-8, ET150-18). Phage clones were incubated with 3T3-GPRC5D cell line, then with anti-M13 mouse antibody. Finally APC-labeled anti-mouse IgG 2nd antibody was added to the reaction after washing again. The binding was measured by FACS and expressed as mean fluorescence intensity (MFI). Cells incubated with M13 K07 helper phage and cells only were used as negative controls.

Example 5—Binding Affinity of Anti-GPRC5D Antibodies

Figure 13:
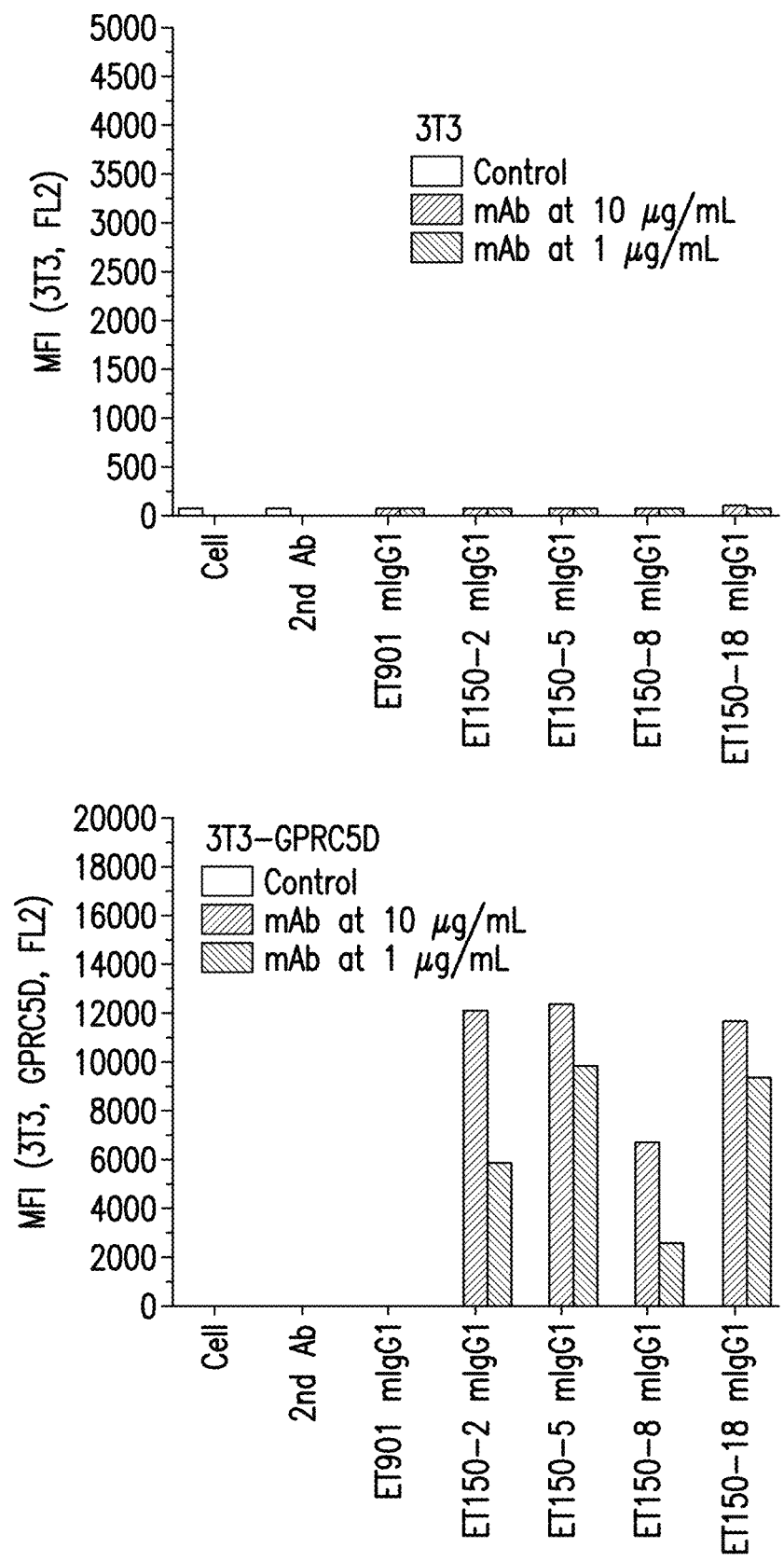
FIG. 13 depicts FACS analysis of anti-GPRC5D antibodies.

FIG. 13 shows FACS analysis of GPRC5D-specific phage antibody clones (ET150-2, ET150-5, ET150-8, ET150-18). Each antibody (ET150-1, ET150-2, ET150-5, ET150-8, ET150-18) was incubated with 3T3 or 3T3-GPRC5D cells at 10 or 1 µg/mL, then with anti-M13 mouse antibody. Finally PE-labeled anti-mouse IgG 2nd antibody was added to the reaction. The binding was measured by FACS and expressed as mean fluorescence intensity (MFI) (FIG. 13). Cells incubated with 2nd antibody alone, ET901 mIgG1 isotype control and cells only were used as negative controls.

Example 6—Bispecific Antibodies Specific for GPRC5D and CD3

Figure 14:
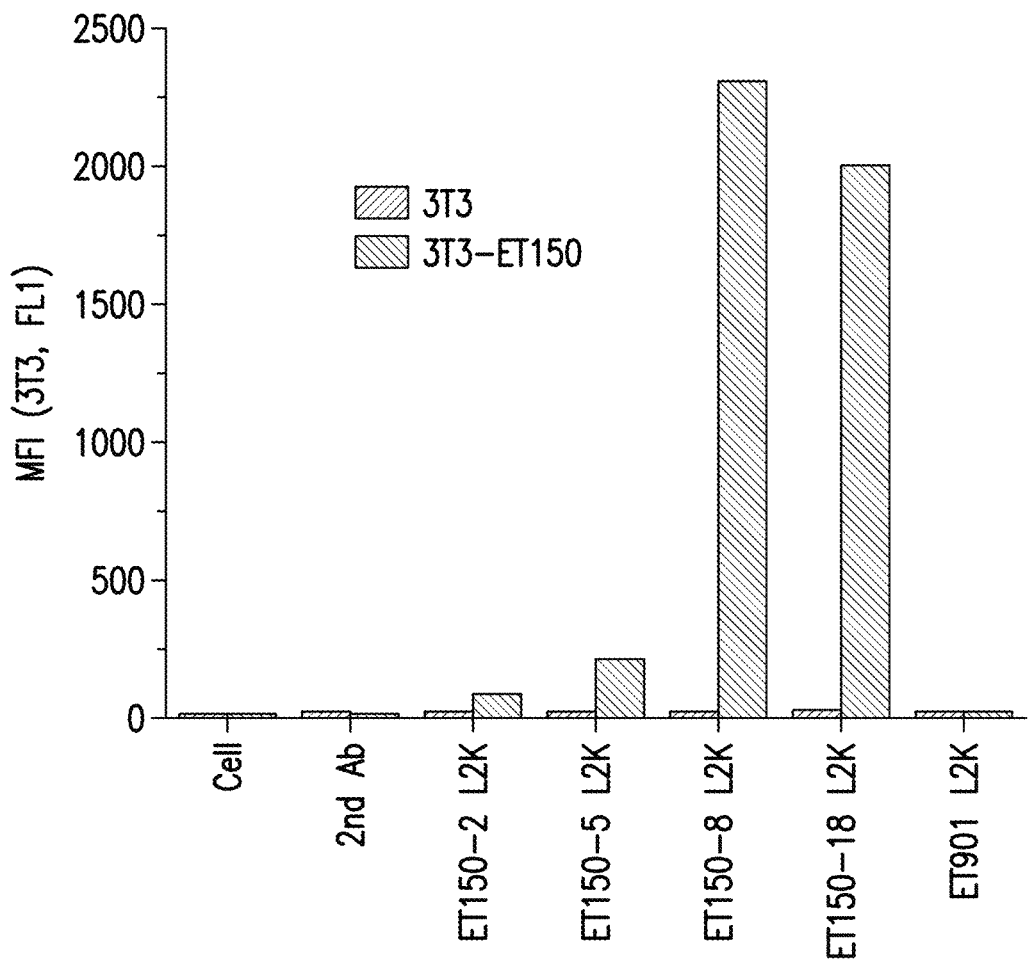
FIG. 14 depicts the FACS analysis of anti-GPRC5D/CD3 bispecific antibodies.

FIG. 14 shows FACS analysis of the anti-GPRC5D/anti-CD3 bispecific antibodies generated using the ET150-2, ET150-5, ET150-8, ET150-18 clones disclosed herein. Each antibody was incubated with 3T3 or 3T3-GPRC5D cells at 10 µg/ml, followed by the incubation with a FITC-conjugated anti-His tag antibody. The binding was measured by FACS and expressed as mean fluorescence intensity (MFI). Cells incubated with 2nd antibody alone, ET901 bispecific antibody control and cells only were used as negative controls. As shown in FIG. 14, the anti-GPRC5D/CD3 bispecific antibodies generated using the disclosed scFvs specifically bound to 3T3 cells expressing GPRC5D.

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

What is claimed is:

1. An anti-human G-protein coupled receptor family C group 5 member D (GPRC5D) antibody or an antigen-binding fragment thereof, comprising:

(i) a heavy chain variable region comprising a CDR1 comprising the amino acid sequence set forth in SEQ ID NO: 130, a CDR2 comprising the amino acid sequence set forth in SEQ ID NO: 131 and a CDR3 comprising the amino acid sequence set forth in SEQ ID NO: 132; and a light chain variable region comprising a CDR1 comprising the amino acid sequence set forth in SEQ ID NO: 133, a CDR2 comprising the amino acid sequence set forth in SEQ ID NO:134 and a CDR3 comprising the amino acid sequence set forth in SEQ ID NO:135;

(ii) a heavy chain variable region comprising a CDR1 comprising the amino acid sequence set forth in SEQ ID NO: 142, a CDR2 comprising the amino acid sequence set forth in SEQ ID NO:143 and a CDR3 comprising the amino acid sequence set forth in SEQ ID NO: 144; and a light chain variable region comprising a CDR1 comprising the amino acid sequence set forth in SEQ ID NO: 145, a CDR2 comprising the amino acid sequence set forth in SEQ ID NO:146 and a CDR3 comprising the amino acid sequence set forth in SEQ ID NO:147;

(iii) a heavy chain variable region comprising a CDR1 comprising the amino acid sequence set forth in SEQ ID NO: 154, a CDR2 comprising the amino acid sequence set forth in SEQ ID NO:155 and a CDR3 comprising the amino acid sequence set forth in SEQ ID NO: 156; and a light chain variable region comprising a CDR1 comprising the amino acid sequence set forth in SEQ ID NO: 157, a CDR2 comprising the amino acid sequence set forth in SEQ ID NO:158 and a CDR3 comprising the amino acid sequence set forth in SEQ ID NO:159;

(iv) a heavy chain variable region comprising a CDR1 comprising the amino acid sequence set forth in SEQ ID NO: 160, a CDR2 comprising the amino acid sequence set forth in SEQ ID NO:161 and a CDR3 comprising the amino acid sequence set forth in SEQ ID NO: 162; and a light chain variable region comprising a CDR1 comprising the amino acid sequence set forth in SEQ ID NO: 163, a CDR2 comprising the amino acid sequence set forth in SEQ ID NO:164 and a CDR3 comprising the amino acid sequence set forth in SEQ ID NO:165;

(v) a heavy chain variable region comprising a CDR1 comprising the amino acid sequence set forth in SEQ ID NO: 166, a CDR2 comprising the amino acid sequence set forth in SEQ ID NO:167 and a CDR3 comprising the amino acid sequence set forth in SEQ ID NO: 168; and a light chain variable region comprising a CDR1 comprising the amino acid sequence set forth in SEQ ID NO: 169, a CDR2 comprising the amino acid sequence set forth in SEQ ID NO:170 and a CDR3 comprising the amino acid sequence set forth in SEQ ID NO:171;

(vi) a heavy chain variable region comprising a CDR1 comprising the amino acid sequence set forth in SEQ ID NO: 172, a CDR2 comprising the amino acid sequence set forth in SEQ ID NO:173 and a CDR3 comprising the amino acid sequence set forth in SEQ ID NO: 174; and a light chain variable region comprising a CDR1 comprising the amino acid sequence set forth in SEQ ID NO: 175, a CDR2 comprising the amino acid sequence set forth in SEQ ID NO:176 and a CDR3 comprising the amino acid sequence set forth in SEQ ID NO:177;

(vii) a heavy chain variable region comprising a CDR1 comprising the amino acid sequence set forth in SEQ ID NO: 178, a CDR2 comprising the amino acid sequence set forth in SEQ ID NO:179 and a CDR3 comprising the amino acid sequence set forth in SEQ ID NO: 180; and a light chain variable region comprising a CDR1 comprising the amino acid sequence set forth in SEQ ID NO: 181, a CDR2 comprising the amino acid sequence set forth in SEQ ID NO:182 and a CDR3 comprising the amino acid sequence set forth in SEQ ID NO:183;

(viii) a heavy chain variable region comprising a CDR1 comprising the amino acid sequence set forth in SEQ ID NO: 184, a CDR2 comprising the amino acid sequence set forth in SEQ ID NO:185 and a CDR3 comprising the amino acid sequence set forth in SEQ ID NO: 186; and a light chain variable region comprising a CDR1 comprising the amino acid sequence set forth in SEQ ID NO: 187, a CDR2 comprising the amino acid sequence set forth in SEQ ID NO:188 and a CDR3 comprising the amino acid sequence set forth in SEQ ID NO:189;

(ix) a heavy chain variable region comprising a CDR1 comprising the amino acid sequence set forth in SEQ ID NO: 190, a CDR2 comprising the amino acid sequence set forth in SEQ ID NO:191 and a CDR3 comprising the amino acid sequence set forth in SEQ ID NO: 192; and a light chain variable region comprising a CDR1 comprising the amino acid sequence set forth in SEQ ID NO: 193, a CDR2 comprising the amino acid sequence set forth in SEQ ID NO:194 and a CDR3 comprising the amino acid sequence set forth in SEQ ID NO:195;

(x) a heavy chain variable region comprising a CDR1 comprising the amino acid sequence set forth in SEQ ID NO: 196, a CDR2 comprising the amino acid sequence set forth in SEQ ID NO:197 and a CDR3 comprising the amino acid sequence set forth in SEQ ID NO: 198; and a light chain variable region comprising a CDR1 comprising the amino acid sequence set forth in SEQ ID NO: 199, a CDR2 comprising the amino acid sequence set forth in SEQ ID NO:200 and a CDR3 comprising the amino acid sequence set forth in SEQ ID NO:201;

(xi) a heavy chain variable region comprising a CDR1 comprising the amino acid sequence set forth in SEQ ID NO: 202, a CDR2 comprising the amino acid sequence set forth in SEQ ID NO:203 and a CDR3 comprising the amino acid sequence set forth in SEQ ID NO: 204; and a light chain variable region comprising a CDR1 comprising the amino acid sequence set forth in SEQ ID NO: 205, a CDR2 comprising the amino acid sequence set forth in SEQ ID NO:206 and a CDR3 comprising the amino acid sequence set forth in SEQ ID NO:207;

(xii) a heavy chain variable region comprising a CDR1 comprising the amino acid sequence set forth in SEQ ID NO: 208, a CDR2 comprising the amino acid sequence set forth in SEQ ID NO:209 and a CDR3 comprising the amino acid sequence set forth in SEQ ID NO: 210; and a light chain variable region comprising a CDR1 comprising the amino acid sequence set forth in SEQ ID NO: 211, a CDR2 comprising the amino acid sequence set forth in SEQ ID NO:212 and a CDR3 comprising the amino acid sequence set forth in SEQ ID NO:213;

(xiii) a heavy chain variable region comprising a CDR1 comprising the amino acid sequence set forth in SEQ ID NO: 214, a CDR2 comprising the amino acid sequence set forth in SEQ ID NO:215 and a CDR3 comprising the amino acid sequence set forth in SEQ ID NO: 216; and a light chain variable region comprising a CDR1 comprising the amino acid sequence set forth in SEQ ID NO: 217, a CDR2 comprising the amino acid sequence set forth in SEQ ID NO:218 and a CDR3 comprising the amino acid sequence set forth in SEQ ID NO:219;

(xiv) a heavy chain variable region comprising a CDR1 comprising the amino acid sequence set forth in SEQ ID NO: 220, a CDR2 comprising the amino acid sequence set forth in SEQ ID NO:221 and a CDR3 comprising the amino acid sequence set forth in SEQ ID NO: 222; and a light chain variable region comprising a CDR1 comprising the amino acid sequence set forth in SEQ ID NO: 223, a CDR2 comprising the amino acid sequence set forth in SEQ ID NO:224 and a CDR3 comprising the amino acid sequence set forth in SEQ ID NO:225;

(xv) a heavy chain variable region comprising a CDR1 comprising the amino acid sequence set forth in SEQ ID NO: 226, a CDR2 comprising the amino acid sequence set forth in SEQ ID NO:227 and a CDR3 comprising the amino acid sequence set forth in SEQ ID NO: 228; and a light chain variable region comprising a CDR1 comprising the amino acid sequence set forth in SEQ ID NO: 229, a CDR2 comprising the amino acid sequence set forth in SEQ ID NO:230 and a CDR3 comprising the amino acid sequence set forth in SEQ ID NO:231;

(xvi) a heavy chain variable region comprising a CDR1 comprising the amino acid sequence set forth in SEQ ID NO: 232, a CDR2 comprising the amino acid sequence set forth in SEQ ID NO:233 and a CDR3 comprising the amino acid sequence set forth in SEQ ID NO: 234; and a light chain variable region comprising a CDR1 comprising the amino acid sequence set forth in SEQ ID NO: 235, a CDR2 comprising the amino acid sequence set forth in SEQ ID NO:236 and a CDR3 comprising the amino acid sequence set forth in SEQ ID NO:237;

(xvii) a heavy chain variable region comprising a CDR1 comprising the amino acid sequence set forth in SEQ ID NO: 238, a CDR2 comprising the amino acid sequence set forth in SEQ ID NO:239 and a CDR3 comprising the amino acid sequence set forth in SEQ ID NO: 240; and a light chain variable region comprising a CDR1 comprising the amino acid sequence set forth in SEQ ID NO: 241, a CDR2 comprising the amino acid sequence set forth in SEQ ID NO:242 and a CDR3 comprising the amino acid sequence set forth in SEQ ID NO:243;

(xviii) a heavy chain variable region comprising a CDR1 comprising the amino acid sequence set forth in SEQ ID NO: 244, a CDR2 comprising the amino acid sequence set forth in SEQ ID NO:245 and a CDR3 comprising the amino acid sequence set forth in SEQ ID NO: 246; and a light chain variable region comprising a CDR1 comprising the amino acid sequence set forth in SEQ ID NO: 247, a CDR2 comprising the amino acid sequence set forth in SEQ ID NO:248 and a CDR3 comprising the amino acid sequence set forth in SEQ ID NO:249;

(xix) a heavy chain variable region comprising a CDR1 comprising the amino acid sequence set forth in SEQ ID NO: 250, a CDR2 comprising the amino acid sequence set forth in SEQ ID NO:251 and a CDR3 comprising the amino acid sequence set forth in SEQ ID NO: 252; and a light chain variable region comprising a CDR1 comprising the amino acid sequence set forth in SEQ ID NO: 253, a CDR2 comprising the amino acid sequence set forth in SEQ ID NO:254 and a CDR3 comprising the amino acid sequence set forth in SEQ ID NO:255;

(xx) a heavy chain variable region comprising a CDR1 comprising the amino acid sequence set forth in SEQ ID NO: 256, a CDR2 comprising the amino acid sequence set forth in SEQ ID NO:257 and a CDR3 comprising the amino acid sequence set forth in SEQ ID NO: 258; and a light chain variable region comprising a CDR1 comprising the amino acid sequence set forth in SEQ ID NO: 259, a CDR2 comprising the amino acid sequence set forth in SEQ ID NO:260 and a CDR3 comprising the amino acid sequence set forth in SEQ ID NO:261;

(xxi) a heavy chain variable region comprising a CDR1 comprising the amino acid sequence set forth in SEQ ID NO: 262, a CDR2 comprising the amino acid sequence set forth in SEQ ID NO:263 and a CDR3 comprising the amino acid sequence set forth in SEQ ID NO: 264; and a light chain variable region comprising a CDR1 comprising the amino acid sequence set forth in SEQ ID NO: 265, a CDR2 comprising the amino acid sequence set forth in SEQ ID NO:266 and a CDR3 comprising the amino acid sequence set forth in SEQ ID NO:267;

(xxii) a heavy chain variable region comprising a CDR1 comprising the amino acid sequence set forth in SEQ ID NO: 292, a CDR2 comprising the amino acid sequence set forth in SEQ ID NO:293 and a CDR3 comprising the amino acid sequence set forth in SEQ ID NO: 294; and a light chain variable region comprising a CDR1 comprising the amino acid sequence set forth in SEQ ID NO: 295, a CDR2 comprising the amino acid sequence set forth in SEQ ID NO:296 and a CDR3 comprising the amino acid sequence set forth in SEQ ID NO:297;

(xxiii) a heavy chain variable region comprising a CDR1 comprising the amino acid sequence set forth in SEQ ID NO: 303, a CDR2 comprising the amino acid sequence set forth in SEQ ID NO:304 and a CDR3 comprising the amino acid sequence set forth in SEQ ID NO: 305; and a light chain variable region comprising a CDR1 comprising the amino acid sequence set forth in SEQ ID NO: 306, a CDR2 comprising the amino acid sequence set forth in SEQ ID NO:307 and a CDR3 comprising the amino acid sequence set forth in SEQ ID NO:308;

(xxiv) a heavy chain variable region comprising a CDR1 comprising the amino acid sequence set forth in SEQ ID NO: 316, a CDR2 comprising the amino acid sequence set forth in SEQ ID NO:317 and a CDR3 comprising the amino acid sequence set forth in SEQ ID NO: 318; and a light chain variable region comprising a CDR1 comprising the amino acid sequence set forth in SEQ ID NO: 319, a CDR2 comprising the amino acid sequence set forth in SEQ ID NO:320 and a CDR3 comprising the amino acid sequence set forth in SEQ ID NO:321;

(xxv) a heavy chain variable region comprising a CDR1 comprising the amino acid sequence set forth in SEQ ID NO: 328, a CDR2 comprising the amino acid sequence set forth in SEQ ID NO:329 and a CDR3 comprising the amino acid sequence set forth in SEQ ID NO: 330; and a light chain variable region comprising a CDR1 comprising the amino acid sequence set forth in SEQ ID NO: 331, a CDR2 comprising the amino acid sequence set forth in SEQ ID NO:332 and a CDR3 comprising the amino acid sequence set forth in SEQ ID NO:333;

(xxvi) a heavy chain variable region comprising a CDR1 comprising the amino acid sequence set forth in SEQ ID NO: 340, a CDR2 comprising the amino acid sequence set forth in SEQ ID NO:341 and a CDR3 comprising the amino acid sequence set forth in SEQ ID NO: 342; and a light chain variable region comprising a CDR1 comprising the amino acid sequence set forth in SEQ ID NO: 343, a CDR2 comprising the amino acid sequence set forth in SEQ ID NO:344 and a CDR3 comprising the amino acid sequence set forth in SEQ ID NO:345; or (xxvii) a heavy chain variable region comprising a CDR1 comprising the amino acid sequence set forth in SEQ ID NO: 352, a CDR2 comprising the amino acid sequence set forth in SEQ ID NO:353 and a CDR3 comprising the amino acid sequence set forth in SEQ ID NO: 354; and a light chain variable region comprising a CDR1 comprising the amino acid sequence set forth in SEQ ID NO: 355, a CDR2 comprising the amino acid sequence set forth in SEQ ID NO:356 and a CDR3 comprising the amino acid sequence set forth in SEQ ID NO:357.

2. The anti-human GPRC5D antibody or antigen-binding fragment thereof of claim 1, wherein the heavy chain variable region comprises an amino acid sequence selected from the group consisting of SEQ ID NOS: 5, 13, 21, 25, 29, 33, 37, 41, 45, 49, 53, 57, 61, 65, 69, 73, 77, 81, 85, 89, 93, 298, 310, 322, 334, 346 and 358.

3. The anti-human GPRC5D antibody or antigen-binding fragment thereof of claim 1, wherein the light chain variable region comprises an amino acid sequence selected from the group consisting of SEQ ID NOS: 6, 14, 22, 26, 30, 34, 38, 42, 46, 50, 54, 58, 62, 66, 70, 74, 78, 82, 86, 90, 94, 299, 311, 323, 335, 347 and 359.

4. The anti-human GPRC5D antibody or antigen-binding fragment thereof of claim 1, wherein:
(a) the heavy chain variable region comprises an amino acid sequence selected from the group consisting of SEQ ID NOS: 5, 13, 21, 25, 29, 33, 37, 41, 45, 49, 53, 57, 61, 65, 69, 73, 77, 81, 85, 89, 93, 298, 310, 322, 334, 346 and 358; and
(b) the light chain variable region comprises an amino acid sequence selected from the group consisting of SEQ ID NOS: 6, 14, 22, 26, 30, 34, 38, 42, 46, 50, 54, 58, 62, 66, 70, 74, 78, 82, 86, 90, 94, 299, 311, 323, 335, 347 and 359.

5. The anti-human GPRC5D antibody or antigen-binding fragment thereof of claim 1, wherein:
(i) the heavy chain variable region comprises an amino acid sequence that is at least about 90% homologous to the amino acid sequence set forth in SEQ ID NO:5, and the light chain variable region comprises an amino acid sequence that is at least about 90% homologous to the amino acid sequence set forth in SEQ ID NO:6;
(ii) the heavy chain variable region comprises an amino acid sequence that is at least about 90% homologous to the amino acid sequence set forth in SEQ ID NO:13, and the light chain variable region comprises an amino acid sequence that is at least about 90% homologous to the amino acid sequence set forth in SEQ ID NO:14;
(iii) the heavy chain variable region comprises an amino acid sequence that is at least about 90% homologous to the amino acid sequence set forth in SEQ ID NO:21, and the light chain variable region comprises an amino acid sequence that is at least about 90% homologous to the amino acid sequence set forth in SEQ ID NO:22;
(iv) the heavy chain variable region comprises an amino acid sequence that is at least about 90% homologous to the amino acid sequence set forth in SEQ ID NO:25, and the light chain variable region comprises an amino acid sequence that is at least about 90% homologous to the amino acid sequence set forth in SEQ ID NO:26;
(v) the heavy chain variable region comprises an amino acid sequence that is at least about 90% homologous to the amino acid sequence set forth in SEQ ID NO:29, and the light chain variable region comprises an amino acid sequence that is at least about 90% homologous to the amino acid sequence set forth in SEQ ID NO:30;
(vi) the heavy chain variable region comprises an amino acid sequence that is at least about 90% homologous to the amino acid sequence set forth in SEQ ID NO:33, and the light chain variable region comprises an amino acid sequence that is at least about 90% homologous to the amino acid sequence set forth in SEQ ID NO:34;
(vii) the heavy chain variable region comprises an amino acid sequence that is at least about 90% homologous to the amino acid sequence set forth in SEQ ID NO:37, and the light chain variable region comprises an amino acid sequence that is at least about 90% homologous to the amino acid sequence set forth in SEQ ID NO:38;
(viii) the heavy chain variable region comprises an amino acid sequence that is at least about 90% homologous to the amino acid sequence set forth in SEQ ID NO:41, and the light chain variable region comprises an amino acid sequence that is at least about 90% homologous to the amino acid sequence set forth in SEQ ID NO:42;
(ix) the heavy chain variable region comprises an amino acid sequence that is at least about 90% homologous to the amino acid sequence set forth in SEQ ID NO:45, and the light chain variable region comprises an amino acid sequence that is at least about 90% homologous to the amino acid sequence set forth in SEQ ID NO:46;
(x) the heavy chain variable region comprises an amino acid sequence that is at least about 90% homologous to the amino acid sequence set forth in SEQ ID NO:49, and the light chain variable region comprises an amino acid sequence that is at least about 90% homologous to the amino acid sequence set forth in SEQ ID NO:50;
(xi) the heavy chain variable region comprises an amino acid sequence that is at least about 90% homologous to the amino acid sequence set forth in SEQ ID NO:53, and the light chain variable region comprises an amino acid sequence that is at least about 90% homologous to the amino acid sequence set forth in SEQ ID NO:54;
(xii) the heavy chain variable region comprises an amino acid sequence that is at least about 90% homologous to the amino acid sequence set forth in SEQ ID NO:57, and the light chain variable region comprises an amino acid sequence that is at least about 90% homologous to the amino acid sequence set forth in SEQ ID NO:58;
(xiii) the heavy chain variable region comprises an amino acid sequence that is at least about 90% homologous to the amino acid sequence set forth in SEQ ID NO:61, and the light chain variable region comprises an amino acid sequence that is at least about 90% homologous to the amino acid sequence set forth in SEQ ID NO:62;
(xiv) the heavy chain variable region comprises an amino acid sequence that is at least about 90% homologous to the amino acid sequence set forth in SEQ ID NO:65, and the light chain variable region comprises an amino acid sequence that is at least about 90% homologous to the amino acid sequence set forth in SEQ ID NO:66;

(xv) the heavy chain variable region comprises an amino acid sequence that is at least about 90% homologous to the amino acid sequence set forth in SEQ ID NO:69, and the light chain variable region comprises an amino acid sequence that is at least about 90% homologous to the amino acid sequence set forth in SEQ ID NO:70;

(xvi) the heavy chain variable region comprises an amino acid sequence that is at least about 90% homologous to the amino acid sequence set forth in SEQ ID NO:73, and the light chain variable region comprises an amino acid sequence that is at least about 90% homologous to the amino acid sequence set forth in SEQ ID NO:74;

(xvii) the heavy chain variable region comprises an amino acid sequence that is at least about 90% homologous to the amino acid sequence set forth in SEQ ID NO:77, and the light chain variable region comprises an amino acid sequence that is at least about 90% homologous to the amino acid sequence set forth in SEQ ID NO:78;

(xviii) the heavy chain variable region comprises an amino acid sequence that is at least about 90% homologous to the amino acid sequence set forth in SEQ ID NO:81, and the light chain variable region comprises an amino acid sequence that is at least about 90% homologous to the amino acid sequence set forth in SEQ ID NO:82;

(xix) the heavy chain variable region comprises an amino acid sequence that is at least about 90% homologous to the amino acid sequence set forth in SEQ ID NO:85, and the light chain variable region comprises an amino acid sequence that is at least about 90% homologous to the amino acid sequence set forth in SEQ ID NO:86;

(xx) the heavy chain variable region comprises an amino acid sequence that is at least about 90% homologous to the amino acid sequence set forth in SEQ ID NO:89, and the light chain variable region comprises an amino acid sequence that is at least about 90% homologous to the amino acid sequence set forth in SEQ ID NO:90;

(xxi) the heavy chain variable region comprises an amino acid sequence that is at least about 90% homologous to the amino acid sequence set forth in SEQ ID NO:93, and the light chain variable region comprises an amino acid sequence that is at least about 90% homologous to the amino acid sequence set forth in SEQ ID NO:94;

(xxii) the heavy chain variable region comprises an amino acid sequence that is at least about 90% homologous to the amino acid sequence set forth in SEQ ID NO:298, and the light chain variable region comprises an amino acid sequence that is at least about 90% homologous to the amino acid sequence set forth in SEQ ID NO:299;

(xxiii) the heavy chain variable region comprises an amino acid sequence that is at least about 90% homologous to the amino acid sequence set forth in SEQ ID NO:310, and the light chain variable region comprises an amino acid sequence that is at least about 90% homologous to the amino acid sequence set forth in SEQ ID NO:311;

(xxiv) the heavy chain variable region comprises an amino acid sequence that is at least about 90% homologous to the amino acid sequence set forth in SEQ ID NO:322, and the light chain variable region comprises an amino acid sequence that is at least about 90% homologous to the amino acid sequence set forth in SEQ ID NO:323;

(xxv) the heavy chain variable region comprises an amino acid sequence that is at least about 90% homologous to amino acids the sequence set forth in SEQ ID NO:334, and the light chain variable region comprises an amino acid sequence that is at least about 90% homologous to the amino acid sequence set forth in SEQ ID NO:335;

(xxvi) the heavy chain variable region comprises an amino acid sequence that is at least about 90% homologous to the amino acid sequence set forth in SEQ ID NO:346, and the light chain variable region comprises an amino acid sequence that is at least about 90% homologous to the amino acid sequence set forth in SEQ ID NO:347; or (xxvii) the heavy chain variable region comprises an amino acid sequence that is at least about 90% homologous to the amino acid sequence set forth in SEQ ID NO:358, and the light chain variable region comprises an amino acid sequence that is at least about 90% homologous to the amino acid sequence set forth in SEQ ID NO:359.

6. The anti-human GPRC5D antibody or antigen-binding fragment thereof of claim 1, wherein:

(i) the heavy chain variable region comprises the amino acid sequence set forth in SEQ ID NO:5, and the light chain variable region comprises the amino acid sequence set forth in SEQ ID NO:6;

(ii) the heavy chain variable region comprises the amino acid sequence set forth in SEQ ID NO:13, and the light chain variable region comprises the amino acid sequence set forth in SEQ ID NO:14;

(iii) the heavy chain variable region comprises the amino acid sequence set forth in SEQ ID NO:21, and the light chain variable region comprises the amino acid sequence set forth in SEQ ID NO:22;

(iv) the heavy chain variable region comprises the amino acid sequence set forth in SEQ ID NO:25, and the light chain variable region comprises the amino acid sequence set forth in SEQ ID NO:26;

(v) the heavy chain variable region comprises the amino acid sequence set forth in SEQ ID NO:29, and the light chain variable region comprises the amino acid sequence set forth in SEQ ID NO:30;

(vi) the heavy chain variable region comprises the amino acid sequence set forth in SEQ ID NO:33, and the light chain variable region comprises the amino acid sequence set forth in SEQ ID NO:34;

(vii) the heavy chain variable region comprises the amino acid sequence set forth in SEQ ID NO:37, and the light chain variable region comprises the amino acid sequence set forth in SEQ ID NO:38;

(viii) the heavy chain variable region comprises the amino acid sequence set forth in SEQ ID NO:41, and the light chain variable region comprises the amino acid sequence set forth in SEQ ID NO:42;

(ix) the heavy chain variable region comprises the amino acid sequence set forth in SEQ ID NO:45, and the light chain variable region comprises the amino acid sequence set forth in SEQ ID NO:46;

(x) the heavy chain variable region comprises the amino acid sequence set forth in SEQ ID NO:49, and the light chain variable region comprises the amino acid sequence set forth in SEQ ID NO:50;

(xi) the heavy chain variable region comprises the amino acid sequence set forth in SEQ ID NO:53, and the light chain variable region comprises the amino acid sequence set forth in SEQ ID NO:54;

(xii) the heavy chain variable region comprises the amino acid sequence set forth in SEQ ID NO:57, and the light chain variable region comprises the amino acid sequence set forth in SEQ ID NO:58;

(xiii) the heavy chain variable region comprises the amino acid sequence set forth in SEQ ID NO:61, and the light chain variable region comprises the amino acid sequence set forth in SEQ ID NO:62;

(xiv) the heavy chain variable region comprises the amino acid sequence set forth in SEQ ID NO:65, and the light chain variable region comprises the amino acid sequence set forth in SEQ ID NO:66;

(xv) the heavy chain variable region comprises the amino acid sequence set forth in SEQ ID NO:69, and the light chain variable region comprises the amino acid sequence set forth in SEQ ID NO:70;

(xvi) the heavy chain variable region comprises the amino acid sequence set forth in SEQ ID NO:73, and the light chain variable region comprises the amino acid sequence set forth in SEQ ID NO:74;

(xvii) the heavy chain variable region comprises the amino acid sequence set forth in SEQ ID NO:77, and the light chain variable region comprises the amino acid sequence set forth in SEQ ID NO:78;

(xviii) the heavy chain variable region comprises the amino acid sequence set forth in SEQ ID NO:81, and the light chain variable region comprises the amino acid sequence set forth in SEQ ID NO:82;

(xix) the heavy chain variable region comprises the amino acid sequence set forth in SEQ ID NO:85, and the light chain variable region comprises the amino acid sequence set forth in SEQ ID NO:86;

(xx) the heavy chain variable region comprises the amino acid sequence set forth in SEQ ID NO:89, and the light chain variable region comprises the amino acid sequence set forth in SEQ ID NO:90;

(xxi) the heavy chain variable region comprises the amino acid sequence set forth in SEQ ID NO:93, and the light chain variable region comprises the amino acid sequence set forth in SEQ ID NO:94;

(xxii) the heavy chain variable region comprises the amino acid sequence set forth in SEQ ID NO:298, and the light chain variable region comprises the amino acid sequence set forth in SEQ ID NO:299;

(xxiii) the heavy chain variable region comprises the amino acid sequence set forth in SEQ ID NO:310, and the light chain variable region comprises the amino acid sequence set forth in SEQ ID NO:311;

(xxix) the heavy chain variable region comprises the amino acid sequence set forth in SEQ ID NO:322, and the light chain variable region comprises the amino acid sequence set forth in SEQ ID NO:323;

(xxv) the heavy chain variable region comprises amino acids the sequence set forth in SEQ ID NO:334, and the light chain variable region comprises the amino acid sequence set forth in SEQ ID NO:335;

(xxvi) the heavy chain variable region comprises the amino acid sequence set forth in SEQ ID NO:346, and the light chain variable region comprises the amino acid sequence set forth in SEQ ID NO:347; or (xxvii) the heavy chain variable region comprises the amino acid sequence set forth in SEQ ID NO:358, and the light chain variable region comprises the amino acid sequence set forth in SEQ ID NO:359.

7. The anti-human GPRC5D antibody or antigen-binding fragment thereof of claim 1, wherein the antibody or antigen-binding fragment thereof binds to human GPRC5D with a binding affinity ($K_d$) of from about $1\times10^{-9}$ M to about $1\times10^{-8}$ M.

8. The anti-human GPRC5D antibody or antigen-binding fragment thereof of claim 1, wherein the antibody or antigen-binding fragment thereof binds to one, two, three or four epitope regions selected from the group consisting of an epitope region in N-terminal region comprising amino acids 1-27 of SEQ ID NO:97, an epitope region in ECL1 region comprising amino acids 85-93 of SEQ ID NO:97, an epitope region in ECL2 region comprising amino acids 145-167 of SEQ ID NO:97, and an epitope region in ECL3 region comprising amino acids 226-239 of SEQ ID NO:97.

9. The anti-human GPRC5D antibody or antigen-binding fragment thereof of claim 1, wherein the antibody or antigen-binding fragment thereof binds to an epitope region selected from the group consisting of:

an epitope region comprising amino acids 16-23 of SEQ ID NO:97, an epitope region comprising amino acids 15-23 of SEQ ID NO:97, an epitope region comprising amino acids 16-25 of SEQ ID NO:97, an epitope region comprising amino acids 10-17 of SEQ ID NO:97, an epitope region comprising amino acids 5-17 of SEQ ID NO:97, an epitope region comprising amino acids 85-95 of SEQ ID NO:97, an epitope region comprising amino acids 157-164 of SEQ ID NO:97, an epitope region comprising amino acids 157-167 of SEQ ID NO:97, an epitope region comprising amino acids 230-237 of SEQ ID NO:97, an epitope region comprising amino acids 229-237 of SEQ ID NO:97, an epitope region comprising amino acids 230-243 of SEQ ID NO:97, and an epitope region comprising amino acids 227-237 of SEQ ID NO:97.

10. The anti-human GPRC5D antibody or antigen-binding fragment thereof of claim 1, wherein the antibody or antigen-binding fragment thereof comprises an amino acid sequence selected from the group consisting of SEQ ID NOS: 101, 103, 105-123, 300, 312, 324, 336, 348 and 360.

11. The anti-human GPRC5D antibody or antigen-binding fragment thereof of claim 1, wherein the antibody comprises a human variable region framework region.

12. The anti-human GPRC5D antibody or antigen-binding fragment thereof of claim 1, which is a fully human antibody or an antigen-binding fragment thereof.

13. The anti-human GPRC5D antibody or antigen-binding fragment thereof of claim 1, which is a chimeric or humanized antibody or an antigen-binding fragment thereof.

14. The anti-human GPRC5D antibody or antigen-binding fragment thereof of claim 1, wherein the antigen-binding fragment of the antibody is a Fab, Fab', F(ab')$_2$, Fv or single chain Fv (scFv).

15. The anti-human GPRC5D antibody or antigen-binding fragment thereof of claim 1, wherein the heavy chain variable region comprises a CDR1 comprising the amino sequence set forth in SEQ ID NO:202, a CDR2 comprising the amino acid sequence set forth in SEQ ID NO:203, and a CDR3 comprising the amino acid sequence set forth in SEQ ID NO:204; and the light chain variable region comprises a CDR1 comprising the amino acid sequence set forth in SEQ ID NO:205, a CDR2 comprising the amino acid sequence set forth in SEQ ID NO:206, and a CDR3 comprising the amino acid sequence set forth in SEQ ID NO:207.

16. The anti-human GPRC5D antibody or antigen-binding fragment thereof of claim 1, wherein the heavy chain variable region comprises a CDR1 comprising the amino acid sequence set forth in SEQ ID NO:214, a CDR2 comprising the amino acid sequence set forth in SEQ ID NO:215, and a CDR3 comprising the amino acid sequence set forth in SEQ ID NO:216; and the light chain variable region comprises a CDR1 comprising the amino acid sequence set forth in SEQ ID NO:217, a CDR2 comprising the amino acid sequence set forth in SEQ ID NO:218, and a CDR3 comprising the amino acid sequence set forth in SEQ ID NO:219.

17. The anti-human GPRC5D antibody or antigen-binding fragment thereof of claim 1, wherein the heavy chain variable region comprises a CDR1 comprising the amino acid sequence set forth in SEQ ID NO:220, a CDR2 comprising the amino acid sequence set forth in SEQ ID NO:221, and the CDR3 comprising the amino acid sequence set forth in SEQ ID NO:222; and the light chain variable region comprises a CDR1 comprises the amino acid sequence set forth in SEQ ID NOs:223, a CDR2 comprising the amino acid sequence set forth in SEQ ID NO:224, and a CDR3 comprising the amino acid sequence set forth in SEQ ID NO:225.

18. The anti-human GPRC5D antibody or antigen-binding fragment thereof of claim 6, wherein the heavy chain variable region comprises the amino acid sequence set forth in SEQ ID NO:53 and the light chain variable region comprises the amino acid sequence set forth in SEQ ID NO:54.

19. The anti-human GPRC5D antibody or antigen-binding fragment thereof of claim 6, wherein the heavy chain variable region comprises the amino acid sequence set forth in SEQ ID NO:61 and the light chain variable region comprises the amino acid sequence set forth in SEQ ID NO:62.

20. The anti-human GPRC5D antibody or antigen-binding fragment thereof of claim 6, wherein the heavy chain variable region comprises the amino acid sequence set forth in SEQ ID NO:65 and the light chain variable region comprises the amino acid sequence set forth in SEQ ID NO:66.

21. The anti-human GPRC5D antibody or antigen-binding fragment thereof of claim 18, wherein the antigen-binding fragment of the antibody is a single chain Fv (scFv).

22. The anti-human GPRC5D antibody or antigen-binding fragment thereof of claim 19, wherein the antigen-binding fragment of the antibody is a single chain Fv (scFv).

23. The anti-human GPRC5D antibody or antigen-binding fragment thereof of claim 20, wherein the antigen-binding fragment of the antibody is a single chain Fv (scFv).

24. A composition comprising the antibody or antigen-binding fragment thereof of claim 1, and a pharmaceutically acceptable carrier.

25. An immunoconjugate comprising the antibody or antigen-binding fragment thereof of claim 1, linked to a therapeutic agent.

26. The immunoconjugate of claim 25, wherein said therapeutic agent is a drug, a cytotoxin, or a radioactive isotope.

27. A composition comprising the immunoconjugate of claim 25 and a pharmaceutically acceptable carrier.

28. A bispecific molecule comprising the antibody or antigen-binding fragment thereof of claim 1, linked to a second functional moiety.

29. The bispecific molecule of claim 28, wherein the second functional moiety has a different binding specificity than said antibody or antigen-binding fragment thereof.

30. The bispecific molecule of claim 28, wherein the second functional moiety has a binding specificity for an immune cell.

31. The bispecific molecule of claim 28, wherein the second functional moiety has a binding specificity for CD3.

32. A composition comprising the bispecific molecule of claim 28 and a pharmaceutically acceptable carrier.

33. An anti-human G-protein coupled receptor family C group 5 member D (GPRC5D) antibody or an antigen-binding fragment thereof, comprising: (a) a heavy chain variable region comprising a CDR1, a CDR2, and a CDR3 of the heavy chain variable region sequence set forth in SEQ ID NO: 5, SEQ ID NO: 13, SEQ ID NO: 21, SEQ ID NO: 25, SEQ ID NO: 29, SEQ ID NO: 33, SEQ ID NO: 37, SEQ ID NO: 41, SEQ ID NO: 45, SEQ ID NO: 49, SEQ ID NO: 53, SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 298, SEQ ID NO: 310, SEQ ID NO: 322, SEQ ID NO: 334, SEQ ID NO: 346, or SEQ ID NO: 358; and (b) a light chain variable region comprising a CDR1, a CDR2, and a CDR3 of the light chain variable region sequence set forth in SEQ ID NO: 6, SEQ ID NO: 14, SEQ ID NO: 22, SEQ ID NO: 26, SEQ ID NO: 30, SEQ ID NO: 34, SEQ ID NO: 38, SEQ ID NO: 42, SEQ ID NO: 46, SEQ ID NO: 50, SEQ ID NO: 54, SEQ ID NO: 58, SEQ ID NO: 62, SEQ ID NO: 66, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 299, SEQ ID NO: 311, SEQ ID NO: 323, SEQ ID NO: 335, SEQ ID NO: 347, or SEQ ID NO: 359.

34. The anti-human GPRC5D antibody or antigen-binding fragment thereof of claim 33, wherein:
   (i) the heavy chain variable region comprises a CDR1, a CDR2, and a CDR3 of the heavy chain variable region sequence set forth in SEQ ID NO:5, and the light chain variable region comprises a CDR1, a CDR2, and a CDR3 of the light chain variable region sequence set forth in SEQ ID NO:6;
   (ii) the heavy chain variable region comprises a CDR1, a CDR2, and a CDR3 of the heavy chain variable region sequence set forth in SEQ ID NO:13, and the light chain variable region comprises a CDR1, a CDR2, and a CDR3 of the light chain variable region sequence set forth in SEQ ID NO:14;
   (iii) the heavy chain variable region comprises a CDR1, a CDR2, and a CDR3 of the heavy chain variable region sequence set forth in SEQ ID NO:21, and the light chain variable region comprises a CDR1, a CDR2, and a CDR3 of the light chain variable region sequence set forth in SEQ ID NO:22;
   (iv) the heavy chain variable region comprises a CDR1, a CDR2, and a CDR3 of the heavy chain variable region sequence set forth in SEQ ID NO:25, and the light chain variable region comprises a CDR1, a CDR2, and a CDR3 of the light chain variable region sequence set forth in SEQ ID NO:26;
   (v) the heavy chain variable region comprises a CDR1, a CDR2, and a CDR3 of the heavy chain variable region sequence set forth in SEQ ID NO:29, and the light chain variable region comprises a CDR1, a CDR2, and a CDR3 of the light chain variable region sequence set forth in SEQ ID NO:30;

(vi) the heavy chain variable region comprises a CDR1, a CDR2, and a CDR3 of the heavy chain variable region sequence set forth in SEQ ID NO:33, and the light chain variable region comprises a CDR1, a CDR2, and a CDR3 of the light chain variable region sequence set forth in SEQ ID NO:34;

(vii) the heavy chain variable region comprises a CDR1, a CDR2, and a CDR3 of the heavy chain variable region sequence set forth in SEQ ID NO:37, and the light chain variable region comprises a CDR1, a CDR2, and a CDR3 of the light chain variable region sequence set forth in SEQ ID NO:38;

(viii) the heavy chain variable region comprises a CDR1, a CDR2, and a CDR3 of the heavy chain variable region sequence set forth in SEQ ID NO:41, and the light chain variable region comprises a CDR1, a CDR2, and a CDR3 of the light chain variable region sequence set forth in SEQ ID NO:42;

(ix) the heavy chain variable region comprises a CDR1, a CDR2, and a CDR3 of the heavy chain variable region sequence set forth in SEQ ID NO:45, and the light chain variable region comprises a CDR1, a CDR2, and a CDR3 of the light chain variable region sequence set forth in SEQ ID NO:46;

(x) the heavy chain variable region comprises a CDR1, a CDR2, and a CDR3 of the heavy chain variable region sequence set forth in SEQ ID NO:49, and the light chain variable region comprises a CDR1, a CDR2, and a CDR3 of the light chain variable region sequence set forth in SEQ ID NO:50;

(xi) the heavy chain variable region comprises a CDR1, a CDR2, and a CDR3 of the heavy chain variable region sequence set forth in SEQ ID NO:53, and the light chain variable region comprises a CDR1, a CDR2, and a CDR3 of the light chain variable region sequence set forth in SEQ ID NO:54;

(xii) the heavy chain variable region comprises a CDR1, a CDR2, and a CDR3 of the heavy chain variable region sequence set forth in SEQ ID NO:57, and the light chain variable region comprises a CDR1, a CDR2, and a CDR3 of the light chain variable region sequence set forth in SEQ ID NO:58;

(xiii) the heavy chain variable region comprises a CDR1, a CDR2, and a CDR3 of the heavy chain variable region sequence set forth in SEQ ID NO:61, and the light chain variable region comprises a CDR1, a CDR2, and a CDR3 of the light chain variable region sequence set forth in SEQ ID NO:62;

(xiv) the heavy chain variable region comprises a CDR1, a CDR2, and a CDR3 of the heavy chain variable region sequence set forth in SEQ ID NO:65, and the light chain variable region comprises a CDR1, a CDR2, and a CDR3 of the light chain variable region sequence set forth in SEQ ID NO:66;

(xv) the heavy chain variable region comprises a CDR1, a CDR2, and a CDR3 of the heavy chain variable region sequence set forth in SEQ ID NO:69, and the light chain variable region comprises a CDR1, a CDR2, and a CDR3 of the light chain variable region sequence set forth in SEQ ID NO:70;

(xvi) the heavy chain variable region comprises a CDR1, a CDR2, and a CDR3 of the heavy chain variable region sequence set forth in SEQ ID NO:73, and the light chain variable region comprises a CDR1, a CDR2, and a CDR3 of the light chain variable region sequence set forth in SEQ ID NO:74;

(xvii) the heavy chain variable region comprises a CDR1, a CDR2, and a CDR3 of the heavy chain variable region sequence set forth in SEQ ID NO:77, and the light chain variable region comprises a CDR1, a CDR2, and a CDR3 of the light chain variable region sequence set forth in SEQ ID NO:78;

(xviii) the heavy chain variable region comprises a CDR1, a CDR2, and a CDR3 of the heavy chain variable region sequence set forth in SEQ ID NO:81, and the light chain variable region comprises a CDR1, a CDR2, and a CDR3 of the light chain variable region sequence set forth in SEQ ID NO:82;

(xix) the heavy chain variable region comprises a CDR1, a CDR2, and a CDR3 of the heavy chain variable region sequence set forth in SEQ ID NO:85, and the light chain variable region comprises a CDR1, a CDR2, and a CDR3 of the light chain variable region sequence set forth in SEQ ID NO:86;

(xx) the heavy chain variable region comprises a CDR1, a CDR2, and a CDR3 of the heavy chain variable region sequence set forth in SEQ ID NO:89, and the light chain variable region comprises a CDR1, a CDR2, and a CDR3 of the light chain variable region sequence set forth in SEQ ID NO:90;

(xxi) the heavy chain variable region comprises a CDR1, a CDR2, and a CDR3 of the heavy chain variable region sequence set forth in SEQ ID NO:93, and the light chain variable region comprises a CDR1, a CDR2, and a CDR3 of the light chain variable region sequence set forth in SEQ ID NO:94;

(xxii) the heavy chain variable region comprises a CDR1, a CDR2, and a CDR3 of the heavy chain variable region sequence set forth in SEQ ID NO:298, and the light chain variable region comprises a CDR1, a CDR2, and a CDR3 of the light chain variable region sequence set forth in SEQ ID NO:299;

(xxiii) the heavy chain variable region comprises a CDR1, a CDR2, and a CDR3 of the heavy chain variable region sequence set forth in SEQ ID NO:310, and the light chain variable region comprises a CDR1, a CDR2, and a CDR3 of the light chain variable region sequence set forth in SEQ ID NO:311;

(xxiv) the heavy chain variable region comprises a CDR1, a CDR2, and a CDR3 of the heavy chain variable region sequence set forth in SEQ ID NO:322, and the light chain variable region comprises a CDR1, a CDR2, and a CDR3 of the light chain variable region sequence set forth in SEQ ID NO:323;

(xxv) the heavy chain variable region comprises a CDR1, a CDR2, and a CDR3 of the heavy chain variable region sequence set forth in SEQ ID NO:334, and the light chain variable region comprises a CDR1, a CDR2, and a CDR3 of the light chain variable region sequence set forth in SEQ ID NO:335;

(xxvi) the heavy chain variable region comprises a CDR1, a CDR2, and a CDR3 of the heavy chain variable region sequence set forth in SEQ ID NO:346, and the light chain variable region comprises a CDR1, a CDR2, and a CDR3 of the light chain variable region sequence set forth in SEQ ID NO:347; or (xxvii) the heavy chain variable region comprises a CDR1, a CDR2, and a CDR3 of the heavy chain variable region sequence set forth in SEQ ID NO:358, and the light chain variable region comprises a CDR1, a CDR2, and a CDR3 of the light chain variable region sequence set forth in SEQ ID NO:359.

35. The anti-human GPRC5D antibody or antigen-binding fragment thereof of claim 33, wherein the antibody or antigen-binding fragment thereof binds to human GPRC5D with a binding affinity ($K_d$) of from about $1\times10^{-9}$ M to about $1\times10^{-8}$ M.

36. The anti-human GPRC5D antibody or antigen-binding fragment thereof of claim 33, wherein the antibody or antigen-binding fragment thereof binds to one, two, three or four epitope regions selected from the group consisting of an epitope region in N-terminal region comprising amino acids 1-27 of SEQ ID NO:97, an epitope region in ECL1 region comprising amino acids 85-93 of SEQ ID NO:97, an epitope region in ECL2 region comprising amino acids 145-167 of SEQ ID NO:97, and an epitope region in ECL3 region comprising amino acids 226-239 of SEQ ID NO:97.

37. The anti-human GPRC5D antibody or antigen-binding fragment thereof of claim 33, wherein the antibody or antigen-binding fragment thereof binds to an epitope region selected from the group consisting of:
  an epitope region comprising amino acids 16-23 of SEQ ID NO:97,
  an epitope region comprising amino acids 15-23 of SEQ ID NO:97,
  an epitope region comprising amino acids 16-25 of SEQ ID NO:97,
  an epitope region comprising amino acids 10-17 of SEQ ID NO:97,
  an epitope region comprising amino acids 5-17 of SEQ ID NO:97,
  an epitope region comprising amino acids 85-95 of SEQ ID NO:97,
  an epitope region comprising amino acids 157-164 of SEQ ID NO:97,
  an epitope region comprising amino acids 157-167 of SEQ ID NO:97,
  an epitope region comprising amino acids 230-237 of SEQ ID NO:97,
  an epitope region comprising amino acids 229-237 of SEQ ID NO:97,
  an epitope region comprising amino acids 230-243 of SEQ ID NO:97, and
  an epitope region comprising amino acids 227-237 of SEQ ID NO:97.

38. The anti-human GPRC5D antibody or antigen-binding fragment thereof of claim 33, wherein the antibody comprises a human variable region framework region.

39. The anti-human GPRC5D antibody or antigen-binding fragment thereof of claim 33, which is a fully human antibody or an antigen-binding fragment thereof.

40. The anti-human GPRC5D antibody or antigen-binding fragment thereof of claim 33, which is a chimeric or humanized antibody or an antigen-binding fragment thereof.

41. The anti-human GPRC5D antibody or antigen-binding fragment thereof of claim 33, wherein the antigen-binding fragment of the antibody is a Fab, Fab', F(ab')$_2$, Fv or single chain Fv (scFv).

42. A composition comprising the antibody or antigen-binding fragment thereof of claim 33, and a pharmaceutically acceptable carrier.

43. An immunoconjugate comprising the antibody or antigen-binding fragment thereof of claim 33, linked to a therapeutic agent.

44. A composition comprising the immunoconjugate of claim 43 and a pharmaceutically acceptable carrier.

45. A bispecific molecule comprising the antibody or antigen-binding fragment thereof of claim 33, linked to a second functional moiety.

46. A composition comprising the bispecific molecule of claim 45 and a pharmaceutically acceptable carrier.

* * * * *